United States Patent
Cumming et al.

(10) Patent No.: US 9,221,839 B2
(45) Date of Patent: Dec. 29, 2015

(54) C5-C6 OXACYCLIC-FUSED THIADIAZINE DIOXIDE COMPOUNDS AS BACE INHIBITORS, COMPOSITIONS, AND THEIR USE

(75) Inventors: Jared N. Cumming, Garwood, NJ (US); Eric J. Gilbert, Scotch Plains, NJ (US); Andrew W. Stamford, Chatham, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/009,883

(22) PCT Filed: Apr. 4, 2012

(86) PCT No.: PCT/US2012/032135
§ 371 (c)(1),
(2), (4) Date: Oct. 4, 2013

(87) PCT Pub. No.: WO2012/138734
PCT Pub. Date: Oct. 11, 2012

(65) Prior Publication Data
US 2014/0023668 A1 Jan. 23, 2014

Related U.S. Application Data

(60) Provisional application No. 61/473,075, filed on Apr. 7, 2011, provisional application No. 61/567,729, filed on Dec. 7, 2011.

(51) Int. Cl.
| | | |
|---|---|---|
| C07D 513/04 | (2006.01) |
| A61K 31/549 | (2006.01) |
| A61K 31/54 | (2006.01) |
| A61K 45/06 | (2006.01) |

(52) U.S. Cl.
CPC .............. *C07D 513/04* (2013.01); *A61K 31/54* (2013.01); *A61K 31/549* (2013.01); *A61K 45/06* (2013.01)

(58) Field of Classification Search
CPC ..... C07D 513/04; A61K 31/549; A61K 31/54
USPC ......................................... 544/10; 514/222.8
See application file for complete search history.

(56) References Cited

U.S. PATENT DOCUMENTS

| | | | |
|---|---|---|---|
| 5,534,520 A | 7/1996 | Fisher et al. |
| 6,225,310 B1 | 5/2001 | Nielsen et al. |
| 6,683,091 B2 | 1/2004 | Asberom et al. |
| 7,648,983 B2 | 1/2010 | Audia et al. |
| 7,994,167 B2 | 8/2011 | Frank et al. |
| 8,338,413 B1 | 12/2012 | Rueeger |
| 8,557,826 B2 | 10/2013 | Stamford et al. |
| 8,563,543 B2 | 10/2013 | Scott et al. |
| 8,569,310 B2 | 10/2013 | Iserloh et al. |
| 8,729,071 B2 | 5/2014 | Scott et al. |
| 8,940,748 B2 | 1/2015 | Scott et al. |
| 9,029,362 B2 | 5/2015 | Scott et al. |
| 2006/0034848 A1 | 2/2006 | Kinoshita et al. |
| 2006/0281730 A1 | 12/2006 | Zhu et al. |
| 2007/0072925 A1 | 3/2007 | Malamas et al. |
| 2007/0287692 A1 | 12/2007 | Wu et al. |
| 2007/0299087 A1 | 12/2007 | Berg et al. |
| 2008/0200445 A1 | 8/2008 | Zhu et al. |
| 2009/0023762 A1 | 1/2009 | Berg et al. |
| 2009/0062282 A1 | 3/2009 | Albert et al. |
| 2009/0209755 A1 | 8/2009 | Suzuki et al. |

(Continued)

FOREIGN PATENT DOCUMENTS

| | | |
|---|---|---|
| EP | 1942105 | 7/2008 |
| JP | 2012250933 | 12/2012 |

(Continued)

OTHER PUBLICATIONS

PCT Search Report for PCT/US2012/32135 mailed on Jul. 23, 2012; 2 pages.
Written Opinion for PCT/US2012/32135 completed on Jun. 26, 2012; 5 pages.
Abramov, et al., Amyloid- as a positive endogenous regulator of release probability at hippocampal synapses, Nature Neuroscience 12, 1567-1576 (2009) Published online: Nov. 22, 2009 | doi:10.1038/nn.2433.
Barton, et al., On the Structure of Some Substituted 4, 6-Pyrimidinones, Department of Organic Chemistry, College of Medicine, Jagiellonian University, Ingardena 3, 30-060-Krakow, Poland, Polish J. Chem., 69, 235-245 (1995), revised manuscript Oct. 25, 1994.

(Continued)

*Primary Examiner* — Kahsay Habte
(74) *Attorney, Agent, or Firm* — Keith D. MacMillan; John C. Todaro

(57) ABSTRACT

In its many embodiments, the present invention provides certain iminothiadiazine dioxide compounds, including compounds Formula

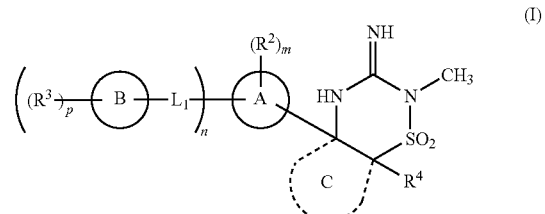

and tautomers and stereoisomers thereof, and pharmaceutically acceptable salts of said compounds, said tautomers and said stereoisomers, wherein each of ring A, ring B, ring C, $R^2$, $R^3$, $R^4$, m, n, p, and -$L_1$- is as defined herein. The novel compounds of the invention may be useful as BACE inhibitors and/or for the treatment and prevention of various pathologies related thereto. Pharmaceutical compositions comprising one or more such compounds (alone and in combination with one or more other active agents), and methods for their preparation and use, including Alzheimer's disease, are also disclosed.

12 Claims, No Drawings

(56) References Cited

U.S. PATENT DOCUMENTS

| | | |
|---|---|---|
| 2010/0069406 A1 | 3/2010 | Zhu et al. |
| 2010/0075957 A1 | 3/2010 | Tamura et al. |
| 2010/0317850 A1 | 12/2010 | Suzuki et al. |
| 2011/0009395 A1 | 1/2011 | Audia et al. |
| 2011/0046122 A1 | 2/2011 | Andreini et al. |
| 2011/0152253 A1 | 6/2011 | Motoki et al. |
| 2012/0035195 A1 | 2/2012 | Banner et al. |
| 2012/0184540 A1 | 7/2012 | Andreini et al. |
| 2012/0189642 A1 | 7/2012 | Scott et al. |
| 2012/0195881 A1 | 8/2012 | Iserloh et al. |
| 2012/0196863 A1 | 8/2012 | Andreini et al. |
| 2012/0258961 A1 | 10/2012 | Suzuki et al. |
| 2012/0258962 A1 | 10/2012 | Hilpert et al. |
| 2012/0302549 A1 | 11/2012 | Narquizian et al. |
| 2014/0023667 A1 | 1/2014 | Stamford et al. |
| 2014/0023668 A1 | 1/2014 | Cumming et al. |
| 2014/0128382 A1 | 5/2014 | Wu et al. |
| 2014/0200213 A1 | 7/2014 | Wu et al. |

FOREIGN PATENT DOCUMENTS

| | | |
|---|---|---|
| WO | WO9004917 | 5/1990 |
| WO | WO9304047 | 3/1993 |
| WO | WO9614844 | 5/1996 |
| WO | WO00051992 | 9/2000 |
| WO | WO2005058311 | 6/2005 |
| WO | WO2006009653 | 1/2006 |
| WO | WO2006009655 | 1/2006 |
| WO | WO2006041404 | 4/2006 |
| WO | WO2006041405 | 4/2006 |
| WO | WO2006044497 | 4/2006 |
| WO | WO2006060109 | 6/2006 |
| WO | WO2006065277 | 6/2006 |
| WO | WO2006076284 | 7/2006 |
| WO | WO2006138192 | 12/2006 |
| WO | WO2006138195 | 12/2006 |
| WO | WO2006138217 | 12/2006 |
| WO | WO2006138264 | 12/2006 |
| WO | WO2006138265 | 12/2006 |
| WO | WO2006138266 | 12/2006 |
| WO | WO2007005366 | 1/2007 |
| WO | WO2007005404 | 1/2007 |
| WO | WO2007011810 | 1/2007 |
| WO | WO2007016012 | 2/2007 |
| WO | WO2007038271 | 4/2007 |
| WO | WO2007078813 | 4/2007 |
| WO | WO2007049532 | 5/2007 |
| WO | WO2007050721 | 5/2007 |
| WO | WO2007053506 | 5/2007 |
| WO | WO2007058580 | 5/2007 |
| WO | WO2007058581 | 5/2007 |
| WO | WO2007058583 | 5/2007 |
| WO | WO2007058601 | 5/2007 |
| WO | WO2007058602 | 5/2007 |
| WO | WO2007073284 | 6/2007 |
| WO | WO2007100536 | 9/2007 |
| WO | WO2007114771 | 10/2007 |
| WO | WO2007145568 | 12/2007 |
| WO | WO2007145569 | 12/2007 |
| WO | WO2007145570 | 12/2007 |
| WO | WO2007145571 | 12/2007 |
| WO | WO2007146225 | 12/2007 |
| WO | WO2008022024 | 2/2008 |
| WO | WO2008063114 | 5/2008 |
| WO | WO2008073365 | 6/2008 |
| WO | WO2008073370 | 6/2008 |
| WO | WO2008076043 | 6/2008 |
| WO | WO2008076044 | 6/2008 |
| WO | WO2008076045 | 6/2008 |
| WO | WO2008076046 | 6/2008 |
| WO | WO2008133273 | 6/2008 |
| WO | WO2008133274 | 6/2008 |
| WO | WO2008103351 | 8/2008 |
| WO | WO2008115552 | 9/2008 |
| WO | WO2008118379 | 10/2008 |
| WO | WO2009020580 | 2/2009 |
| WO | WO2009091016 | 7/2009 |
| WO | WO2009108550 | 9/2009 |
| WO | WO2009131974 | 10/2009 |
| WO | WO2009131975 | 10/2009 |
| WO | WO2009134617 | 11/2009 |
| WO | WO2009136350 | 11/2009 |
| WO | WO2009151098 | 12/2009 |
| WO | WO2010013302 | 2/2010 |
| WO | WO2010013794 | 2/2010 |
| WO | WO2010021680 | 2/2010 |
| WO | WO2010030954 | 3/2010 |
| WO | WO2010038686 | 4/2010 |
| WO | WO2010047372 | 4/2010 |
| WO | WO2010128058 | 11/2010 |
| WO | WO2011005738 | 1/2011 |
| WO | WO2011009897 | 1/2011 |
| WO | WO2011009898 | 1/2011 |
| WO | WO2011009943 | 1/2011 |
| WO | WO2011020806 | 2/2011 |
| WO | WO2011029803 | 3/2011 |
| WO | WO2011044181 | 4/2011 |
| WO | WO2011044184 | 4/2011 |
| WO | WO2011044185 | 4/2011 |
| WO | WO2011044187 | 4/2011 |
| WO | WO2011058763 | 5/2011 |
| WO | WO2011069934 | 6/2011 |
| WO | WO2011070029 | 6/2011 |
| WO | WO2011070781 | 6/2011 |
| WO | WO2011071057 | 6/2011 |
| WO | WO2011071109 | 6/2011 |
| WO | WO2011071135 | 6/2011 |
| WO | WO2011072064 | 6/2011 |
| WO | WO2011077726 | 6/2011 |
| WO | WO2011080176 | 7/2011 |
| WO | WO2011106414 | 9/2011 |
| WO | WO2011115928 | 9/2011 |
| WO | WO2011115938 | 9/2011 |
| WO | WO2011123674 | 10/2011 |
| WO | WO2011130347 | 10/2011 |
| WO | WO2011130741 | 10/2011 |
| WO | WO2011138293 | 11/2011 |
| WO | WO2011154374 | 12/2011 |
| WO | WO2011154431 | 12/2011 |
| WO | WO2012006953 | 1/2012 |
| WO | WO2012040641 | 3/2012 |
| WO | WO2012057247 | 5/2012 |
| WO | WO2012057248 | 5/2012 |
| WO | WO2012071279 | 5/2012 |
| WO | WO2012071458 | 5/2012 |

OTHER PUBLICATIONS

Bayden, et al., Web application for studying the free energy of binding and protonation states of protein-ligand complexes based on HINT, J Comput Aided Mol Des (2009) 23:621-632.

Chiriano, et al., Sequential Virtual Screening Approach to the Identification of Small Organic Molecules as Potential BACE-1 Inhibitors, Chem Biol Drug Des 2011; 77: 268-271.

Cho, et al, S-Nitrosylation of Drp1 Mediates β-Amyloid-Related Mitochondrial Fission and Neuronal Injury, Science Apr. 3, 2009: vol. 324 No. 5923 pp. 102-105.

Cole, et al., Review: The Alzheimer's disease B-secretase enzyme, BACEI, Molecular Neurodegeneration 2007, 2:22, Published Nov. 15, 2007.

Cumming JN, et al. Piperazine sulfonamide BACE1 inhibitors: Design, synthesis, and in vivo characterization. Bioorg Med Chem Lett. 2010;20:2837-42.

Cumming JN, et al. Rational design of novel, potent piperazinone and imidazolidinone BACE1 inhibitors. Bioorg Med Chem Lett. 2008;18:3236-41.

Cumming JN, et al. Structure based design of iminohydantoin BACE1 inhibitors: identification of an orally available, centrally active BACE1 inhibitor. Bioorg Med Chem Lett. Apr. 1, 2012;22(7):2444-9. doi: 10.1016/j.bmcl.2012.02.013.

Cumming, et al., Design and development of cyclic amine BACE1 inhibitors, Current Opinion in Drug Discovery and Development, 2004, 7(4), 536-556.

(56) References Cited

OTHER PUBLICATIONS

Edwards, et al., Application of Fragment-Based Lead Generation to the Discovery of Novel, Cyclic Amidine p-Secretase Inhibitors with Nanomolar Potency, Cellular Activity, and High Ligand Efficiency, 1. Med. Chenl. 2007, 50, 5912-5925.

Evin, et al., BACE Inhibitors as Potential Drugs for the Treatment of Alzheimer's Disease: Focus on Bioactivity, Recent Patents on CNS Drug Discovery, 2011, 6, 91-106.

Farah, et al., Reduced BACE1 Activity Enhances Clearance of Myelin Debris and Regeneration of Axons in the Injured Peripheral Nervous System, The Journal of Neuroscience, Apr. 13, 2011 • 31(15):5744-5754.

Getchell, et al., 3-Nitrotyrosine immunoreactivity in olfactory receptor neurons of patients with Alzheimer's disease: implications for impaired odor sensitivity, Neurobiology of Aging 24 (2003) 663-673., accepted Oct. 8, 2002, pp. 663-673.

Ginman, et al., "Core refinement toward permeable B-Secretase (BACE-1) Inhibitors with low hERG Activity", Journal of Medicinal Chemistry, Rec'd Aug. 12, 2012.

Gravenfors, et al., "New Aminimidazoles as B-Secretase (BACE-1) inhibitors Showing amylod-B (AB) lowering in the brain", Journal of Medicinal Chemistry, 2012, 9297-9311.

Guo, et al., Targeting Amyloid-B in Glaucoma Treatment, pp. 13444-13449, PNAS, Aug. 14, 2007, vol. 104, No. 33.

Hilpert, et al., "B-Secretase (BACE1) Inhibitors with high in vivo efficacy suitable for clinical evaluation of Alzheimer's disease", Journal of Medicinal Chemistry, 2013, 3980-3995.

Huang, et al., "Structure- and Property-Based Design of Aminooxazoline Xanthines as selective, orally efficacious, and CNS Penetrable BACE inhibitors for the treatment of Alzheimer's disease", Journal of Medicinal Chemistry, Special Issue: Alzheimer's Disease, 2012, 55, 9156-9169.

Huang, et al., Pharmacophore Model Construction of, 8-Secretase Inhibitors, Acta Chimica Sinica, vol. 66, No. 16, 2008, pp. 1889-1897. (English Abstract).

Hunt, et al., "Spirocyclic B-Site Amyloid Precursor Protein Cleaving Enzyme 1 (BACE1) Inhibitors: From hit to Lowering of Cerebralspinal fluid (CSF) Amyloid-B in a higher species", Journal of Medicinal Chemistry 2013, 56, 3379-3403.

lserloh U, et al. Discovery of an orally efficacious 4-phenoxypyrrolidine-based BACE1 inhibitor. Bioorg Med Chem Lett. 2008;18:418-22.

Iserloh U, et al. Potent pyrrolidine- and piperidine-based BACE-1 inhibitors. Bioorg Med Chem Lett. 2008;18:414-7.

Jin, et al., Evidence for dimeric BACE-mediated APP processing, Biochemical and Biophysical Research Communications 393 (2010) 21-27.

Loane, et al., Amyloid Precursor Protein Secretases as Therapeutic Targets for Traumatic Brain Injury, Nature Medicine, Advance Online Publication, Received Aug. 27, 2008; accepted Feb. 18, 2009; published online Mar. 15, 2009; doi:10.1038/nm.1940, pp. 1-3.

Luo, et al., mice deficient in BACE1, the Alzheimer's B-secretase, have normal phenotype and abolished B-amyloid, Nature Neuroscience, vol. 4, No. 3, Mar. 2001.

Malamas, et al., Aminoimidazoles as potent and selective human B-secretase (BACE1) inhibitors, J. Med. Chem., 2009, 52, 6314-6323.

Malamas, et al., Design and Synthesis of 5, 50-Disubstituted Aminohydantoins as Potent and Selective Human β-Secretase (BACE1) Inhibitors, J. Med. Chem. 2010, 53, 1146-1158 (Published on Web Dec. 7, 2009).

Malamas, et al., Design and synthesis of aminohydantoins as potent and selective human b-secretase (BACE1) inhibitors with enhanced brain permeability, Bioorganic & Medicinal Chemistry Letters 20 (2010) 6597-6605.

Malamas, et al., Di-substituted pyridinyl aminohydantoins as potent and highly selective human b-secretase (BACE1) inhibitors, Bioorganic & Medicinal Chemistry 18 (2010) 630-639.

Malamas, et al., New pyrazolyl and thienyl aminohydantoins as potent BACE1 inhibitors: Exploring the S20 region, Bioorganic & Medicinal Chemistry Letters 21 (2011) 5164-5170.

Malamas, et al., Novel pyrrolyl 2-aminopyridines as potent and selective human b-secretase (BACE1) inhibitors, Bioorganic & Medicinal Chemistry Letters 20 (2010) 2068-2073 (Available online Feb. 23, 2010).

Mandal M, et al., Design and validation of bicyclic iminopyrimidinones as beta amyloid cleaving enzyme-1 (BACE1) inhibitors: conformational constraint to favor a bioactive conformation. J Med Chem. Nov. 8, 2012;55(21):9331-45. doi:10.1021/jm301039c.

May, et al., Robust Central Reduction of B Amyloid in Humans with an Orally Available, Non-Peptidic B-Secretase Inhibitor, The Journal of Neuroscience, Nov. 16, 2011 • 31(46):16507-16516 • 16507.

McConlogue, et al., Partial reduction of BACE1 as dramatic effects on Alzheimer's plaque and synaptic pathology in APP transgenic mice, J. Biological Chem., vol. 282, No. 36, pp. 26326-26334, Sep. 7, 2007.

Nowak, et al., Discovery and initial optimization of 5, 50-disubstituted aminohydantoins as potent b-secretase (BACE1) inhibitors,Bioorganic & Medicinal Chemistry Letters 20 (2010) 632-635. (Available online Nov. 20, 2009).

Ohno, et al., BACE1 deficiency rescues memory deficits and Cholinergic function in a mouse model of Alzheimer's disease, Neuron, vol. 41, 27-33, Jan. 8, 2004.

Ohno, et al.BACE1 gene deletion prevents neuron loss and memory deficits in 5XFAD APP/PS1 transgenic mice, Neurobiology of disease 26 (2006), pp. 134-145.

Osherovich, L. AB's Dry (AMD) Humor, SciBX 4(26); doi:10.1038/scibx.2011.727, Published online Jun. 30, 2011.

Probst, et al., Small-molecule BACE1 inhibitors: a patent literature review, Expert Opinion on Therapeutic Patents, (2006-2011), 2012, 22(5):511-540.

Roberds, et al., BACE knockout mice are healthy despite lacking the primary B-secretase activity in the brain: implications for Alzheimer's disease therapeutics, Human Mol. Genetics, vol. 10, No. 12, pp. 1317-1324. Apr. 3, 2004.

Salloway, et al., A randomized, double-blind, placebo-controlled clinical trial of intravenous bapineuzumab in patients with mild-to-moderate Alzheimer's disease who are alipoprotein E4 non-carriers, European Federation of Neurological Societies, Stockholm, Sweden, Sep. 12, 2012.

Scott, et al., "Novel Imino Pyrimidinone B-Secretase (BACE1) Inhibitors. P1 Thiophenes", Poster presentation, American Chemical Society, 2011.

Silvestri, Romano, Boom in the Development of Non-Peptidic b-Secretase (BACE1) Inhibitors for the Treatment of Alzheimer's Disease, Istituto Pasteur, Fondazione Cenci Bolognetti, Dipartimento di Chimica e Tecnologie del Farmaco, Sapienza Universita' di Roma, Piazzale Aldo Moro 5, I-00185 Roma, Italy, Published online Jul. 23, 2008 in Wiley InterScience (www.interscience.wiley.com).

Southan, BACE2 as a New Diabetes Target: a patent review 2010-2012, Expert Opinion on Therapeutic Patents, 2013, Informa UK, Ltd., ISSN 1354-3776, e-1744-7674.

Sperling, et al., A randomized, double-blind, placebo-controlled clinical trial of intravenous bapineuzumab in patients with mild-to-moderate Alzheimer's disease who are alipoprotein E4 non-carriers, European Federation of Neurological Societies, Stockholm, Sweden, Sep. 11, 2012.

Stachel, et al., Structure-Based Design of Potent and Selective Cell-Permeable Inhibitors of Human Beta-Secretase (BACE-1), J. Med. Chem., 2004, vol. 47, pp. 6447-6450.

Stamford, et al., "Fragment-based discovery of BACE1 inhibitors, Potential disease-modifying agents for the treatment of Alzheimer's disease", Slide Presentation R. Bryan Miller Symposium, UC Davis, Mar. 7-8, 2013.

Stamford, et al., Discovery of an Orally Available, Brain Penetrant BACE1 Inhibitor That Affords Robust CNS Aβ Reduction, ACS Med. Chem. Lett. Jul. 12, 2012, 3, 897-902.

(56) References Cited

OTHER PUBLICATIONS

Stamford, et al., Inhibitors of BACE for treating Alzheimer's disease: a fragment-based drug discovery story, Current Opinion in Chemical Biology; v:17 i:3 p. 320-328; Jun. 2013 Elsevier.

Statchel, et al., Conformationally biased P3 amide replacements of b-secretase inhibitors, S. J. Stachel et al./Bioorg. Med. Chem. Lett. 16 (2006) 641-644.

Statchel, et al., Discovery of aminoheterocycles as a novel b-secretase inhibitor class: pH dependence on binding activity part 1, Bioorganic & Medicinal Chemistry Letters 19 (2009) 2977-2980.

Swahn, et al., "Aminimidazoles as BACE-1 inhibitors: The challenge to achieve in vivo brain efficacy", Bioorganic and Medicinal Chemistry Letters, 22 (2012) 1854-1859.

Swahn, et al., "Design and synthesis of beta-site amyloid precursor protein cleaving enzyme (BACE1) inhibitors with in vivo brain reduction of B-amyloid peptides", Journal of Medicinal Chemistry, 2012, 55, 9346-9361.

Tresadern, et al., Rational design and synthesis of aminopiperazinones as b-secretase (BACE) inhibitors, Bioorganic & Medicinal Chemistry Letters 21 (2011) 7255-7260.

Wang YS, et al., Application of fragment-based NMR screening, X-ray crystallography, structure-based design, and focused chemical library design to identify novel microM leads for the development of nM BACE-1 (beta-site APP cleaving enzyme 1) inhibitors. J Med Chem. 2010;53:942-50.

Weiner, Further insights into Alzheimer disease pathogenesis, Weiner, M. W. Nat. Rev. Neurol. 9, 65-66 (2013); published online Jan. 22, 2013.

Welch, J.T., et al., The synthesis and biological activity of pentafluorosulfanyl analogs of fluoxetine, fenfluramine, and norfenfluramine, Bioorganic & Medicinal Chemistry; v:15 i:21 p. 6659-6666; Nov. 1, 2007.

Wyss DF, et al., Combining NMR and X-ray crystallography in fragment-based drug discovery: discovery of highly potent and selective BACE-1 inhibitors. Top Curr Chem. 2012;317:83-114. doi: 10.1007/128_2011_183.

Zhi, et al., Self-organizing molecular field analysis on human b-secretase nonpeptide inhibitors: 5, 5-disubstituted aminohydantoins, European Journal of Medicinal Chemistry 46 (2011) 58-64.

Zhou, et al., An efficient synthesis of 2-amino-4-(4-fluoro-3-(2-fluoropyridin-3-yl)phenyl)-4-(4-methoxy-3-methylphenyl)-1-methyl-1H-imidazol-5(4H)-one, a potent BACE1 inhibitor, ARKIVOC 2010 (vi) 84-88.

Zhou, et al., Pyridinyl aminohydantoins as small molecule BACE1 inhibitors, Bioorganic & Medicinal Chemistry Letters 20 (2010) 2326-2329 (Available online Feb. 12, 2010).

Zhu, et al., Discovery of Cyclic Acylguanidines as Highly Potent and Selective β-Site Amyloid Cleaving Enzyme (BACE) Inhibitors: Part I; Inhibitor Design and Validation), 1, J. Med. Chem. 2010, 53, 951-965.

C5-C6 OXACYCLIC-FUSED THIADIAZINE DIOXIDE COMPOUNDS AS BACE INHIBITORS, COMPOSITIONS, AND THEIR USE

CROSS-REFERENCE TO RELATED APPLICATIONS

This Application is a U.S. National Stage Application under 35 U.S.C. 371 of PCT Application No. PCT/US2012/032135, filed Apr. 4, 2012, which claims priority under 35 U.S.C. 199(e) to U.S. Provisional Application No. 61/567,729, filed Dec. 7, 2011, and U.S. Provisional Application No. 61/473,075, filed Apr. 7, 2011.

FIELD OF THE INVENTION

This invention provides certain imino thiadiazine dioxide compounds and compositions comprising these compounds, which may be useful as inhibitors of BACE, and for treating or preventing pathologies related thereto

BACKGROUND OF THE INVENTION

Amyloid beta peptide ("Aβ") is a primary component of β amyloid fibrils and plaques, which are regarded playing a role in an increasing number of pathologies. Examples of such pathologies include, but are not limited to, Alzheimer's Disease, Down's syndrome, Parkinson's disease, memory loss (including memory loss associated with Alzheimer's disease and Parkinson's disease), attention deficit symptoms (including attention deficit symptoms associated with Alzheimer's disease ("AD"), Parkinson's disease, and Down's syndrome), dementia (including pre-senile dementia, senile dementia, dementia associated with Alzheimer's disease, Parkinson's disease, and Down's syndrome), progressive supranuclear palsy, cortical basal degeneration, neurodegeneration, olfactory impairment (including olfactory impairment associated with Alzheimer's disease, Parkinson's disease, and Down's syndrome), β-amyloid angiopathy (including cerebral amyloid angiopathy), hereditary cerebral hemorrhage, mild cognitive impairment ("MCI"), glaucoma, amyloidosis, type II diabetes, hemodialysis ($β_2$ microglobulins and complications arising therefrom), neurodegenerative diseases such as scrapie, bovine spongiform encephalitis, and Creutzfeld-Jakob disease and the like.

Aβ peptides are short peptides which are made from the proteolytic break-down of the transmembrane protein called amyloid precursor protein ("APP"). Aβ peptides are made from the cleavage of APP by β-secretase activity at the position corresponding to the N-terminus of Aβ, and by γ-secretase activity at the position corresponding to the C-terminus of Aβ. (APP is also cleaved by α-secretase activity, resulting in the secreted, non-amyloidogenic fragment known as soluble APPα.) Beta site APP Cleaving Enzyme ("BACE-1") is regarded as the primary aspartyl protease responsible for the production of abnormal Aβ by β-secretase activity. The inhibition of BACE-1 has been shown to inhibit the production of Aβ.

Alzheimer's disease is estimated to afflict more than 20 million people worldwide and is believed to be the most common cause of dementia. AD is a disease characterized by degeneration and loss of neurons and also by the formation of senile plaques and neurofibrillary tangles. Presently, treatment of Alzheimer's disease is limited to the treatment of its symptoms rather than the underlying causes. Symptom-improving agents approved for this purpose include, for example, N-methyl-D-aspartate receptor antagonists such as memantine (Namenda®, Forrest Pharmaceuticals, Inc.), cholinesterase inhibitors such as donepezil (Aricept®, Pfizer), rivastigmine (Exelon®, Novartis), galantamine (Razadyne Reminyl®), and tacrine (Cognex®).

In AD, Aβ peptides, formed through β-secretase and γ-secretase activity, can form tertiary structures that aggregate to form amyloid fibrils. Aβ peptides have also been shown to form Aβ oligomers (sometimes referred to as "Abeta aggretates" or "Abeta oligomers"). Aβ oligomers are small multimeric structures composed of 2 to 12 Aβ peptides that are structurally distinct from Aβ fibrils. Amyloid fibrils can deposit outside neurons in dense formations known as senile plaques, neuritic plaques, or diffuse plaques in regions of the brain important to memory and cognition. Aβ oligomers are cytotoxic when injected in the brains of rats or in cell culture. This Aβ plaque formation and deposition and/or Aβ oligomer formation, and the resultant neuronal death and cognitive impairment, are among the hallmarks of AD pathophysiology. Other hallmarks of AD pathophysiology include intracellular neurofibrillary tangles comprised of abnormally phosphorylated tau protein, and neuroinflammation.

Evidence suggests that Aβ and Aβ fibrils and plaque play a causal role in AD pathophysiology. (See Ohno et al., *Neurobiology of Disease*, No. 26 (2007), 134-145.) Mutations in the genes for APP and presenilins 1/2 (PS1/2) are known to cause familial AD and an increase in the production of the 42-amino acid form of Aβ is regarded as causative. Aβ has been shown to be neurotoxic in culture and in vivo. For example, when injected into the brains of aged primates, fibrillar Aβ causes neuron cell death around the injection site. Other direct and circumstantial evidence of the role of Aβ in Alzheimer etiology has also been published.

BACE-1 has become an accepted therapeutic target for the treatment of Alzheimer's disease. For example, McConlogue et al., *J. Bio. Chem.*, vol. 282, No. 36 (September 2007), have shown that partial reductions of BACE-1 enzyme activity and concomitant reductions of Aβ levels lead to a dramatic inhibition of Aβ-driven AD-like pathology (while minimizing side effects of full inhibition), making β-secretase a target for therapeutic intervention in AD. Ohno et al. *Neurobiology of Disease*, No. 26 (2007), 134-145, report that genetic deletion of BACE-1 in 5×FAD mice abrogates Aβ generation, blocks amyloid deposition, prevents neuron loss found in the cerebral cortex and subiculum (brain regions manifesting the most severe amyloidosis in 5×FAD mice), and rescues memory deficits in 5×FAD mice. The group also reports that Aβ is ultimately responsible for neuron death in AD and conclude that BACE-1 inhibition has been validated as an approach for the treatment of AD. Roberds et al., Human Mol. Genetics, 2001, Vol. 10, No. 12, 1317-1324, established that inhibition or loss of β-secretase activity produces no profound phenotypic defects while inducing a concomitant reduction in β-amyloid peptide. Luo et al., *Nature Neuroscience*, vol. 4, no. 3, March 2001, report that mice deficient in BACE-1 have normal phenotype and abolished β-amyloid generation.

BACE-1 has also been identified or implicated as a therapeutic target for a number of other diverse pathologies in which Aβ or Aβ fragments have been identified to play a role. One such example is in the treatment of AD-type symptoms of patients with Down's syndrome. The gene encoding APP is found on chromosome 21, which is also the chromosome found as an extra copy in Down's syndrome. Down's syndrome patients tend to acquire AD at an early age, with almost all those over 40 years of age showing Alzheimer's-type pathology. This is thought to be due to the extra copy of the APP gene found in these patients, which leads to overexpression of APP and therefore to increased levels of Aβ causing the prevalence of AD seen in this population. Furthermore, Down's patients who have a duplication of a small region of chromosome 21 that does not include the APP gene do not develop AD pathology. Thus, it is thought that inhibitors of BACE-1 may be useful in reducing Alzheimer's type pathology in Down's syndrome patients.

Another example is in the treatment of glaucoma (Guo et al., *PNAS*, vol. 104, no. 33, Aug. 14, 2007). Glaucoma is a retinal disease of the eye and a major cause of irreversible blindness worldwide. Guo et al. report that Aβ colocalizes with apoptotic retinal ganglion cells (RGCs) in experimental glaucoma and induces significant RGC cell loss in vivo in a dose- and time-dependent manner. The group report having demonstrated that targeting different components of the Aβ formation and aggregation pathway, including inhibition of β-secretase alone and together with other approaches, can effectively reduce glaucomatous RGC apoptosis in vivo. Thus, the reduction of Aβ production by the inhibition of BACE-1 could be useful, alone or in combination with other approaches, for the treatment of glaucoma.

Another example is in the treatment of olfactory impairment. Getchell et al., *Neurobiology of Aging*, 24 (2003), 663-673, have observed that the olfactory epithelium, a neuroepithelium that lines the posterior-dorsal region of the nasal cavity, exhibits many of the same pathological changes found in the brains of AD patients, including deposits of Aβ, the presence of hyperphosphorylated tau protein, and dystrophic neurites among others. Other evidence in this connection has been reported by Bacon A W, et al., *Ann NY Acad Sci* 2002; 855:723-31; Crino P B, Martin J A, Hill W D, et al., *Ann Otol Rhinol Laryngol*, 1995; 104:655-61; Davies D C, et al., *Neurobiol Aging*, 1993; 14:353-7; Devanand D P, et al., *Am J Psychiatr*, 2000; 157:1399-405; and Doty R L, et al., *Brain Res Bull*, 1987; 18:597-600. It is reasonable to suggest that addressing such changes by reduction of Aβ by inhibition of BACE-1 could help to restore olfactory sensitivity in patients with AD.

Other diverse pathologies characterized by the inappropriate formation and deposition of Aβ or fragments thereof, and/or by the presence of amyloid fibrils, include neurodegenerative diseases such as scrapie, bovine spongiform encephalitis, Creutzfeld-Jakob disease and the like, type II diabetes (which is characterized by the localized accumulation of cytotoxic amyloid fibrils in the insulin producing cells of the pancreas), and amyloid angiopathy. In this regard reference can be made to the patent literature. For example, Kong et al., *US*2008/0015180, disclose methods and compositions for treating amyloidosis with agents that inhibit Aβ peptide formation. Another example is the treatment of traumatic brain injury. As another example, Loane, et al. report the targeting of amyloid precursor protein secretases as therapeutic targets for traumatic brain injury. (Loane et al., "Amyloid precursor protein secretases as therapeutic targets for traumatic brain injury", *Nature Medicine, Advance Online Publication*, published online Mar. 15, 2009.) Still other diverse pathologies characterized by the inappropriate formation and deposition of Aβ or fragments thereof, and/or by the presence of amyloid fibrils, and/or for which inhibitor(s) of BACE-1 is expected to be of therapeutic value are discussed further hereinbelow.

The therapeutic potential of inhibiting the deposition of Aβ has motivated many groups to characterize BACE-1 and to identify inhibitors of BACE-1 and of other secretase enzyme inhibitors. Examples from the patent literature are growing and include US2005/0282826, WO2006009653, WO2007005404, WO2007005366, WO2007038271, WO2007016012, US2007072925, WO2007149033, WO2007145568, WO2007145569, WO2007145570, WO2007145571, WO2007114771, US20070299087, US2007/0287692, WO2005/016876, WO2005/014540, WO2005/058311, WO2006/065277, WO2006/014762, WO2006/014944, WO2006/138195, WO2006/138264, WO2006/138192, WO2006/138217, WO2007/050721, WO2007/053506, WO2007/146225, WO2006/138230, WO2006/138265, WO2006/138266, WO2007/053506, WO2007/146225, WO2008/073365, WO2008/073370, WO2008/103351, US2009/041201, US2009/041202, WO2009/131975, WO2009091016, and WO2010/047372.

BACE inhibitors, particularly BACE-2 inhibitors, are an art-recognized target for the treatment of diabetes. Type 2 diabetes (T2D) is caused by insulin resistance and inadequate insulin secretion from the pancreatic beta-cells, leading to poor blood-glucose control and hyperglycemia (M Prentki & C J Nolan, "Islet beta-cell failure in type 2 diabetes." *J. Clin. Investig.*, 2006, 116(7), 1802-1812). Patients with T2D have an increased risk of microvascular and macrovascular disease and a range of related complications including diabetic neuropathy, retinopathy, and cardiovascular disease.

Beta-cell failure and consequent dramatic decline in insulin secretion and hyperglycemia marks the onset of T2D M Prentki & C J Nolan, "Islet beta-cell failure in type 2 diabetes." *J. Clin. Investig.*, 2006, 116(7), 1802-1812). Most current treatments do not prevent the loss of beta-cell mass characterizing overt T2D. However, recent developments with GLP-1 analogues, gastrin and other agents show that prevention and proliferation of beta-cells is possible to achieve, leading to an improved glucose tolerance and slower progression to overt T2D. (L L. Baggio & D J. Drucker, "Therapeutic approaches to preserve islet mass in type 2 diabetes", *Annu. Rev. Med.* 2006, 57, 265-281.)

Tmem27 has been identified as a protein promoting beta-cell proliferation (P. Akpinar, S. Juqajima, J. Krutzfeldt, M. Stoffel, "Tmem27: A cleaved and shed plasma membrane protein that stimulates pancreatic beta-cell proliferation", *Cell. Metab.* 2005, 2, 385-397) and insulin secretion (K. Fukui, Q. Yang, Y. Cao, N. Takahashi et al., "The HNF-1 target Collectrin controls insulin exocytosis by SNARE complex formation", *Cell. Metab.* 2005, 2, 373-384.) Tmem27 is a 42 kDa membrane glycoprotein which is a constitutively shed from the surface of beta-cells, resulting from a degradation of the full-length cellular Tmem27. Over expression of Tmem27 in a transgenic mouse increases beta-cell mass and improves glucose tolerance in a DIO model of diabetes. (P. Akpinar, S. Juqajima, J. Krutzfeldt, M. Stoffel, "Tmem27: A cleaved and shed plasma membrane protein that stimulates pancreatic beta-cell proliferation", *Cell. Metab.* 2005, 2, 385-397; (K. Fukui, Q. Yang, Y. Cao, N. Takahashi et al., "The HNF-1 target Collectrin controls insulin exocytosis by SNARE complex formation", *Cell. Metab.* 2005, 2, 373-384.) Furthermore, siRNA knockout of Tmem27 in a rodent beta-cell proliferation assay (e.g., using INS1e cells) reduces the proliferation rate, indicating a role for Tmem27 in control of beta-cell mass.

In vitro, BACE-2 (but reportedly not BACE-1) cleaves a peptide based on the sequence of Tmem27. BACE-2 is a membrane-bound aspartyl protease and is colocalized with Tmem27 in rodent pancreatic beta-cells (G. Finzi, F. Franzi, C. Placidi, F. Acquati, et al., "BACE-2 is stored in secretory granules of mouse and rat pancreatic beta cells", *Ultrastruct. Pathol.* 2008, 32(6), 246-251). It is also known to be capable of degrading APP (I. Hussain, D. Powell, D. Howlett, G. Chapman, et al., "ASP1 (BACE2) cleaves the amyloid precursor protein at the beta-secretase site", *Mol. Cell. Neurosci.* 2000, 16, 609-619), IL-1 R2 (P. Kuhn, E. Marjaux, A. Imhof, B. De Strooper, et al., "Regulated intramembrane proteolysis of the interleukin-1 receitpro II by alpha-, beta-, and gamma-secretase", *J. Biol. Chem.*, 2007, 282(16), 11982-11995). Inhibition of BACE-2 is therefore proposed as a treatment for T2D with the potential to preserve and restore beta-cell mass and stimulate insulin secretion in pre-diabetic and diabetic patients. See, e.g., WO2010128058.

SUMMARY OF THE INVENTION

The present invention provides certain imino thiadiazine dioxide compounds which are collectively or individually referred to herein as "compound(s) of the invention", as described herein. The compounds of the invention are expected to be useful as inhibitors of BACE-1. In some embodiments, the compounds of the invention are expected to be inhibitors of BACE-2. In some embodiments, the compounds of the present invention may also exhibit improved solution stability compared to the corresponding iminopyrimidinones.

In one embodiment, the compounds of the invention have the structural Formula (I):

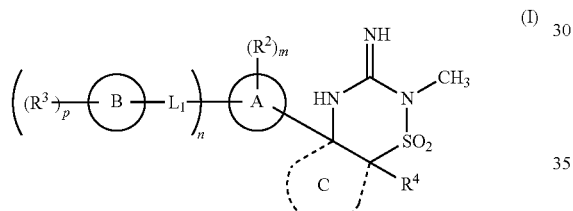
(I)

or a tautomer thereof having the structural Formula (I'):

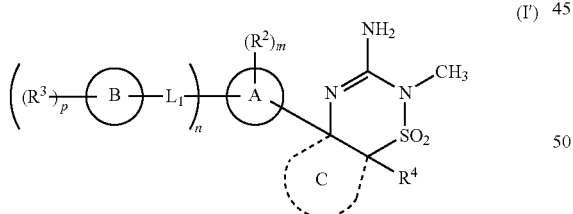
(I')

or pharmaceutically acceptable salt thereof, wherein:
ring C is selected from the group consisting of:

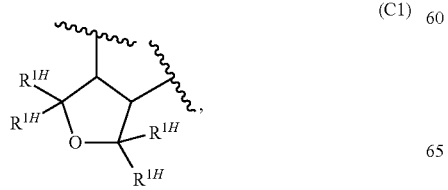
(C1)

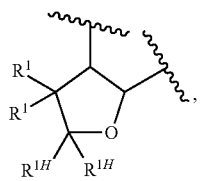
(C2)

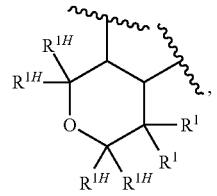
(C3)

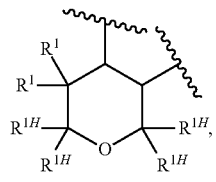
(C4)

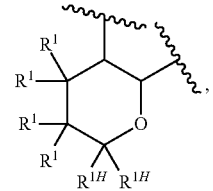
(C5)

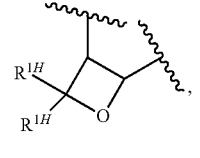
(C6)

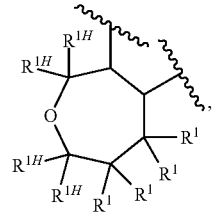
(C7)

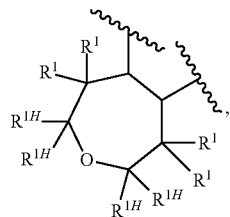
(C8)

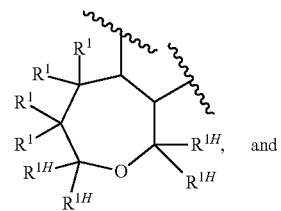
(C9)

and

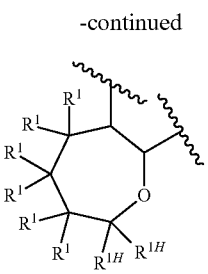
(C10)

ring A is selected from the group consisting of aryl, monocyclic heteroaryl, monocyclic cycloalkyl, monocyclic cycloalkenyl, monocyclic heterocycloalkyl, monocyclic heterocycloalkenyl, and a multicyclic group;

each ring B (when present) is independently selected from the group consisting of aryl, monocyclic heteroaryl, monocyclic cycloalkyl, monocyclic cycloalkenyl, monocyclic heterocycloalkyl, monocyclic heterocycloalkenyl, and a multicyclic group;

-$L_1$- (when present) independently represents a bond or a divalent moiety selected from the group consisting of -alkyl-, -haloalkyl-, -heteroalkyl-, -alkenyl-, -alkynyl-, —N($R^6$)—, —NHC(O)—, —C(O)NH—, NHS($O)_2$—, —S$(O)_2$NH—, —O—$CH_2$—, —$CH_2$—O—, —NH$CH_2$—, —$CH_2$NH—, and —CH($CF_3$)NH—, —NHCH($CF_3$)—;

m, n, and p are each independently selected integers, wherein:
m is 0 or more;
n is 0 or 1; and
p is 0 or more,
wherein the maximum value of m is the maximum number of available substitutable hydrogen atoms on ring A, and wherein the maximum value of p is the maximum number of available substitutable hydrogen atoms on ring B;

each $R^1$ (when present) is independently selected from the group consisting of: H, halogen, —OH, —CN, —$SF_5$, —$OSF_5$, —Si$(R^5)_3$, —N$(R^6)_2$, —$NR^7$C(O)$R^6$, —$NR^7$S$(O)_2R^6$, —$NR^7$C(O)N$(R^6)_2$, —$NR^7$C(O)O$R^6$, —O$R^6$, —S$R^6$, —C(O)$R^6$, —C(O)$_2R^6$, —C(O)$_N(R^6)_2$, —P(O)(O$R^5)_2$, —P(O)(O$R^5$)($R^5$), —S(O)$R^6$, —S$(O)_2R^6$, —S$(O)_2$N$(R^6)_2$, alkyl, haloalkyl, heteroalkyl, alkenyl, alkynyl, aryl, -alkyl-aryl, monocyclic heteroaryl, -alkyl-(monocyclic heteroaryl), monocyclic cycloalkyl, -alkyl-(monocyclic cycloalkyl), monocyclic heterocycloalkyl, a multicyclic group, and -alkyl-(multicyclic group);
wherein said alkyl, said haloalkyl, said heteroalkyl, said alkenyl, said alkynyl, said aryl, said -alkyl-aryl, said monocyclic heteroaryl, said -alkyl-(monocyclic heteroaryl), said monocyclic cycloalkyl, said -alkyl-(monocyclic cycloalkyl), said monocyclic heterocycloalkyl, said multicyclic group, and said -alkyl-(multicyclic group) of $R^1$ is optionally unsubstituted or substituted with one or more groups independently selected from $R^8$;

each $R^{1H}$ is independently selected from the group consisting of: H, alkyl, haloalkyl, heteroalkyl, alkenyl, alkynyl, aryl, -alkyl-aryl, monocyclic heteroaryl, -alkyl-(monocyclic heteroaryl), monocyclic cycloalkyl, -alkyl-(monocyclic cycloalkyl), monocyclic heterocycloalkyl, a multicyclic group, -alkyl-(multicyclic group), —C(O)$R^6$, —C(O)$_2R^6$, —C(O)N$(R^6)_2$, —P(O)(O$R^5)_2$, —P(O)(O$R^5$)($R^5$), —S(O)$R^6$, —S$(O)_2R^6$, and —S$(O)_2$N$(R^6)_2$.
wherein said alkyl, said haloalkyl, said heteroalkyl, said alkenyl, said alkynyl, said aryl, said -alkyl-aryl, said monocyclic heteroaryl, said -alkyl-(monocyclic heteroaryl), said monocyclic cycloalkyl, said -alkyl-(monocyclic cycloalkyl), said monocyclic heterocycloalkyl, said multicyclic group, and said -alkyl-(multicyclic group), of $R^{1H}$ is optionally unsubstituted or substituted with one or more groups independently selected from $R^8$;

each $R^2$ (when present) is independently selected from the group consisting of: halogen, —OH, —CN, —$SF_5$, $OSF_5$, —$NO_2$, —Si$(R^5)_3$, —P(O)(O$R^5)_2$, —P(O)(O$R^5$)($R^5$), —N$(R^6)_2$, —$NR^7$C(O)$R^6$, —$NR^7$S$(O)_2R^6$, —$NR^7$C(O)N$(R^6)_2$, —$NR^7$C(O)O$R^6$, —C(O)$R^6$, —C(O)$_2R^6$, —C(O)N$(R^6)_2$, —S(O)$R^6$, —S$(O)_2R^6$, —S$(O)_2$N$(R^6)_2$, —O$R^6$, —S$R^6$, alkyl, haloalkyl, heteroalkyl, alkenyl, alkynyl, cycloalkyl, -alkyl-cycloalkyl, aryl, -alkyl-aryl, heteroaryl, -alkyl-heteroaryl, and heterocycloalkyl,
wherein said alkyl, haloalkyl, heteroalkyl, alkenyl, alkynyl, cycloalkyl, -alkyl-cycloalkyl, aryl, -alkyl-aryl, heteroaryl, -alkyl-heteroaryl, and heterocycloalkyl of $R^2$ are each optionally unsubstituted or substituted with one or more groups independently selected from $R^8$;

each $R^3$ (when present) is independently selected from the group consisting of: halogen, —OH, —CN, —$SF_5$, $OSF_5$, —$NO_2$, —Si$(R^5)_3$, —P(O)(O$R^5)_2$, —P(O)(O$R^5$)($R^5$), —N$(R^6)_2$, —$NR^7$C(O)$R^6$, —$NR^7$S$(O)_2R^6$, —$NR^7$C(O)N$(R^6)_2$, —$NR^7$C(O)O$R^6$, —C(O)$R^6$, —C(O)$_2R^6$, —C(O)N$(R^6)_2$, —S(O)$R^6$, —S$(O)_2R^6$, —S$(O)_2$N$(R^6)_2$, —O$R^6$, —S$R^6$, alkyl, haloalkyl, heteroalkyl, alkenyl, alkynyl, cycloalkyl, -alkyl-cycloalkyl, aryl, -alkyl-aryl, heteroaryl, -alkyl-heteroaryl, and heterocycloalkyl,
wherein said alkyl, haloalkyl, heteroalkyl, alkenyl, alkynyl, cycloalkyl, -alkyl-cycloalkyl, aryl, -alkyl-aryl, heteroaryl, -alkyl-heteroaryl, and heterocycloalkyl of $R^2$ are each optionally unsubstituted or substituted with one or more groups independently selected from $R^8$;

$R^4$ is selected from the group consisting of H, halogen, optionally substituted alkyl, optionally substituted -alkyl-OH, optionally substituted heteroalkyl, optionally substituted -alkyl-cycloalkyl, optionally substituted -alkyl-aryl, and optionally substituted -alkyl-heteroaryl, wherein said optional substituents are each independently selected from $R^8$;

each $R^5$ (when present) is independently selected from the group consisting of H, alkyl, aryl, arylalkyl-, haloalkyl, cycloalkyl, -alkyl-cycloalkyl, heteroaryl, and heteroarylalkyl-;

each $R^6$ (when present) is independently selected from the group consisting of H, alkyl, -alkyl-OH, alkenyl, heteroalkyl, -heteroalkyl-OH, haloalkyl, -haloalkyl-OH, cycloalkyl, lower alkyl-substituted cycloalkyl, lower alkyl-substituted -alkyl-cycloalkyl, aryl, -alkyl-aryl, heteroaryl, and -alkyl-heteroaryl,
wherein each said aryl, -alkyl-aryl, heteroaryl, and -alkyl-heteroaryl of $R^6$ is unsubstituted or substituted with one or more groups independently selected from halogen, alkyl, heteroalkyl, haloalkyl, alkoxy, heteroalkoxy, and haloalkoxy;

each $R^7$ (when present) is independently selected from the group consisting of H, alkyl, cycloalkyl, -alkyl-cycloalkyl, aryl, -alkyl-aryl, heteroaryl, and -alkyl-heteroaryl; and each $R^8$ (when present) is independently selected from the group consisting of halogen, —OH, —CN, —$SF_5$, —$OSF_5$, alkyl, alkoxy, haloalkyl, haloalkoxy, cycloalkyl, -alkyl-cycloalkyl, —O-cycloalkyl, —O-alkyl-cycloalkyl, heteroalkyl, —O-heteroalkyl, and -alkyl-OH.

In other embodiments, the invention provides compositions, including pharmaceutical compositions, comprising one or more compounds of the invention (e.g., one compound of the invention), or a tautomer thereof, or a pharmaceutically acceptable salt or solvate of said compound(s) and/or said tautomer(s), optionally together with one or more additional therapeutic agents, optionally in an acceptable (e.g., pharmaceutically acceptable) carrier or diluent.

In other embodiments, the invention provides various methods of treating, preventing, ameliorating, and/or delaying the onset of an Aβ pathology and/or a symptom or symptoms thereof, comprising administering a composition comprising an effective amount of one or more compounds of the invention, or a tautomer thereof, or pharmaceutically acceptable salt or solvate of said compound(s) and/or said tautomer(s), to a patient in need thereof. Such methods optionally additionally comprise administering an effective amount of one or more additional therapeutic agents suitable for treating the patient being treated.

These and other embodiments of the invention, which are described in detail below or will become readily apparent to those of ordinary skill in the art, are included within the scope of the invention.

DETAILED DESCRIPTION OF THE INVENTION

In one embodiment, the compounds of the invention have the structural Formula (I) as described above.

In another embodiment, the compounds of the invention have the structural Formula (IA):

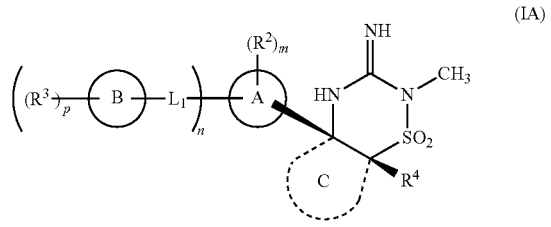

(IA)

or a tautomer thereof having the structural Formula (IA'):

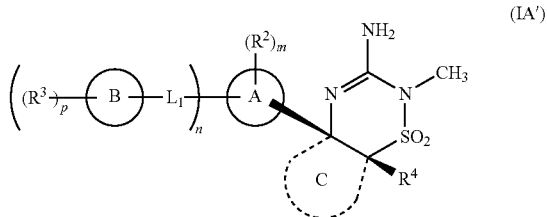

(IA')

or a pharmaceutically acceptable salt thereof, wherein:
wherein ring A, ring B, ring C, -L$_1$-, R$^2$, R$^3$, R$^4$, m, n, and p are each as defined in Formula (I).

In another embodiment, in each of Formulas (I), (I'), (IA), and (IA'):
each R$^1$ (when present) is independently selected from the group consisting of H, fluoro, methyl, ethyl, cyclopropyl, —OCH$_3$, —OCH$_2$CH$_3$, —O-cyclopropyl, —OCHF$_2$, —OCF$_3$, —CH$_2$-cyclopropyl, —CH$_2$OH, —CH$_2$OCH$_3$, —CH$_2$OCH$_2$CH$_3$, trifluoromethyl, —CH$_2$F, —CHF$_2$, phenyl, pyridyl, pyrimidinyl, pyrazinyl, benzyl, —CH$_2$-pyridyl, —CH$_2$-pyrimidinyl, —CH$_2$-pyrazinyl, —O-phenyl, —O-pyridyl, —O-pyrimidinyl, —O-pyrazinyl, —O-benzyl, —O—CH$_2$-pyridyl, —O—CH$_2$-pyrimidinyl, and —O—CH$_2$-pyrazinyl;

wherein each said phenyl, pyridyl, pyrimidinyl, pyrazinyl, benzyl, —CH$_2$-pyridyl, —CH$_2$-pyrimidinyl, —CH$_2$-pyrazinyl, —O-phenyl, —O-pyridyl, —O-pyrimidinyl, —O-pyrazinyl, O-benzyl, —O—CH$_2$-pyridyl, —O—CH$_2$-pyrimidinyl, and —O—CH$_2$-pyrazinyl of R$^1$ is unsubstituted or substituted with one or more groups independently selected from the group consisting of halogen, alkyl, heteroalkyl, and haloalkyl.

In another embodiment, in each of Formulas (I), (I'), (IA), and (IA'):
each R$^{1H}$ is independently selected from the group consisting of H, methyl, ethyl, cyclopropyl, —CH$_2$-cyclopropyl, —CH$_2$OCH$_3$, —CH$_2$OCH$_2$CH$_3$, trifluoromethyl, —CH$_2$F, —CHF$_2$, phenyl, pyridyl, pyrimidinyl, pyrazinyl, benzyl, —CH$_2$-pyridyl, —CH$_2$-pyrimidinyl, and —CH$_2$-pyrazinyl, wherein each said phenyl, pyridyl, pyrimidinyl, pyrazinyl, benzyl, —CH$_2$-pyridyl, —CH$_2$-pyrimidinyl, and —CH$_2$-pyrazinyl, of R$^{1H}$ is unsubstituted or substituted with one or more groups independently selected from the group consisting of halogen, alkyl, heteroalkyl, and haloalkyl.

In another embodiment, in each of Formulas (I), (I'), (IA), and (IA'):
each R$^1$ (when present) is independently selected from the group consisting of H, methyl, ethyl, —OCH$_3$, —OCF$_3$, phenyl, pyridyl, pyrimidinyl, pyrazinyl, —CF$_3$, —CHF$_2$, and —CH$_2$F, wherein each said phenyl, pyridyl, pyrimidinyl, and said pyrazinyl of R$^1$ is unsubstituted or substituted with one or more groups independently selected from the group consisting of halogen, alkyl, heteroalkyl, and haloalkyl; and each R$^{1H}$ is independently selected from the group consisting of H, methyl, cyclopropyl, —CH$_2$-cyclopropyl, —CH$_2$OCH$_3$, trifluoromethyl, —CH$_2$F, —CHF$_2$, phenyl, pyridyl, pyrimidinyl, and pyrazinyl, wherein said phenyl, pyridyl, and pyrimidinyl and said pyrazinyl of R$^{1H}$ is unsubstituted or substituted with one or more groups independently selected from the group consisting of halogen, alkyl, heteroalkyl, and haloalkyl.

In another embodiment, in each of Formulas (I), (I'), (IA), and (IA'):
each R$^1$ (when present) is H; and each R$^{1H}$ (when present) is H.

In another embodiment, the compounds of the invention have the structural Formula (II):

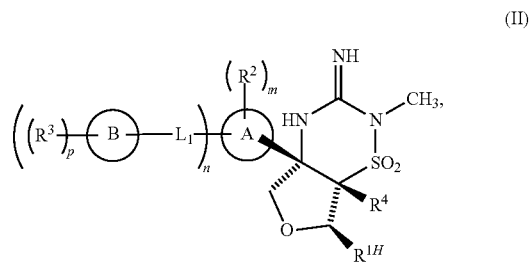

(II)

or its tautomeric form, Formula (II'):

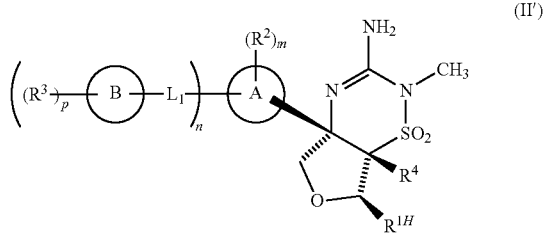

or a pharmaceutically acceptable salt thereof, wherein:
$R^{1H}$ is selected from the group consisting of H, methyl, ethyl, cyclopropyl, —CH$_2$-cyclopropyl, —CH$_2$OH, —CH$_2$OCH$_3$, —CH$_2$OCH$_2$CH$_3$, trifluoromethyl, —CH$_2$F, —CHF$_2$, phenyl, pyridyl, pyrimidinyl, pyrazinyl, benzyl, —CH$_2$-pyridyl, —CH$_2$-pyrimidinyl, and —CH$_2$-pyrazinyl;

wherein said phenyl, pyridyl, pyrimidinyl, pyrazinyl, benzyl, —CH$_2$-pyridyl, —CH$_2$-pyrimidinyl, and —CH$_2$-pyrazinyl of $R^{1H}$ is unsubstituted or substituted with one or more groups independently selected from the group consisting of halogen, alkyl, heteroalkyl, and haloalkyl; and ring A, ring B, -L$_1$-, R$^2$, R$^3$, R$^4$, m, n, and p are each as defined in Formula (I).

In another embodiment, in each of Formulas (I), (I'), (IA), (IA'), (II), and (II'):
each $R^{1H}$ is selected from the group consisting of H, methyl, cyclopropyl, —CH$_2$-cyclopropyl, —CH$_2$OCH$_3$, trifluoromethyl, —CH$_2$F, and —CHF$_2$.

In another embodiment, in each of Formulas (I), (I'), (IA), (IA'), (II), and (II'): $R^{1H}$ is H, methyl, and —CH$_2$F.

In another embodiment, in each of Formulas (I), (I'), (IA), (IA'), (II), and (II'): $R^{1H}$ is H.

In another embodiment, in each of Formulas (II), and (II'), $R^{1H}$ is H; H and R$^4$ is H.

In another embodiment, the compounds of the invention have the structural Formula (III):

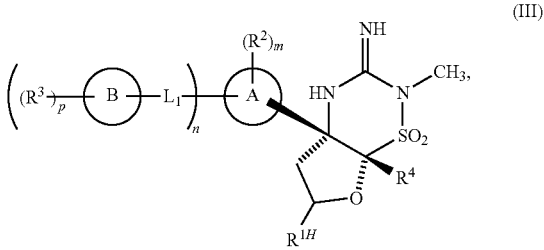

or its tautomeric form, Formula (III'):

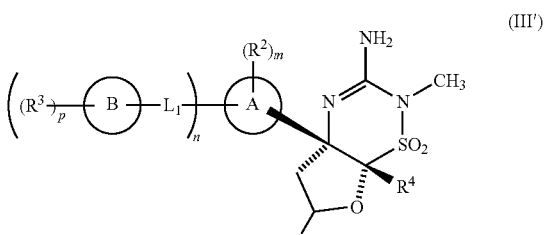

or a pharmaceutically acceptable salt thereof, wherein:
$R^{1H}$ is selected from the group consisting of H, methyl, ethyl, cyclopropyl, —CH$_2$-cyclopropyl, —CH$_2$OH, —CH$_2$OCH$_3$, —CH$_2$OCH$_2$CH$_3$, trifluoromethyl, —CH$_2$F, —CHF$_2$, phenyl, pyridyl, pyrimidinyl, pyrazinyl, benzyl, —CH$_2$-pyridyl, —CH$_2$-pyrimidinyl, and —CH$_2$-pyrazinyl;

wherein said phenyl, pyridyl, pyrimidinyl, pyrazinyl, benzyl, —CH$_2$-pyridyl, —CH$_2$-pyrimidinyl, and —CH$_2$-pyrazinyl of $R^{1H}$ is unsubstituted or substituted with one or more groups independently selected from the group consisting of halogen, alkyl, heteroalkyl, and haloalkyl; and ring A, ring B, -L$_1$-, R$^2$, R$^3$, R$^4$, m, n, and p are each as defined in Formula (I).

In another embodiment, in each of Formulas (I), (I'), (IA), (IA'), (III), and (III'):
each $R^{1H}$ is independently selected from the group consisting of H, methyl, cyclopropyl, —CH$_2$-cyclopropyl, —CH$_2$OCH$_3$, trifluoromethyl, —CHF$_2$, phenyl, pyridyl, pyrimidinyl, and pyrazinyl, wherein said phenyl, said pyridyl, said pyrimidinyl, and said pyrazinyl of $R^{1H}$ is unsubstituted or substituted with one or more groups independently selected from the group consisting of halogen, alkyl, heteroalkyl, and haloalkyl.

In another embodiment, in each of Formulas (I), (I'), (IA), (IA'), (III), and (III'):
each $R^{1H}$ is selected from the group consisting of H, methyl, cyclopropyl, —CH$_2$-cyclopropyl, —CH$_2$OCH$_3$, trifluoromethyl, —CH$_2$F, and —CHF$_2$.

In another embodiment, in each of Formulas (I), (I'), (IA), (IA'), (III), and (III'): each $R^{1H}$ is H.

In another embodiment, in each of Formulas (III), and (III'): $R^{1H}$ is H; H and R$^4$ is H In another embodiment, the compounds of the invention have the structural Formula (IV):

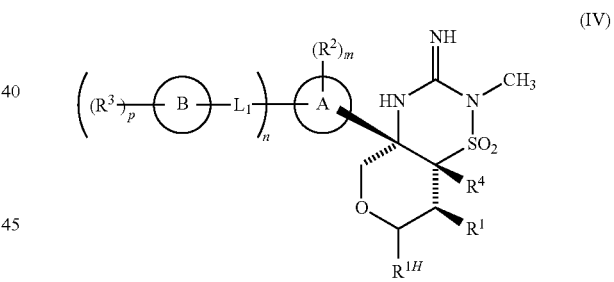

or a tautomer thereof having the structural Formula (IV'):

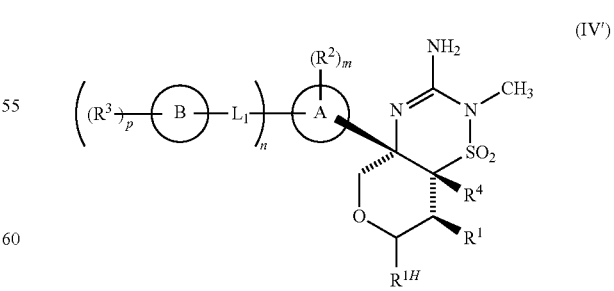

or pharmaceutically acceptable salt thereof, wherein:
R$^1$ is selected from the group consisting of H, fluoro, methyl, ethyl, cyclopropyl, —OCH$_3$, OCH$_2$CH$_3$, —O-cyclopropyl, —OCHF$_2$, —OCF$_3$, —CH$_2$-cyclopropyl, —CH$_2$OH, —CH₂OCH₃, —CH₂OCH₂CH₃, trifluoromethyl, —CH₂F, —CHF₂, phenyl, pyridyl, pyrimidinyl, pyrazinyl, benzyl, —CH₂-pyridyl, and —CH₂-pyrimidinyl, —CH₂-pyrazinyl, wherein said phenyl, pyridyl, pyrimidinyl, pyrazinyl, benzyl, —CH₂-pyridyl, —CH₂-pyrimidinyl, and —CH₂-pyrazinyl of $R^1$ may be unsubstituted or substituted with one or more groups independently selected from the group consisting of halogen, alkyl, heteroalkyl, and haloalkyl;

$R^{1H}$ is selected from the group consisting of H, methyl, ethyl, cyclopropyl, —CH₂-cyclopropyl, —CH₂OH, —CH₂OCH₃, —CH₂OCH₂CH₃, trifluoromethyl, —CH₂F, —CHF₂, phenyl, pyridyl, pyrimidinyl, pyrazinyl, benzyl, —CH₂-pyridyl, and —CH₂-pyrimidinyl, —CH₂-pyrazinyl, wherein said phenyl, pyridyl, pyrimidinyl, pyrazinyl, benzyl, —CH₂-pyridyl, —CH₂-pyrimidinyl, and —CH₂-pyrazinyl of $R^{1H}$ is unsubstituted or substituted with one or more groups independently selected from the group consisting of halogen, alkyl, heteroalkyl, and haloalkyl; and ring A, ring B, -L₁-, $R^2$, $R^3$, $R^4$, m, n, and p are each as defined in Formula (I).

In another embodiment, in each of Formulas (I), (I'), (IA), (IA'), (IV), and (IV'):

each $R^1$ (when present) is independently selected from the group consisting of H, methyl, ethyl, —OCH₃, —CH₂OCH₃, —OCF₃, —CF₃, —CHF₂, and —CH₂F; and each $R^{1H}$ is independently selected from the group consisting of H, methyl, cyclopropyl, —CH₂-cyclopropyl, —CH₂OCH₃, trifluoromethyl, —CH₂F, —CHF₂, phenyl, pyridyl, pyrimidinyl, and pyrazinyl, wherein each said phenyl, pyridyl, pyrimidinyl, and pyrazinyl of $R^{1H}$ is independently unsubstituted or substituted with one or more groups independently selected from the group consisting of halogen, alkyl, heteroalkyl, and haloalkyl.

In another embodiment, in each of Formulas (I), (I'), (IA), (IA'), (IV), and (IV'), ring C is selected from the group consisting of:

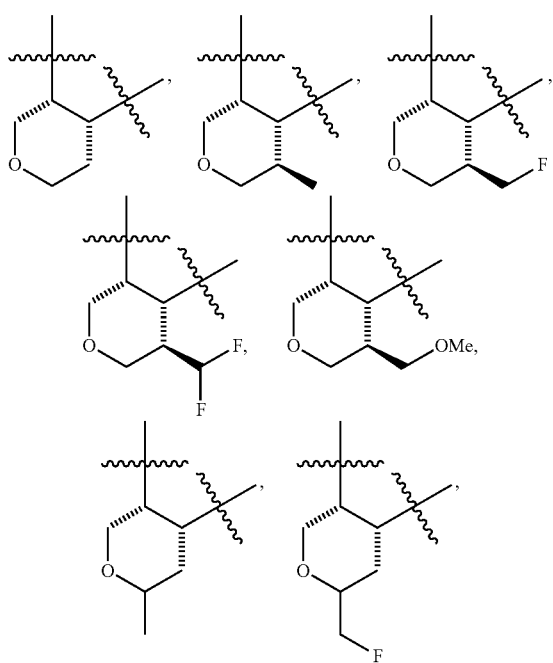

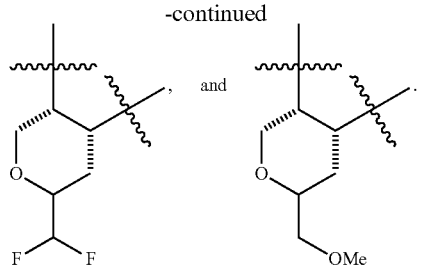

In another embodiment, in each of Formulas (I), (I'), (IA), (IA'), (IV), and (IV'):
$R^1$ (when present) is H; and $R^{1H}$ is H.

In another embodiment, the compounds of the invention have the structural Formula (V):

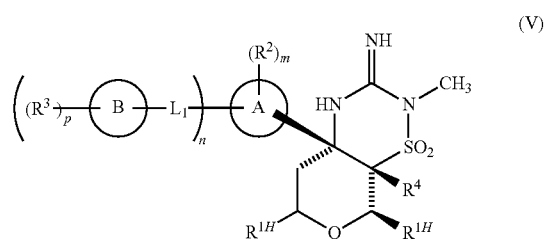

or a tautomer thereof having the structural Formula (V'):

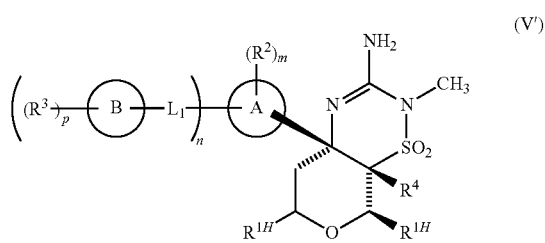

or pharmaceutically acceptable salt thereof, wherein:

each $R^{1H}$ is independently selected from the group consisting of H, methyl, ethyl, cyclopropyl, —CH₂-cyclopropyl, —CH₂OH, —CH₂OCH₃, —CH₂OCH₂CH₃, trifluoromethyl, —CH₂F, —CHF₂, phenyl, pyridyl, pyrimidinyl, pyrazinyl, benzyl, —CH₂-pyridyl, and —CH₂-pyrimidinyl, —CH₂-pyrazinyl, wherein said phenyl, pyridyl, pyrimidinyl, pyrazinyl, benzyl, —CH₂-pyridyl, —CH₂-pyrimidinyl, and —CH₂-pyrazinyl of $R^{1H}$ is unsubstituted or substituted with one or more groups independently selected from the group consisting of halogen, alkyl, heteroalkyl, and haloalkyl; and ring A, ring B, -L₁-, $R^2$, $R^3$, $R^4$, m, n, and p are each as defined in Formula (I).

In another embodiment, in each of Formulas (I), (I'), (IA), (IA'), (V), and (V'):

each $R^{1H}$ is independently selected from the group consisting of H, methyl, cyclopropyl, —CH₂-cyclopropyl, —CH₂OCH₃, trifluoromethyl, —CH₂F, —CHF₂, phenyl, pyridyl, pyrimidinyl, and pyrazinyl, wherein each said phenyl, pyridyl, pyrimidinyl, and pyrazinyl of $R^{1H}$ is independently unsubstituted or substituted with one or more groups independently selected from the group consisting of halogen, alkyl, heteroalkyl, and haloalkyl.

In another embodiment, in each of Formulas (I), (I'), (IA), (IA'), (V), and (V'), Ring C is selected from the group consisting of:

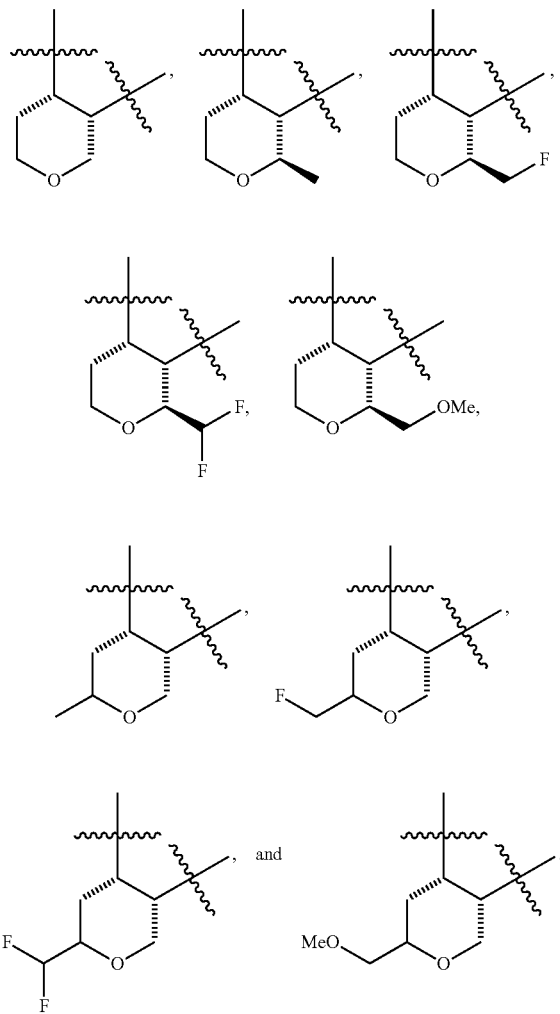

In another embodiment, in each of Formulas (I), (I'), (IA), (IA'), (V), and (V'):
each $R^{1H}$ is H.

In another embodiment, in each of Formulas (V), and (V'): each $R^{1H}$ is H; and $R^4$ is H.

In another embodiment, the compounds of the invention have the structural Formula (VI):

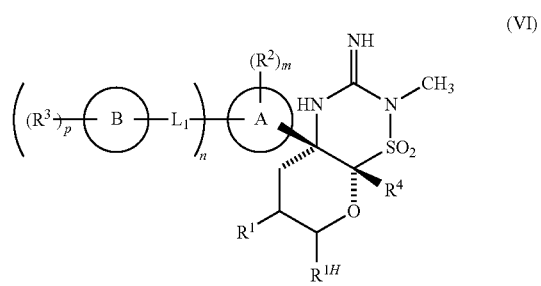

(VI)

or a tautomer thereof having the structural Formula (VI'):

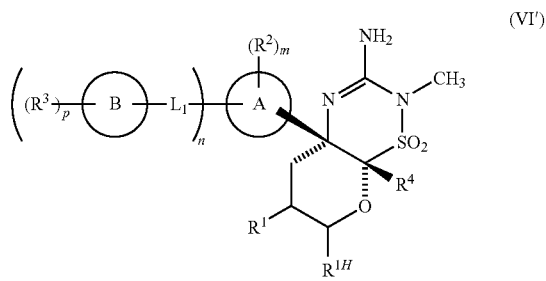

(VI')

or pharmaceutically acceptable salt thereof, wherein:

$R^1$ is selected from the group consisting of H, fluoro, methyl, ethyl, cyclopropyl, —$OCH_3$, $OCH_2CH_3$, —O-cyclopropyl, —$OCHF_2$, —$OCF_3$, —$CH_2$-cyclopropyl, —$CH_2OH$, —$CH_2OCH_3$, —$CH_2OCH_2CH_3$, trifluoromethyl, —$CH_2F$, —$CHF_2$, phenyl, pyridyl, pyrimidinyl, pyrazinyl, benzyl, —$CH_2$-pyridyl, and —$CH_2$-pyrimidinyl, —$CH_2$-pyrazinyl, wherein said phenyl, pyridyl, pyrimidinyl, pyrazinyl, benzyl, —$CH_2$-pyridyl, —$CH_2$-pyrimidinyl, and —$CH_2$-pyrazinyl of $R^1$ may be unsubstituted or substituted with one or more groups independently selected from the group consisting of halogen, alkyl, heteroalkyl, and haloalkyl; and $R^{1H}$ is selected from the group consisting of H, methyl, ethyl, cyclopropyl, —$CH_2$-cyclopropyl, —$CH_2OH$, —$CH_2OCH_3$, —$CH_2OCH_2CH_3$, trifluoromethyl, —$CH_2F$, —$CHF_2$, phenyl, pyridyl, pyrimidinyl, pyrazinyl, benzyl, —$CH_2$-pyridyl, and —$CH_2$-pyrimidinyl, —$CH_2$-pyrazinyl, wherein said phenyl, pyridyl, pyrimidinyl, pyrazinyl, benzyl, —$CH_2$-pyridyl, —$CH_2$-pyrimidinyl, and —$CH_2$-pyrazinyl of $R^{1H}$ is unsubstituted or substituted with one or more groups independently selected from the group consisting of halogen, alkyl, heteroalkyl, and haloalkyl; and ring A, ring B, -$L_1$-, $R^2$, $R^3$, $R^4$, m, n, and p are each as defined in Formula (I).

In another embodiment, in each of Formulas (I), (I'), (IA), (IA'), (VI), and (VI'):

each $R^1$ (when present) and each $R^{1H}$ are independently selected from the group consisting of H, methyl, cyclopropyl, —$CH_2$-cyclopropyl, —$CH_2OCH_3$, trifluoromethyl, —$CH_2F$, —$CHF_2$, phenyl, pyridyl, pyrimidinyl, and pyrazinyl, wherein each said each phenyl, pyridyl, pyrimidinyl, and each said pyrazinyl of $R^1$ and $R^{1H}$ is independently unsubstituted or substituted with one or more groups independently selected from the group consisting of halogen, alkyl, heteroalkyl, and haloalkyl.

In another embodiment, in each of Formulas (I), (I'), (IA), (IA'), (VI), and (VI'), ring C is selected from the group consisting of:

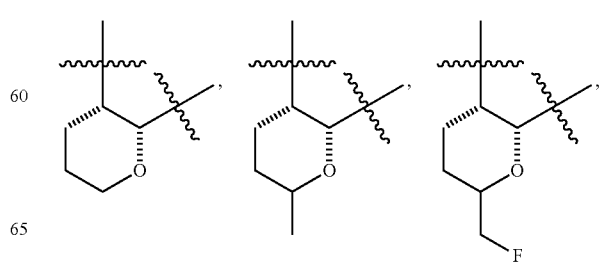

-continued

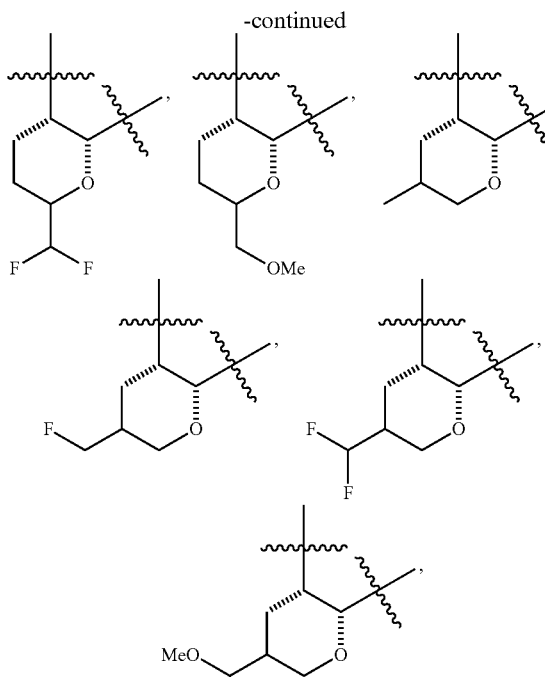

In another embodiment, in each of Formulas (I), (I'), (IA), (IA'), (VI), and (VI'):

each $R^1$ (when present) is H; and each $R^{1H}$ is H.

In another embodiment, in each of Formulas (I), (I'), (IA), (IA'), (II), (II'), (III), (III'), (IV), (IV'), (V), (V'), (VI) and (VI'):

$R^4$ is selected from the group consisting of H, fluoro, methyl, ethyl, —$CH_2$-cyclopropyl, benzyl, —$CH_2$-pyridyl, —$CH_2OCH_3$ and —$CH_2OCH_2CH_3$, wherein said benzyl and said —$CH_2$-pyridyl of $R^4$ is unsubstituted or substituted with one or more groups independently selected from the group consisting of halogen, alkyl, heteroalkyl, haloalkyl, alkoxy, —O-cyclopropyl, heteroalkoxy, haloalkoxy, —CN, —$SF_5$, and —$OSF_5$.

In another embodiment, in each of Formulas (I), (I'), (IA), (IA'), (II), (II'), (III), (III'), (IV), (IV'), (V), (V'), (VI) and (VI'):

$R^4$ is selected from the group consisting of H, fluoro, methyl, —$CH_2$-cyclopropyl, and —$CH_2OCH_3$.

In another embodiment, in each of Formulas (I), (I'), (IA), (IA'), (II), (II'), (III), (III'), (IV), (IV'), (V), (V'), (VI) and (VI'):

$R^4$ is H.

In another embodiment, in each of Formulas (VI), and (VI'): each R' (when present) is H; each $R^{1H}$ is H; and $R^4$ is H.

In some embodiments, in each of Formulas (I), (I'), (IA), (IA'), (II), (II'), (III), (III'), (IV), (IV'), (V), (V'), (VI) and (VI'):

n is 1. In these embodiments, the moiety:

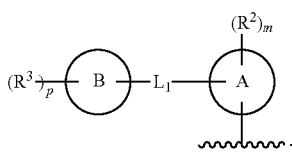

has the form:

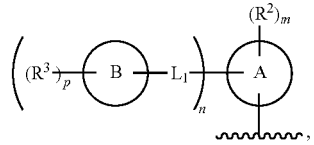

In another embodiment, in each of Formulas (I), (I'), (IA), (IA'), (II), (II'), (III), (III'), (IV), (IV'), (V), (V'), (VI) and (VI'):

n is 1;

m is 0 or more; and ring A is selected from the group consisting of phenyl, pyridyl, pyrazinyl, furanyl, thienyl, pyrimidinyl, pyridazinyl, thiazolyl, oxazolyl, imidazolyl, pyrazolyl, quinazolinyl, benzofuranyl, benzimidazolyl, benzoxazolyl, benzothiazolyl, benzothienyl, naphthyl, quinolyl, isoquinolyl, indazolyl, indolyl, and thienopyrazolyl.

In another embodiment, in each of Formulas (I), (I'), (IA), (IA'), (II), (II'), (III), (III'), (IV), (IV'), (V), (V'), (VI) and (VI'):

n is 1;

m is 0 or more; and ring A is selected from the group consisting of phenyl, pyridyl, thienyl, thiazolyl, naphthyl, isoquinolinyl, benzothienyl, benzimidazolyl, indazolyl, indolyl, and thienopyrazolyl.

In another embodiment, in each of Formulas (I), (I'), (IA), (IA'), (II), (II'), (III), (III'), (IV), (IV'), (V), (V'), (VI) and (VI'):

n is 1;

m is 0 or more; and ring A is selected from the group consisting of phenyl, thienyl, and pyridyl.

In another embodiment, in each of Formulas (I), (I'), (IA), (IA'), (II), (II'), (III), (III'), (IV), (IV'), (V), (V'), (VI) and (VI'):

n is 1;

m is 0 or more; and each $R^2$ (when present) is independently selected from the group consisting of halogen, —CN, —$SF_5$, —$OSF_5$, —$NO_2$, —$NH_2$, —$N(alkyl)_2$, —NH(alkyl), —NHC(O)$R^6$, —NHS$(O)_2R^6$, —NHC(O)N($R^6$)$_2$, —NHC(O)O$R^6$, —C(O)$R^6$, —C(O)$_2R^6$, —C(O)N($R^6$)$_2$, —S(O)$R^6$, —S(O)$_2R^6$, —S(O)$_2$N($R^6$)$_2$, —O$R^6$, —S$R^6$, lower alkyl, lower haloalkyl, lower heteroalkyl, lower alkenyl, lower alkynyl, phenyl, benzyl, lower cycloalkyl, monocyclic heteroaryl, and —$CH_2$—(monocyclic heteroaryl), wherein said phenyl, benzyl, lower cycloalkyl, monocyclic heteroaryl, and —$CH_2$— (monocyclic heteroaryl) of $R^2$ is unsubstituted or substituted with one or more groups independently selected from the group consisting of halogen, alkyl, heteroalkyl, haloalkyl, alkoxy, —O-cyclopropyl, heteroalkoxy, haloalkoxy, —CN, —$SF_5$, and —$OSF_5$.

In one such embodiment, each $R^6$ (when present) is independently selected from the group consisting of H, lower alkyl, lower cycloalkyl, lower haloalkyl, and lower heteroalkyl.

In another embodiment, in each of Formulas (I), (I'), (IA), (IA'), (II), (II'), (III), (III'), (IV), (IV'), (V), (V'), (VI) and (VI'):

each $R^3$ group (when present) is independently selected from the group consisting of halogen, —CN, —$SF_5$, —$NH_2$, —NH(alkyl), —$N(alkyl)_2$, —OH, —O-alkyl, —SH, —S(alkyl), methyl, ethyl, propyl, haloalkyl, —C≡C—$CH_3$, cyclopropyl, —$CH_2$-cyclopropyl, —C(O)OH, —C(O)O- alkyl, —O-haloalkyl, optionally substituted phenyl, and optionally substituted monocyclic heteroaryl, wherein each said optional substituent is, independently, as defined in Formula (I).

In another embodiment, in each of Formulas (I), (I'), (IA), (IA'), (II), (II'), (III), (III'), (IV), (IV'), (V), (V'), (VI) and (VI'):

n is 1;
m is 0 or more; and
each $R^2$ group (when present) is independently selected from the group consisting of halogen, —CN, —SF$_5$, —NHCH$_3$, —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, and —OCHF$_2$.

In another embodiment, in each of Formulas (I), (I'), (IA), (IA'), (II), (II'), (III), (III'), (IV), (IV'), (V), (V'), (VI) and (VI'):

n is 1;
m is 0, 1, or 2; and
each $R^2$ group (when present) is independently selected from F, Cl, Br, —CN, —CF$_3$, —CHF$_2$, cyclopropyl, —OCF$_3$, and —OCHF$_2$.

In another embodiment, in each of Formulas (I), (I'), (IA), (IA'), (II), (II'), (III), (III'), (IV), (IV'), (V), (V'), (VI) and (VI'):

n is 1;
ring A is selected from the group consisting of phenyl, thienyl, and pyridyl;
m is 0, 1, or 2; and
each $R^2$ group (when present) is independently selected from the group consisting F, Cl, Br, —CN, —CF$_3$, —CHF$_2$, cyclopropyl, —OCF$_3$, and —OCHF$_2$.

In another embodiment, in each of Formulas (I), (I'), (IA), (IA'), (II), (II'), (III), (III'), (IV), (IV'), (V), (V'), (VI) and (VI'):

n is 1; and
-L$_1$- represents a bond or a divalent moiety selected from the group consisting of —NHC(O), —C(O)NH—, —NHS(O)$_2$—, —S(O)$_2$NH—, —O—CH$_2$—, —CH$_2$—O—, —NHCH$_2$—, —CH$_2$NH—, and —CH(CF$_3$)NH—.

In another embodiment, in each of Formulas (I), (I'), (IA), (IA'), (II), (II'), (III), (III'), (IV), (IV'), (V), (V'), (VI) and (VI'):

n is 1; and
-L$_1$- represents a bond or a divalent moiety selected from the group consisting of —NHC(O)— and —C(O)NH—.

In another embodiment, in each of Formulas (I), (I'), (IA), (IA'), (II), (II'), (III), (III'), (IV), (IV'), (V), (V'), (VI) and (VI'):

n is 1; and
-L$_1$- represents a bond.

In another embodiment, in each of Formulas (I), (I'), (IA), (IA'), (II), (II'), (III), (III'), (IV), (IV'), (V), (V'), (VI) and (VI'):

n is 1; and
-L$_1$- represents a divalent moiety selected from the group consisting of —NHC(O)— and —C(O)NH—.

In another embodiment, in each of Formulas (I), (I'), (IA), (IA'), (II), (II'), (III), (III'), (IV), (IV'), (V), (V'), (VI) and (VI'):

n is 1;
p is 0 or more; and
ring B is selected from the group consisting of phenyl, monocyclic heterocycloalkyl, monocyclic heteroaryl, and a multicyclic group.

In another embodiment, in each of Formulas (I), (I'), (IA), (IA'), (II), (II'), (III), (III'), (IV), (IV'), (V), (V'), (VI) and (VI'):

n is 1;
p is 0 or more; and
ring B is selected from the group consisting of phenyl, pyridyl, pyrimidinyl, pyrrolyl, oxazolyl, isoxazolyl, pyrazinyl, thienyl, pyrazolyl, furanyl, thiazolyl, pyridazinyl, isothiazolyl, isoxazolyl, isothiazolyl, indolyl, pyrrolopyridinyl, and pyrrolopyrimidinyl.

In another embodiment, in each of Formulas (I), (I'), (IA), (IA'), (II), (II'), (III), (III'), (IV), (IV'), (V), (V'), (VI) and (VI'):

n is 1;
p is 0 or more; and
ring B is selected from the group consisting of phenyl, pyridinyl, pyrimidinyl, oxazolyl, pyrrolyl, and a multicyclic group.

In another embodiment, in each of Formulas (I), (I'), (IA), (IA'), (II), (II'), (III), (III'), (IV), (IV'), (V), (V'), (VI) and (VI'):

n is 1;
p is 0 or more; and
ring B is selected from the group consisting of phenyl, pyridinyl, pyrimidinyl, oxazolyl, pyrrolyl, and indolyl.

In another embodiment, in each of Formulas (I), (I'), (IA), (IA'), (II), (II'), (III), (III'), (IV), (IV'), (V), (V'), (VI) and (VI'):

n is 1;
p is 0 or more; and
each $R^3$ (when present) is independently selected from the group consisting of halogen, —CN, —SF$_5$, —OSF$_5$, —NO$_2$, —NH$_2$, —N(alkyl)$_2$, —NH(alkyl), —NHC(O)R$^6$, —NHS(O)$_2$R$^6$, —NHC(O)N(R$^6$)$_2$, —NHC(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, lower alkyl, lower haloalkyl, lower heteroalkyl, lower alkenyl, lower alkynyl, phenyl, benzyl, lower cycloalkyl, monocyclic heteroaryl, and —CH$_2$—(monocyclic heteroaryl), wherein said phenyl, benzyl, lower cycloalkyl, monocyclic heteroaryl, and —CH$_2$— (monocyclic heteroaryl) of $R^3$ is unsubstituted or substituted with one or more groups independently selected from the group consisting of halogen, alkyl, heteroalkyl, haloalkyl, alkoxy, —O-cyclopropyl, heteroalkoxy, haloalkoxy, —CN, —SF$_5$, and OSF$_5$.

In one such embodiment, each $R^6$ (when present) is independently selected from the group consisting of H, lower alkyl, lower cycloalkyl, lower haloalkyl, and lower heteroalkyl.

In another embodiment, in each of Formulas (I), (I'), (IA), (IA'), (II), (II'), (III), (III'), (IV), (IV'), (V), (V'), (VI) and (VI'):

n is 1;
p is 0 or more; and
each $R^3$ group (when present) is independently selected from the group consisting of halogen, —OH, —CN, —SF$_5$, —NH$_2$, —NH(CH$_3$), —N(CH$_3$)$_2$, —OCH$_3$, —OCH$_2$CH$_3$, O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, —OCH$_2$CF$_3$, and —OCHF$_2$.

In another embodiment, in each of Formulas (I), (I'), (IA), (IA'), (II), (II'), (III), (III'), (IV), (IV'), (V), (V'), (VI) and (VI'):

n is 1;
ring A is selected from the group consisting of phenyl, thienyl, and pyridyl;

m is 0 or 1;

each $R^2$ group (when present) is independently selected from the group consisting of halogen, —CN, —SF$_5$, —NHCH$_3$, —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, and —OCHF$_2$.

-L$_1$- is a bond or a divalent moiety selected from the group consisting of —NHC(O)— and —C(O)NH—;

ring B is selected from the group consisting of phenyl, monocyclic heterocycloalkyl, and monocyclic heteroaryl;

p is 0 or more; and each $R^3$ group (when present) is independently selected from the group consisting of halogen, —OH, —CN, —SF$_5$, —NH$_2$, —NH(CH$_3$), —N(CH$_3$)$_2$, —OCH$_3$, —OCH$_2$CH$_3$, O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, —OCH$_2$CF$_3$, and —OCHF$_2$.

In another embodiment, in each of Formulas (I), (I'), (IA), (IA'), (II), (II'), (III), (III'), (IV), (IV'), (V), (V'), (VI) and (VI'):

n is 1; ring A is phenyl or pyridyl; and the moiety

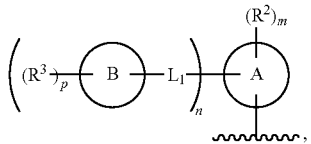

has the form:

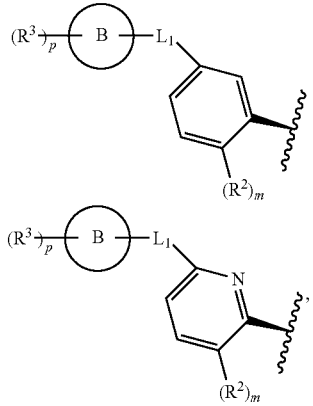

or wherein:

m is 0 or 1;

each $R^2$ group (when present) is independently selected from the group consisting of halogen, —CN, —SF$_5$, —NHCH$_3$, —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, and —OCHF$_2$;

-L$_1$- is a bond or a divalent moiety selected from the group consisting of —NHC(O)— and —C(O)NH—;

ring B is selected from the group consisting of phenyl, pyridyl, pyrimidinyl, pyrrolyl, oxazolyl, isoxazolyl, pyrazinyl, thienyl, pyrazolyl, furanyl, thiazolyl, pyridazinyl, isothiazolyl, isoxazolyl, and isothiazolyl;

p is 0 or more; and each $R^3$ group (when present) is independently selected from the group consisting of halogen, —OH, —CN, —SF$_5$, —NH$_2$, —NH(CH$_3$), —N(CH$_3$)$_2$, —OCH$_3$, —OCH$_2$CH$_3$, O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, —OCH$_2$CF$_3$, and —OCHF$_2$.

In another embodiment, in each of Formulas (I), (I'), (IA), (IA'), (II), (II'), (III), (III'), (IV), (IV'), (V), (V'), (VI) and (VI'):

n is 1; ring A is thienyl; and the moiety

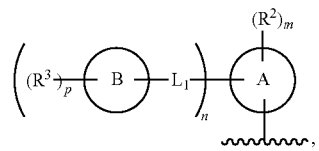

has the form:

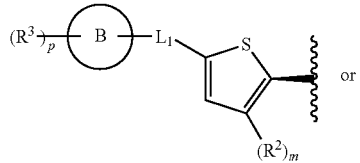

or

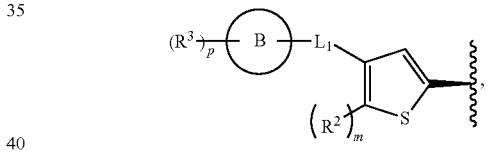

wherein:

m is 0 or 1;

each $R^2$ group (when present) is independently selected from the group consisting of halogen, —CN, —SF$_5$, —NHCH$_3$, —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, and —OCHF$_2$.

-L$_1$- is a bond or a divalent moiety selected from the group consisting of —NHC(O)— and —C(O)NH—;

ring B is selected from the group consisting of phenyl, pyridyl, pyrimidinyl, pyrrolyl, oxazolyl, isoxazolyl, pyrazinyl, thienyl, pyrazolyl, furanyl, thiazolyl, pyridazinyl, isothiazolyl, isoxazolyl, and isothiazolyl;

p is 0 or more; and each $R^3$ group (when present) is independently selected from the group consisting of halogen, —OH, —CN, —SF$_{55}$—NH$_2$, —NH(CH$_3$), —N(CH$_3$)$_2$, —OCH$_3$, —OCH$_2$CH$_3$, O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, —OCH$_2$CF$_3$, and —OCHF$_2$.

In another embodiment, in each of Formulas (I), (I'), (IA), (IA'), (II), (II'), (III), (III'), (IV), (IV'), (V), (V'), (VI) and (VI'), n is 1, and the moiety
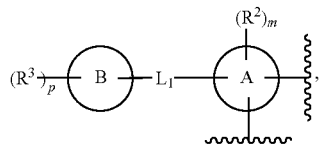
is selected from the group consisting of:
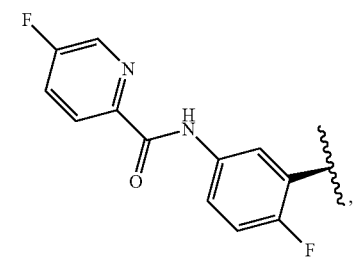
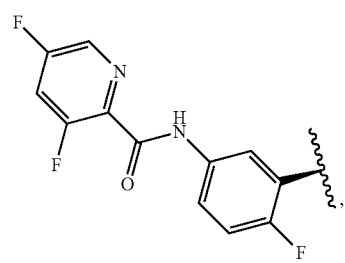
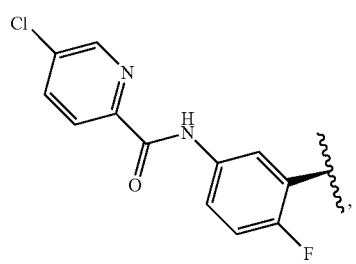
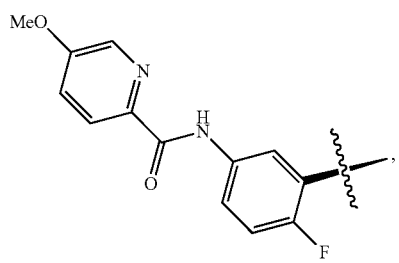
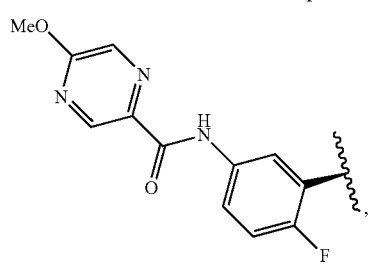
-continued
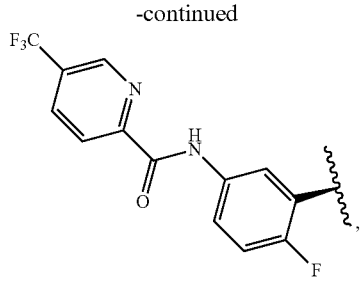
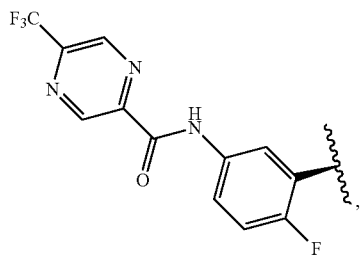
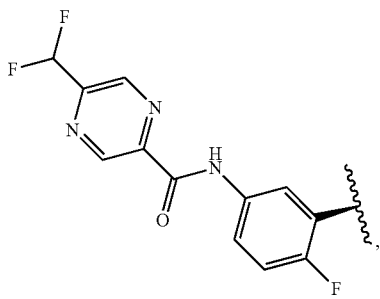
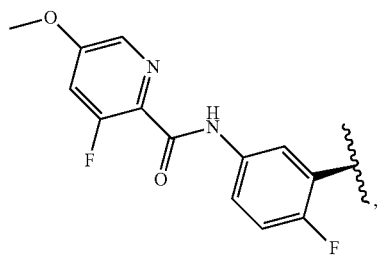
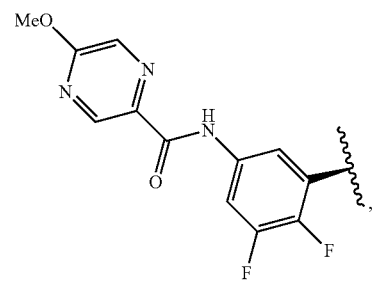
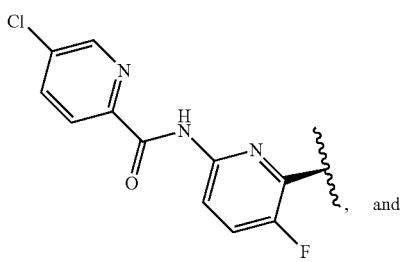, and

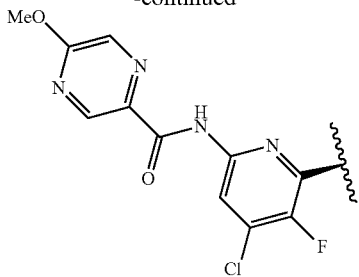
In another embodiment, in each of Formulas (I), (I'), (IA), (IA'), (II), (II'), (III), (III'), (IV), (IV'), (V), (V'), (VI) and (VI'), n is 1 and the moiety
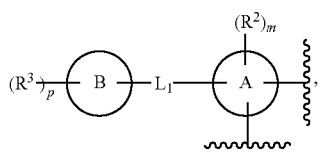
is selected from the group consisting of:
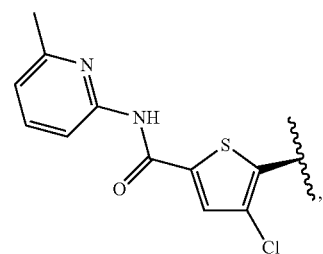
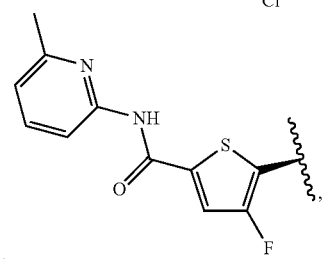
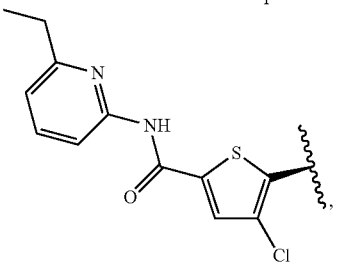
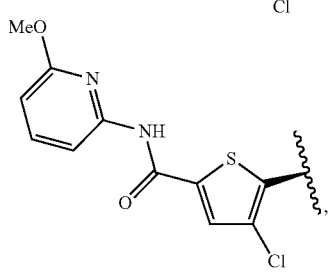
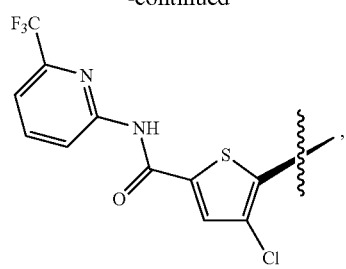
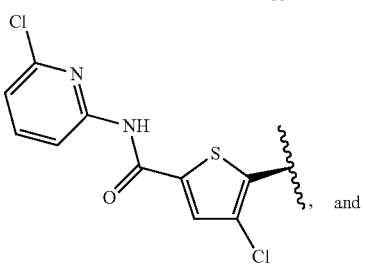
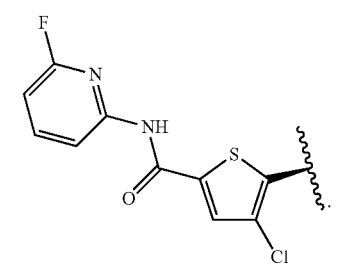
In another embodiment, in each of Formulas (I), (I'), (IA), (IA'), (II), (II'), (III), (III'), (IV), (IV'), (V), (V'), (VI) and (VI'), n is 1, -L$_1$- is a bond, and the moiety
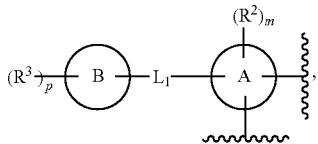
is selected from the group consisting of:
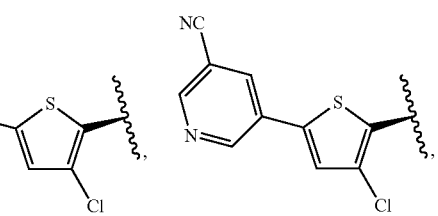
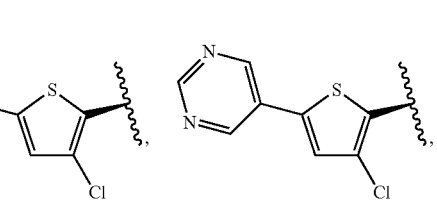

-continued

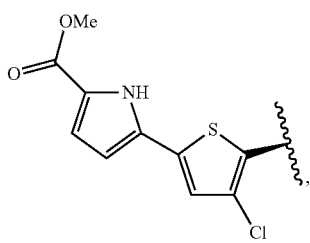,

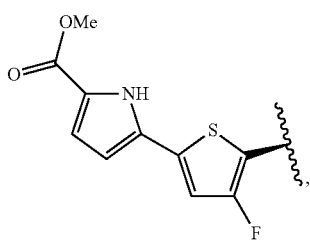,

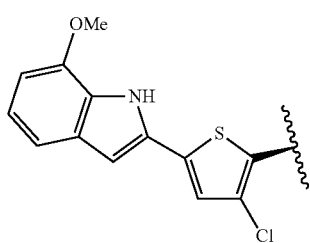,

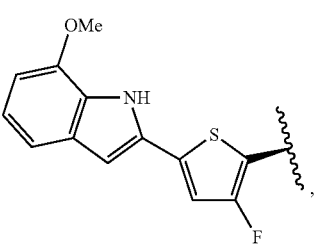,

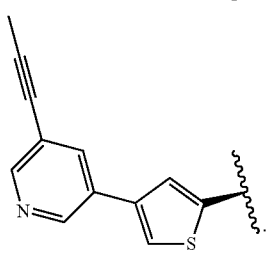.

In some embodiments, in each of Formulas (I), (I'), (IA), (IA'), (II), (II'), (III), (III'), (IV), (IV'), (V), (V'), (VI) and (VI'), n is 0. In these embodiments, the moiety:

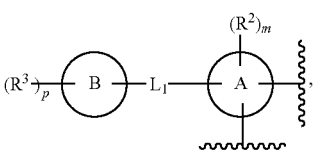

has the form

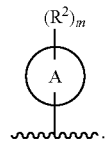.

In another embodiment, in each of Formulas (I), (I'), (IA), (IA'), (II), (II'), (III), (III'), (IV), (IV'), (V), (V'), (VI) and (VI'):
n is 0;
ring A is selected from the group consisting of phenyl, pyridyl, pyrazinyl, furanyl, thienyl, pyrimidinyl, pyridazinyl, thiazolyl, and oxazolyl; and
$R^2$ and m are each as defined in Formula (I).

In another embodiment, in each of Formulas (I), (I'), (IA), (IA'), (II), (II'), (III), (III'), (IV), (IV'), (V), (V'), (VI) and (VI'):
n is 0;
ring A is selected from the group consisting of phenyl, pyridyl, pyrazinyl, furanyl, thienyl, pyrimidinyl, pyridazinyl, thiazolyl, and oxazolyl;
m is 0 to 5; and
each $R^2$ (when present) is independently selected from the group consisting of halogen, —OH, —CN, —SF$_5$, —OSF$_5$, —NO$_2$, —N(R$^6$)$_2$, —NR$^7$C(O)R$^6$, —NR$^7$S(O)$_2$R$^6$, —NR$^7$C(O)N(R$^6$)$_2$, —NR$^7$C(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, lower alkyl, -(lower alkyl)-OH, lower haloalkyl, lower heteroalkyl, lower alkenyl, lower alkynyl, phenyl, benzyl, lower cycloalkyl, monocyclic heteroaryl, and —CH$_2$— (monocyclic heteroaryl),
wherein said phenyl, benzyl, lower cycloalkyl, monocyclic heteroaryl, and —CH$_2$— (monocyclic heteroaryl) of $R^2$ is unsubstituted or substituted with one or more groups independently selected from the group consisting of halogen, alkyl, heteroalkyl, haloalkyl, alkoxy, —O-cyclopropyl, heteroalkoxy, haloalkoxy, —CN, —SF$_5$, and OSF$_5$.

In one such embodiment,
each $R^6$ (when present) is independently selected from the group consisting of H, lower alkyl, lower haloalkyl, and lower heteroalkyl,
and $R^7$ (when present) is selected from the group consisting of H, lower alkyl.

In another embodiment, in each of Formulas (I), (I'), (IA), (IA'), (II), (II'), (III), (III'), (IV), (IV'), (V), (V'), (VI) and (VI'):
n is 0;
ring A is selected from the group consisting of phenyl, pyridyl, and thienyl; and
$R^2$ and m are each as defined in Formula (I).

In another embodiment, in each of Formulas (I), (I'), (IA), (IA'), (II), (II'), (III), (III'), (IV), (IV'), (V), (V'), (VI) and (VI'):
n is 0;
ring A is phenyl; and
$R^2$ and m are each as defined in Formula (I).

In another embodiment, in each of Formulas (I), (I'), (IA), (IA'), (II), (II'), (III), (III'), (IV), (IV'), (V), (V'), (VI) and (VI'):
n is 0;
ring A is phenyl;
m is 0 to 5; and
each $R^2$ (when present) is independently selected from the group consisting of halogen, —CN, —SF$_5$, —OSF$_5$, —NO$_2$, —NH$_2$, —N(alkyl)$_2$, —NH(alkyl), —NHC(O)R$^6$, —NHS (O)$_2$R$^6$, —NHC(O)N(R$^6$)$_2$, —NHC(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, lower alkyl, lower haloalkyl, lower heteroalkyl, lower alkenyl, lower alkynyl, phenyl, benzyl, lower cycloalkyl, monocyclic heteroaryl, and —CH$_2$— (monocyclic heteroaryl), wherein said phenyl, benzyl, lower cycloalkyl, monocyclic heteroaryl, and —CH$_2$— (monocyclic heteroaryl) of R$^2$ is unsubstituted or substituted with one or more groups independently selected from the group consisting of halogen, alkyl, heteroalkyl, haloalkyl, alkoxy, —O-cyclopropyl, heteroalkoxy, haloalkoxy, —CN, —SF$_5$, and OSF$_5$.

In one such embodiment, each R$^6$ (when present) is independently selected from the group consisting of H, lower alkyl, lower haloalkyl, lower cycloalkyl, and lower heteroalkyl.

In another embodiment, in each of Formulas (I), (I'), (IA), (IA'), (II), (II'), (III), (III'), (IV), (IV'), (V), (V'), (VI) and (VI'):
n is 0;
ring A is phenyl;
m is 0 to 4; and
each R$^2$ group (when present) is independently selected from the group consisting of halogen, —CN, —SF$_5$, —NH$_2$, —NHCH$_3$, —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, and —OCHF$_2$.

In another embodiment, in each of Formulas (I), (I'), (IA), (IA'), (II), (II'), (III), (III'), (IV), (IV'), (V), (V'), (VI) and (VI'):
n is 0;
ring A is phenyl;
m is 0 to 4; and
each R$^2$ group (when present) is independently selected from the group consisting of halogen, haloalkyl, cyclopropyl, and —CN.

In another embodiment, in each of Formulas (I), (I'), (IA), (IA'), (II), (II'), (III), (III'), (IV), (IV'), (V), (V'), (VI) and (VI'):
n is 0;
ring A is phenyl;
m is 0 to 4; and
each R$^2$ group (when present) is independently selected from the group consisting of fluorine, chlorine, bromo, cyclopropyl, —CF$_3$, and —CN.

Non-limiting examples, in each of Formulas (I), (I'), (IA), (IA'), (II), (II'), (III), (III'), (IV), (IV'), (V), (V'), (VI) and (VI'), when n is 0, of the moiety

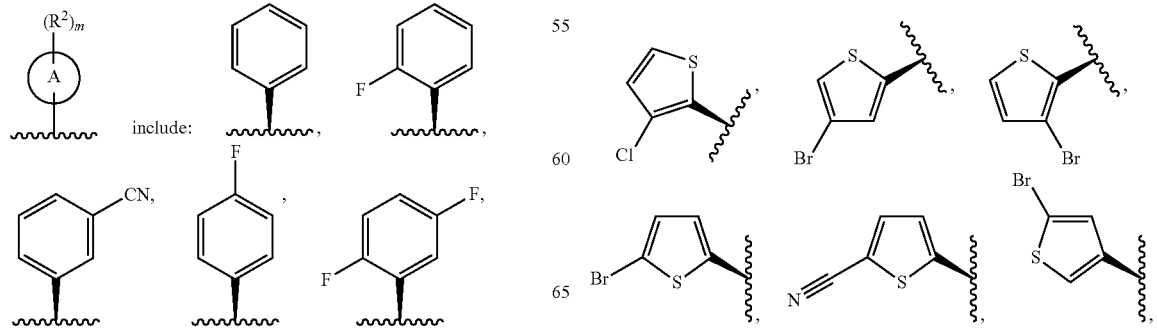

include:

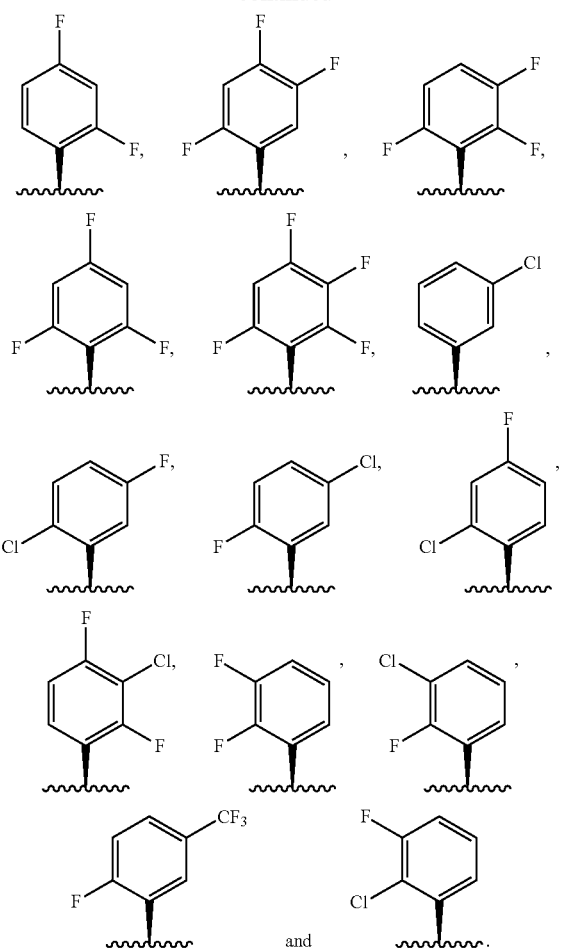

Additional non-limiting examples, in each of Formulas (I), (I'), (IA), (IA'), (II), (II'), (III), (III'), (IV), (IV'), (V), (V'), (VI) and (VI'), when n is 0, of the moiety

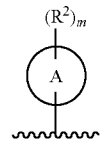

include:

-continued

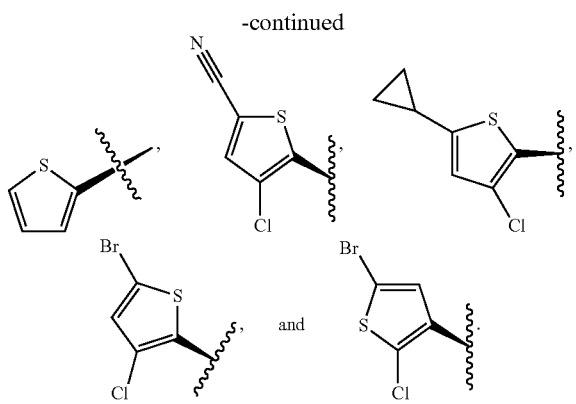

Specific non-limiting examples of compounds of the invention are shown in the table of examples below. While only one tautomeric form of each compound is shown in the tables, it shall be understood that all tautomeric forms of the compounds are contemplated as being within the scope of the non-limiting examples.

In another embodiment, 1 to 3 carbon atoms of the compounds of the invention may be replaced with 1 to 3 silicon atoms so long as all valency requirements are satisfied.

In another embodiment, there is provided a composition comprising a compound of the invention and a pharmaceutically acceptable carrier or diluent.

Another embodiment provides a composition comprising a compound of the invention, either as the sole active agent, or optionally in combination with one or more additional therapeutic agents, and a pharmaceutically acceptable carrier or diluent. Non-limiting examples of additional therapeutic agents for use in combination with the compounds of the invention include those selected from the group consisting of: (a) drugs useful for the treatment of Alzheimer's disease and/or drugs useful for treating one or more symptoms of Alzheimer's disease, (b) drugs useful for inhibiting the synthesis Aβ, (c) drugs useful for treating neurodegenerative diseases, and (d) drugs useful for the treatment of type II diabetes and/or one or more symptoms or associated pathologies thereof.

Additional non-limiting examples of additional therapeutic agents for use in combination with the compounds of the invention include drugs useful for the treatment, prevention, delay of onset, amelioration of any pathology associated with Aβ and/or a symptom thereof. Non-limiting examples of pathologies associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $\beta_2$ microglobulins and complications arising therefrom in hemodialysis patients), scrapie, bovine spongiform encephalitis, and Creutzfeld-Jakob disease, comprising administering to said patient at least one compound of the invention, or a tautomer or isomer thereof, or pharmaceutically acceptable salt or solvate of said compound or said tautomer, in an amount effective to inhibit or treat said pathology or pathologies.

Additional non-limiting examples of additional therapeutic agents for use in combination with compounds of the invention include: muscarinic antagonists (e.g., $m_1$ agonists (such as acetylcholine, oxotremorine, carbachol, or McNa343), or $m_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®), (±)-2,3-dihydro-5,6-dimethoxy-2-[[1-(phenylmethyl)-4-piperidinyl]methyl]-1H-inden-1-one hydrochloride), galantamine (Razadyne®), and rivastigimine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies (such as bapineuzemab, Wyeth/Elan); vitamin E; nicotinic acetylcholine receptor agonists; CB1 receptor inverse agonists or CB1 receptor antagonists; antibiotics; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Tau kinase inhibitors (e.g., GSK3beta inhibitors, cdk5 inhibitors, or ERK inhibitors); Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g, PBT2); and $GPR^3$ modulators; and antihistamines such as Dimebolin (e.g., Dimebon®, Pfizer).

Another embodiment provides a method of preparing a pharmaceutical composition comprising the step of admixing at least one compound of the invention, or a tautomer or stereoisomer thereof, or pharmaceutically acceptable salt or solvate of said compound, said stereoisomer, or said tautomer, and a pharmaceutically acceptable carrier or diluent.

Another embodiment provides a method of inhibiting β-secretase (BACE-1 and/or BACE-2) comprising exposing a population of cells expressing β-secretase to at least one compound of the invention, or a tautomer or stereoisomer thereof, or pharmaceutically acceptable salt or solvate of said compound, said stereoisomer, or said tautomer, in an amount effective to inhibit β-secretase. In one such embodiment, said population of cells is in vivo. In another such embodiment, said population of cells is ex vivo. In another such embodiment, said population of cells is in vitro.

Another embodiment provides a method of inhibiting β-secretase in a patient in need thereof. Another embodiment provides a method of inhibiting the formation of Aβ from APP in a patient in need thereof. Another embodiment, the invention provides a method of inhibiting the formation of Aβ plaque and/or Aβ fibrils and/or Aβ oligomers and/or senile plaques and/or neurofibrillary tangles and/or inhibiting the deposition of amyloid protein (e.g., amyloid beta protein) in, on or around neurological tissue (e.g., the brain), in a patient in need thereof. Each such embodiment comprises administering at least one compound of the invention, or a tautomer or stereoisomer thereof, or pharmaceutically acceptable salt or solvate of said compound, said stereoisomer, or said tautomer, in a therapeutically effective amount to inhibit said pathology or condition in said patient.

In another embodiment, the invention provides a method of treating, preventing, and/or delaying the onset of one or more pathologies associated with Aβ and/or one or more symptoms of one or more pathologies associated with Aβ. Non-limiting examples of pathologies associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $\beta_2$ microglobulins and complications arising therefrom in hemodialysis patients), scrapie, bovine spongiform encephalitis, and Creutzfeld-Jakob disease, comprising administering to said patient at least one compound of the invention, or a tautomer or stereoisomer thereof, or pharmaceutically acceptable salt or solvate of said compound, said stereoisomer, or said tautomer, in an amount effective to inhibit said pathology or pathologies.

In one embodiment, the invention provides a method of treating Alzheimer's disease, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer), optionally in further combination with one or more additional therapeutic agents effective to treat Alzheimer's disease or a disease or condition associated therewith, to a patient in need of treatment. In embodiments wherein one or more additional therapeutic agents are administered, such agents may be administered sequentially or together. Non-limiting examples of associated diseases or conditions, and non-limiting examples of suitable additional therapeutically active agents, are as described above.

In one embodiment, the invention provides a method of treating Down's syndrome, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer) to a patient in need of treatment.

In one embodiment, the invention provides a kit comprising, in separate containers, in a single package, pharmaceutical compositions for use in combination, wherein one container comprises an effective amount of a compound of the invention (or a tautomer or stereoisomer thereof, or pharmaceutically acceptable salt or solvate of said compound, said stereoisomer, or said tautomer) in a pharmaceutically acceptable carrier, and another container (i.e., a second container) comprises an effective amount of another pharmaceutically active ingredient, the combined quantities of the compound of the invention and the other pharmaceutically active ingredient being effective to: (a) treat Alzheimer's disease, or (b) inhibit the deposition of amyloid protein in, on or around neurological tissue (e.g., the brain), or (c) treat neurodegenerative diseases, or (d) inhibit the activity of BACE-1.

In various embodiments, the compositions and methods disclosed above and below wherein the compound(s) of the invention is a compound or compounds selected from the group consisting of the exemplary compounds of the invention described below.

In another embodiment, the invention provides for the use of a compound of the invention, or a tautomer or stereoisomer thereof, or pharmaceutically acceptable salt or solvate of said compound, said stereoisomer, or said tautomer, in the manufacture of a medicament for use in the treatment, the delay of onset, and/or the prevention of one or more Aβ pathologies and/or in the treatment, the delay of onset, and/or the prevention of one or more symptoms of one or more Aβ pathologies.

DEFINITIONS

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" portion of "hydroxyalkyl", "haloalkyl", arylalkyl-, alkylaryl-, "alkoxy" etc.

It shall be understood that, in the various embodiments of the invention described herein, any variable not explicitly defined in the context of the embodiment is as defined in Formula (I). All valences not explicitly filled are assumed to be filled by hydrogen.

In the various embodiments described herein, each variable is selected independently of the others unless otherwise indicated.

As described herein, variables of the formulas presented herein, such as ring A and ring B may be unsubstituted or substituted with "one or more" groups. For example, ring A may be unsubstituted or substituted with one or more $R^2$ groups; ring B may be unsubstituted or substituted with one or more $R^3$ groups. It shall be understood that the upper limit of the number of substituents (referred to in the phrase "one or more substituents") is the number of available hydrogen atoms on the relevant moiety (e.g., ring A or ring B) that are available for replacement by a substituent which will result in a chemically stable and chemically neutral moiety. Thus, for example, in the various Formulas of the compounds of the invention, e.g., in Formula (I), m, n, and p are each independently selected integers, wherein:
m is 0 or more,
n is 0 or 1, and
p is 0 or more,
wherein the maximum value of m is the maximum number of available substitutable hydrogen atoms on ring A, and wherein the maximum value of p is the maximum number of available substitutable hydrogen atoms on ring B. By way of non-limiting illustration, when ring A is a

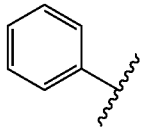 [SMILES: *c1ccccc1]

group, the maximum value of m is 5. When ring A is a

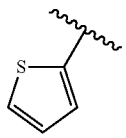 [SMILES: *c1cccs1]

group, the maximum value of m is 3. When ring A is a

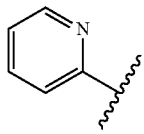

group, the maximum value of m is 4.

"Patient" includes both human and non-human animals. Non-human animals include those research animals and companion animals such as mice, primates, monkeys, great apes, canine (e.g., dogs), and feline (e.g., house cats).

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, or they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the aforesaid "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the aforesaid bulk composition and individual dosage units.

"Halogen" and "halo" mean fluorine, chlorine, bromine, or iodine. Preferred are fluorine, chlorine and bromine.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being as described herein or independently selected from the group consisting of halo, alkyl, haloalkyl, spirocycloalkyl, aryl, cycloalkyl, cyano, hydroxy, alkoxy, alkylthio, amino, —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Haloalkyl" means an alkyl as defined above wherein one or more hydrogen atoms on the alkyl is replaced by a halo group defined above.

"Heteroalkyl" means an alkyl moiety as defined above, having one or more carbon atoms, for example one, two or three carbon atoms, replaced with one or more heteroatoms, which may be the same or different, where the point of attachment to the remainder of the molecule is through a carbon atom of the heteroalkyl radical. Suitable such heteroatoms include O, S, S(O), S(O)$_2$, and —NH—, —N(alkyl)-. Non-limiting examples include ethers, thioethers, amines, and the like.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene. More generally, the suffix "ene" on alkyl, aryl, heterocycloalkyl, etc. indicates a divalent moiety, e.g., —CH$_2$CH$_2$— is ethylene, and

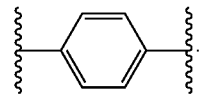

is para-phenylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Alkenylene" means a difunctional group obtained by removal of a hydrogen from an alkenyl group that is defined above. Non-limiting examples of alkenylene include —CH=CH—, —C(CH$_3$)=CH—, and —CH=CHCH$_2$—.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl. "Monocyclic aryl" means phenyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more substituents, which may be the same or different, as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The term "monocyclic heteroaryl" refers to monocyclic versions of heteroaryl as described above and includes 4- to 7-membered monocyclic heteroaryl groups comprising from 1 to 4 ring heteroatoms, said ring heteroatoms being independently selected from the group consisting of N, O, and S, and oxides thereof. The point of attachment to the parent moiety is to any available ring carbon or ring heteroatom. Non-limiting examples of monocyclic heteroaryl moities include pyridyl, pyrazinyl, furanyl, thienyl, pyrimidinyl, pyridazinyl, pyridoneyl, thiazolyl, isothiazolyl, oxazolyl, oxadiazolyl, isoxazolyl, pyrazolyl, furazanyl, pyrrolyl, pyrazolyl, triazolyl, thiadiazolyl (e.g., 1,2,4-thiadiazolyl), imidazolyl, and triazinyl (e.g., 1,2,4-triazinyl), and oxides thereof.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like. Further non-limiting examples of cycloalkyl include the following:

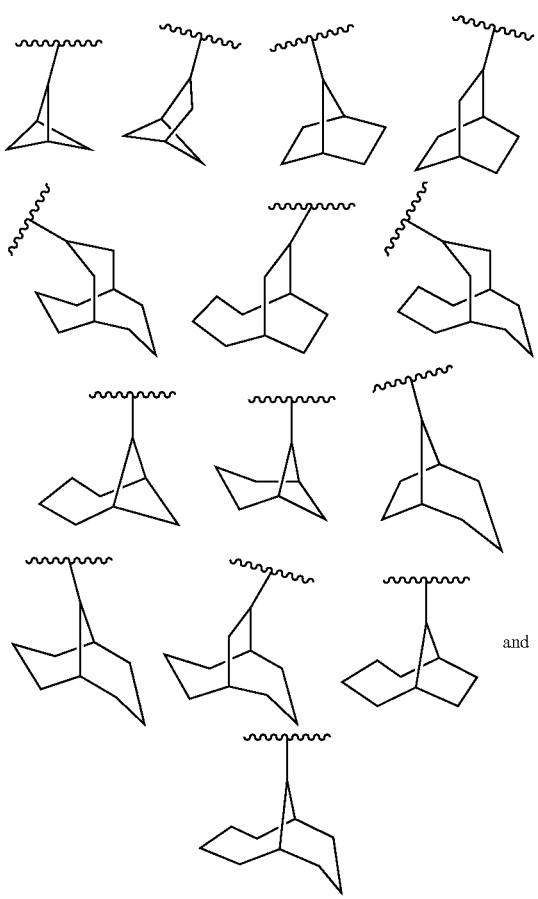

and

"Cycloalkenyl" means a non-aromatic mono or multicyclic ring system comprising about 3 to about 10 carbon atoms, preferably about 5 to about 10 carbon atoms which contain at least one carbon-carbon double bond. Preferred cycloalkenyl rings contain about 5 to about 7 ring atoms. The cycloalkenyl can be optionally substituted with one or more substituents, which may be the same or different, as described herein. The term "monocyclic cycloalkenyl" refers to monocyclic versions of cycloalkenyl groups described herein and includes non-aromatic 3- to 7-membered monocyclic cycloalkyl groups which contains one or more carbon-carbon double bonds. Non-limiting examples include cyclopropenyl, cyclobutenyl, cyclopentenyl, cyclohexenyl, cyclohetpenyl, cyclohepta-1,3-dienyl, and the like. Non-limiting example of a suitable multicyclic cycloalkenyl is norbornylenyl.

"Heterocycloalkyl" (or "heterocyclyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

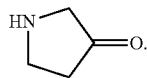

As used herein, the term "monocyclic heterocycloalkyl" refers monocyclic versions of the heterocycloalkyl moieties described herein and include a 4- to 7-membered monocyclic heterocycloalkyl groups comprising from 1 to 4 ring heteroatoms, said ring heteroatoms being independently selected from the group consisting of N,N-oxide, O, S, S-oxide, S(O), and S(O)$_2$. The point of attachment to the parent moiety is to any available ring carbon or ring heteroatom. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof. Non-limiting examples of lower alkyl-substituted oxetanyl include the moiety:

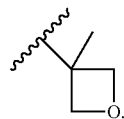

"Heterocycloalkenyl" (or "heterocyclenyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more substituents, which may be the same or different, as described herein. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes rings wherein =O replaces two available hydrogens on the same carbon atom (i.e., heterocyclyl includes rings having a carbonyl group in the ring). Example of such moiety is pyrrolidenone (or pyrrolone):

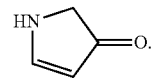

As used herein, the term "monocyclic heterocycloalkenyl" refers to monocyclic versions of the heterocycloalkenyl moities described herein and include 4- to 7-membered monocyclic heterocycloalkenyl groups comprising from 1 to 4 ring heteroatoms, said ring heteroatoms being independently selected from the group consisting of N,N-oxide, O, S, S-oxide, S(O), and S(O)$_2$. The point of attachment to the parent moiety is to any available ring carbon or ring heteroatom. Non-limiting examples of monocyclic heterocyloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, dihydrothiophenyl, and dihydrothiopyranyl, and oxides thereof.

It should be noted that in hetero-atom containing ring systems of this invention, there are no hydroxyl groups on carbon atoms adjacent to a N, O or S, as well as there are no N or S groups on carbon adjacent to another heteroatom.

there is no —OH attached directly to carbons marked 2 and 5.

As used herein, the term "multicyclic group" refers to a fused ring system comprising two (bicyclic), three (tricyclic), or more fused rings, wherein each ring of the fused ring system is independently selected from the group consisting of phenyl, monocyclic heteroaryl, monocyclic cycloalkyl, monocyclic cycloalkenyl, monocyclic heterocycloalkyl, and monocyclic heterocycloalkenyl. The point of attachment to the parent moiety is to any available ring carbon or (if present) ring heteroatom on any of the fused rings. It shall be understood that each of the following multicyclic groups pictured may be unsubstituted or substituted, as described herein. Only the point of attachment to the parent moiety is shown by the wavy line.

The term multicyclic groups includes bicyclic aromatic groups. Non-limiting examples of multicyclic groups which are bicyclic aromatic groups include:

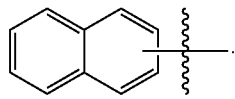

The term multicyclic groups includes bicyclic heteroaromatic groups comprising from 1 to 3 ring heteroatoms, each said ring heteroatom being independently selected from the group consisting of N, O, and S, S(O), S(O)$_2$, and oxides of N, O, and S, and oxides thereof.

The term multicyclic group includes saturated bicyclic cycloalkyl groups. Non-limiting examples of multicyclic groups which are saturated bicyclic cycloalkyl groups include the following:

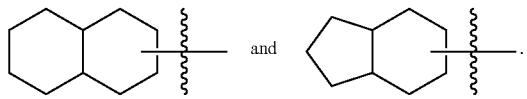

The term multicyclic group includes partially unsaturated bicyclic cycloalkyl groups. Non-limiting examples of multicyclic groups which comprise partially unsaturated bicyclic cycloalkyl groups include the following:

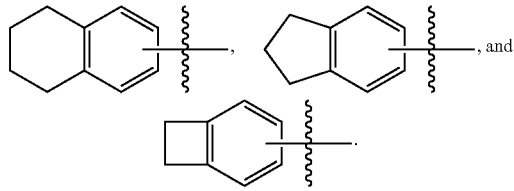

The term multicyclic groups includes partially or fully saturated bicyclic groups comprising from 1 to 3 ring heteroatoms, each said ring heteroatom is independently selected from the group consisting of N, O, and S, S(O), S(O)$_2$, and oxides of N, O, and S.

The term multicyclic group includes aromatic tricyclic groups, cycloalkyl tricyclic groups, as well as heteroaromatic and partially and fully saturated tricyclic groups. For tricyclic groups comprising ring heteroatoms, said tricyclic groups comprise one or more (e.g., from 1 to 5) ring heteroatoms, wherein each said ring heteroatom is independently selected from N, O, and S, S(O), S(O)$_2$, and oxides of N, O, and S:

"Arylalkyl" (or "aralkyl") means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl. The term (and similar terms) may be written as "arylalkyl-" to indicate the point of attachment to the parent moiety. Similarly, "heteroarylalkyl", "cycloalkylalkyl", "cycloalkenylalkyl", "heterocycloalkylalkyl", "heterocycloalkenylalkyl", etc., mean a heteroaryl, cycloalkyl, cycloalkenyl, heterocycloalkyl, heterocycloalkenyl, etc. as described herein bound to a parent moiety through an alkyl group. Preferred groups contain a lower alkyl group. Such alkyl groups may be straight or branched, unsubstituted and/or substituted as described herein.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclylalkyl" (or "heterocycloalkylalkyl") means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenylalkyl" means a heterocyclenyl moiety as defined above linked via an alkyl moiety (defined above) to a parent core.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Cyanoalkyl" means a NC-alkyl- group in which alkyl is as previously defined. Preferred cyanoalkyls contain lower alkyl. Non-limiting examples of suitable cyanoalkyl groups include cyanomethyl and 2-cyanoethyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkyoxyalkyl" means a group derived from an alkoxy and alkyl as defined herein. The bond to the parent moiety is through the alkyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl- moiety or the like includes substitution on any ring portion and/or on the alkyl portion of the group.

When a variable appears more than once in a group, e.g., $R^8$ in —N($R^6$)$_2$, or a variable appears more than once in a structure presented herein, the variables can be the same or different.

The line ----, as a bond generally indicates a mixture of, or either of, the possible isomers, e.g., containing (R)- and (S)-stereochemistry. For example:

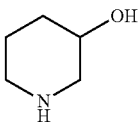

means containing both

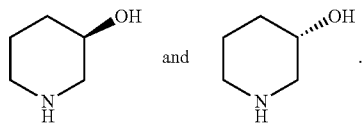

The wavy line ～ as used herein, indicates a point of attachment to the rest of the compound. Lines drawn into the ring systems, such as, for example:

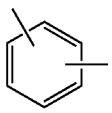

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, heterocyclenyl, or other ring described herein, e.g.,

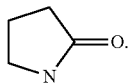

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

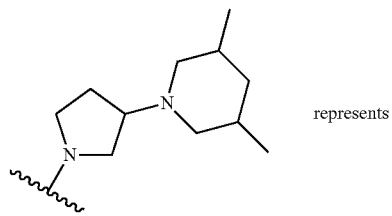 represents

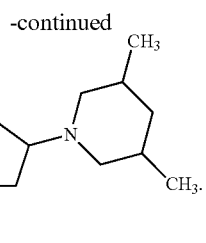

In another embodiment, the compounds of the invention, and/or compositions comprising them, are present in isolated and/or purified form. The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer or stereoisomer thereof, or pharmaceutically acceptable salt or solvate of said compound, said stereoisomer, or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

It shall be understood that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

Another embodiment provides prodrugs and/or solvates of the compounds of the invention. A discussion of prodrugs is provided in T. Higuchi and V. Stella, Pro-drugs as Novel Delivery Systems (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the invention or a pharmaceutically acceptable salt thereof, contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as (β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl, and the like.

Similarly, if a compound of the invention contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of the invention incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$)cycloalkyl, benzyl, or R-carbonyl is a natural α-aminoacyl or natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl, carboxy ($C_1$-$C_6$)alkyl, amino($C_1$-$C_4$)alkyl or mono-N— or di-N,N—($C_1$-$C_6$)alkylaminoalkyl, —C(Y$^4$)Y$^5$ wherein Y$^4$ is H or methyl and Y$^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

Another embodiment provides pharmaceutically acceptable salts of the compounds of the invention. Thus, reference to a compound of the invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the invention may be formed, for example, by reacting a compound of the invention with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Another embodiment provides pharmaceutically acceptable esters of the compounds of the invention. Such esters include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Another embodiment provides tautomers of the compounds of the invention, and salts, solvates, esters and prodrugs thereof. Also, for example, all keto-enol and imine-enamine forms of the compounds are included in the invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Another embodiment provides for diastereomeric mixtures and individual enantiomers of the compounds of the invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

All stereoisomers (for example, geometric isomers, optical isomers and the like) of the compounds of the invention (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated as embodiments within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Another embodiment provides isotopically-labelled compounds of the invention. Such compounds are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of the invention (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of the invention can generally be prepared by following procedures analogous to those disclosed in the Schemes and/or in the Examples hereinbelow, by substituting an appropriate isotopically labelled reagent for a non-isotopically labelled reagent.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1H$), and deuterium ($^2H$). Protium is the predominant hydrogen isotope found in nature. Additional examples of isotopes that can be incorporated into compounds of the invention include (when present) isotopes of hydrogen, carbon, nitrogen, oxygen, phosphorus, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

In another embodiment, the compounds of the invention are isotopically labeled for use as research or diagnostic agents. For example, compounds of the invention can be labeled for use in compound and/or substrate tissue distribution assays. Tritiated (i.e., $^3H$) and carbon-14 (i.e., $^{14}C$) isotopes may be prepared for their ease of preparation and detectability. In another embodiment, the compounds of the invention can be labeled with isotopes such as deuterium (i.e., $^2H$). Deuterium enrichment of the compounds of the invention may afford certain therapeutic advantages resulting from greater metabolic stability (e.g., increased in vivo half-life or reduced dosage requirements), or may provide a compound useful as a standard for characterization of biological samples, and hence may be preferred in some circumstances. Isotopically labelled compounds of the invention can generally be prepared without undue experimentation by following procedures analogous to those disclosed in the Schemes and/or in the examples hereinbelow, by substituting an appropriate isotopically labelled reagent for a non-isotopically labelled reagent. Labels suitable for use in such research or diagnostic agents include, but are not limited to, nuclear spin markers, e.g. a $^{19}F$ magnetic resonance imaging (MRI) probe, radioactive markers, e.g., $^{18}F$, $^{11}C$, $^{15}N$, $^{125}I$, and $^3H$ (also referred to as "tritium") isotope marker, and complexes of metal atoms or metal ions and chelating agents. Such labeled compounds can be used for in vitro or in vivo imaging of BACE, especially in tissues such as brain, heart, liver, kidney, and lungs, to obtain quantitative measurements of BACE and determine the distribution and regional binding characteristics of these receptors in tissue. These assay-type probes may be used, inter alia, in connection with such diagnostic techniques as MRI and positron emission tomography (PET), and single photon emission computed tomography (SPECT).

Thus, for example, some of the compounds of the invention contain one or more methyl ether groups. Those of ordinary skill in the art will recognize that carbon-11 isotopic analogs of methyl ether groups can be readily made by methods well known in the art. Some of the compounds of the invention include fluoro groups. Those of ordinary skill in the art will also recognize that $^{18}F$ can be used as an isotopic replacement for fluoro groups present in a compound of the invention, and $^{18}F$ analogs of the compounds of the invention that contain a fluoro group can be made by a variety of methods known in the art.

Polymorphic forms of the compounds of the invention, and of the salts, solvates, esters and prodrugs of the compounds of the invention, are intended to be included in the present invention.

Another embodiment provides suitable dosages and dosage forms of the compounds of the invention. Suitable doses for administering compounds of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from about 0.001 to 500 mg/kg of body weight/day of the compound of the invention. In one embodiment, the dosage is from about 0.01 to about 25 mg/kg of body weight/day of a compound of the invention, or a pharmaceutically acceptable salt or solvate of said compound. In another embodiment, the quantity of active compound in a unit dose of preparation may be varied or adjusted from about 1 mg to about 100 mg, preferably from about 1 mg to about 50 mg, more preferably from about 1 mg to about 25 mg, according to the particular application. In another embodiment, a typical recommended daily dosage regimen for oral administration can range from about 1 mg/day to about 500 mg/day, preferably 1 mg/day to 200 mg/day, in two to four divided doses.

As discussed above, the amount and frequency of administration of the compounds of the invention and/or the pharmaceutically acceptable salts thereof will be regulated according to the judgment of the attending clinician considering such factors as age, condition and size of the patient as well as severity of the symptoms being treated.

When used in combination with one or more additional therapeutic agents, the compounds of this invention may be administered together or sequentially. When administered sequentially, compounds of the invention may be administered before or after the one or more additional therapeutic agents, as determined by those skilled in the art or patient preference.

If formulated as a fixed dose, such combination products employ the compounds of this invention within the dosage range described herein and the other pharmaceutically active agent or treatment within its dosage range.

Accordingly, another embodiment provides combinations comprising an amount of at least one compound of the invention, or a pharmaceutically acceptable salt, solvate, ester or prodrug thereof, and an effective amount of one or more additional agents described above.

The pharmacological properties of the compounds of this invention may be confirmed by a number of pharmacological assays. Certain assays are exemplified elsewhere in this document.

Another embodiment provides for pharmaceutically acceptable compositions comprising a compound of the invention, either as the neat chemical or optionally further comprising additional ingredients. For preparing pharmaceutical compositions from the compounds of the invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences,* 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

Another embodiment provides for compositions comprising a compound of the invention formulated for transdermal delivery. The transdermal compositions can take the form of creams, lotions, aerosols and/or emulsions and can be included in a transdermal patch of the matrix or reservoir type as are conventional in the art for this purpose.

Another embodiment provides for compositions comprising a compound of the invention formulated for subcutaneous delivery. Another embodiment provides for compositions suitable for oral delivery. In some embodiments, it may be advantageous for the pharmaceutical preparation comprising one or more compounds of the invention be prepared in a unit dosage form. In such forms, the preparation is subdivided into suitably sized unit doses containing appropriate quantities of the active component, e.g., an effective amount to achieve the desired purpose. Each of the foregoing alternatives, together with their corresponding methods of use, are considered as included in the various embodiments of the invention.

PREPARATIVE EXAMPLES

Compounds of the invention can be made using procedures known in the art. The following reaction schemes show typical procedures, but those skilled in the art will recognize that other procedures can also be suitable. For examples in which $R^1$ and $R^{1H}$ are other than hydrogen, and for examples in which the oxacyclic-fused ring size is other than enumerated below, those skilled in the art will recognize that changes to the requisite reagents can be made at the appropriate Steps in the Methods outlined below. Non-limiting examples of said Steps and Methods in which such changes could be made include (1) Steps 4 and 5 of Method A, (2) Step 3 of Method I, (3) Steps 4 and 5 of Method Q, (4) Steps 4 and 5 of Method Y, and (5) Step 3 of Method Ag. In some of the Methods shown below (such as Methods A, B, D, and F), an exocyclic ring nitrogen of a synthetic intermediate is protected with a tert-butoxycarbonyl (Boc) group. Where a bond is present between the nitrogen and Boc group, no particular stereochemical orientation is implied by the direction of the bond. Reactions may involve monitoring for consumption of starting material, and there are many methods for said monitoring, including but not limited to thin layer chromatography (TLC) and liquid chromatography mass spectrometry (LCMS), and those skilled in the art will recognize that where one method is specified, other non-limiting methods may be substituted.

Techniques, solvents and reagents may be referred to by their abbreviations as follows Acetic acid: AcOH
Acetonitrile: MeCN
Allyl carbamate: Alloc
Aqueous: aq.
Benzyl: Bn
Benzyltrimethylammonium hydroxide: Triton B
[1,1'-Bis(diphenylphosphino)ferrocene]-dichloropalladium (II): PdCl$_2$dppf
Bis(2-oxo-3-oxazolidinyl)phosphonic chloride: BOPCl
tert-Butyl: t-Bu or tBu
Calculated: Calc'd
Centimeters: cm
3-Chloroperoxybenzoic acid: mCPBA
Diethylaminosulfur trifluoride: DAST
Dibenzylideneacetone: dba
Dichloromethane: DCM
2-Dicyclohexylphosphino-2',4',6'-triisopropylbiphenyl: XPhos Diisopropylamine: iPr$_2$NH or DIPA
Diisopropylethylamine: DIEA or iPr$_2$NEt
1,2-Dimethoxyethane: DME
Dimethylacetamide: DMA
1-(3-Dimethylaminopropyl)-3-ethylcarbodiimide: EDC or EDCI
Dimethylformamide: DMF
Dimethylsulfoxide: DMSO
Diphenylphosphoryl azide: DPPA
Equivalents: equiv.
Ether or diethyl ether: Et$_2$O
Ethyl: Et
Ethyl acetate: AcOEt, EtOAc, or EA
Example: Ex.
Expected: Exp.
Grams: g
Hexanes: hex
High performance liquid chromatography: HPLC
High resolution mass spectrometry: HRMS
Hydroxybenzotriazole: HOBt
Inhibition: Inh.
Iron(III) acetylacetonate: Fe(acac)$_3$
Isopropyl alcohol: IPA
Liquid chromatography mass Spectrometry: LCMS
Lithium diisopropylamide: LDA
Methanesulfonyl chloride: MeSO$_2$Cl or MsCl
Methanol: MeOH
Methoxymethyl: MOM
Methyl t-butyl ether: MTBE
Methyl chloromethyl ether: MOMCl
Methyl iodide: MeI
N-Methyl morpholine: NMM
Methyl magnesium bromide: MeMgBr
Microliters: µl or µL Milligrams: mg
Milliliters: mL
Millimoles: mmol
Minutes: min
N-bromosuccinimide: NBS
n-Butyllithium: nBuLi or n-BuLi
Nuclear magnetic resonance spectroscopy: NMR
Number: no. or No.
Observed: Obs.
Palladium(II) acetate: Pd(OAc)$_2$
Para-methoxy benzyl: PMB
Petroleum ether: PE
Retention time: t$_R$
Room temperature (ambient, about 25° C.): rt or RT
tert-Butoxycarbonyl: t-Boc or Boc
SFC: Supercritical Fluid Chromatography
Temperature: temp.
Tetrahydrofuran: THF
Thin layer chromatography: TLC
para-Toluenesulfonyl chloride: TsCl
1,1,1-Triacetoxy-1,1-dihydro-1,2-benziodoxol-3(1H)-one: DMP
Triethylamine: Et$_3$N or TEA
Trifluoroacetic acid: TFA
Trimethylsilyl: TMS
2-(Trimethylsilyl)ethoxycarbonyl: Teoc
2,4,6-tripropyl-1,3,5,2,4,6-trioxatriphosphorinane-2,4-6-trioxide: T3P
Ultra performance liquid chromatography: UPLC
Method A

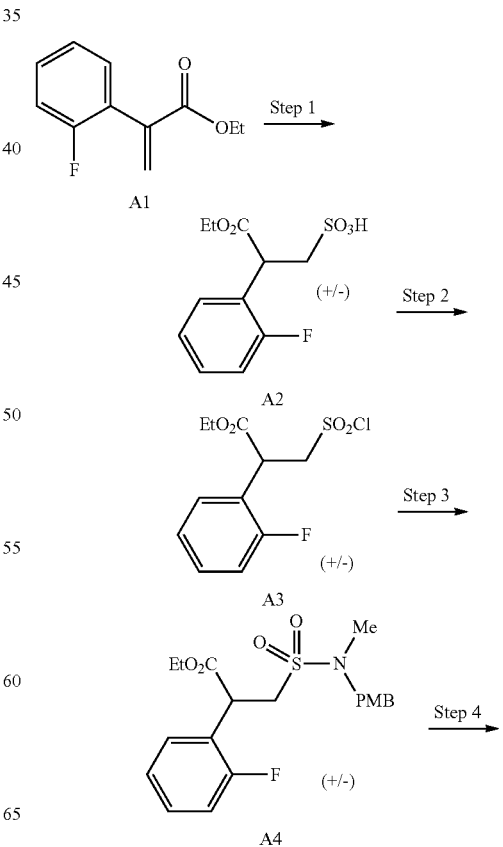

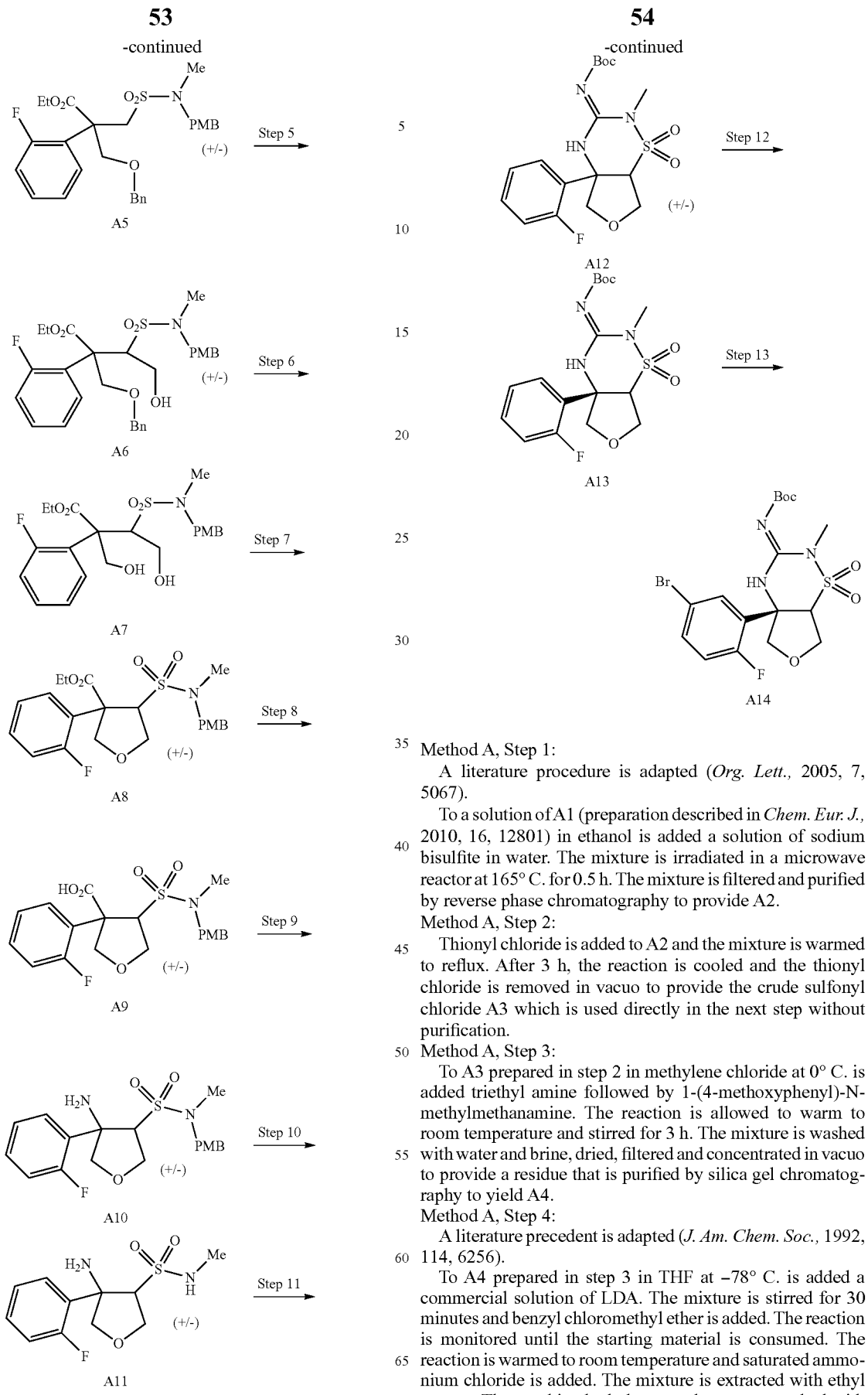

Method A, Step 1:
 A literature procedure is adapted (*Org. Lett.*, 2005, 7, 5067).
 To a solution of A1 (preparation described in *Chem. Eur. J.*, 2010, 16, 12801) in ethanol is added a solution of sodium bisulfite in water. The mixture is irradiated in a microwave reactor at 165° C. for 0.5 h. The mixture is filtered and purified by reverse phase chromatography to provide A2.

Method A, Step 2:
 Thionyl chloride is added to A2 and the mixture is warmed to reflux. After 3 h, the reaction is cooled and the thionyl chloride is removed in vacuo to provide the crude sulfonyl chloride A3 which is used directly in the next step without purification.

Method A, Step 3:
 To A3 prepared in step 2 in methylene chloride at 0° C. is added triethyl amine followed by 1-(4-methoxyphenyl)-N-methylmethanamine. The reaction is allowed to warm to room temperature and stirred for 3 h. The mixture is washed with water and brine, dried, filtered and concentrated in vacuo to provide a residue that is purified by silica gel chromatography to yield A4.

Method A, Step 4:
 A literature precedent is adapted (*J. Am. Chem. Soc.*, 1992, 114, 6256).
 To A4 prepared in step 3 in THF at −78° C. is added a commercial solution of LDA. The mixture is stirred for 30 minutes and benzyl chloromethyl ether is added. The reaction is monitored until the starting material is consumed. The reaction is warmed to room temperature and saturated ammonium chloride is added. The mixture is extracted with ethyl acetate. The combined ethyl acetate layers are washed with water and brine, dried, filtered and concentrated in vacuo to provide a residue that is purified by silica gel chromatography to yield A5.

Method A, Step 5:

A literature precedent is adapted (*J. Org. Chem.*, 1984, 49, 1700).

To A5 prepared in step 4 in THF at −78° C. is added NaHMDS. The reaction is warmed to −30° C. for 30 minutes and subsequently cooled to −78° C. Paraformaldehyde is added to the reaction mixture and the reaction is allowed to warm to room temperature. Once starting material is consumed as evidenced by monitoring by, for instance, TLC, water is added to the reaction. The mixture is extracted with ethyl acetate. The combined ethyl acetate layers are washed with water and brine, dried, filtered, and concentrated in vacuo to provide a residue that is purified by silica gel chromatography to yield A6.

Method A, Step 6:

The benzyl group of A6 is removed by treating A6 in ethanol with a palladium hydrogenation catalyst such as Pd(OH)$_2$ or Pd/C. The mixture is put under an atmosphere of hydrogen gas. The reaction is monitored until the starting material is consumed, and the reaction is filtered through a bed of Celite washing with DCM. The filtrate is concentrated in vacuo and the residue is purified by silica gel chromatography to provide A7.

Method A, Step 7:

A literature precedent is adapted (*J. Am. Chem. Soc.*, 1985, 107, 5210).

To A7 prepared in step 6 is added a solution of diethoxytriphenylphosphorane in toluene (preparation of which is described in *J. Am. Chem. Soc.*, 1985, 107, 5210). The reaction is warmed to 45° C. and stirred for 60 h or until TLC shows the disappearance of starting material. The reaction is then cooled to room temperature. Water is added and the mixture is extracted with ethyl acetate. The combined ethyl acetate layers are washed with water and brine, dried, and filtered and concentrated in vacuo to provide a residue that is purified by silica gel chromatography to yield A8.

Method A, Step 8:

To A8 prepared in step 7 in THF is added 2N LiOH$_{(aq)}$. The reaction is warmed to 60° C. and stirred for several hours until TLC shows the disappearance of starting material. The reaction is then cooled to room temperature and acidified to pH~3 using 1N HCl$_{(aq)}$. The mixture is then extracted with ethyl acetate. The combined ethyl acetate layers are washed with water and brine, dried, filtered, and concentrated in vacuo to provide the carboxylic acid A9.

Method A, Step 9:

A literature precedent is adapted (*J. Org. Chem.*, 1992, 57, 6188).

To acid A9 prepared in step 8 in THF at rt is added TEA followed by diphenylphosphonic azide. The reaction mixture is stirred at room temperature for 24 h and then most of the solvent is removed in vacuo. To the residue is added acetonitrile. The resulting solution is added dropwise to a mixture of acetonitrile, water, and trifluoroacetic acid which is heated to 80° C. The reaction is then stirred at 80° C. for 1.5 h. The reaction is cooled to room temperature and concentrated in vacuo. Ethyl acetate is added and the mixture is washed with saturated NaHCO$_3$, water, and brine. The organic layer is dried, filtered, and concentrated in vacuo to provide a residue that is purified by silica gel chromatography to yield A10.

Method A, Step 10:

To the amine A10 prepared in step 9 in chloroform is added m-dimethoxybenzene and trifluoroacetic acid. The mixture is stirred for 18 h or until TLC shows the disappearance of starting material. Additional TFA may be added if the reaction does not go to completion. Once the starting material is consumed, the mixture is concentrated in vacuo and then taken up into DCM. The mixture is washed with saturated NaHCO$_3$, water and brine. The organic layer is dried, filtered, and concentrated in vacuo to provide a residue that is purified by silica gel chromatography to yield A11.

Method A, Step 11:

To A11 prepared in step 10 in a suitable solvent, for example t-butanol or acetonitrile, is added a solution of cyanogen bromide. The resultant mixture is heated to reflux for 4 hours or until monitoring shows the disappearance of starting material and the formation of desired product. The solvent is removed in vacuo and ethyl acetate is added. The mixture is washed with water and brine. The organic layer is dried (MgSO$_4$), filtered, and concentrated in vacuo to provide a residue that is taken up into DCM and TEA and (Boc)$_2$O is added. The mixture is stirred at room temperature for 12 h and then washed with saturated NaHCO$_3$, water, and brine. The organic layer is dried (MgSO$_4$), filtered, and concentrated in vacuo to provide a residue that is purified by silica gel chromatography to yield A12.

Method A, Step 12:

The racemic mixture A12 is separated into enantiomers using chiral HPLC to provide the desired enantiomer Aβ.

Method A, Step 13

(A literature precedent is adapted, *J. Med. Chem.*, 2006, 49, 2600).

To A13 prepared in step 12 in acetonitrile is added dibromodimethylhydantoin. The mixture is cooled to 0° C. using an ice bath and sulfuric acid is added. The mixture is allowed to warm to room temperature and stirring is continued at room temperature for 10 minutes. The mixture is then heated to 55° C. and stirred for 2 h. The mixture is cooled to room temperature and most of the solvent is removed in vacuo. The residue is neutralized with 4N NaOH and the resulting mixture is extracted with EtOAc. The organic phase is dried (MgSO$_4$), filtered, and concentrated in vacuo. The residue is taken up into DCM and (Boc)$_2$O is added. The reaction is stirred at room temperature for 12 h. The reaction is concentrated in vacuo and the residue is purified by silica gel chromatography to provide A14.

Method A2

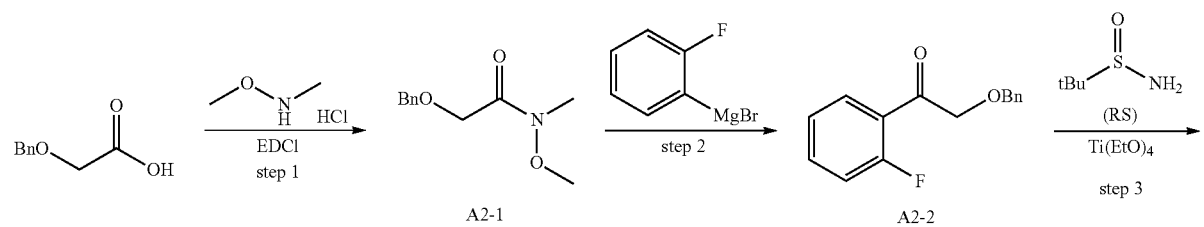

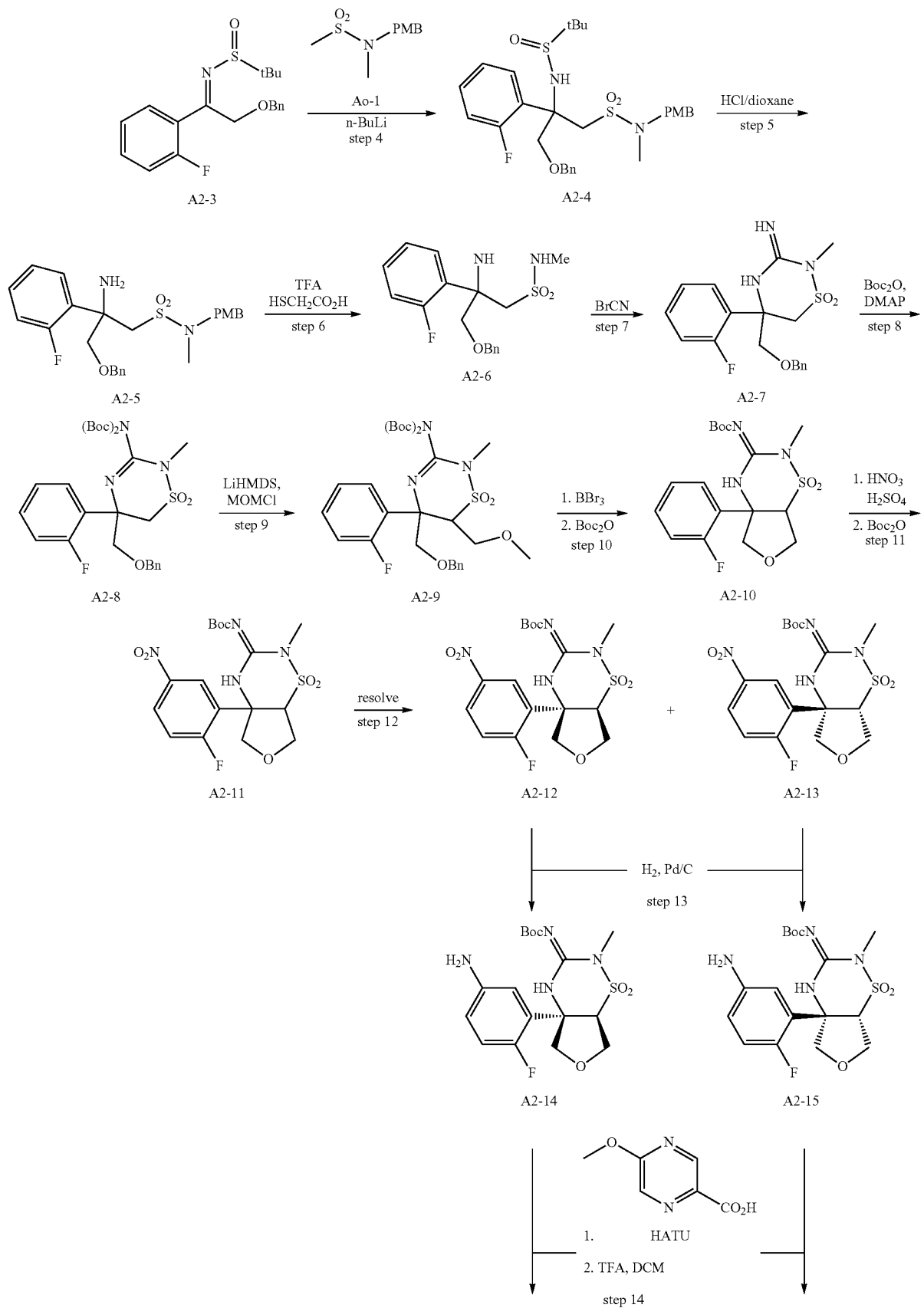

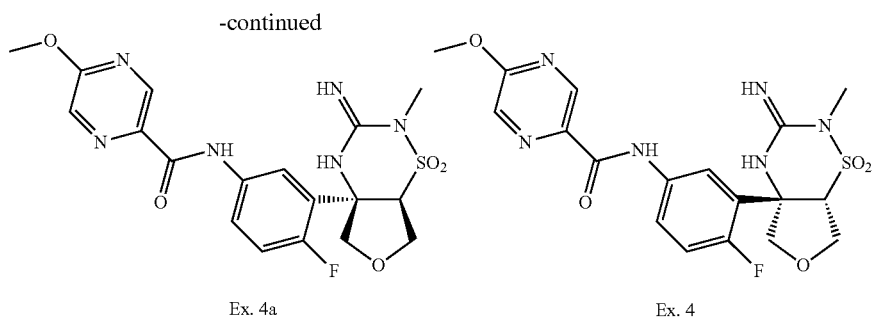

Ex. 4a          Ex. 4

Method A2, Step 1

To a solution of 2-(benzyloxy)acetic acid (3.23 g, 19.5 mmol) in DCM (60 mL) was added EDCI (6.1 g, 29.2 mmol), followed by N,O-dimethylhydroxylamine hydrochloride (2.8 g, 29.2 mmol) and pyridine (10 mL). The mixture was stirred at 25° C. for 16 h, washed with 0.1 M HCl and brine, dried over $Na_2SO_4$ and concentrated. The residue was purified by column chromatography (PE:EA=10:1) to afford compound A2-1 (3.6 g, 90%). $^1$H NMR (CDCl$_3$, 400 MHz): 7.25-7.40 (m, 5H), 4.67 (s, 2H), 4.28 (s, 2H), 3.62 (s, 3H), 3.19 (s, 3H).

Method A2, Step 2

To a suspension of magnesium (207 mg, 8.64 mmol) in THF (16 mL) was added one drop of 1,2-dibromoethane, followed by a solution of 1-bromo-2-fluorobenzene (756 mg, 4.32 mmol) in THF (8 mL) at 25° C. The mixture was stirred at 25° C. for 1 h and was then added to a solution of compound A2-1 (500 mg, 2.4 mmol) in THF (8 mL) at 0° C. The mixture was stirred at 0° C. for 1 h, quenched with saturated aq. $NH_4Cl$, and extracted with EtOAc. The combined extracts were washed with brine, dried over $Na_2SO_4$, concentrated and purified by column chromatography (PE:EA=30:1) to afford compound A2-2 (430 mg, 74%). $^1$H NMR (CDCl$_3$, 400 MHz): 7.93-7.97 (m, 1H), 7.50-7.55 (m, 1H), 7.23-7.40 (m, 6H), 7.08-7.13 (m, 1H), 4.70 (s, 2H), 4.69 (s, 2H).

Method A2, Step 3

A mixture of compound A2-2 (5.8 g, 23.8 mmol), (RS)-tert-butylsulfinamide (4.4 g, 35.7 mmol) and Ti(OEt)$_4$ (16.3 g, 71.4 mmol) in THF (60 mL) was stirred at 25° C. under $N_2$ for 16 h, diluted with ice-water, and then filtered. The filtrate was extracted with EtOAc. The combined extracts were washed with water and brine, dried over $Na_2SO_4$ and concentrated. The residue was purified by column chromatography to afford compound A2-3 (1.7 g, 21%). $^1$H NMR (CD$_3$OD, 400 MHz): 7.87-7.50 (m, 1H), 7.11-7.36 (m, 8H), 4.80 (s, 2H), 4.65 (s, 2H), 1.25 (s, 9H).

Method A2, Step 4

To a solution of N-(4-methoxybenzyl)-N-methylmethanesulfonamide Ao-1 (2.64 g, 11.5 mmol) in THF (30 mL) at −78° C. was added n-BuLi (4.6 mL, 11.5 mmol, 2.5 M in hexane). The mixture was stirred at −78° C. for 1 h and a solution of compound A2-3 (2 g, 5.8 mmol) in THF (10 mL) was added. The resulting mixture was stirred at −78° C. for 3 h, quenched with saturated aq. $NH_4Cl$ and extracted with EtOAc. The combined extracts were washed with brine, dried over $Na_2SO_4$, concentrated and purified by column chromatography (PE:EA=3:1) to afford compound A2-4 (580 mg, 45%). $^1$H NMR (CD$_3$OD, 400 MHz): 7.04-7.39 (m, 11H), 6.82-6.85 (m, 2H), 5.45-5.65 (m, 1H), 4.45-4.65 (m, 3H), 4.05-4.25 (m, 3H), 3.85-3.95 (m, 2H), 3.78 (s, 3H), 2.69 (s, 3H), 1.25 (s, 9H).

Method A2, Step 5

To a solution of compound A2-4 (800 mg, 1.4 mmol) in DCM (10 mL) was added HCl/dioxane (2 mL, 4M) at 0° C. and stirred 25° C. for 1 h. The reaction mixture was concentrated to afford compound A2-5 as HCl salt, which was used directly in next step without further purification.

Method A2, Step 6

To a solution of compound A2-5 (706 mg, 1.4 mmol) in TFA (6 mL) at 0° C. was added thioglycolic acid (1.3 g, 14 mmol). The reaction mixture was stirred 25° C. for 16 h, and concentrated. The residue was basified with aq. $NaHCO_3$ solution to pH 8, and then extracted with DCM. The combined extracts were washed with brine, dried over $Na_2SO_4$, concentrated and purified by column chromatography (PE:EA=2:1) to afford compound A2-6 (390 mg, 80%). $^1$H NMR (CD$_3$OD, 400 MHz): 7.59-7.63 (m, 1H), 7.19-7.37 (m, 7H), 7.03-7.08 (m, 1H), 4.47-4.54 (m, 2H), 3.80-3.84 (m, 2H), 3.68 (d, J=9.2 Hz, 1H), 3.56 (d, J=9.2 Hz, 1H), 2.52 (s, 3H).

Method A2, Step 7

A solution of compound A2-6 (390 mg, 1.1 mmol) and BrCN (460 mg, 5.2 mmol) in CH$_3$CN (8 mL) was stirred at 60° C. for 16 h. The reaction mixture was concentrated and purified by column chromatography (0-3% MeOH in CH$_2$Cl$_2$) to afford compound A2-7 (300 mg, 72%). $^1$H NMR (CD$_3$OD, 400 MHz): 7.42-7.51 (m, 2H), 7.18-7.36 (m, 7H), 4.54-4.64 (m, 2H), 4.52 (d, J=14.2 Hz, 1H), 4.32 (d, J=14.2 Hz, 1H), 4.03 (d, J=10.0 Hz, 1H), 3.95 (d, J=10.0 Hz, 1H), 2.52 (s, 3H).

Method A2, Step 8

A solution of compound A2-7 (365 mg, 0.97 mmol), Boc$_2$O (627 mg, 2.9 mmol), DIEA (374 mg, 2.9 mmol) and DMAP (50 mg, 0.3 mmol) in DCM (5 mL) was stirred at 30° C. for 16 h. The reaction mixture was concentrated and purified by column chromatography (PE:EA=10:1) to afford compound A2-8 (400 mg, 71%). $^1$H NMR (CDCl$_3$, 400 MHz): 7.59-7.64 (m, 1H), 7.26-7.32 (m, 6H), 7.06-7.13 (m, 1H), 7.00-7.04 (m, 1H), 4.60-4.63 (m, 1H), 4.52-4.55 (m, 1H), 4.12-4.16 (m, 1H), 3.89-3.93 (m, 2H), 3.77-3.80 (m, 1H), 3.11 (s, 3H), 1.49 (s, 18H).

Method A2, Step 9

To a solution of compound A2-8 (500 mg, 0.87 mmol) in THF (6 mL) at −78° C. was added n-BuLi (0.45 mL, 1.13 mmol, 2.5 M in hexane). The mixture was stirred at −78° C. for 1 h and chloro(methoxy)methane (91 g, 1.13 mmol) was added. The resulting mixture was stirred at −78° C. for 1 h, quenched with saturated aq. $NH_4Cl$, and extracted with EtOAc. The combined extracts were dried over $Na_2SO_4$, concentrated and purified by column chromatography (PE:EA=5:1) to afford compound A2-9 (300 mg, 56%). $^1$H NMR (CDCl$_3$, 400 MHz): 7.65-7.69 (m, 1H), 7.29-7.37 (m, 6H), 7.14-7.18 (m, 1H), 6.99-7.04 (m, 1H), 5.45 (s, 1H), 4.89-4.91 (m, 1H), 4.80-4.82 (m, 1H), 4.66-4.69 (m, 1H), 4.59-4.62 (m, 1H), 4.33-4.35 (m, 1H), 3.94-3.96 (m, 1H), 3.77 (s, 3H), 3.25 (s, 3H), 1.53 (s, 18H).

Method A2, Step 10

To a solution of compound A2-9 (300 mg, 0.483 mmol) in DCM (3 mL) at −78° C. was added BBr$_3$ (1.21 g, 4.83 mmol) dropwise. The mixture was stirred at −78° C. for 4 h and then allowed to warm to room temperature slowly overnight. The reaction mixture was diluted with MeOH and concentrated. The residue was dissolved in DCM (3 mL), and then Boc$_2$O (156 mg, 0.72 mmol) and DIEA (186 mg, 1.44 mmol) were added. The mixture was stirred at RT for 4 h, concentrated and purified by preparative TLC to afford compound A2-10 (80 mg, 42%). $^1$H NMR (CDCl$_3$, 400 MHz): 10.62 (s, 1H), 7.59-7.64 (m, 1H), 7.39-7.45 (m, 1H), 7.25-7.29 (m, 1H), 7.14-7.20 (m, 1H), 4.55-4.58 (m, 1H), 4.45-4.49 (m, 1H), 4.37-4.40 (m, 1H), 4.28-4.30 (m, 1H), 4.15-4.18 (m, 1H), 3.34 (s, 3H), 1.52 (s, 9H).

Method A2, Step 11

To a solution of compound A2-10 (1 g, 2.51 mmol) in conc. H$_2$SO$_4$ (7 mL) at −10° C. was slowly added a solution of fuming HNO$_3$ (1.58 g, 25.1 mmol) in conc. H$_2$SO$_4$ (3 mL). The mixture was stirred at −10° C. for 1 h, poured into ice water and quenched with NH$_4$OH. The mixture was extracted with DCM. The combined extracts were washed with brine, dried over Na$_2$SO$_4$ and concentrated. The residue was dissolved in DCM (5 mL), and then Boc$_2$O (813 mg, 3.77 mmol) and DIEA (971 mg, 7.53 mmol) were added. The mixture was stirred at 30° C. for 12 h, concentrated and purified by column chromatography (PE:EA=5:1) to afford compound A2-11 (600 mg, 54%). $^1$H NMR (CDCl$_3$, 400 MHz): 10.81 (s, 1H), 8.57-8.59 (m, 1H), 8.33-8.37 (m, 1H), 7.34-7.39 (m, 1H), 4.52-4.55 (m, 1H), 4.41-4.52 (m, 2H), 4.31-4.33 (m, 1H), 4.19-4.23 (m, 1H), 3.36 (s, 3H), 1.54 (s, 9H).

Method A2, Step 12

Compound A2-11 (600 mg) was separated by SFC column to afford two isomers compound A2-12 (250 mg) and compound A2-13 (250 mg). Instrument: Thar 80 Column: AD 250 mm×20 mm, 20 um; Mobile phase: A: Supercritical CO$_2$, B: MeOH (0.05% NH$_3$H$_2$O), A:B=65:35 at 80 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm Method A2, Step 13

A mixture of compound A2-12 (250 mg, 0.56 mmol), Pd/C (50 mg) and MeOH (10 mL) was stirred at 25° C. for 16 h under H$_2$ (25 psi), and filtered. The filtrate was concentrated to afford compound A2-14 (230 mg, 100%). Compound A2-15 was synthesized from A2-13 in a similar method as compound A2-14.

Method A2, Step 14

The mixture of compound A2-14 (130 mg, 0.32 mmol), 5-methoxypyrazine-2-carboxylic acid (73 mg, 0.47 mmol), HATU (358 mg, 0.94 mmol) and DIEA (162 mg, 1.26 mmol) in DMF (2 mL) was stirred at 25° C. for 3 h. The mixture was diluted with water and extracted with EtOAc. The combined extracts were washed with brine, dried over Na$_2$SO$_4$ and concentrated. The residue was dissolved in DCM (3 mL), and then TFA (1 mL) was added. The resulting mixture was stirred at 25° C. for 1 h, concentrated and purified by HPLC to afford Ex. 4a (54 mg). HPLC Instrument: LC 8A & Gilson 215 fraction collector; Column: Phenomenex Synergi max-RP 150×30 mm, 5 μm; Mobile phase A: purified water (0.075% TFA, VAT) Mobile phase B: acetonitrile Gradient: 15-45% B, 0-8 min. $^1$H NMR of Example 4a (CD$_3$OD, 400 MHz): 8.92 (s, 1H), 8.31 (s, 1H), 8.17-8.20 (m, 1H), 7.91-7.94 (m, 1H), 7.29-7.35 (m, 1H), 5.04-5.07 (m, 2H), 4.41-4.52 (m, 2H), 4.54-4.57 (m, 1H), 4.49-4.52 (m, 1H), 4.40-4.44 (m, 1H), 4.31-4.34 (m, 1H), 4.09 (s, 3H), 3.50 (s, 3H).

Method A3

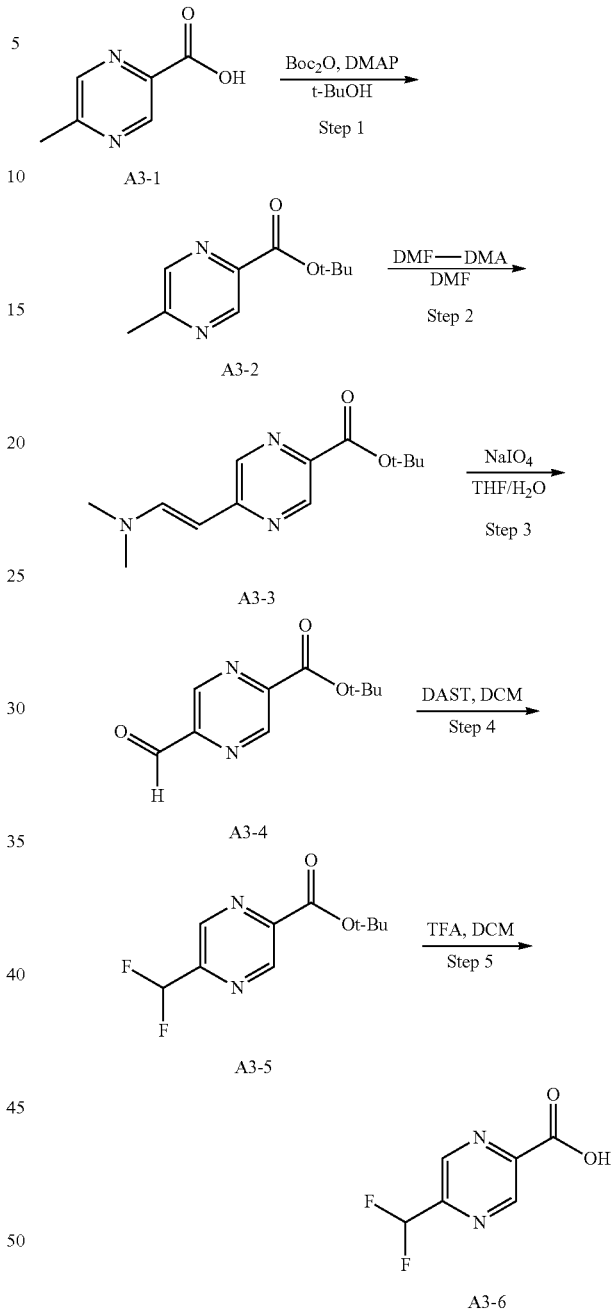

Step 1:

A solution of compound A3-1 (30 g, 216 mmol), Boc$_2$O (56.2 g, 260 mmol) and DMAP (7.9 g, 640 mmol) in t-BuOH (800 mL) was stirred at 60° C. for 18 h. The solution was concentrated and purified by column (PE:EA=3:1) to afford compound A3-2 (40 g, 95%). $^1$H NMR (400 MHz, CDCl$_3$): 9.05 (d, J=1.2 Hz, 1H), 8.52 (d, J=0.8 Hz, 1H), 2.60 (s, 3H), 1.60 (s, 9H).

Step 2:

A solution of compound A3-2 (40 g, 215 mmol) in DMF-DMA (750 mL) and DMF (750 mL) was stirred at 130° C. for 5 h. The solution was concentrated and purified by column (PE:EA=3:1) to afford compound A3-3 (25 g, 50%). $^1$H NMR (400 MHz, CDCl$_3$): 8.80 (d, J=1.2 Hz, 1H), 8.15 (d, J=1.2 Hz, 1H), 7.71 (d, J=12.8 Hz, 1H), 5.14 (d, J=12.8 Hz, 1H), 2.99 (s, 6H), 1.61 (s, 9H).

Step 3:

A solution of compound A3-3 (15 g, 60 mmol), NaIO$_4$ (38.5 g, 180 mmol) in THF (300 mL) and H$_2$O (300 mL) was stirred at RT for 4 h, and then the reaction was quenched with sat. aq. Na$_2$S$_2$O$_3$. The solution was extracted with EtOAc. The combined extracts were washed with brine, dried over Na$_2$SO$_4$, concentrated and purified by column (PE:EA=5:1) to afford compound A3-4 (10 g, 80%).

Step 4:

To a solution of compound A3-4 (2 g, 10 mmol) in THF (100 mL) at 0° C. under N$_2$ was added DAST (6.63 g, 30 mmol) dropwise. The solution was stirred at RT for 4 h, and then quenched with water, extracted with EtOAc. The combined extracts were washed with brine, dried over Na$_2$SO$_4$, concentrated and purified by column (PE:EA=5:1) to afford compound A3-5 (1.5 g, 68%). $^1$H NMR (400 MHz, CDCl$_3$): 9.20 (s, 1H), 8.97 (s, 1H), 6.71 (t, J=14.4 Hz, 1H), 1.61 (s, 9H).

Step 5:

To a solution of A3-5 (1.5 g, 6.5 mmol) in DCM (20 mL) at 0° C. was added TFA (2 mL) dropwise. The solution was stirred at RT for 4 h, and then concentrated to afford A3-6 (1 g, 88%). $^1$H NMR (400 MHz, MeOD): 9.30 (s, 1H), 8.98 (s, 1H), 6.92 (t, J=14.4 Hz, 1H).

Method A4

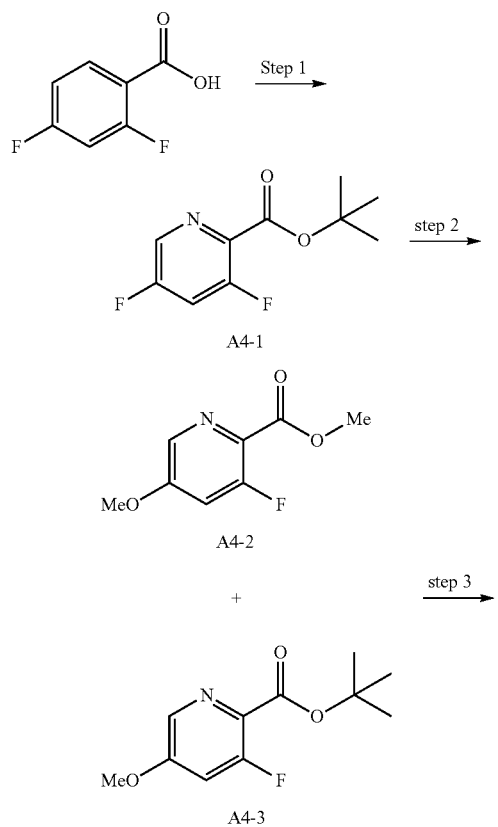

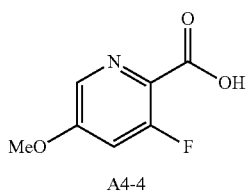

Step 1:

To 3,5-difluoropyridine-2-carboxylic acid (1.0 g, 6.3 mmol) in t-butanol (10 mL) and pyridine (3 mL) at 0° C. was added p-toluenesulfonyl chloride (2.8 g, 2.4 mmol). After 1 h, saturated NaHCO$_{3\ (aq)}$ was added and the mixture was stirred for 15 minutes. The mixture was then extracted with ether. The combined ether extracts were washed with water and brine, dried (MgSO$_4$), filtered, and concentrated in vacuo. The residue was purified by silica gel chromatography (0-10% EtOAc/hex) over 25 minutes to provide A4-1 (1.3 g, 96%).

Step 2:

To 4-1 (0.21 g, 1 mmol) was added NaOMe in MeOH (0.5 M, 3 mL, 1.5 mmol). The reaction was stirred at room temperature for 1.5 h. The reaction was acidified with saturated aq. citric acid to pH~4. The mixture was then concentrated in vacuo. The residue was taken up into EtOAc, washed with saturated aq. NaHCO$_3$, water, and brine. The organic layer was dried (MgSO$_4$), filtered, and concentrated in vacuo. The residue was taken up into 30% EtOAc/hex and the resultant solid was filtered off to provide A4-2 (25 mg, 14%). The filtrate was concentrated in vacuo and the residue was purified by silica gel chromatography (0-40% EtOAc/hex) over 30 minutes to provide A4-2 (43 mg, 23%) and A4-3 (53 mg, 23%).

Step 3:

To A4-2 (0.059 g, 0.32 mmol) in THF was added 2N LiOH (0.5 mL, 1 mmol). The reaction was stirred at room temperature for 30 minutes. The reaction was adjusted to pH~5 with saturated citric acid$_{(aq)}$. Brine was added and the mixture was extracted with EtOAc. The combined organic layers were washed with brine, dried (MgSO$_4$), filtered, and concentrated in vacuo to provide A4-4 (0.031 g, 57%).

Method B

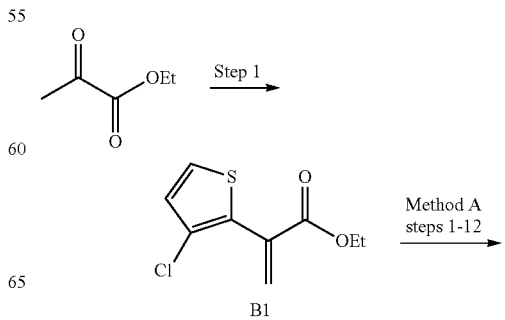

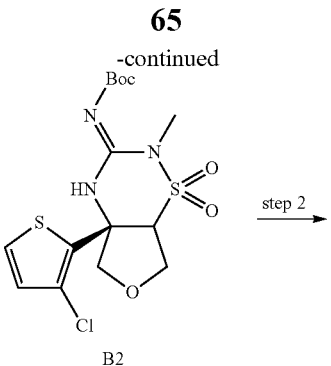

B2

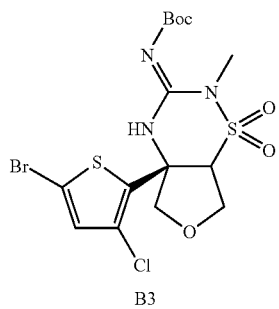

B3

Method B, Step 1:

A literature procedure is adapted (*Chem. Eur. J.*, 2010, 16, 12801). To a flask containing ethyl pyruvate in dioxane is added p-toluenesulfonylhydrazide. The reaction is heated to 70° C. and stirred for 2 hours. The reaction is cooled to room temperature and Xphos and tris(dibenzylideneacetone)dipalladium and lithium t-butoxide is added followed by 2-bromo-3-chlorothiophene. Nitrogen is bubbled through the reaction for 5 minutes after which time the reaction is heated to 110° C. After starting material is determined to be consumed by TLC, the mixture is allowed to cool to room temperature. DCM is added and the mixture is passed through a plug of Celite. The filtrate is washed with water and brine, dried ($MgSO_4$), filtered, and concentrated in vacuo to provide a residue that is purified by silica gel chromatography to yield B1.

B1 is converted to B2 using steps 1-12 described in Method A.

Method B, Step 2:

To B2 in DMF is added NBS. The reaction is stirred at 55° C. for 5 h or until TLC indicates the disappearance of starting material. The reaction is cooled to room temperature and water is added. The mixture is extracted with ethyl acetate. The combined organic layers are washed with water and brine, dried ($MgSO_4$), filtered, and concentrated in vacuo. The residue is purified by silica gel chromatography to provide B3.

Method C

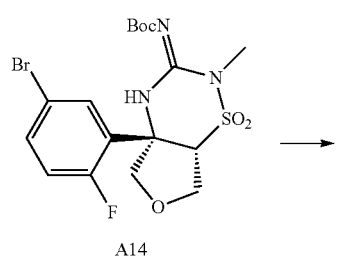

A14

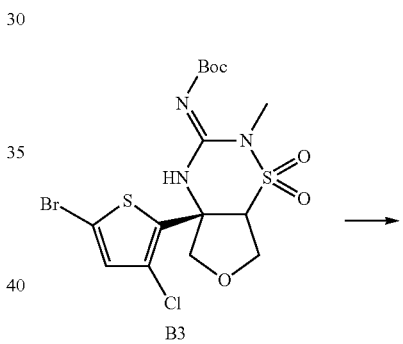

A2-15

Method C, Step1:

To A14 in toluene in a reaction tube is added diphenyl imine, di-t-butylphosphinobiphenyl, $Pd_2(dba)_3$, and sodium tert-butoxide. The reaction vessel is sealed and heated to 65° C. until monitoring indicates that starting material is consumed. The reaction is cooled to room temperature and ethyl acetate is added. The mixture is filtered through a pad of Celite. The filtrate is concentrated in vacuo.

The residue is taken up into methanol and sodium acetate is added followed by hydroxylamine hydrochloride. The mixture is stirred at room temperature for 12 h. The reaction is then concentrated in vacuo. The residue is taken up into ethyl acetate and washed with saturated sodium bicarbonate, water, and brine. The organic layer is dried ($MgSO_4$), filtered, and concentrated in vacuo. The residue is purified by silica gel chromatography to provide A2-15.

Method D

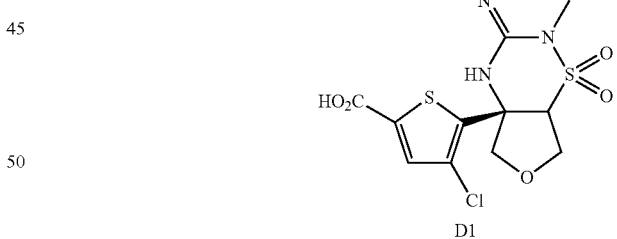

B3        D1

Method D, Step 1:

To B3 in THF at 0° C. is added methyl magnesium bromide. The reaction is stirred at 0° C. for 30 minutes and then cooled to −78° C. A hexane solution of n-butyllithium is added over 10 minutes and the reaction is stirred for an additional hour at −78° C. $CO_2$ gas is then bubbled through the reaction for 5 minutes at which time the cold bath is removed. After the mixture warms to room temperature, 1N HCl and ethyl acetate are added. The mixture is extracted with ethyl acetate. The combined organic layers are washed with water and brine, dried ($MgSO_4$), filtered, and concentrated in vacuo. The residue is purified by silica gel chromatography to provide D1.

Method E

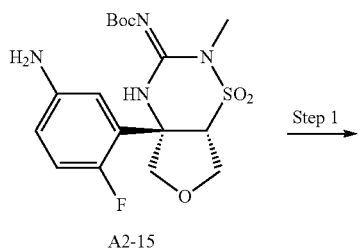

A2-15

Step 1 →

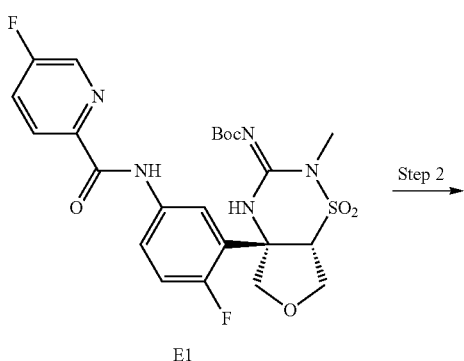

E1

Step 2 →

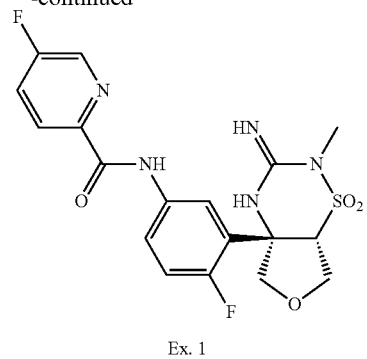

Ex. 1

Method E, Step 1:

To A2-15 in THF at 0° C. is added 5-fluoropyridine-2-carboxylic acid, diisopropylethylamine, and T3P (50% wt/wt in EtOAc). The cold bath is removed and the reaction is stirred at room temperature until starting material is consumed as determined by TLC. Water is added and the mixture is stirred for 10 minutes at room temperature. The mixture is then extracted with ethyl acetate. The combined organic layers are washed with water and brine, dried (MgSO$_4$), filtered, and concentrated in vacuo. The residue is purified by silica gel chromatography to provide E1.

Method E, Step 2:

To E1 prepared in Step 1 in DCM is added TFA. The reaction is stirred at room temperature until starting material is consumed as determined by LCMS or TLC. The reaction is then concentrated in vacuo. DCM is added and the mixture is washed with saturated NaHCO$_3$, water, and brine. The organic layer is dried (MgSO$_4$), filtered, and concentrated in vacuo to provide Ex. 1.

Using the procedures described in step 1 and step 2 of Method E, A2-15 is coupled with the carboxylic acids to provide the examples shown in Table 1. Alternatively, examples in Table 1 with the exception of Example 2 were prepared using the procedures described in Method A2. Example 2 can be prepared according to Method A2 as well.

TABLE 1

| Carboxylic Acid | Ex. No. | Example | BACE1 Ki (nM) | BACE2 Ki (nM) | Exact Mass [M + H]$^+$ | t$_r$ (min) | LCMS Cond. |
|---|---|---|---|---|---|---|---|
| (5-fluoropyridine-2-carboxylic acid) | 1 | (Ex. 1 structure) | 13 | 1.9 | Calc'd 438.1 Found 438.1 | 2.26 | A2 |
| (4-fluoropyridine-2-carboxylic acid) | 1a | (Ex. 1a structure) | 3529 | 491 | Calc'd 438.1 Found 438.1 | 2.27 | A2 |

TABLE 1-continued

| Carboxylic Acid | Ex. No. | Example | BACE1 Ki (nM) | BACE2 Ki (nM) | Exact Mass [M + H]+ | t_r (min) | LCMS Cond. |
|---|---|---|---|---|---|---|---|
| 3,5-difluoropyridine-2-carboxylic acid | 2 | (structure) | | | | | |
| 5-methoxypyridine-2-carboxylic acid | 3 | (structure) | 18.18 | 8.20 | Calc'd 450.1 Found 450.1 | 2.30 | A2 |
| 5-methoxypyridine-2-carboxylic acid | 3a | (structure) | 871.5 | 475.7 | Calc'd 450.1, Found 450.1 | 2.31 | A2 |
| 5-methoxypyrazine-2-carboxylic acid | 4 | (structure) | 54.12 | 48.4 | Calc'd 451.1, Found 451.1 | 2.26 | A2 |
| 5-methoxypyrazine-2-carboxylic acid | 4a | (structure) | 1326 | 1509 | Calc'd 451.1, Found 451.1 | 2.26 | A2 |
| 5-chloropyridine-2-carboxylic acid | 5 | (structure) | 5.07 | 1.3 | Calc'd 454.1, Found 454.1 | 3.48 | A1 |

TABLE 1-continued

| Carboxylic Acid | Ex. No. | Example | BACE1 Ki (nM) | BACE2 Ki (nM) | Exact Mass [M + H]+ | t$_r$ (min) | LCMS Cond. |
|---|---|---|---|---|---|---|---|
| 5-chloropyridine-2-carboxylic acid | 5a | | 197 | 55.2 | Calc'd 454.1, Found 454.1 | 3.49 | A1 |
| 5-(trifluoromethyl)pyridine-2-carboxylic acid | 6 | | 9.79 | 19.5 | Calc'd 488.1, Found 488.1 | 3.55 | A1 |
| 5-(trifluoromethyl)pyridine-2-carboxylic acid | 6a | | 354 | 472.8 | Calc'd 488.1, Found 488.1 | 3.55 | A1 |
| 5-(difluoromethyl)pyrazine-2-carboxylic acid A3-6 | 6b | | 27.2 | 17.4 | Calc'd 471.1, Found 471.1 | 2.26 | A2 |
| 5-(difluoromethyl)pyrazine-2-carboxylic acid A3-6 | 6c | | 999 | 857.5 | Calc'd 471.1, Found 471.1 | 2.27 | A2 |

TABLE 1-continued
| Carboxylic Acid | Ex. No. | Example | BACE1 Ki (nM) | BACE2 Ki (nM) | Exact Mass [M + H]+ | t_r (min) | LCMS Cond. |
|---|---|---|---|---|---|---|---|
| 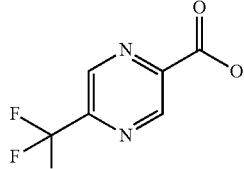 | 6d | 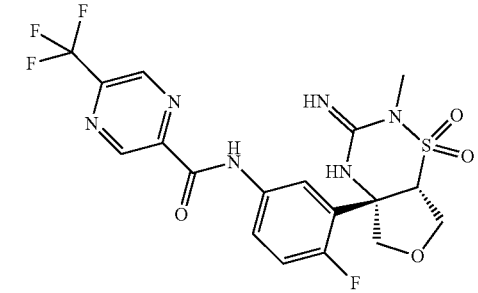 [SMILES: CN1C(=N)N[C@@]2(c3cc(NC(=O)c4cnc(C(F)(F)F)cn4)ccc3F)COC[C@H]2S1(=O)=O] | 28.4 | 55.0 | Calc'd 489.1, Found 489.1 | 2.38 | A2 |
| 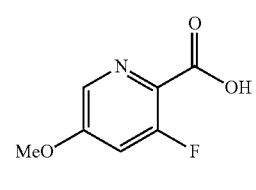 [SMILES: COc1cnc(C(=O)O)c(F)c1] A4-4 | 6e | 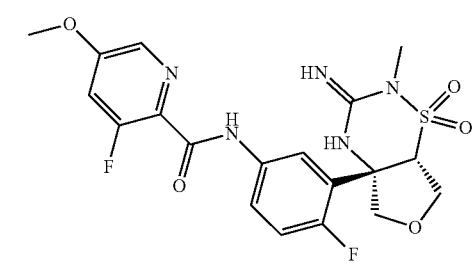 [SMILES: COc1cnc(C(=O)Nc2ccc(F)c([C@]34COC[C@H]3S(=O)(=O)N(C)C(=N)N4)c2)c(F)c1] | 15.8 | 6.9 | Calc'd 468.1, Found 468.2 | 2.26 | A2 |
Method E2
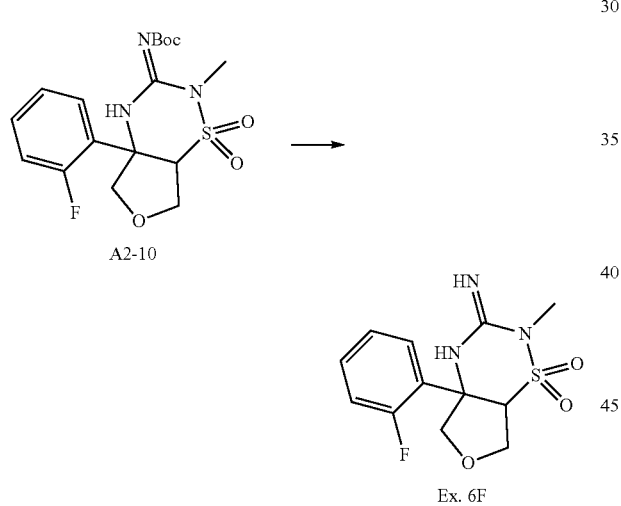
A2-10 was treated to conditions described in Method E, step 2 to provide Ex. 6F.
TABLE 1A
| Ex. # | Structure | BACE1 Ki (nM) | BACE-2 Ki (nM) | Exact Mass [M + H]+ | t_r (min) | LCMS conditions |
|---|---|---|---|---|---|---|
| 6f | 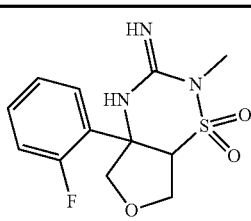 | 7846 | 4204 | Calc'd 300.1, Found 300.1 | 2.03 | A2 |

Method E3
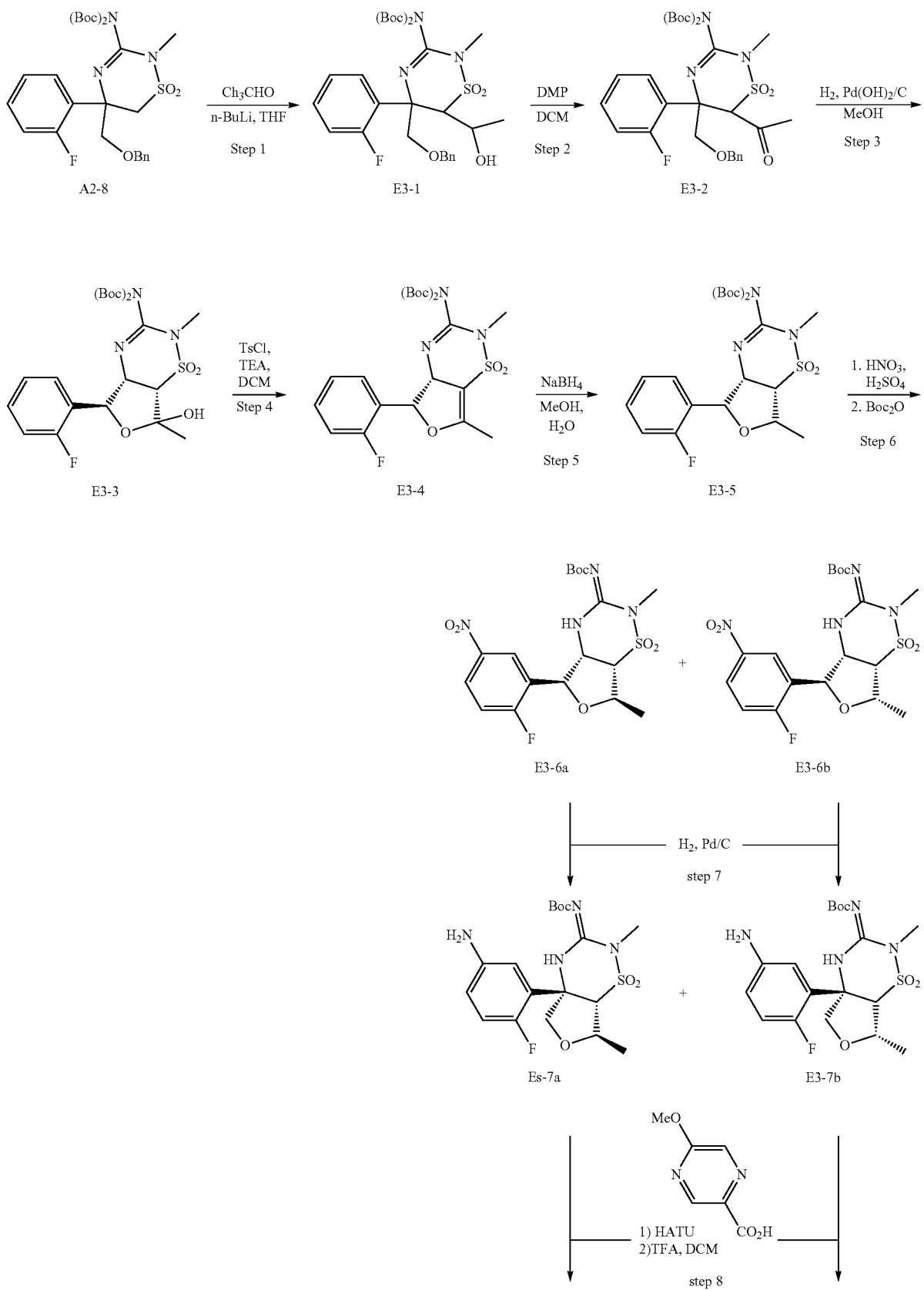

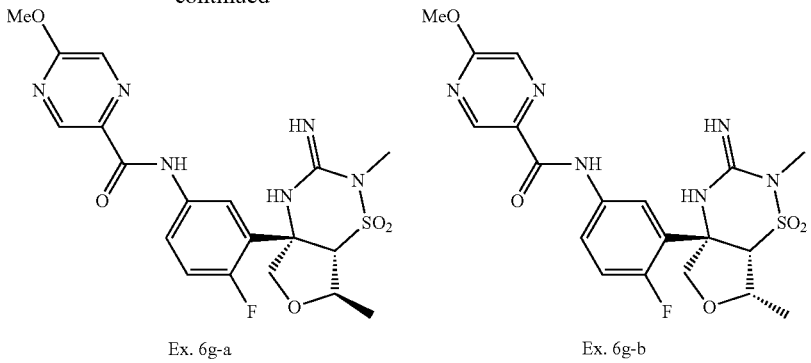

Ex. 6g-a             Ex. 6g-b

Step 1:

To a solution of compound A2-8 (577 mg, 1 mmol) in THF (5 mL) at −78° C. was added n-BuLi (0.6 mL, 1.5 mmol, 2.5M in hexane). The mixture was stirred at −78° C. for 1 h and then acetaldehyde (66 mg, 1.5 mmol) was added. After 1 h at −78° C., the mixture was quenched with sat. aq. NH$_4$Cl, and extracted with EtOAc. The combined extracts were washed with brine, dried (Na$_2$SO$_4$), concentrated, and purified by silica gel chromatography (PE:EA=5:1) to afford a 3:1 mixture of compounds E3-1 and A2-8 (600 mg total mass).

Step 2:

To a solution of the mixture in step 1 (900 mg) in DCM (15 mL) was added DMP (900 mg, 2.59 mmol) at 0° C. The mixture was stirred at RT for 1 h, quenched with NaHCO$_3$ solution (15 mL) and Na$_2$S$_2$O$_3$ solution (15 mL) at 0° C. The resulting mixture was stirred at RT for 0.5 h, extracted with DCM. The DCM layers were washed with brine, dried over Na$_2$SO$_4$, concentrated and purified by silica gel chromatography (PE:EA=20:1) to afford compound E3-2 (600 mg). $^1$H NMR (400 MHz, CDCl$_3$): 7.59~7.64 (m, 1H), 7.18~7.37 (m, 5H), 7.07~7.10 (m, 2H), 6.97~7.00 (m, 1H), 5.19 (s, 2H), 4.49~4.55 (m, 1H), 4.36~4.43 (m, 1H), 3.96~3.98 (m, 1H), 3.27 (s, 3H), 2.39 (s, 3H), 1.53 (s, 18H).

Step 3:

To a solution of compound E3-2 (500 mg, 0.96 mmol) in MeOH (10 mL) was added Pd(OH)$_2$/C (100 mg, 10%) and stirred under H$_2$ (25 psi) at 40° C. for 16 h. The mixture was filtered. The filtrate was concentrated to afford compound E3-3 (300 mg, 73%). $^1$H NMR (400 MHz, CDCl$_3$): 7.27~7.32 (m, 2H), 7.05~7.15 (m, 2H), 5.09 (dd, $J_1$=2.0 Hz, $J_2$=10.8 Hz, 1H), 4.92 (dd, $J_1$=2.0 Hz, $J_2$=10.8 Hz, 1H), 2.87~2.91 (m, 1H), 2.28 (s, 3H), 2.22 (s, 3H), 1.46 (s, 18H).

Step 4:

A mixture of compound E3-3 (200 mg, 0.39 mmol), TsCl (110 mg, 0.58 mmol), TEA (195 mg, 1.93 mmol) in DCM (4 mL) was stirred at 40° C. for two days, and quenched with water, extracted with DCM. The DCM layers were washed with brine, dried over Na$_2$SO$_4$ and concentrated. The residue was purified by silica gel chromatography (PE:EA=10:1) to afford compound E3-4 (60 mg, 30%). $^1$H NMR (400 MHz, CDCl$_3$): 7.57~7.61 (m, 2H), 7.28~7.33 (m, 2H), 7.05~7.11 (m, 2H), 4.90 (dd, $J_1$=2.0 Hz, $J_2$=10.0 Hz, 1H), 4.76 (dd, $J_1$=2.0 Hz, $J_2$=10.0 Hz, 1H), 3.09 (s, 3H), 2.29 (s, 3H), 1.49 (s, 18H).

Step 5:

To a solution of compound E3-4 (50 mg, 0.1 mmol) in MeOH (1 mL) and H$_2$O (1 mL) was added NaBH$_4$ (38 mg, 1 mmol) at 0° C. The mixture was stirred at RT for 4 h, and quenched by water and extracted with DCM. The DCM layers were dried over Na$_2$SO$_4$ and concentrated to afford compound E3-5 (50 mg), which was used in next step directly.

Step 6:

To a solution of compound E3-5 (100 mg, 0.195 mmol) in conc. H$_2$SO$_4$ (2 mL) was added a solution of fuming HNO$_3$ (123 mg, 1.95 mmol) in conc. H$_2$SO$_4$ (1 mL) at −10° C. The mixture was stirred at −10° C. for 1 h and poured onto ice water and basified with NH$_4$OH to pH 9. The solution was extracted with DCM. The DCM layers were washed with brine, dried over Na$_2$SO$_4$ and concentrated. The residue was dissolved in DCM (3 mL), and then Boc$_2$O (63 mg, 0.293 mmol) and DIEA (101 mg, 0.784 mmol) were added. The mixture was stirred at RT for 12 h, concentrated and purified by prep-TLC to afford compound E3-6a (30 mg) and compound E3-6b (30 mg). $^1$H NMR (400 MHz, CD$_3$OD) for E3-6a: 8.51~8.54 (m, 1H), 8.32~8.37 (m, 1H), 7.46~7.51 (m, 1H), 4.60 (d, J=9.6 Hz, 2H), 4.15~4.17 (m, 2H), 3.29 (s, 3H), 1.50 (s, 9H), 1.43~1.44 (m, 3H). $^1$H NMR (400 MHz, CD$_3$OD) for compound E3-6b: 8.47~8.49 (m, 1H), 8.34~8.40 (m, 1H), 7.46~7.51 (m, 1H), 4.40~4.47 (m, 2H), 4.10~4.17 (m, 2H), 3.28 (s, 3H), 1.49 (s, 9H), 1.58 (d, J=6.4 Hz, 3H).

Step 7:

To a solution of compound E3-6a (130 mg, 0.28 mmol) in MeOH (10 mL) was added Pd/C (50 mg, 10%) and stirred under H$_2$ balloon at 25° C. overnight. The mixture was filtered. The filtrate was concentrated to afford compound E3-7a (100 mg, 83%). Compound E3-7b was synthesized in a similar manner to compound E3-7a.

Step 8:

Using the procedure described in Method A2, step 14, E3-7a and E3-7b are converted to Ex. 6g-a and Ex. 6g-b.

Using the carboxylic acids in Table 1B and either E3-7a or E3-7b as appropriate, the following Examples can be prepared using the procedure described in Method A2, step 14.

TABLE 1B

| Carboxylic Acid | Ex. Number | Example |
|---|---|---|
| 5-methoxypyrazine-2-carboxylic acid | 6g-a | |
| 5-methoxypyrazine-2-carboxylic acid | 6g-b | |
| 5-fluoropyridine-2-carboxylic acid | 6h-a | |
| 5-fluoropyridine-2-carboxylic acid | 6h-b | |

TABLE 1B-continued
| Carboxylic Acid | Ex. Number | Example |
|---|---|---|
| 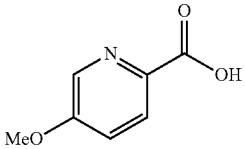 | 6i-a | 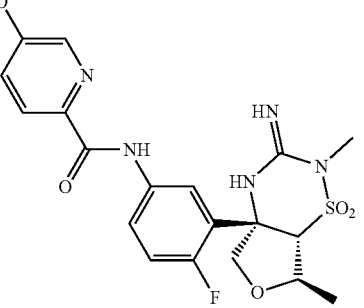 |
| 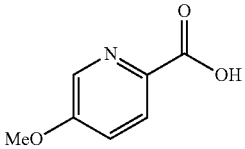 [SMILES: COc1ccc(C(=O)O)nc1] | 6i-b | 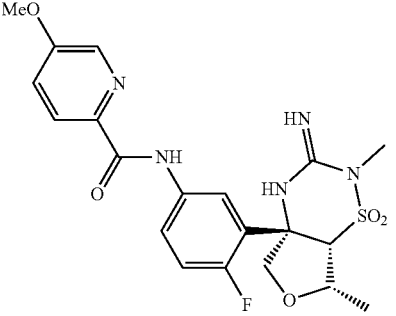 [SMILES: COc1ccc(C(=O)Nc2ccc(F)c([C@]34CO[C@@H](C)[C@H]3S(=O)(=O)N(C)C(=N)N4)c2)nc1] |
| 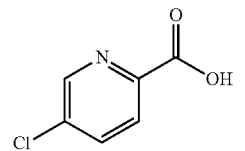 | 6j-a | 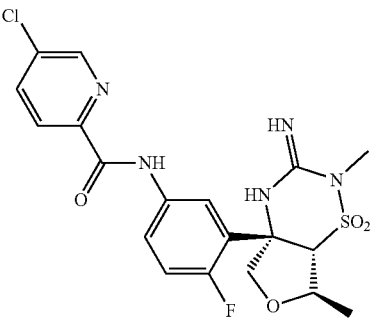 [SMILES: C[C@H]1OC[C@]2(c3cc(NC(=O)c4ccc(Cl)cn4)ccc3F)NC(=N)N(C)S(=O)(=O)[C@H]12] |
| 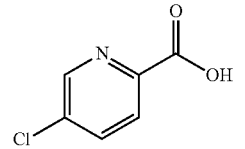 | 6j-b | 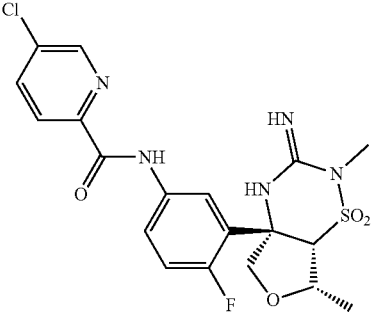 [SMILES: C[C@@H]1OC[C@]2(c3cc(NC(=O)c4ccc(Cl)cn4)ccc3F)NC(=N)N(C)S(=O)(=O)[C@H]12] |

TABLE 1B-continued

| Carboxylic Acid | Ex. Number | Example |
| --- | --- | --- |
| 5-(trifluoromethyl)pyridine-2-carboxylic acid | 6k-a | |
| 5-(trifluoromethyl)pyridine-2-carboxylic acid | 6k-b | |
| 5-(difluoromethyl)pyrazine-2-carboxylic acid (A3-6) | 6l-a | |
| 5-(difluoromethyl)pyrazine-2-carboxylic acid (A3-6) | 6l-b | |

TABLE 1B-continued
| Carboxylic Acid | Ex. Number | Example |
|---|---|---|
| 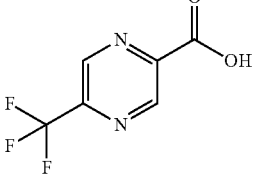 | 6m-a | 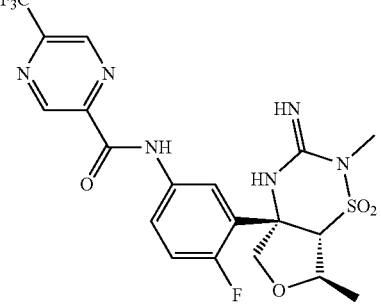 |
| 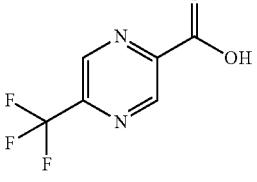 | 6m-b | 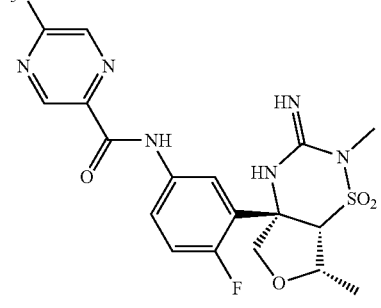 |
| 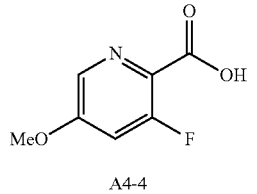<br>A4-4 | 6n-a | 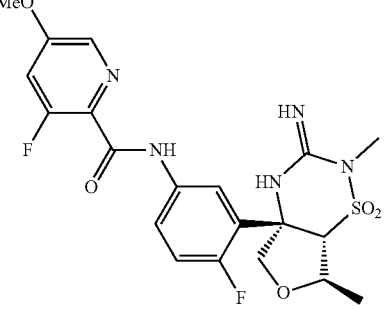 |
| 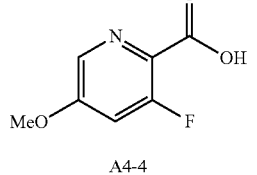<br>A4-4 | 6n-b | 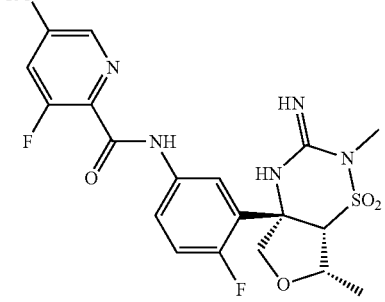 |

Method E4
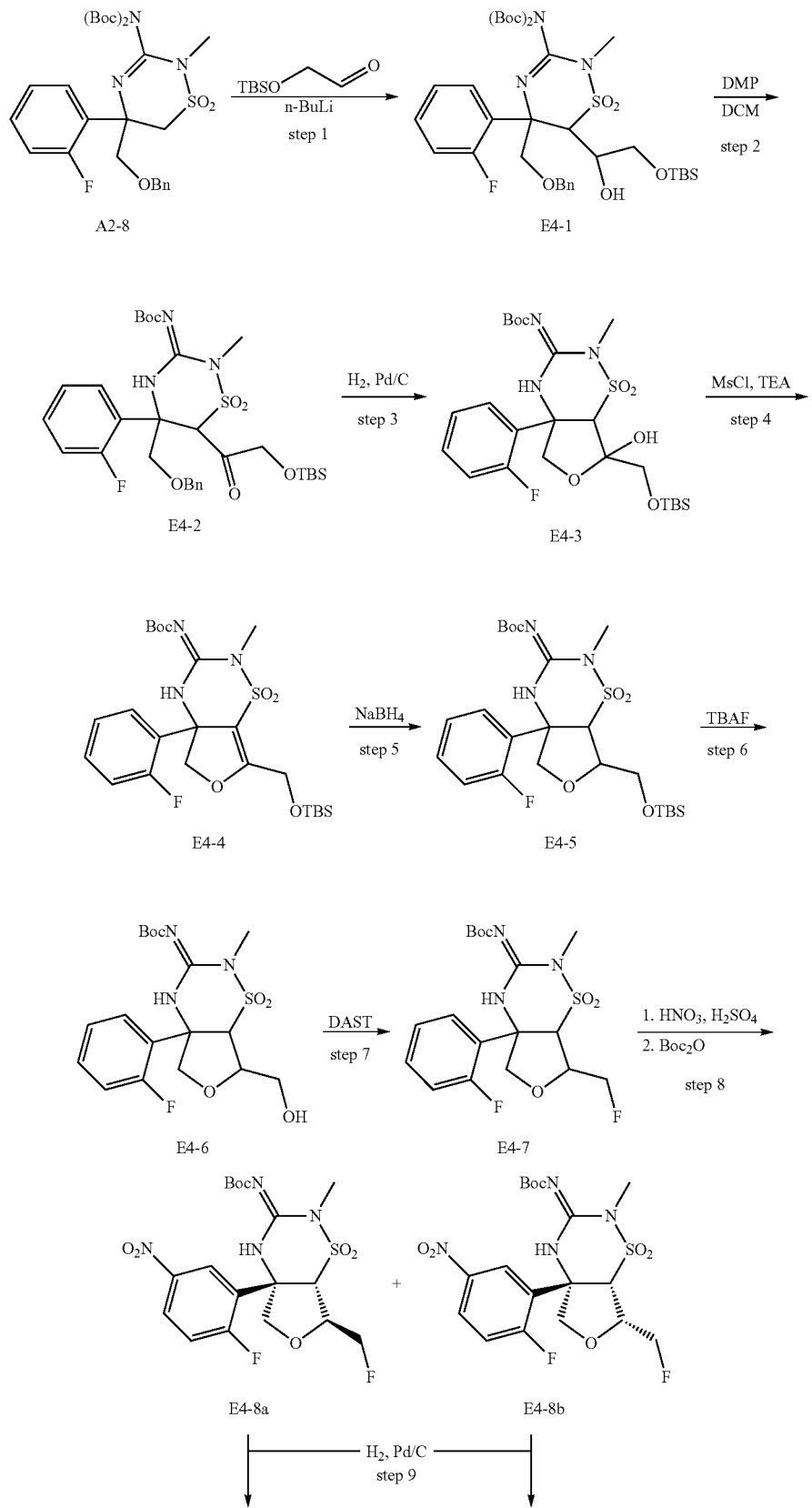

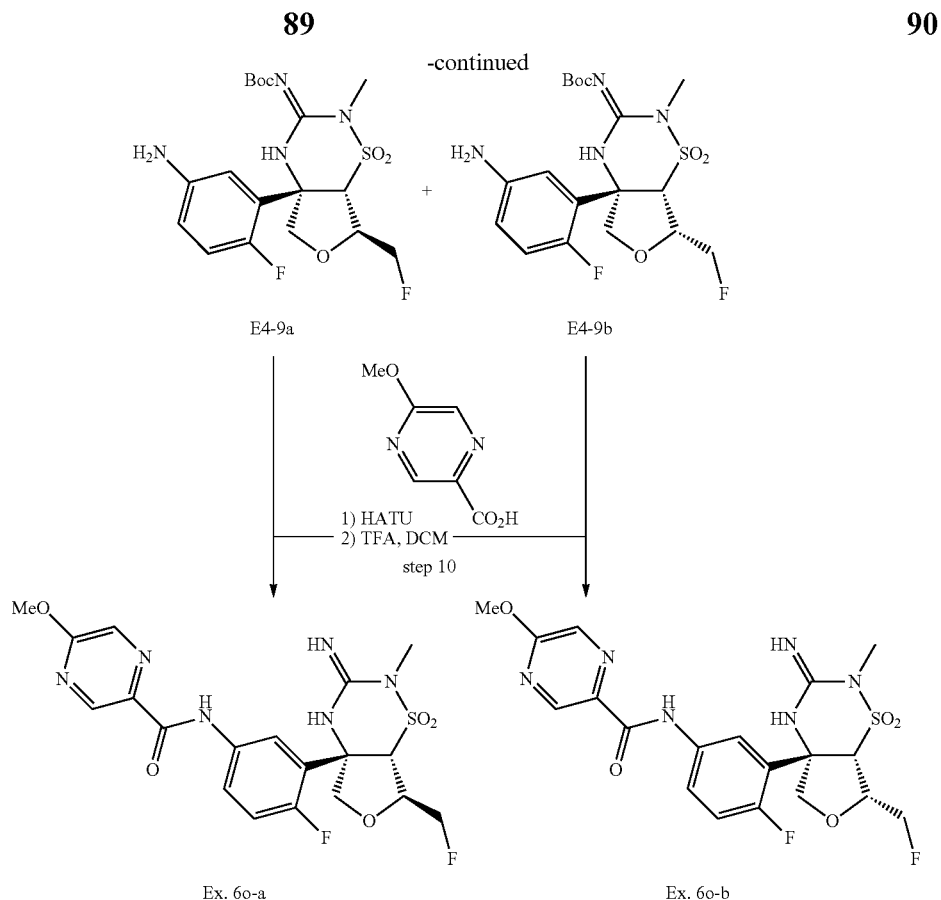

Step 1:
To a stirred solution of compound A2-8 (2.8 g, 4.8 mmol) in 20 mL of THF at −78° C. was added n-butyllithium (2.9 mL, 7.2 mmol, 2.5 M in hexane). After stirring for 30 min, 2-((tert-butyldimethylsilyl)oxy)acetaldehyde (1.3 g, 7.2 mmol) was added dropwise. The solution was stirred at −78° C. for additional 3 h, and quenched with 10 mL of water and extracted with EtOAc. The combined extracts were dried over $Na_2SO_4$, filtered, concentrated and purified by silica gel chromatography (PE:EA=10:1) to afford compound E4-1 (2 g).

Step 2
To a solution of compound E4-1 (2 g) in 20 mL of DCM under $N_2$ was added Dess-Martin periodinane (1.2 g, 2.7 mmol) at 0° C. The mixture was stirred at RT overnight, quenched with aq. $NaHCO_3$ solution (15 mL) and aq. $Na_2S_2O_3$ solution (15 mL) at 0° C. The resulting mixture was stirred at RT for 0.5 h and extracted with DCM. The DCM layers were washed with brine, dried over $Na_2SO_4$, concentrated and purified by silica gel chromatography (PE:EA=20:1) to afford compound E4-2 (300 mg).

Step 3
To a solution of compound E4-2 in MeOH is added Pd$(OH)_2$/C and the reaction is stirred under $H_2$ (25 psi) at 40° C. for 16 h. The mixture is filtered. The filtrate is concentrated to afford compound E4-3.

Step 4
A mixture of compound E4-3, methanesulfonyl chloride, and TEA in DCM is stirred at 40° C. for two days, quenched with water, and extracted with DCM. The DCM layers are washed with brine, dried over $Na_2SO_4$, and concentrated. The residue is purified by silica gel chromatography to afford compound E4-4.

Step 5
To a solution of compound E4-4 in MeOH and $H_2O$ (1:1) is added $NaBH_4$ at 0° C. The mixture is stirred at RT for 4 h, quenched with water, and extracted with DCM. The DCM layers are dried over $Na_2SO_4$, and concentrated to afford compound E4-5, which is used in next step directly without further purification.

Step 6
To a solution of E4-5 in THF at room temperature is added a THF solution of TBAF. The reaction is stirred at room temperature until TLC determines that starting material has been consumed. The reaction is poured into water and the mixture is extracted with EtOAc. The combined organic layers are washed with water and brine, dried ($MgSO_4$), filtered, and concentrated in vacuo. The residue is purified by silica gel chromatography to provide E4-6.

Step 7
To a solution of E4-6 in THF at room temperature is added DAST. The reaction is stirred until starting material is consumed as determined by TLC. The reaction is poured into water, and the mixture is extracted with EtOAc. The combined organic layers are washed with water and brine, dried ($MgSO_4$), filtered, and concentrated in vacuo. The residue is purified by silica gel chromatography to provide E4-7.

Step 8
To a solution of compound E4-7 in conc. $H_2SO_4$ is added a solution of fuming $HNO_3$ in conc. $H_2SO_4$ at −10° C. The mixture is stirred at −10° C. for 1 h and poured onto ice water, and basified with $NH_4OH$ to pH 9. The solution is extracted with DCM. The DCM layers are washed with brine, dried over $Na_2SO_4$, and concentrated in vacuo. The residue is dissolved in DCM, and then $Boc_2O$ and DIEA are added. The mixture is stirred at RT for 12 h, concentrated and purified by silica gel chromatography to afford compound E4-8a and compound E4-8b.

Step 9

To a solution of compound E4-8a in MeOH is added Pd/C and stirred under H₂ balloon at 25° C. overnight. The mixture is filtered. The filtrate is concentrated to afford compound E4-9a. Compound E4-9b is synthesized from E4-8b in a method similar to compound E4-9a.

Step 10

Using the procedure described in Method A2, step 14, E4-9a and E4-9b are converted to Ex. 6o-a and Ex. 6o-b.

Using the carboxylic acids in Table 1C and either E4-9a or E4-9b as appropriate, the examples in Table 1C can be prepared using the procedure described in Method A2, step 14.

TABLE 1C

| Carboxylic Acid | Ex. Number | Example |
|---|---|---|
| 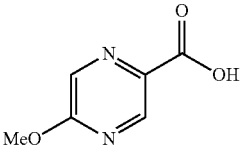 | 6o-a | 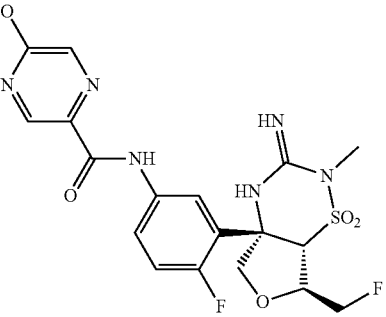 |
| 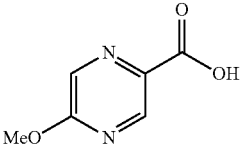 | 6o-b | 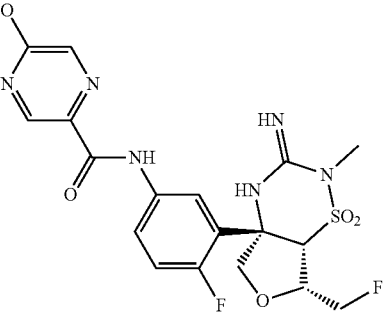 |
| 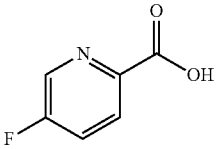 | 6p-a | 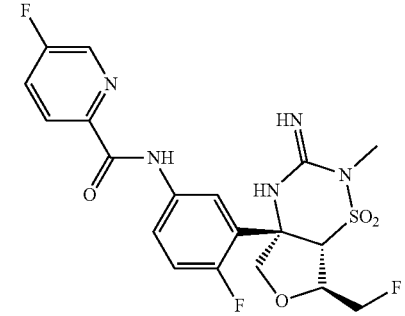 [SMILES: CN1C(=N)N[C@@]2(c3cc(NC(=O)c4ccc(F)cn4)ccc3F)CO[C@H](CF)[C@H]2S1(=O)=O] |
| 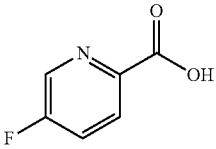 | 6p-b | 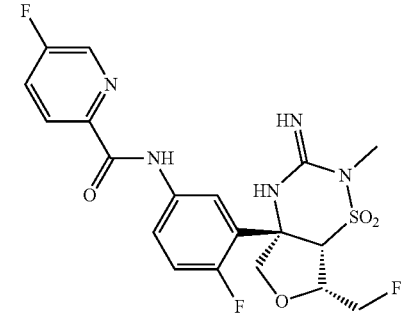 [SMILES: CN1C(=N)N[C@@]2(c3cc(NC(=O)c4ccc(F)cn4)ccc3F)CO[C@@H](CF)[C@H]2S1(=O)=O] |

TABLE 1C-continued

| Carboxylic Acid | Ex. Number | Example |
|---|---|---|
| 5-methoxypyridine-2-carboxylic acid (MeO at 5-position) | 6q-a | structure |
| 5-methoxypyridine-2-carboxylic acid | 6q-b | structure |
| 5-chloropyridine-2-carboxylic acid | 6r-a | structure |
| 5-chloropyridine-2-carboxylic acid | 6r-b | structure |

TABLE 1C-continued
| Carboxylic Acid | Ex. Number | Example |
|---|---|---|
| 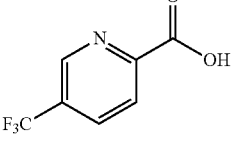 | 6s-a | 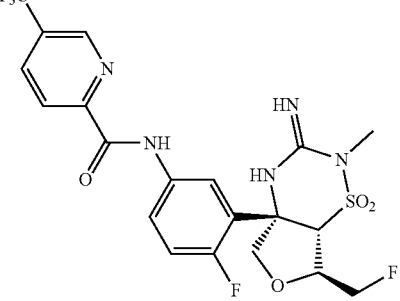 |
| 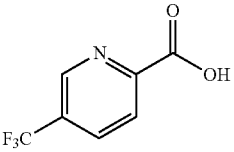 [SMILES: O=C(O)c1ccc(C(F)(F)F)cn1] | 6s-b | 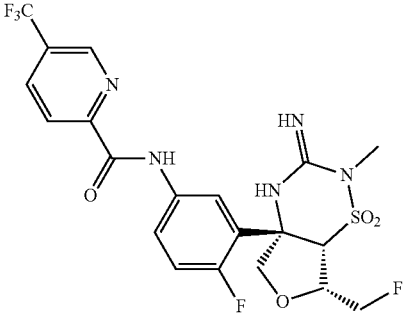 |
| 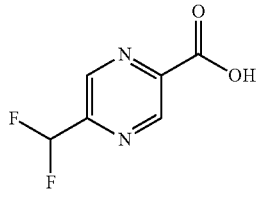<br>A3-6 | 6t-a | 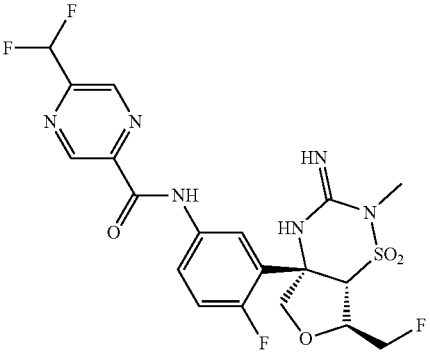 [SMILES: CN1C(=N)N[C@@]2(c3cc(NC(=O)c4cnc(C(F)F)cn4)ccc3F)CO[C@H](CF)[C@H]2S1(=O)=O] |
| 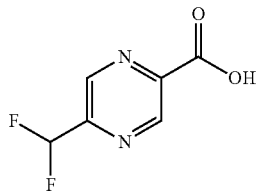 [SMILES: O=C(O)c1cnc(C(F)F)cn1]<br>A3-6 | 6t-b | 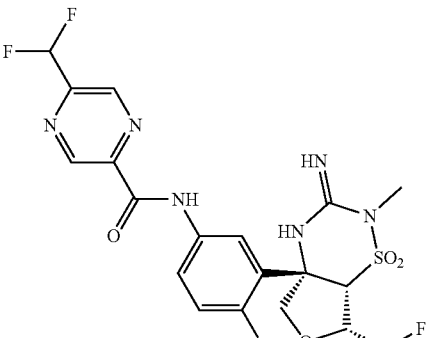 |

TABLE 1C-continued
| Carboxylic Acid | Ex. Number | Example |
|---|---|---|
| 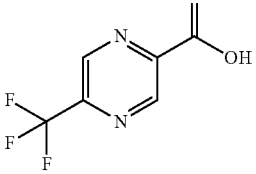 | 6u-a | 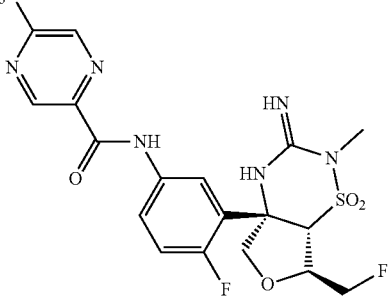 |
| 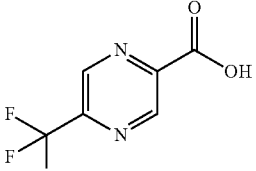 | 6u-b | 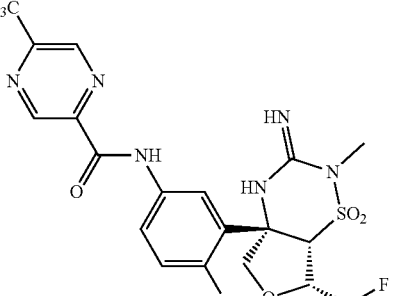 |
| 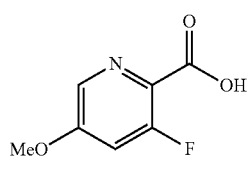<br>A4-4 | 6v-a | 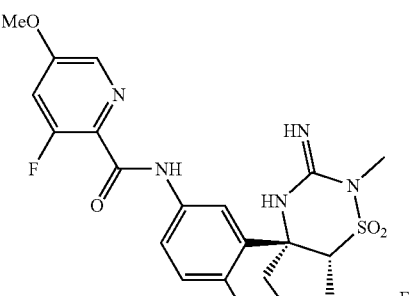 |
| 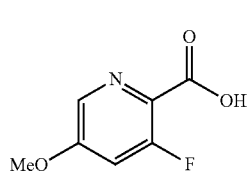<br>A4-4 | 6v-b | 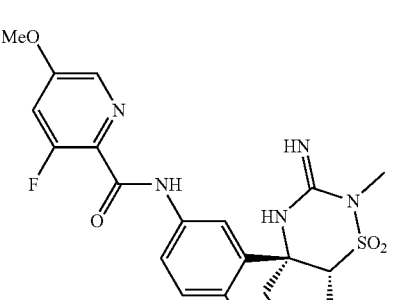 |

Method F

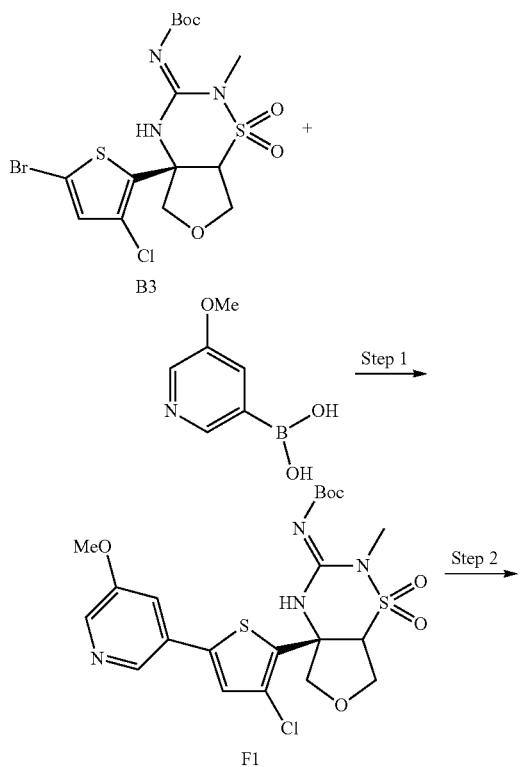

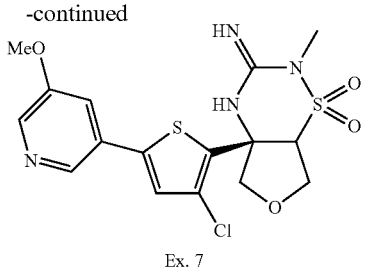

Ex. 7

Method F, Step 1:

To B3 in tert-butanol is added 5-methoxypyridine-3-boronic acid, aqueous potassium carbonate, and $PdCl_2(dppf)$. The reaction is warmed to 65° C. and stirred for 3 h. The reaction is cooled to room temperature and water is added. The mixture is extracted with EtOAc. The combined organics are washed with water and brine, dried ($MgSO_4$), filtered, and concentrated in vacuo. The residue is purified by silica gel chromatography to provide F1.

Method F, Step 2:

F1 is treated to conditions described in Method E, step 2 to provide Ex. 7.

Using the conditions described in Method F step 1 and step 2, the following boronic acids in Table 2 are coupled with B3 to provide the Examples shown.

TABLE 2

| Boronic Acid | Example Number | Example |
|---|---|---|
| ![CN-pyridine-B(OH)2] | Ex. 8 | ![Ex. 8 structure] |
| ![pyrimidine-B(OH)2] | Ex. 9 | ![Ex. 9 structure] |
| ![OMe-indole-Boc-B(OH)2] | Ex. 10 | ![Ex. 10 structure] |

TABLE 2-continued

| Boronic Acid | Example Number | Example |
|---|---|---|
| (5-ethynylpyridin-3-yl)boronic acid | Ex. 11 | Example 11 structure |
| methyl 1-Boc-5-(B(OH)₂)-pyrrole-2-carboxylate | Ex. 12 | Example 12 structure |

Method G

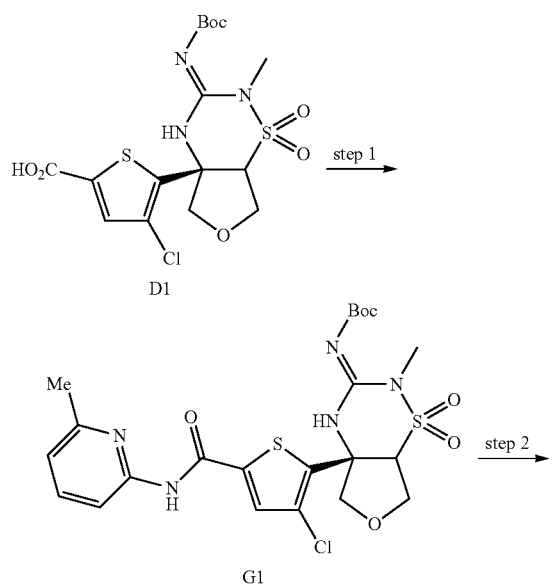

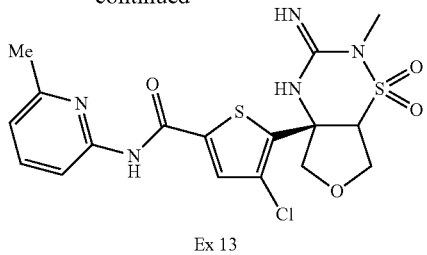

Ex 13

Method G, Step 1:
To D1 in pyridine is added 2-amino-6-methylpyridine followed by bis(2-oxo-3-oxazolidinyl)phosphinic chloride. The reaction is stirred for 18 h at room temperature and then concentrated in vacuo. Water is added and the mixture is extracted with EtOAc. The combined organic layers are washed with water and brine, dried (MgSO₄), filtered, and concentrated in vacuo. The residue is purified by silica gel chromatography to provide G1.

Method G, Step 2:
G1 is treated to conditions described in Method E, step 2 to provide Ex. 13.

Using the procedures described in Method G, the examples in Table 3 are prepared using the aminopyridine shown.

TABLE 3

| Aminopyridine | Example Number | Example |
|---|---|---|
| 6-methoxypyridin-2-amine | Ex. 14 | Example 14 structure |

TABLE 3-continued

| Aminopyridine | Example Number | Example |
|---|---|---|
| Me, pyridine-NH2 | Ex. 15 | (structure) |
| Cl-pyridine-NH2 | Ex. 16 | (structure) |
| F-pyridine-NH2 | Ex. 17 | (structure) |
| CF3-pyridine-NH2 | Ex. 18 | (structure) |

Method H

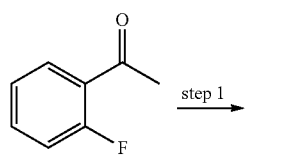

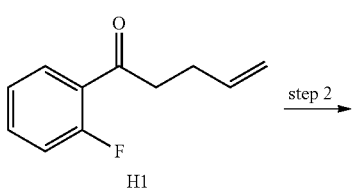

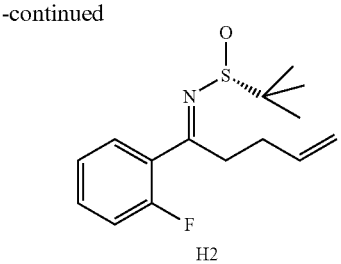

Method H, Step 1:

A literature procedure is adapted (*J. Am. Chem. Soc.,* 2005, 127, 8294).

A solution of 1-(2-fluorophenyl)ethanone in THF is added to a suspension of potassium hydride in THF at 0° C. over 10 minutes. After 30 minutes, triethylboron is added and the mixture is stirred for an additional 15 minutes. Allyl bromide is then added and the reaction is allowed to warm to room temperature and is stirred for 4 h. The reaction mixture is quenched with a mixture (1:1) of 30% NaOH and 30% $H_2O_2$. The mixture is extracted with ether. The combined ether layers are washed with water and brine, dried ($MgSO_4$), filtered, and concentrated in vacuo. The residue is purified by silica gel chromatography to provide H1.

Method H, Step 2:

To H1 in THF is added (R)-2-methyl-2-propanesulfinamide and Ti(OEt)$_4$. The solution is heated to reflux and stirred for 12 h. The solution is cooled to room temperature and poured onto ice. To this mixture is added DCM and the resultant mixture is stirred for 10 minutes at room temperature. The mixture is extracted with DCM. The combined organic layers are washed with water and brine, dried (MgSO$_4$), filtered, and concentrated in vacuo. The residue is purified by silica gel chromatography to provide H2.

Method I

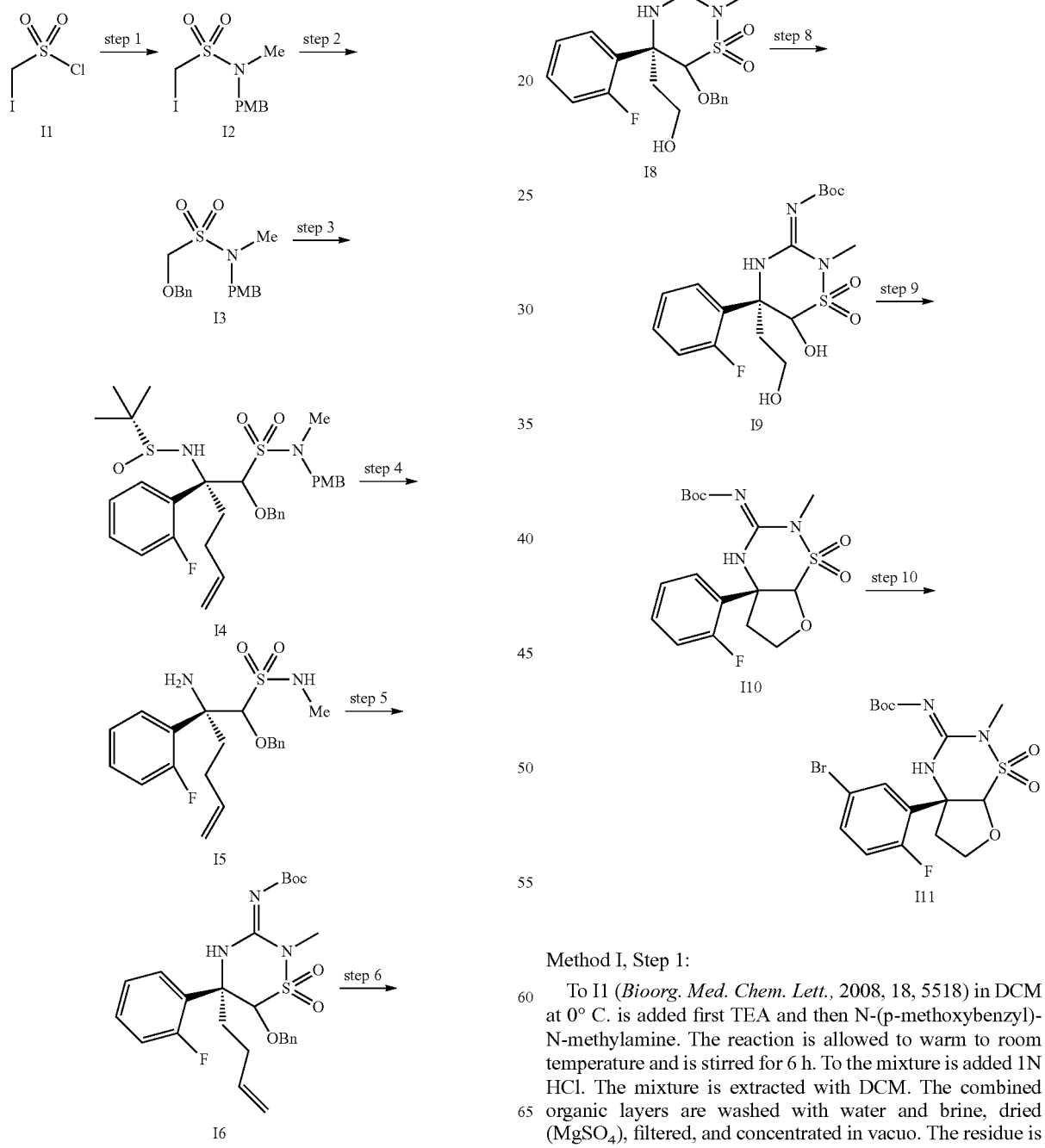

Method I, Step 1:

To I1 (*Bioorg. Med. Chem. Lett.*, 2008, 18, 5518) in DCM at 0° C. is added first TEA and then N-(p-methoxybenzyl)-N-methylamine. The reaction is allowed to warm to room temperature and is stirred for 6 h. To the mixture is added 1N HCl. The mixture is extracted with DCM. The combined organic layers are washed with water and brine, dried (MgSO$_4$), filtered, and concentrated in vacuo. The residue is purified by silica gel chromatography to provide I2.

Method I, Step 2:

A literature procedure is adapted (WO 2006117306).

To I2 in DMF is added benzyl alcohol and cesium carbonate. The reaction is heated to 55° C. for 4 h and then cooled to room temperature. To the mixture is added 3N HCl. The mixture is then extracted with EtOAc. The combined organic layers are washed with water and brine, dried ($MgSO_4$), filtered, and concentrated in vacuo. The residue is purified by silica gel chromatography to provide I3.

Method I, Step 3:

To I3 in THF at −78° C. is added dropwise a solution of n-butyllithium. The resultant mixture is stirred at −78° C. for 30 minutes. After that time, a solution of H2 in THF precooled to −78° C. in a separate round bottom flask is transferred via cannula to the solution above. The resultant solution is stirred at −78° C. for 4 h. Water is added and the mixture is allowed to warm to room temperature. The mixture is extracted with ethyl acetate. The combined organic layers are washed with water and brine, dried ($MgSO_4$), filtered, and concentrated in vacuo. The residue is purified by silica gel chromatography to provide I4.

Method I, Step 4:

To I4 in DCM/methanol (3:1) is added 4M HCl in dioxane. The solution is stirred for 2 h at room temperature and then concentrated in vacuo. The residue is taken up into chloroform and TFA (1:1). To this solution is added 1,3-dimethoxybenzene. The mixture is stirred at room temperature for 12 h. The solution is then concentrated in vacuo. The resultant oil is partitioned between ether and 1N $HCl_{(aq)}$. The aqueous layer is extracted with ether. The aqueous layer is then adjusted to pH 10 with the addition of saturated $Na_2CO_{3(aq)}$. The aqueous layer is then extracted with DCM. The combined DCM layers are washed with water and brine, dried ($MgSO_4$), filtered, and concentrated in vacuo to provide I5.

Method I, Step 5:

To a slurry of I5 in n-butanol is added a solution of cyanogen bromide (5M in MeCN). The resultant mixture is heated to reflux for 4 hours. The mixture is concentrated to ⅓ of the original volume. The product is then isolated by methods known to those in the art. In one such non-limiting method, $Et_2O$ (200 mL) is added to the mixture, the resultant solid is removed via filtration and washed with $Et_2O$. Once isolated. the material is partitioned between EtOAc and sat. $Na_2CO_3$ (aq.). The aqueous layer is extracted with EtOAc (3×). The combined organic layers are washed with brine, dried over $Na_2SO_4$, filtered and concentrated in vacuo. The residue is taken up into DCM and $(Boc)_2O$ is added. The reaction is stirred at room temperature for 12 h. The reaction mixture is washed with water and brine, dried ($MgSO_4$), filtered, and concentrated in vacuo. The residue is purified by silica gel chromatography to provide I6.

Method I, Step 6:

Using the catalyst system and conditions described in *J. Am. Chem. Soc.*, 2007, 129, 9592, 16 is converted to I7.

Method I, Step 7:

Ozone is passed through a solution of DCM containing I7 at −78° C. until TLC determined that starting material had been consumed. Sodium borohydride is added and the reaction is allowed to warm to room temperature. The mixture is then washed with water and brine, dried ($MgSO_4$), filtered, and concentrated in vacuo. The residue is purified by silica gel chromatography to provide I8.

Method I, Step 8:

To I8 in ethanol is added palladium on charcoal. The mixture is placed under 1 atmosphere of hydrogen gas. The reaction is stirred until TLC determines that starting material is consumed. The mixture is then filtered through a bed of Celite. The filtrate is concentrated in vacuo. The residue is purified by silica gel chromatography to provide I9.

Method I, Step 9:

A literature precedent is adapted (*J. Am. Chem. Soc.*, 1985, 107, 5210).

To I9 is added a solution of diethoxytriphenylphosphorane in toluene (preparation of which is described in *J. Am. Chem. Soc.*, 1985, 107, 5210). The reaction is warmed to 45° C. and stirred for 60 h or until TLC shows the disappearance of starting material. The reaction is then cooled to room temperature. Water is added and the mixture is extracted with ethyl acetate. The combined ethyl acetate layers are washed with water and brine, dried, and filtered and concentrated in vacuo to provide a residue that is purified by silica gel chromatography to yield I10.

Method I, Step 10:

A literature precedent is adapted (*J. Med. Chem.*, 2006, 49, 2600). I10 is treated according to Method A, Step 13 to provide I11.

Method J

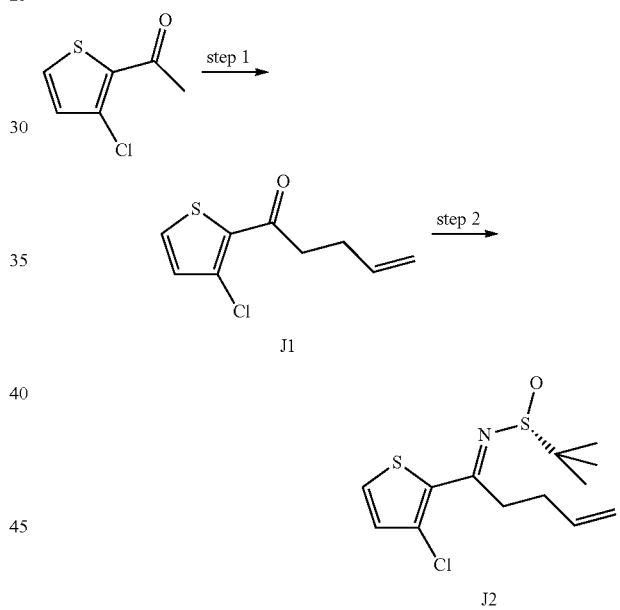

Using the conditions described in step 1 and step 2 of Method H, 1-(3-chlorothiophen-2-yl)ethanone is converted to J2.

Method K

-continued

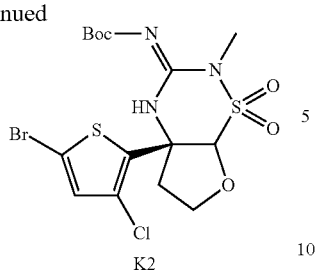
K2

Method K, Step 1:
Using the procedures described in Method I steps 1-9 and substituting J2 for H2 in step 3, I1 is converted to K1.

Method K, Step 2:
To K1 in DMF is added NBS. The reaction is stirred at 55° C. for 5 h or until TLC indicates the disappearance of starting material. The reaction is cooled to room temperature and water is added. The mixture is extracted with ethyl acetate. The combined organic layers are washed with water and brine, dried (MgSO$_4$), filtered, and concentrated in vacuo. The residue is purified by silica gel chromatography to provide K2.

Method L

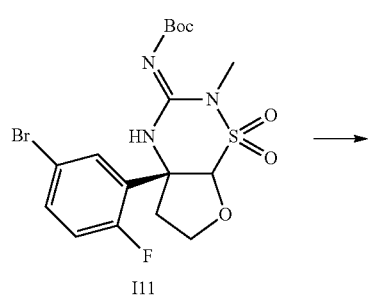
I11

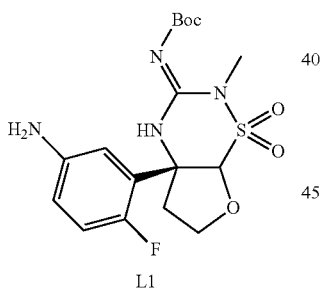
L1

Method L, Step 1:
I11 is treated according to Method C to provide L1.

Method M

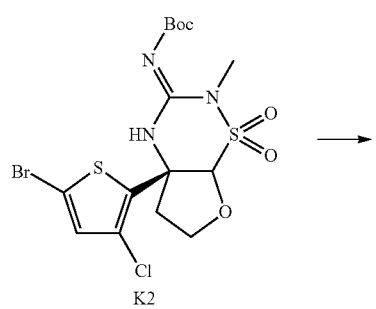
K2

-continued

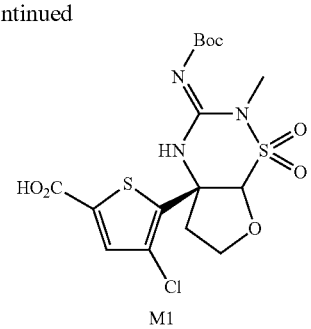
M1

Method M, Step 1:
K2 is treated according to Method D to provide M1.

Method N

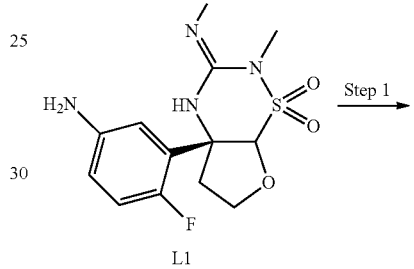
L1

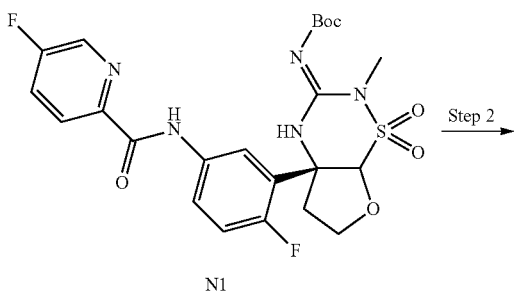
N1

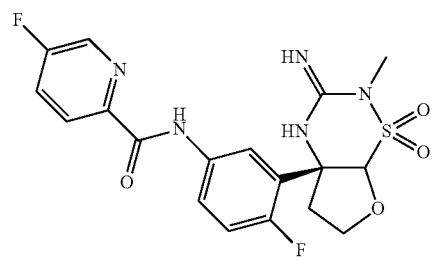
Ex. 19

Method N, Step 1:
L1 is treated according to Method E to provide Ex. 19.
Using the procedures described in Method N, L1 is coupled with the carboxylic acids to provide the examples shown in Table 4.

TABLE 4

| Carboxylic Acid | Example Number | Example |
| --- | --- | --- |
| 3,5-difluoropyridine-2-carboxylic acid | Ex. 20 | |
| 5-methoxypyridine-2-carboxylic acid | Ex. 21 | |
| 5-methoxypyrazine-2-carboxylic acid | Ex. 22 | |
| 5-chloropyridine-2-carboxylic acid | Ex. 23 | |
| 5-(trifluoromethyl)pyridine-2-carboxylic acid | Ex. 24 | |

Method O
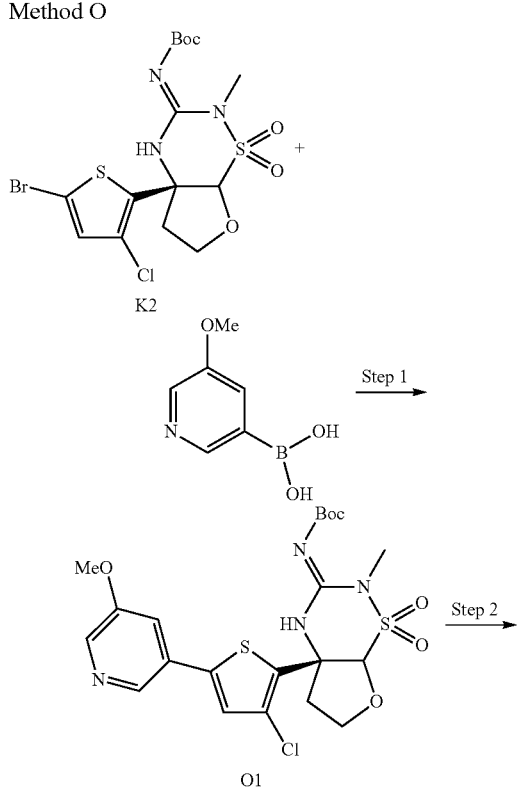
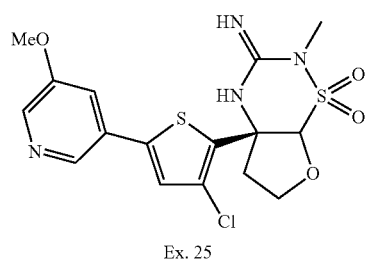
Method O, Step 1:
K2 is treated according to Method F to provide Ex. 25.
Using the conditions described in Method O, the following boronic acids in Table 5 are coupled with K2 to provide the Examples shown.
TABLE 5
| Boronic Acid | Example Number | Example |
|---|---|---|
|  | Ex. 26 |  |
|  | Ex. 27 |  |
|  | Ex. 28 |  |

TABLE 5-continued

| Boronic Acid | Example Number | Example |
|---|---|---|
| (5-ethynylpyridin-3-yl)boronic acid | Ex. 29 | Ex. 29 structure |
| methyl 1-Boc-5-(B(OH)₂)-pyrrole-2-carboxylate | Ex. 30 | Ex. 30 structure |

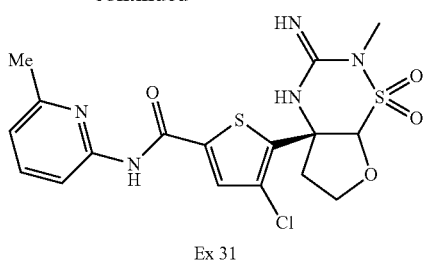

Method P

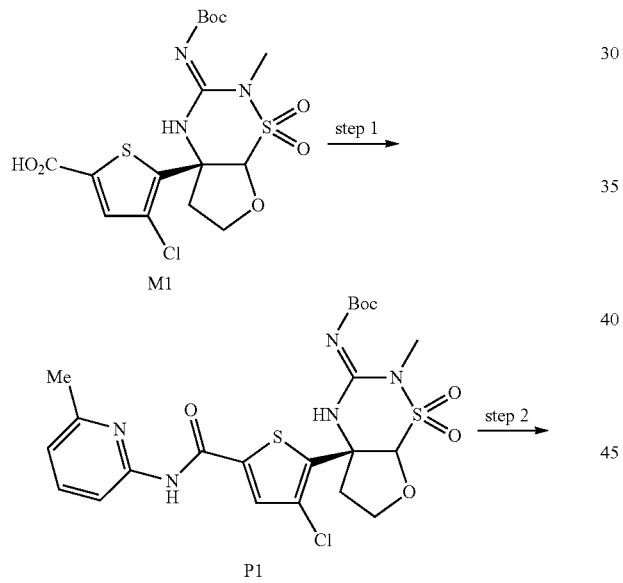

Method P, Step 1:

M1 is treated according to Method G to provide Ex. 31.

Using the procedures described in Method P, the examples in Table 6 are prepared using the aminopyridine shown.

TABLE 6

| Aminopyridine | Example Number | Example |
|---|---|---|
| 6-methoxypyridin-2-amine | Ex. 32 | Ex. 32 structure |

TABLE 6-continued
| Aminopyridine | Example Number | Example |
|---|---|---|
| Me-pyridine-NH2 | Ex. 33 | (structure) |
| Cl-pyridine-NH2 | Ex. 34 | (structure) |
| F-pyridine-NH2 | Ex. 35 | (structure) |
| CF3-pyridine-NH2 | Ex. 36 | (structure) |
Method Q
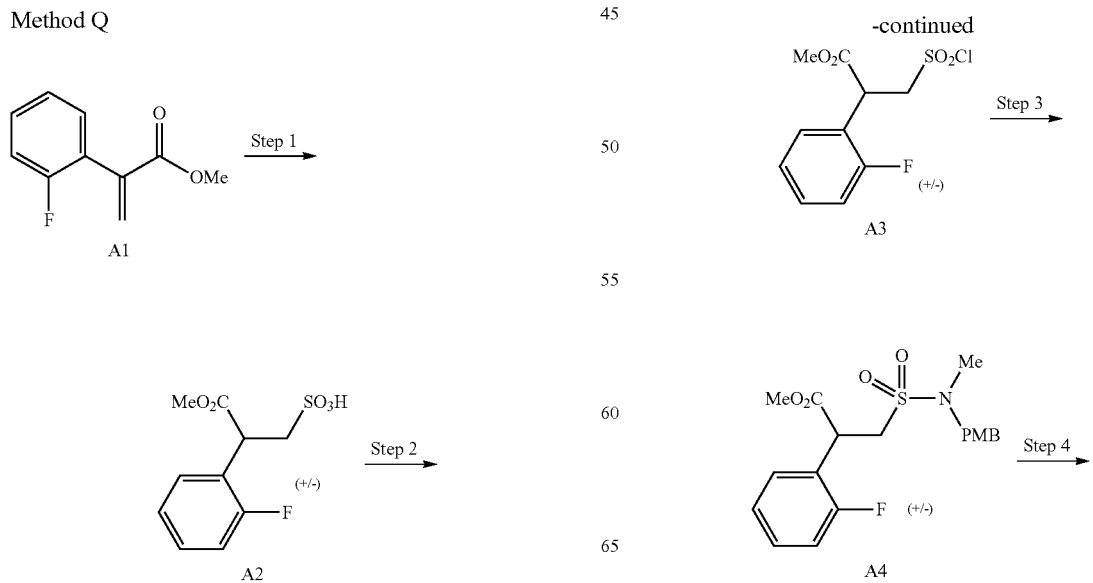

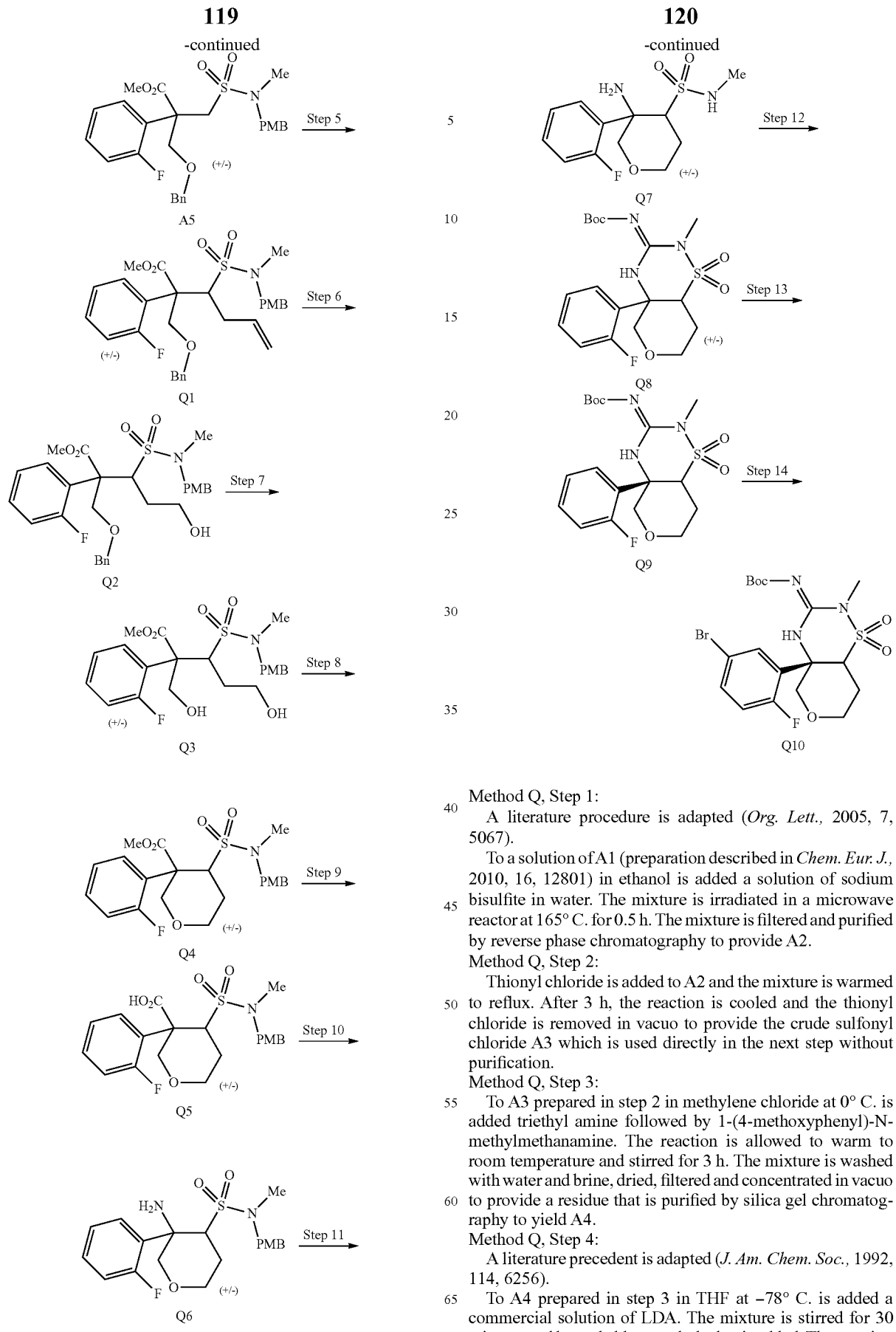

Method Q, Step 1:
A literature procedure is adapted (*Org. Lett.*, 2005, 7, 5067).

To a solution of A1 (preparation described in *Chem. Eur. J.*, 2010, 16, 12801) in ethanol is added a solution of sodium bisulfite in water. The mixture is irradiated in a microwave reactor at 165° C. for 0.5 h. The mixture is filtered and purified by reverse phase chromatography to provide A2.

Method Q, Step 2:
Thionyl chloride is added to A2 and the mixture is warmed to reflux. After 3 h, the reaction is cooled and the thionyl chloride is removed in vacuo to provide the crude sulfonyl chloride A3 which is used directly in the next step without purification.

Method Q, Step 3:
To A3 prepared in step 2 in methylene chloride at 0° C. is added triethyl amine followed by 1-(4-methoxyphenyl)-N-methylmethanamine. The reaction is allowed to warm to room temperature and stirred for 3 h. The mixture is washed with water and brine, dried, filtered and concentrated in vacuo to provide a residue that is purified by silica gel chromatography to yield A4.

Method Q, Step 4:
A literature precedent is adapted (*J. Am. Chem. Soc.*, 1992, 114, 6256).

To A4 prepared in step 3 in THF at −78° C. is added a commercial solution of LDA. The mixture is stirred for 30 minutes and benzyl chloromethyl ether is added. The reaction is stirred until TLC indicated the disappearance of starting material. The reaction is warmed to room temperature and saturated ammonium chloride is added. The mixture is extracted with ethyl acetate. The combined ethyl acetate layers are washed with water and brine, dried, filtered and concentrated in vacuo to provide a residue that is purified by silica gel chromatography to yield A5.

Method Q, Step 5:

A literature precedent is adapted (*Tetrahedron*, 2005, 61, 5615).

To a solution of A5 in THF at −78° C. is added LDA. The reaction is stirred at −78° C. for 30 minutes after which a solution of allyl bromide in THF is added over 15 minutes. The reaction is allowed to warm to room temperature and the reaction is stirred for 8 h. The reaction is added to 2N $HCl_{(aq)}$ and the mixture is extracted with EtOAc. The combined organic layers are washed with water and brine, dried ($MgSO_4$), filtered, and concentrated in vacuo. The residue is purified by silica gel chromatography to provide Q1.

Method Q, Step 6:

Ozone is passed through a solution of DCM containing Q1 at −78° C. until TLC determined that starting material had been consumed. Sodium borohydride is added and the reaction is allowed to warm to room temperature. The mixture is then washed with water and brine, dried ($MgSO_4$), filtered, and concentrated in vacuo. The residue is purified by silica gel chromatography to provide Q2.

Method Q, Step 7:

To Q2 in ethanol is added palladium on carbon. The mixture is placed under 1 atmosphere of hydrogen gas. The reaction is stirred until TLC indicates that starting material is consumed. The mixture is then filtered through a bed of Celite. The filtrate is concentrated in vacuo. The residue is purified by silica gel chromatography to provide Q3.

Method Q, Step 8:

A literature precedent is adapted (*J. Am. Chem. Soc.*, 1985, 107, 5210).

To Q3 is added a solution of diethoxytriphenylphosphorane in toluene (preparation of which is described in J. Am. Chem. Soc., 1985, 107, 5210). The reaction is warmed to 45° C. and stirred for 60 h or until TLC shows the disappearance of starting material and the formation of Q4. The reaction is then cooled to room temperature. Water is added and the mixture is extracted with ethyl acetate. The combined ethyl acetate layers are washed with water and brine, dried, and filtered and concentrated in vacuo to provide a residue that is purified by silica gel chromatography to yield Q4.

Method Q, Step 9:

To Q4 in THF at room temperature is added 2N $LiOH_{(aq)}$. The reaction is warmed to 60° C. for several hours until TLC shows the disappearance of starting material. The reaction is then cooled to room temperature and acidified to pH~3 using 1N $HCl_{(aq)}$. The mixture is then extracted with ethyl acetate. The combined ethyl acetate layers are washed with water and brine, dried, filtered, and concentrated in vacuo to provide the carboxylic acid Q5.

Method Q, Step 10:

A literature precedent is adapted (*J. Org. Chem.*, 1992, 57, 6188).

To the carboxylic acid Q5 THF at room temperature is added TEA followed by diphenylphosphonic azide. The reaction mixture is stirred at RT or 24 h and then most of the solvent is removed in vacuo. To the residue is added acetonitrile. The resulting solution is added dropwise to a mixture of acetonitrile, water, and trifluoroacetic acid which is heated to 80° C. The reaction is then stirred at 80° C. for 1.5 h. The reaction is cooled to room temperature and concentrated in vacuo. Ethyl acetate is added and the mixture is washed with saturated $NaHCO_3$, water, and brine. The organic layer is dried, filtered, and concentrated in vacuo to provide a residue that is purified by silica gel chromatography to yield Q6.

Method Q, Step 11:

To the amine Q6 in chloroform is added m-dimethoxybenzene and trifluoroacetic acid. The mixture is stirred for 18 h or until TLC shows the disappearance of starting material. Additional TFA may be added if the reaction does not go to completion. Once the starting material is consumed, the mixture is concentrated in vacuo and then taken up into DCM. The mixture is washed with saturated $NaHCO_3$, water and brine. The organic layer is dried, filtered, and concentrated in vacuo to provide a residue that is purified by silica gel chromatography to yield Q7.

Method Q, Step 12:

To Q7 in a suitable solvent, for example t-butanol or acetonitrile, is added a solution of cyanogen bromide. The resultant mixture is heated to reflux for 4 hours or until TLC shows the disappearance of starting material and the formation of desired product. The solvent is removed in vacuo and ethyl acetate is added. The mixture is washed with water and brine. The organic layer is dried, filtered, and concentrated in vacuo to provide a residue that is taken up into DCM and TEA and $(Boc)_2O$ is added. The mixture is stirred at room temperature for 12 h and then washed with saturated $NaHCO_3$, water, and brine. The organic layer is dried, filtered, and concentrated in vacuo to provide a residue that is purified by silica gel chromatography to yield Q8.

Method Q, Step 13:

The racemic mixture Q8 is separated into enantiomers using chiral HPLC to provide the desired enantiomer Q9.

Method Q, Step 14:

A literature precedent is adapted (*J. Med. Chem.*, 2006, 49, 2600).

To Q9 in acetonitrile is added dibromodimethylhydantoin. The mixture is cooled to 0° C. using an ice bath and sulfuric acid is added. The mixture is allowed to warm to room temperature and stirring is continued at room temperature for 10 minutes. The mixture is then heated to 55° C. and stirred for 2 h. The mixture is cooled to room temperature and most of the solvent is removed in vacuo. The residue is neutralized with 4N NaOH and the resulting mixture is extracted with EtOAc. The organic phase is dried ($MgSO_4$), filtered, and concentrated in vacuo. The residue is taken up into DCM and $(Boc)_2O$ is added. The reaction is stirred at room temperature for 12 h. The reaction is concentrated in vacuo and the residue is purified by silica gel chromatography to provide Q10.

Method R

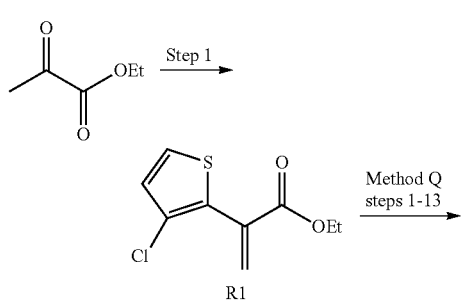

-continued

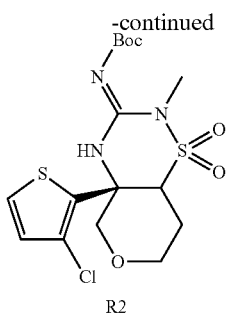
R2

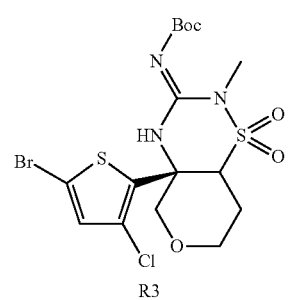
R3

Method R, Step 1:

A literature procedure is adapted (*Chem. Eur. J.,* 2010, 16, 12801).

To a flask containing ethyl pyruvate in dioxane is added p-toluenesulfonylhydrazide. The reaction is heated to 70° C. and stirred for 2 hours. The reaction is cooled to room temperature and Xphos and tris(dibenzylideneacetone)dipalladium and lithium t-butoxide is added followed by 2-bromo-3-chlorothiophene. Nitrogen is bubbled through the reaction for 5 minutes after which time the reaction is heated to 110° C. After starting material is determined to be consumed by TLC, the mixture is allowed to cool to room temperature. DCM is added and the mixture is passed through a plug of Celite. The filtrate is washed with water and brine, dried (MgSO$_4$), filtered, and concentrated in vacuo to provide a residue that is purified by silica gel chromatography to yield R1.

R1 is then converted to R2 using the procedures described in steps 1-13 of Method Q.

Method R, Step 2:

To R2 in DMF is added NBS. The reaction is stirred at 55° C. for 5 h or until TLC indicates the disappearance of starting material. The reaction is cooled to room temperature and water is added. The mixture is extracted with ethyl acetate. The combined organic layers are washed with water and brine, dried (MgSO$_4$), filtered, and concentrated in vacuo. The residue is purified by silica gel chromatography to provide R3.

Method S

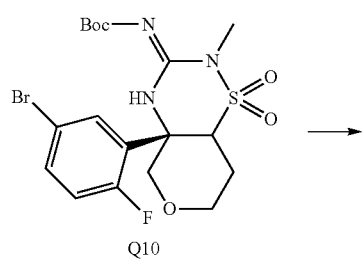
Q10

-continued

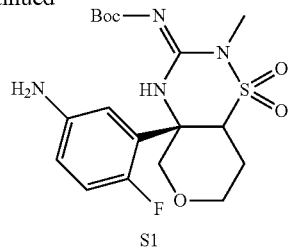
S1

Method S, Step 1:

Q10 is treated according to Method C to provide S1.

Method T

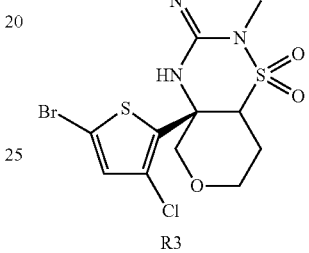
R3

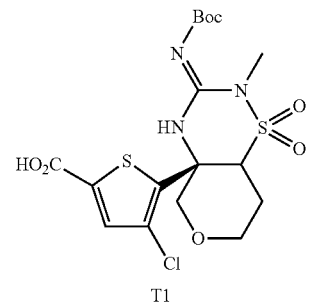
T1

Method T, Step 1:

R3 is treated according to Method D to provide T1.

Method U

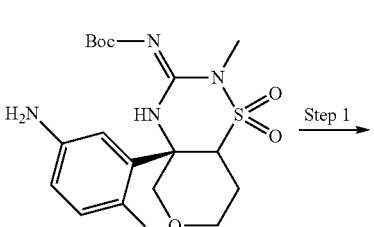
S1

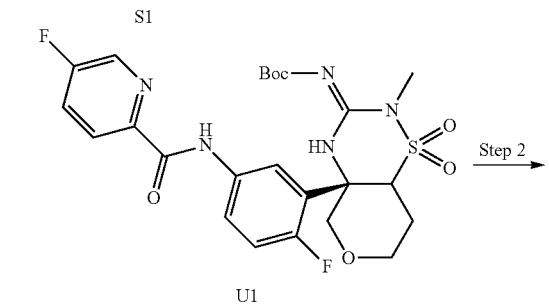
U1

Method U, Step 1:
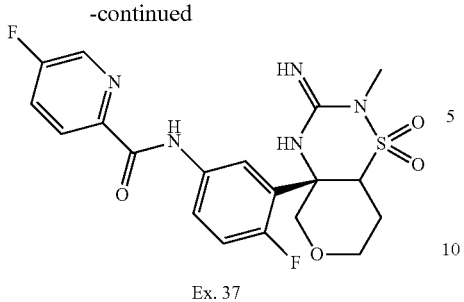
Ex. 37
S1 is treated according to Method E to provide Ex. 37.
Using the procedures described Method U, S1 is coupled with the carboxylic acids to provide the examples shown in Table 7.
TABLE 7
| Carboxylic Acid | Example Number | Example |
| --- | --- | --- |
|  | Ex. 38 |  |
|  | Ex. 39 |  |
|  | Ex. 40 |  |
|  | Ex. 41 |  |

127
TABLE 7-continued
| Carboxylic Acid | Example Number | Example |
|---|---|---|
| 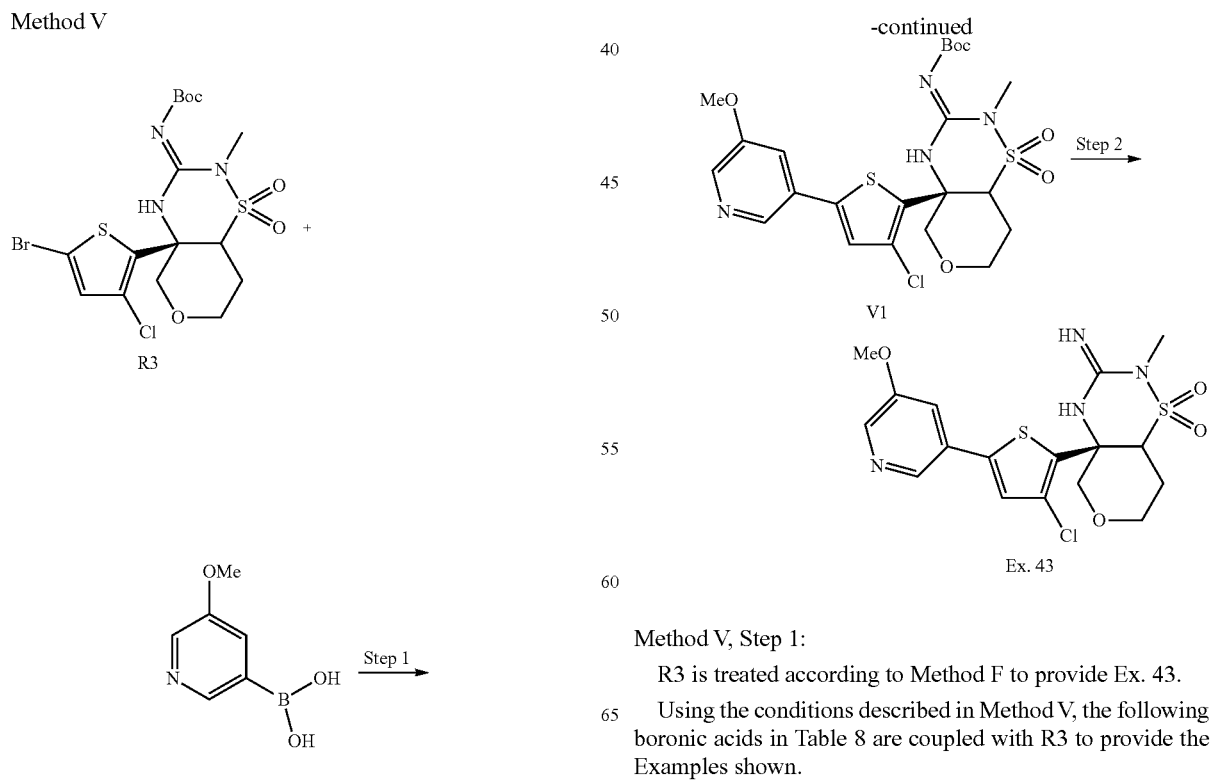 | Ex. 42 | |
| | Ex. 42a A3-6 | |
| | Ex. 42b A4-4 | |
Method V
Method V, Step 1:
R3 is treated according to Method F to provide Ex. 43.
Using the conditions described in Method V, the following boronic acids in Table 8 are coupled with R3 to provide the Examples shown.

TABLE 8
| Boronic Acid | Example Number | Example |
|---|---|---|
| 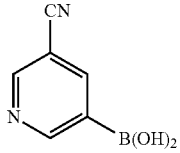 | Ex. 44 | 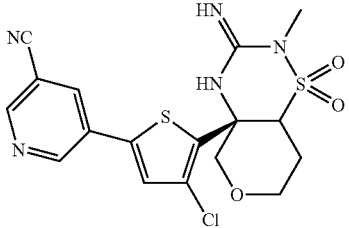 [SMILES: CN1C(=N)N[C@@]2(c3sc(-c4cncc(C#N)c4)cc3Cl)COCCC2S1(=O)=O] |
| 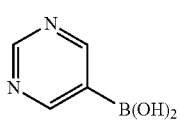 | Ex. 45 | 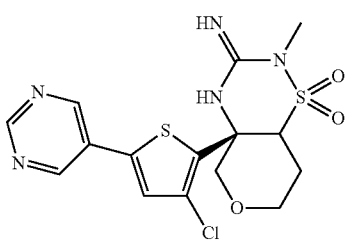 [SMILES: CN1C(=N)N[C@@]2(c3sc(-c4cncnc4)cc3Cl)COCCC2S1(=O)=O] |
| 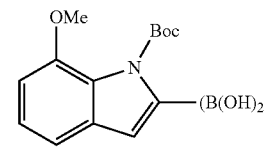 | Ex. 46 | 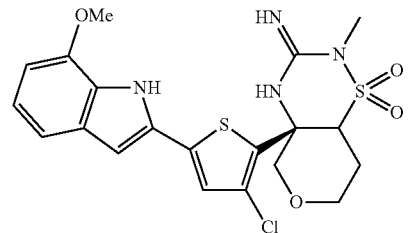 |
| 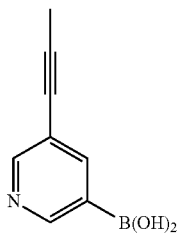 | Ex. 47 | 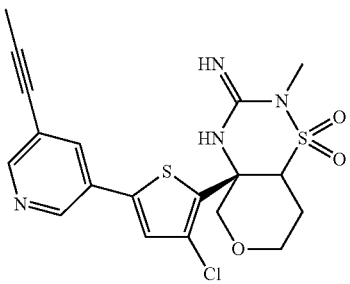 [SMILES: CC#Cc1cncc(-c2cc(Cl)c([C@]34COCCC3S(=O)(=O)N(C)C(=N)N4)s2)c1] |
| 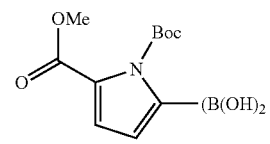 | Ex. 48 | 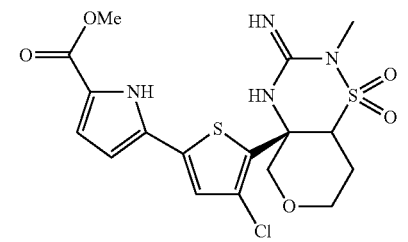 |

Method X

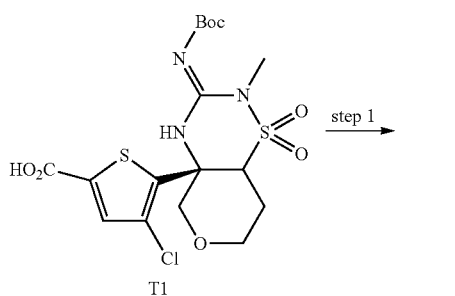
T1

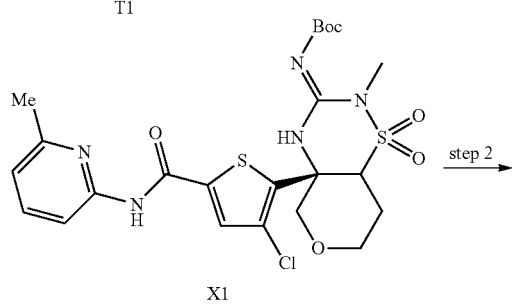
X1

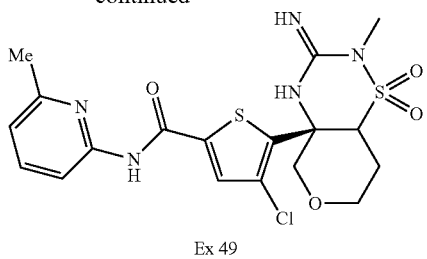
Ex 49

Method X, Step 1:

T1 is treated according to Method G to provide Ex. 49.

Using the procedures described in Method X, the examples in Table 9 are prepared using the aminopyridine shown.

TABLE 9

| Aminopyridine | Example Number | Example |
|---|---|---|
| OMe pyridine NH2 | Ex. 50 | MeO-pyridine-NH-C(O)-thiophene(Cl)-spiro structure |
| Me pyridine NH2 | Ex. 51 | Me-pyridine-NH-C(O)-thiophene(Cl)-spiro structure |
| Cl pyridine NH2 | Ex. 52 | Cl-pyridine-NH-C(O)-thiophene(Cl)-spiro structure |

TABLE 9-continued
| Aminopyridine | Example Number | Example |
|---|---|---|
| | Ex. 53 | |
| | Ex. 54 | |
Method Y
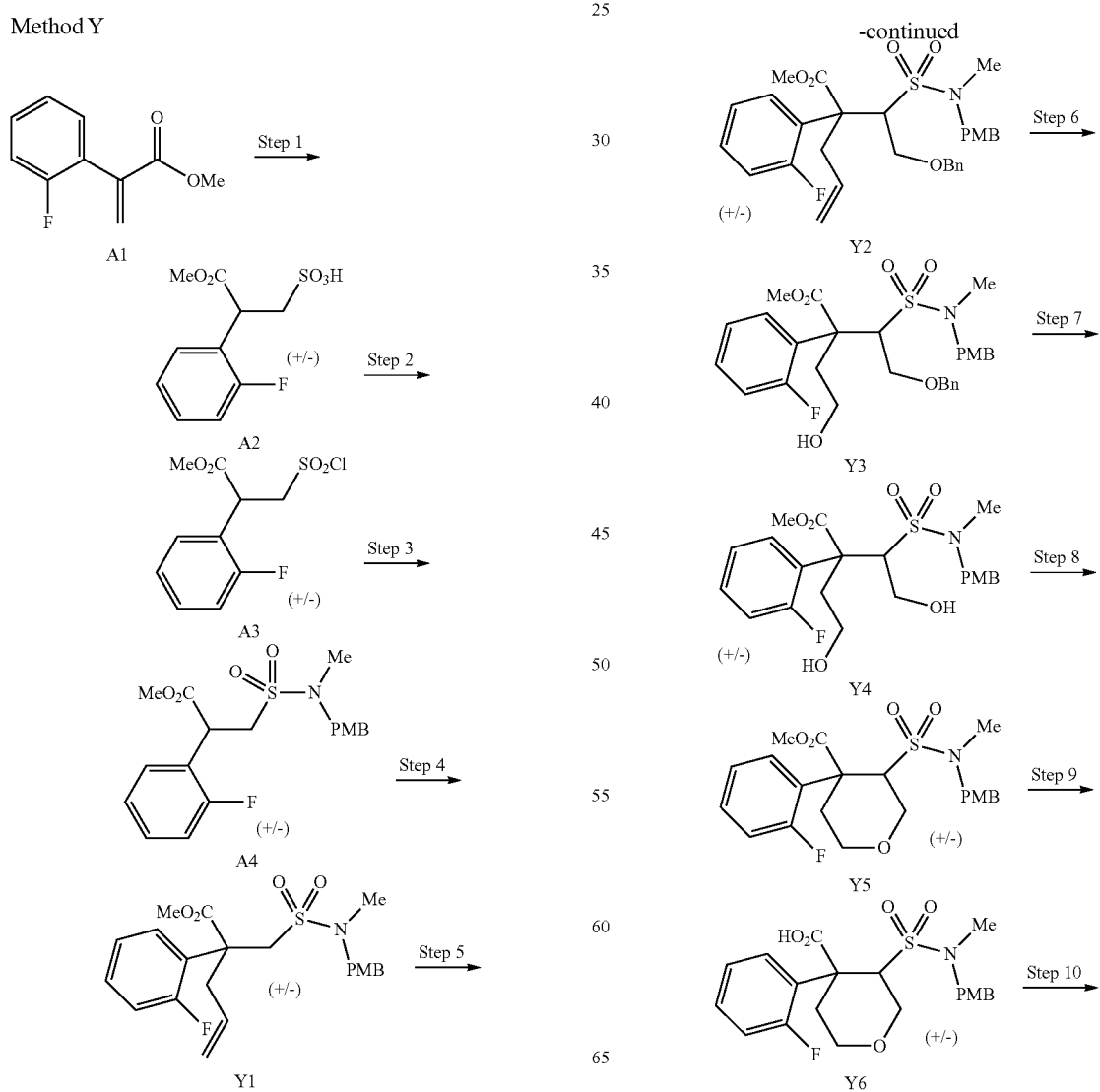

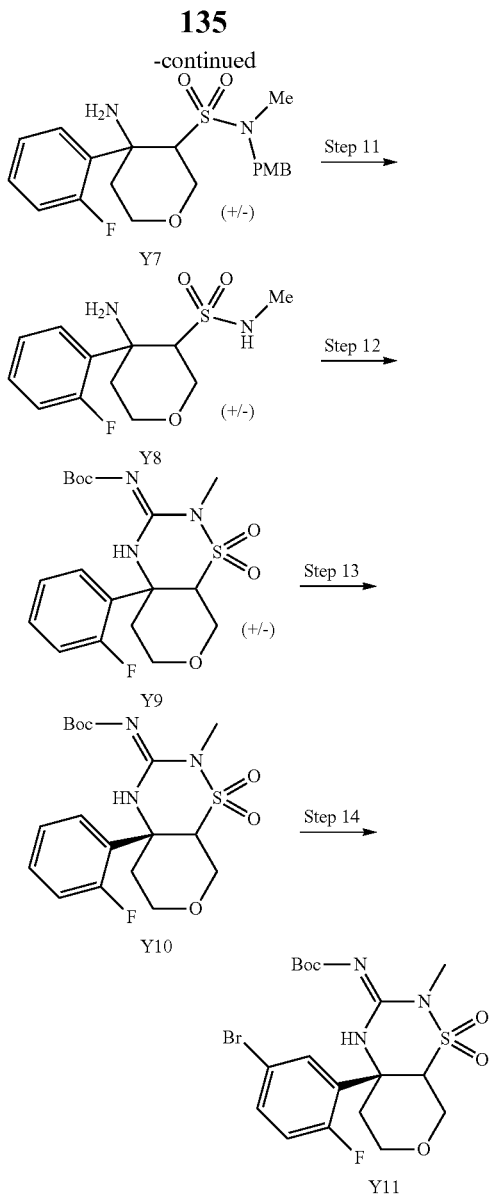

Method Y, Steps 1-4:
Compound A4 is formed from A1 as described in Method A.

Method Y, Step 4:
To a solution of A4 in THF at −78° C. is added LDA. The reaction is stirred at −78° C. for 30 minutes after which a solution of allyl bromide in THF is added over 15 minutes. The reaction is allowed to warm to room temperature and the reaction is stirred for 8 h. The reaction is added to 2N HCl$_{(aq)}$ and the mixture is extracted with EtOAc. The combined organic layers are washed with water and brine, dried (MgSO$_4$), filtered, and concentrated in vacuo. The residue is purified by silica gel chromatography to provide Y1.

Method Y, Step 5:
A literature procedure is adapted (WO 2008030902).
To a solution of Y1 in THF at 0° C. is added LiHMDS. The reaction is stirred at 0° C. for 30 minutes after which it is cooled to −78° C. A THF solution of benzyl chloromethyl ether is added dropwise and the cold bath is removed and the reaction is allowed to warm to room temperature. After 1 h at room temperature, saturated aqueous ammonium chloride is added. The mixture is extracted with EtOAc. The combined organic layers are washed with water and brine, dried (MgSO$_4$), filtered, and concentrated in vacuo. The residue is purified by silica gel chromatography to provide Y2.

Method Y, Step 6:
Ozone is passed through a solution of DCM containing Y2 at −78° C. until TLC indicates that starting material is consumed. Sodium borohydride is added and the reaction is allowed to warm to room temperature. The mixture is then washed with water and brine, dried (MgSO$_4$), filtered, and concentrated in vacuo. The residue is purified by silica gel chromatography to provide Y3.

Method Y, Step 7:
To Y3 in ethanol is added palladium on carbon. The mixture is place under 1 atmosphere of hydrogen gas. The reaction is stirred until TLC determines that starting material is consumed. The mixture is then filtered through a bed of Celite. The filtrate is concentrated in vacuo. The residue is purified by silica gel chromatography to provide Y4.

Method Y, Step 8:
A literature precedent is adapted (*J. Am. Chem. Soc.*, 1985, 107, 5210).
To Y4 is added a solution of diethoxytriphenylphosphorane in toluene (preparation described in *J. Am. Chem. Soc.*, 1985, 107, 5210). The reaction is warmed to 45° C. and stirred for 60 h or until TLC shows the disappearance of starting material. The reaction is then cooled to room temperature. Water is added and the mixture is extracted with ethyl acetate. The combined ethyl acetate layers are washed with water and brine, dried, and filtered and concentrated in vacuo to provide a residue that is purified by silica gel chromatography to yield Y5.

Method Y, Step 9:
To Y5 in THF at room temperature is added 2N LiOH$_{(aq)}$. The reaction is warmed to 60° C. for several hours until TLC shows the disappearance of starting material. The reaction is then cooled to room temperature and acidified to pH~3 using 1N HCl$_{(aq)}$. The mixture is then extracted with ethyl acetate. The combined ethyl acetate layers are washed with water and brine, dried, filtered, and concentrated in vacuo to provide the carboxylic acid Y6.

Method Y, Step 10:
A literature precedent is adapted (*J. Org. Chem.*, 1992, 57, 6188).
To the carboxylic acid Y6 THF at rt is added TEA followed by diphenylphosphonic azide. The reaction mixture is stirred at room temperature for 24 h and then most of the solvent is removed in vacuo. To the residue is added acetonitrile. The resulting solution is added dropwise to a mixture of acetonitrile, water, and trifluoroacetic acid which is heated to 80° C. The reaction is then stirred at 80° C. for 1.5 h. The reaction is cooled to room temperature and concentrated in vacuo. Ethyl acetate is added and the mixture is washed with saturated NaHCO$_3$, water, and brine. The organic layer is dried, filtered, and concentrated in vacuo to provide a residue that is purified by silica gel chromatography to yield Y7.

Method Y, Step 11:
To the amine Y7 in chloroform is added m-dimethoxybenzene and trifluoroacetic acid. The mixture is stirred for 18 h or until TLC shows the disappearance of starting material. Additional TFA may be added if the reaction does not go to completion. Once the starting material is consumed, the mixture is then concentrated in vacuo and then taken up into DCM. The mixture is washed with saturated NaHCO$_3$, water and brine. The organic layer is dried, filtered, and concentrated in vacuo to provide a residue that is purified by silica gel chromatography to yield Y8.

Method Y, Step 12:

To Y8 in a suitable solvent, for example t-butanol or acetonitrile, is added a solution of cyanogen bromide. The resultant mixture is heated to reflux for 4 hours or until TLC shows the disappearance of starting material and the formation of desired product. The solvent is removed in vacuo and ethyl acetate is added. The mixture is washed with water and brine. The organic layer is dried, filtered, and concentrated in vacuo to provide a residue that is taken up into DCM and TEA and (Boc)$_2$O is added. The mixture is stirred at room temperature for 12 h and then washed with saturated NaHCO$_3$, water, and brine. The organic layer is dried, filtered, and concentrated in vacuo to provide a residue that is purified by silica gel chromatography to yield Y9.

Method Y, Step 13:

The racemic mixture Y9 is separated into enantiomers using chiral HPLC to provide the desired enantiomer Y10.

Method Y, Step 14:

A literature precedent is adapted (*J. Med. Chem.*, 2006, 49, 2600).

To Y10 in acetonitrile is added dibromodimethylhydantoin. The mixture is cooled to 0° C. using an ice bath and sulfuric acid is added. The mixture is allowed to warm to room temperature and stirring is continued at room temperature for 10 minutes. The mixture is then heated to 55° C. and stirred for 2 h. The mixture is cooled to room temperature and most of the solvent is removed in vacuo. The residue is neutralized with 4N NaOH and the resulting mixture is extracted with EtOAc. The organic phase is dried (MgSO$_4$), filtered, and concentrated in vacuo. The residue is taken up into DCM and (Boc)$_2$O is added. The reaction is stirred at room temperature for 12 h. The reaction is concentrated in vacuo and the residue is purified by silica gel chromatography to provide Y11.

Method Z

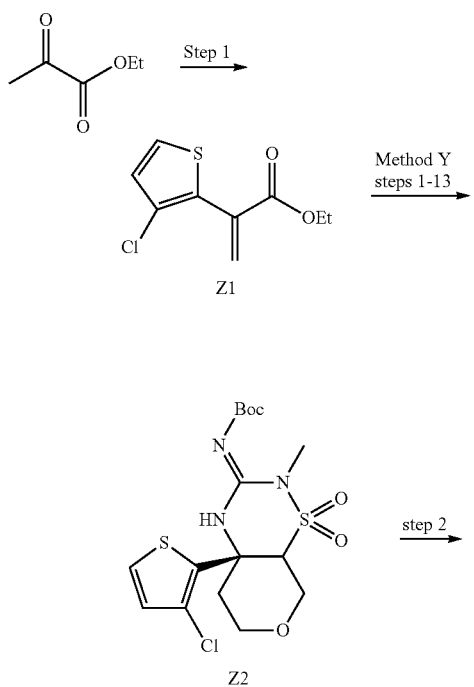

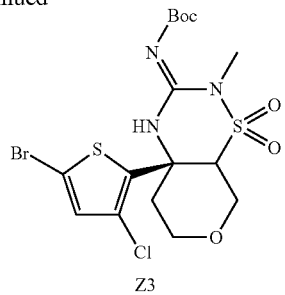

Method Z, Step 1:

A literature procedure is adapted (*Chem. Eur. J.*, 2010, 16, 12801).

To a flask containing ethyl pyruvate in dioxane is added p-toluenesulfonylhydrazide. The reaction is heated to 70° C. and stirred for 2 hours. The reaction is cooled to room temperature and Xphos and tris(dibenzylideneacetone)dipalladium and lithium t-butoxide is added followed by 2-bromo-3-chlorothiophene. Nitrogen is bubbled through the reaction for 5 minutes after which time the reaction is heated to 110° C. After starting material is determined to be consumed by TLC, the mixture is allowed to cool to room temperature. DCM is added and the mixture is passed through a plug of Celite. The filtrate is washed with water and brine, dried (MgSO$_4$), filtered, and concentrated in vacuo to provide a residue that is purified by silica gel chromatography to yield Z1.

Z1 is then converted to Z2 using the procedures described in steps 1-13 of Method Y.

Method Z, Step 2:

To Z2 in DMF is added NBS. The reaction is stirred at 55° C. for 5 h or until TLC indicates the disappearance of starting material. The reaction is cooled to room temperature and water is added. The mixture is extracted with ethyl acetate. The combined organic layers are washed with water and brine, dried (MgSO$_4$), filtered, and concentrated in vacuo. The residue is purified by silica gel chromatography to provide Z3.

Method Aa

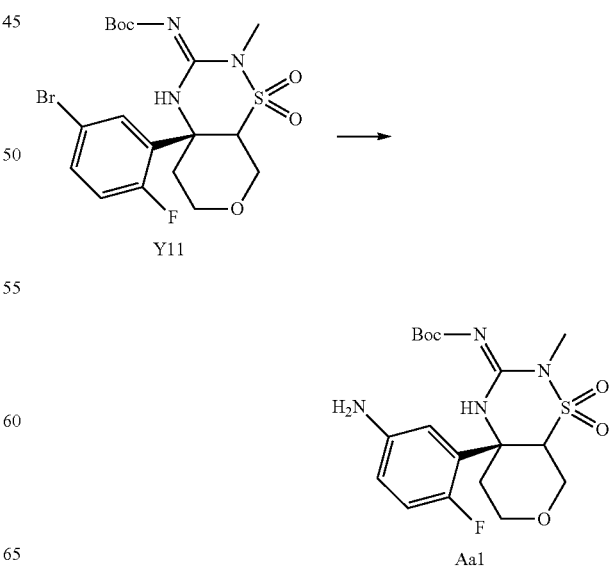

Method Aa, Step1:
 Y11 is treated according to Method C to provide Aa1.
Method Ab

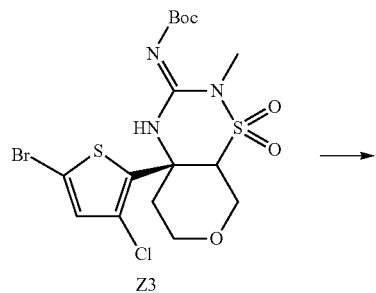

Z3

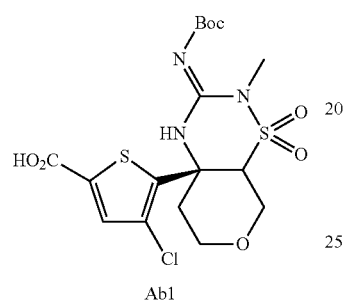

Ab1

Method Ab, Step 1:
 Z3 is treated according to Method D to provide Ab1.
Method Ac

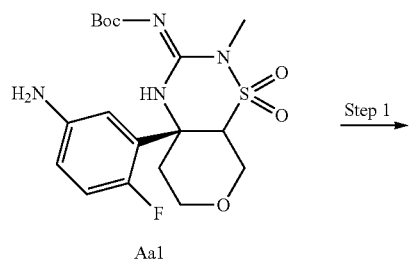

Aa1

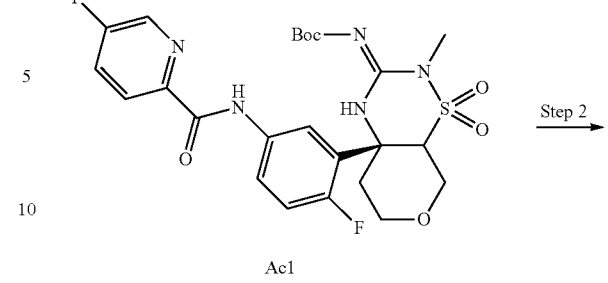

Ac1

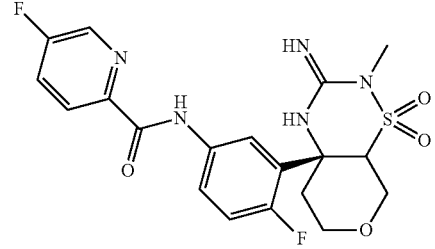

Ex. 55

Method Ac, Step 1:
 Aa1 is treated according to Method E to provide Ex. 55.

Using the procedures described in Method Ac, Aa1 is coupled with the carboxylic acids to provide the examples shown in Table 10.

TABLE 10

| Carboxylic Acid | Example Number | Example |
|---|---|---|
|  | Ex. 56 |  |

141
TABLE 10-continued
| Carboxylic Acid | Example Number | Example |
|---|---|---|
| Ex. 57 | | |
| Ex. 58 | | |
| Ex. 59 | | |
| Ex. 60 | | |
Method Ad
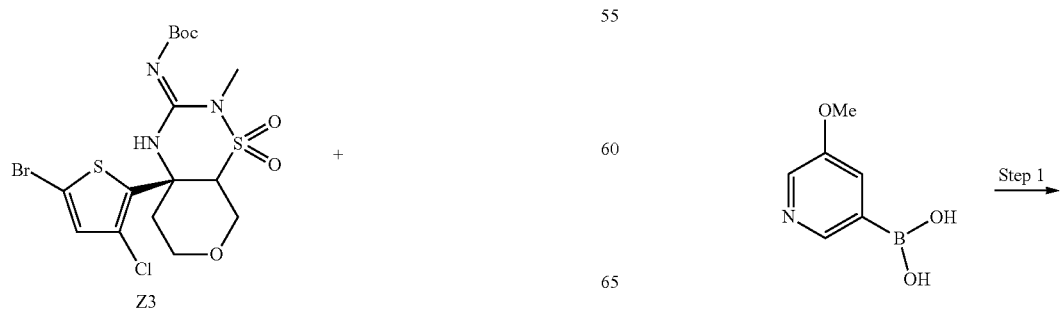
-continued 143
-continued

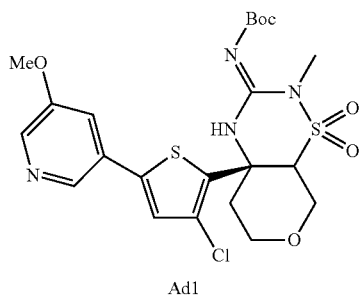

Ad1

Step 2 →

144
-continued

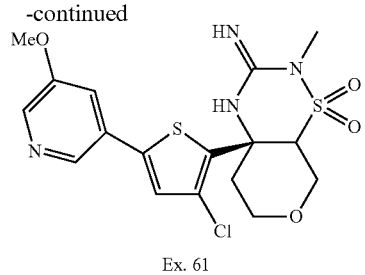

Ex. 61

Method Ad, Step 1:
Z3 is treated according to Method F to provide Ex. 61.
Using the conditions described in Method Ad, the following boronic acids in Table 11 are coupled with Z3 to provide the Examples shown.

TABLE 11

| Boronic Acid | Example Number | Example |
|---|---|---|
| ![CN-pyridine-B(OH)2] | Ex. 62 | ![Ex62 structure] |
| ![pyrimidine-B(OH)2] | Ex. 63 | ![Ex63 structure] |
| ![OMe-Boc-indole-B(OH)2] | Ex. 64 | ![Ex64 structure] |
| ![ethynyl-pyridine-B(OH)2] | Ex. 65 | ![Ex65 structure] |

TABLE 11-continued
| Boronic Acid | Example Number | Example |
|---|---|---|
| 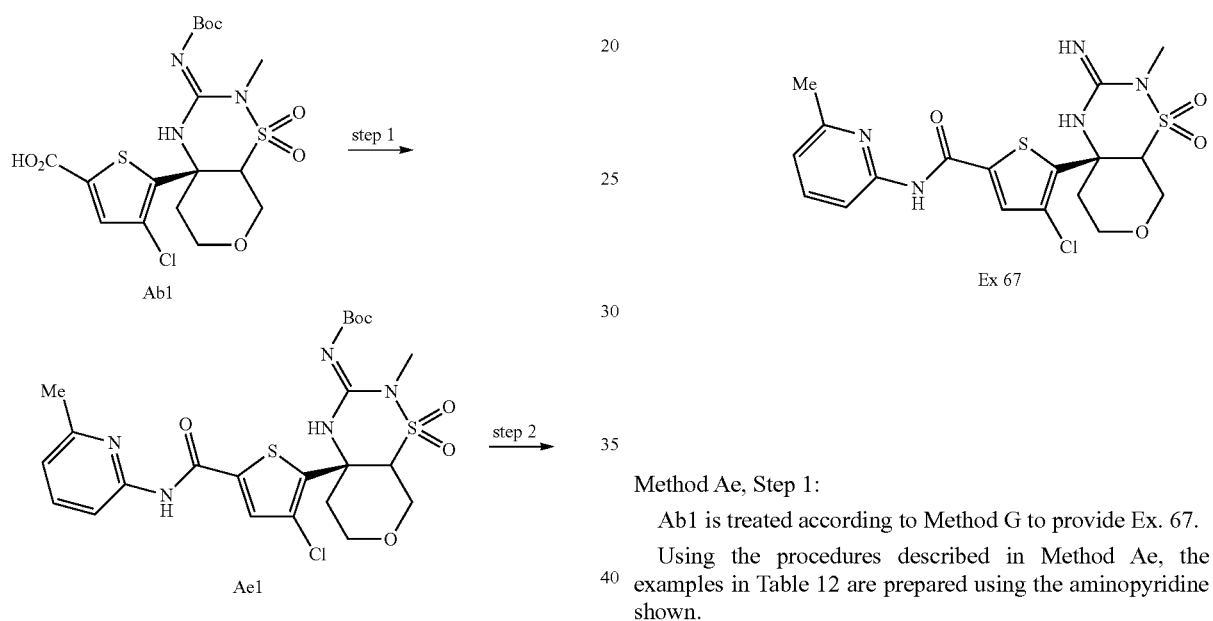 | Ex. 66 | |
Method Ae
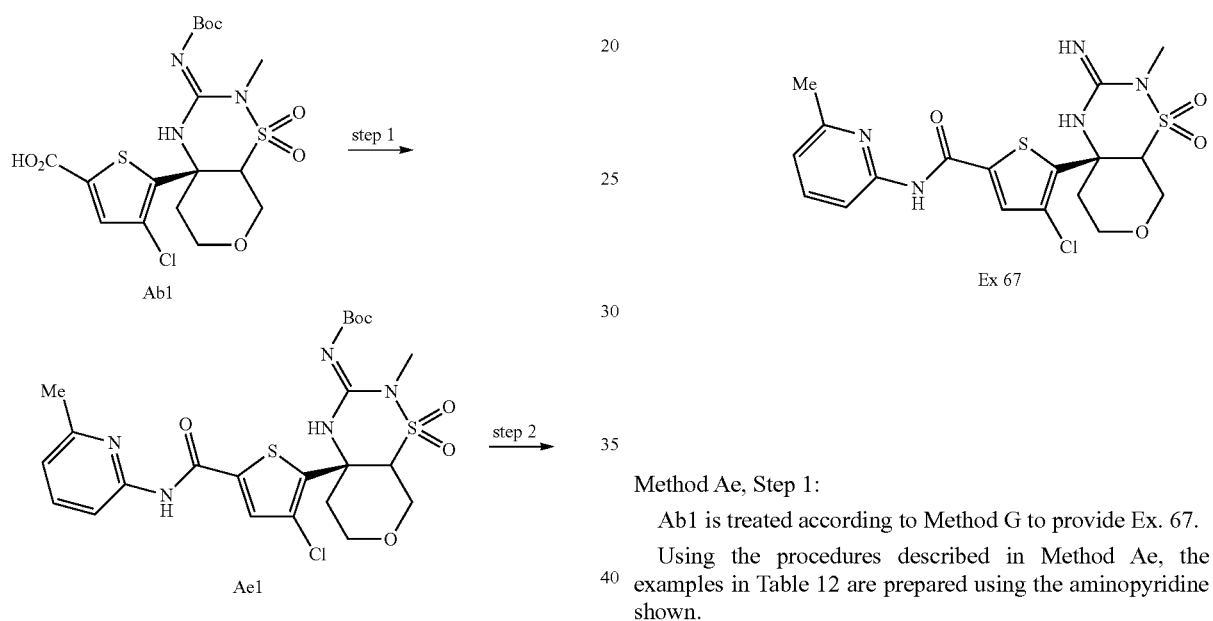
Method Ae, Step 1:
Ab1 is treated according to Method G to provide Ex. 67.
Using the procedures described in Method Ae, the examples in Table 12 are prepared using the aminopyridine shown.
TABLE 12
| Aminopyridine | Example Number | Example |
|---|---|---|
| | Ex. 68 | |
| | Ex. 69 | |

TABLE 12-continued
| Aminopyridine | Example Number | Example |
|---|---|---|
| | Ex. 70 | |
| | Ex. 71 | |
| | Ex. 72 | |
Method Ag
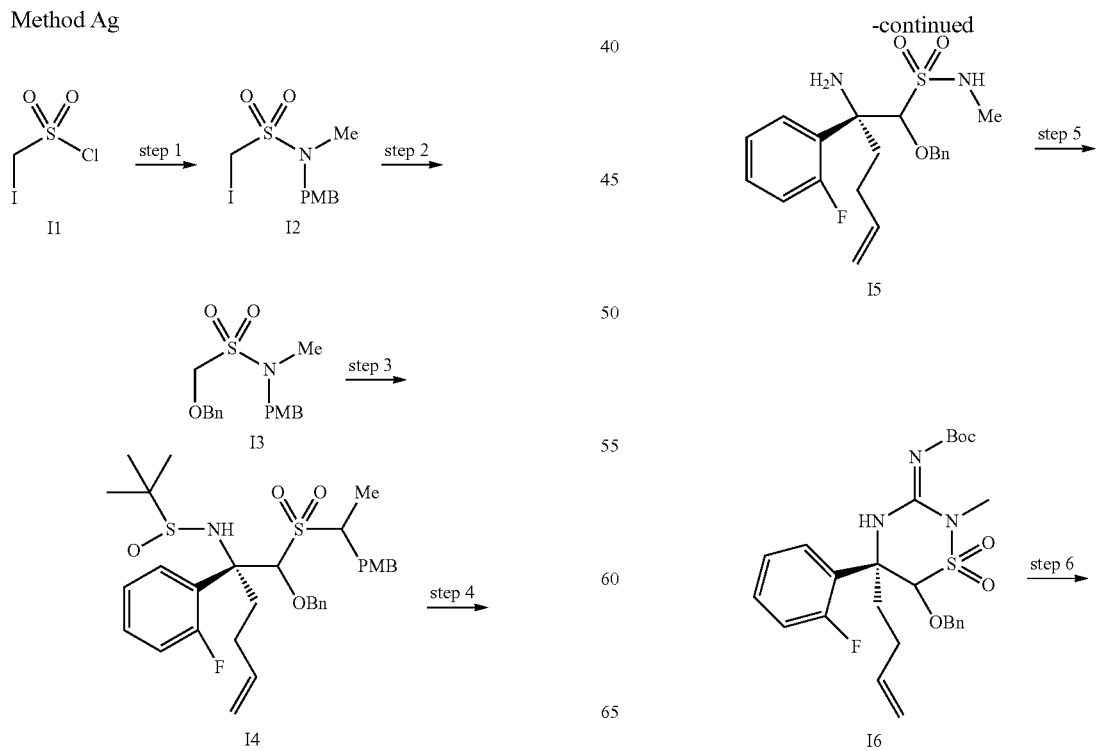

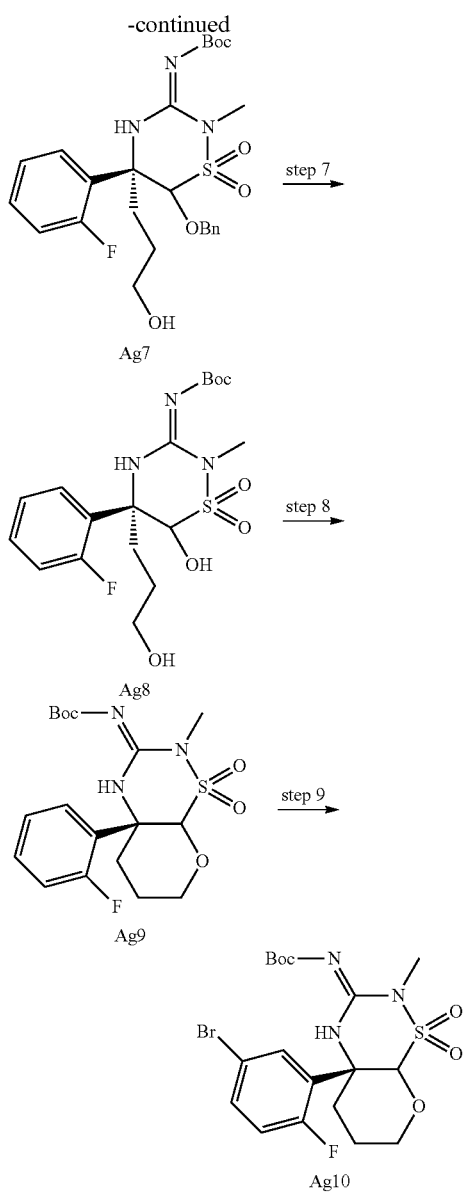

Method Ag, Step 1:

To I1 (*Bioorg. Med. Chem. Lett.*, 2008, 18, 5518) in DCM at 0° C. is added first TEA and then N-(p-methoxybenzyl)-N-methylamine. The reaction is allowed to warm to room temperature and is stirred for 6 h. To the mixture is added 1N HCl. The mixture is extracted with DCM. The combined organic layers are washed with water and brine, dried (MgSO$_4$), filtered, and concentrated in vacuo. The residue is purified by silica gel chromatography to provide I2.

Method Ag, Step 2:

A literature procedure is adapted (WO 2006117306).

To I2 in DMF is added benzyl alcohol and cesium carbonate. The reaction is heated to 55° C. for 4 h and then cooled to room temperature. To the mixture is added 3N HCl. The mixture is then extracted with EtOAc. The combined organic layers are washed with water and brine, dried (MgSO$_4$), filtered, and concentrated in vacuo. The residue is purified by silica gel chromatography to provide I3.

Method Ag, Step 3:

To I3 in THF at −78° C. is added dropwise a solution of n-butyllithium. The resultant mixture is stirred at −78° C. for 30 minutes. After that time, a solution of H2 in THF precooled to −78° C. in a separate round bottom flask is transferred via cannula to the solution above. The resultant solution is stirred at −78° C. for 4 h. Water is added and the mixture is allowed to warm to room temperature. The mixture is extracted with ethyl acetate. The combined organic layers are washed with water and brine, dried (MgSO$_4$), filtered, and concentrated in vacuo. The residue is purified by silica gel chromatography to provide I4.

Method Ag, Step 4:

To I4 in DCM/methanol (3:1) is added 4M HCl in dioxane. The solution is stirred for 2 h at room temperature and then concentrated in vacuo. The residue is taken up into chloroform and TFA (1:1). To this solution is added 1,3-dimethoxybenzene. The mixture is stirred at room temperature for 12 h. The solution is then concentrated in vacuo. The resultant oil is partitioned between ether and 1N HCl$_{(aq)}$. The aqueous layer is extracted with ether. The aqueous layer is then adjusted to pH 10 with the addition of saturated Na$_2$CO$_{3(aq)}$. The aqueous layer is then extracted with DCM. The combined DCM layers are washed with water and brine, dried (MgSO$_4$), filtered, and concentrated in vacuo to provide I5.

Method Ag, Step 5:

To a slurry of I5 in n-butanol is added a solution of cyanogen bromide (5M in MeCN). The resultant mixture is heated to reflux for 4 hours. The mixture is concentrated to ⅓ of the original volume. The product is then isolated by methods known to those in the art. In one such non-limiting method, Et$_2$O (200 mL) is added to the mixture, the resultant solid is removed via filtration and washed with Et$_2$O. Once isolated, the material is partitioned between EtOAc and sat. Na$_2$CO$_3$ (aq.). The aqueous layer is extracted with EtOAc (3×). The combined organic layers are washed with brine, dried over Na$_2$SO$_4$, filtered and concentrated in vacuo. The residue is taken up into DCM and (Boc)$_2$O is added. The reaction is stirred at room temperature for 12 h. The reaction mixture is washed with water and brine, dried (MgSO$_4$), filtered, and concentrated in vacuo. The residue is purified by silica gel chromatography to provide I6.

Method Ag, Step 6:

Ozone is passed through a solution of DCM containing I6 at −78° C. until TLC determined that starting material had been consumed. Sodium borohydride is added and the reaction is allowed to warm to room temperature. The mixture is then washed with water and brine, dried (MgSO$_4$), filtered, and concentrated in vacuo. The residue is purified by silica gel chromatography to provide Ag7.

Method Ag, Step 7:

To Ag7 in ethanol is added palladium on charcoal. The mixture is place under 1 atmosphere of hydrogen gas. The reaction is stirred until TLC determines that starting material is consumed. The mixture is then filtered through a bed of Celite. The filtrate is concentrated in vacuo. The residue is purified by silica gel chromatography to provide Ag8.

Method Ag, Step 8:

A literature precedent is adapted (*J. Am. Chem. Soc.*, 1985, 107, 5210).

To Ag8 is added a solution of diethoxytriphenylphosphorane in toluene (preparation of which is described in *J. Am. Chem. Soc.*, 1985, 107, 5210). The reaction is warmed to 45° C. and stirred for 60 h or until TLC shows the disappearance of starting material and the formation of Ag9. The reaction is then cooled to room temperature. Water is added and the mixture is extracted with ethyl acetate. The combined ethyl acetate layers are washed with water and brine, dried, and filtered and concentrated in vacuo to provide a residue that is purified by silica gel chromatography to yield Ag9.

Method Ag, Step 9:

A literature precedent is adapted (*J. Med. Chem.,* 2006, 49, 2600).

To Ag9 in acetonitrile is added dibromodimethylhydantoin. The mixture is cooled to 0° C. using an ice bath and sulfuric acid is added. The mixture is allowed to warm to room temperature and stirring is continued at room temperature for 10 minutes. The mixture is then heated to 55° C. and stirred for 2 h. The mixture is cooled to room temperature and most of the solvent is removed in vacuo. The residue is neutralized with 4N NaOH and the resulting mixture is extracted with EtOAc. The organic phase is dried (MgSO$_4$), filtered, and concentrated in vacuo. The residue is taken up into DCM and (Boc)$_2$O is added. The reaction is stirred at room temperature for 12 h. The reaction is concentrated in vacuo and the residue is purified by silica gel chromatography to provide Ag10.

Method Ai

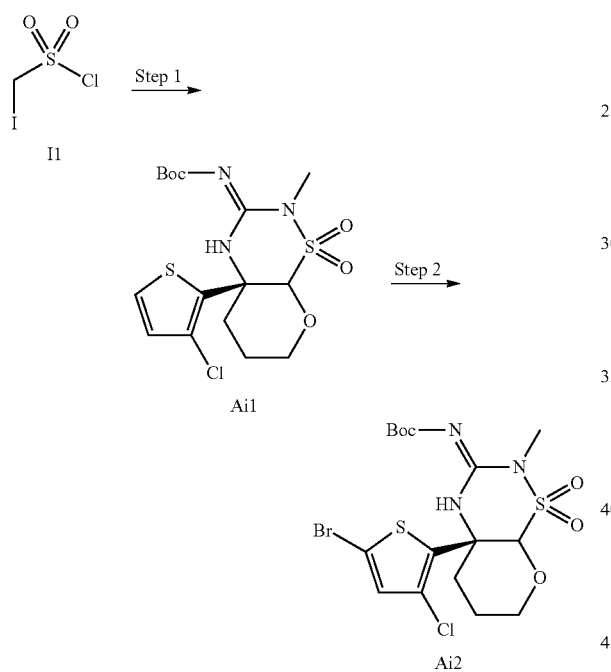

Method Ai, Step 1:

Using the procedures described in Method Ag steps 1-8 and substituting J2 for H2 in step 3, I1 is converted to Ai1.

Method Ai, Step 2:

Using the procedure described in Method B step 2, Ai1 was converted to Ai2.

Method Aj

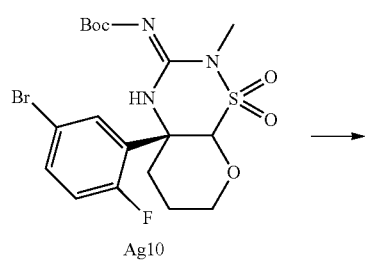

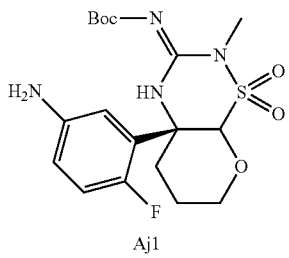

Method Aj, Step1:

Ag10 is treated according to Method C to provide Aj1.

Method Ak

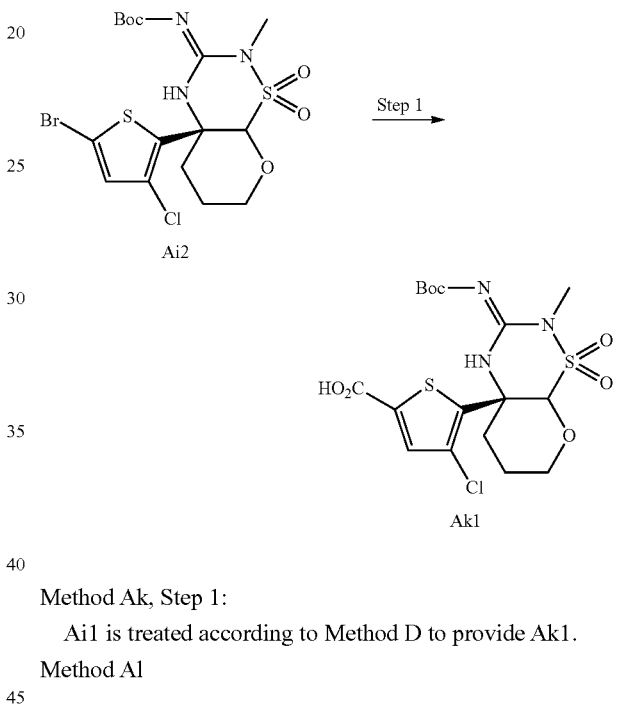

Method Ak, Step 1:

Ai1 is treated according to Method D to provide Ak1.

Method Al

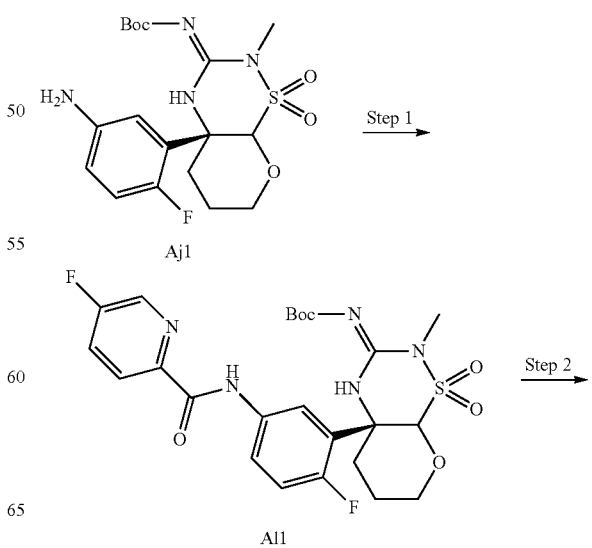

-continued
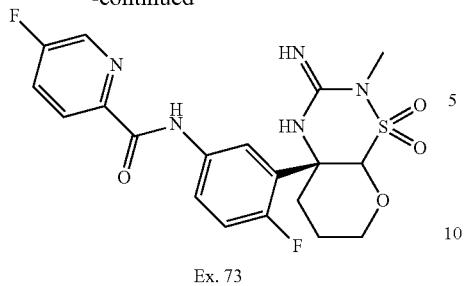
Ex. 73
Method Al, Step 1:
Aj1 is treated according to Method E to provide Ex. 73.
Using the procedures described in Method Al, Aj1 is coupled with the carboxylic acids to provide the examples shown in Table 13.
TABLE 13
| Carboxylic Acid | Example Number | Example |
| --- | --- | --- |
|  | Ex. 74 |  |
|  | Ex. 75 |  |
|  | Ex. 75 |  |
|  | Ex. 76 |  |

TABLE 13-continued
| Carboxylic Acid | Example Number | Example |
| --- | --- | --- |
| 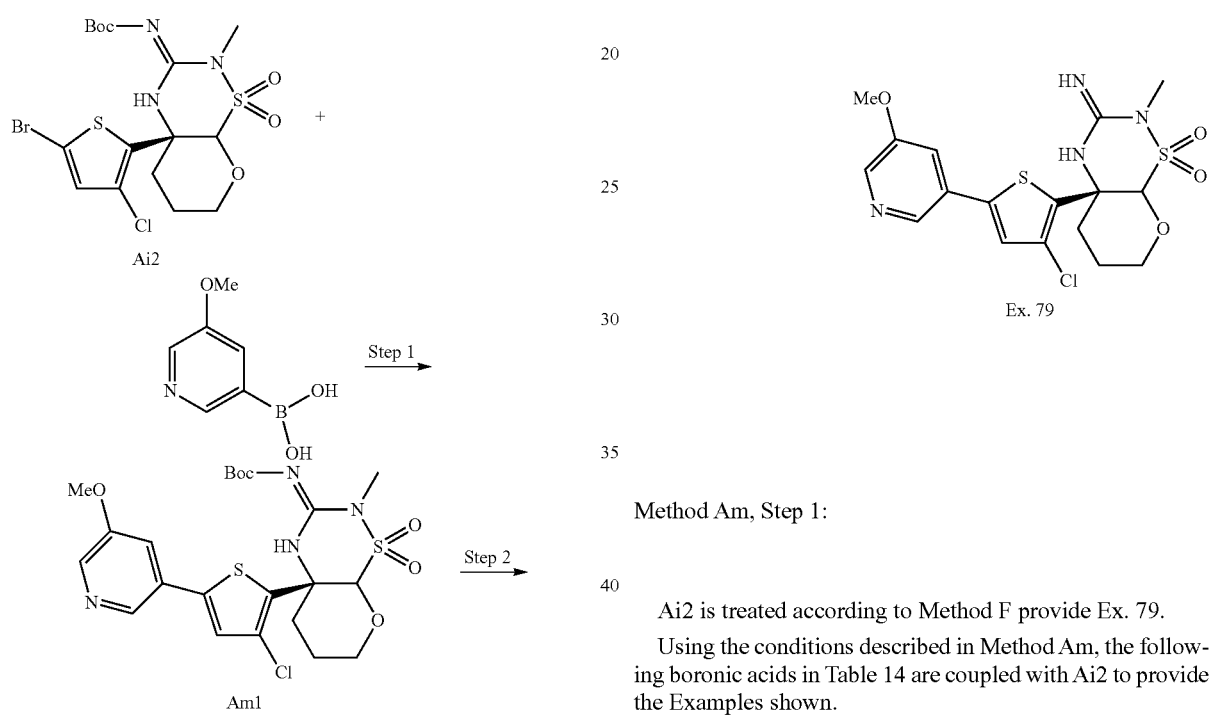 | Ex. 77 | |
Method Am
Method Am, Step 1:
Ai2 is treated according to Method F provide Ex. 79.
Using the conditions described in Method Am, the following boronic acids in Table 14 are coupled with Ai2 to provide the Examples shown.
TABLE 14
| Boronic Acid | Example Number | Example |
| --- | --- | --- |
| | Ex. 80 | |

TABLE 14-continued
| Boronic Acid | Example Number | Example |
|---|---|---|
| 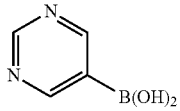 | Ex. 81 | 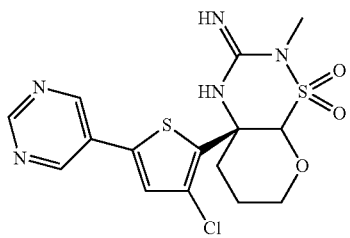 [SMILES: CN1C(=N)N[C@@]2(c3sc(-c4cncnc4)cc3Cl)CCCOC2S1(=O)=O] |
| 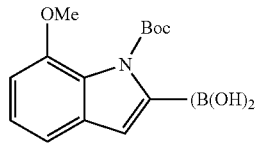 | Ex. 82 | 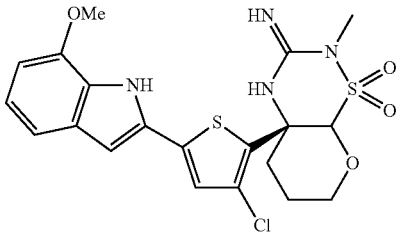 [SMILES: COc1cccc2cc(-c3cc(Cl)c([C@]45CCCOC4S(=O)(=O)N(C)C(=N)N5)s3)[nH]c12] |
| 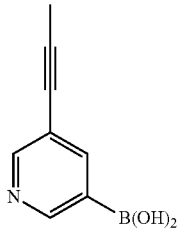 | Ex. 83 | 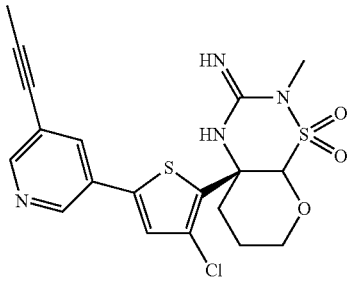 |
| 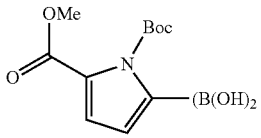 | Ex. 84 | 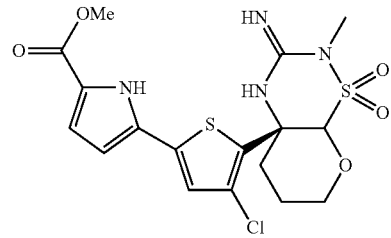 [SMILES: COC(=O)c1ccc(-c2cc(Cl)c([C@]34CCCOC3S(=O)(=O)N(C)C(=N)N4)s2)[nH]1] |
Method An
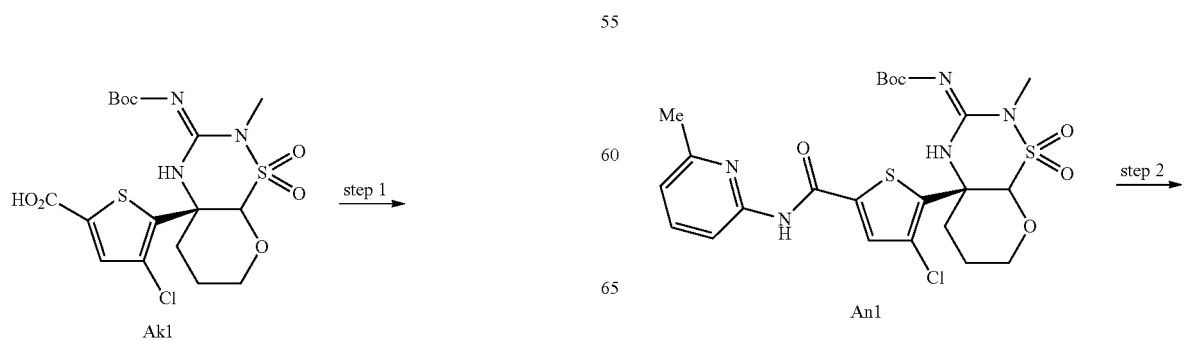

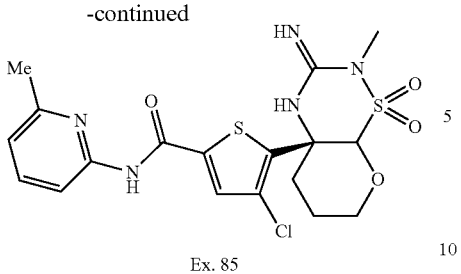

Ex. 85

Method An, Step 1:

Ak1 is treated according to Method G to provide Ex. 85.

Using the procedures described in Method An, the examples in Table 15 are prepared using the aminopyridine shown.

TABLE 15

| Aminopyridine | Example Number | Example |
|---|---|---|
| OMe-pyridine-NH2 | Ex. 86 | MeO-pyridyl-carboxamide-thiophene-Cl-spiro-pyran-sulfonamidine |
| Me-pyridine-NH2 | Ex. 87 | Me-pyridyl-carboxamide-thiophene-Cl-spiro-pyran-sulfonamidine |
| Cl-pyridine-NH2 | Ex. 88 | Cl-pyridyl-carboxamide-thiophene-Cl-spiro-pyran-sulfonamidine |
| F-pyridine-NH2 | Ex. 89 | F-pyridyl-carboxamide-thiophene-Cl-spiro-pyran-sulfonamidine |
| CF3-pyridine-NH2 | Ex. 90 | F3C-pyridyl-carboxamide-thiophene-Cl-spiro-pyran-sulfonamidine |

Method Ao

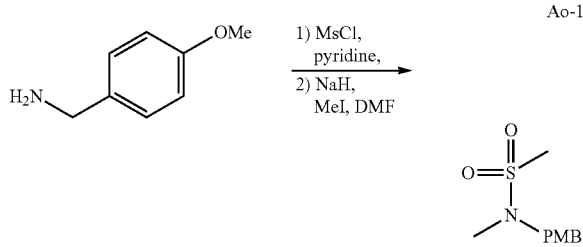

To a stirred solution of 4-methoxybenzyl amine (198.9 g, 1.45 mol) in anhydrous pyridine (400 mL) at 0° C. was added dropwise via an addition funnel methanesulfonyl chloride (116 mL, 1.45 mol) over 45 min. After the addition was complete, the cooling bath was removed and the resultant solution was stirred at RT overnight. The reaction was concentrated in vacuo (water bath 60-65° C.) to remove most of the pyridine. The residue was taken up in $CH_2Cl_2$ (1 L). The organic solution was washed with 1 N $HCl_{(aq.)}$ (2×1 L), sat. $NaHCO_3$ (aq) (2×1 L) and brine (1×500 mL). The organic layer was dried over $Na_2SO_4$, filtered and concentrated to afford a crude solid. This solid was dissolved in 95% EtOH (430 mL) using a steam bath to warm the solution. The solution was allowed to cool, causing the product to precipitate from solution. The product was removed by filtration and the solid was washed with cold EtOH (3×150 mL). A second crop was obtained after allowing the mother liquor to stir at RT overnight. The overall yield of the product was 246.5 g (79% yield).

This product was dissolved in anhydrous DMF (3.0 L), cooled to 0° C. and placed under an atmosphere of $N_2$. To this solution was added in small portions sodium hydride (60% in mineral oil, 60.2 g, 1.51 mol, 1.3 eq.). After the addition was complete, the mixture was stirred for an additional 10 min. To this mixture was added dropwise via an addition funnel methyl iodide (250 g, 1.76 mol, 1.5 eq.). After the addition was complete, the cooling bath was removed and the mixture was allowed to stir at RT overnight. The mixture was then concentrated in vacuo (p=10 torr, bath temp=55-60° C.) to remove ca. 2.5 L of DMF. Some solids precipitated from the solution. The remaining mixture was partitioned between 5 L ice water, 5 L $Et_2O$ and 500 mL of EtOAc. The organic layer was separated. The aqueous layer was extracted with $Et_2O$ (2×1 L). The combined organic layers were washed with brine (2×1 L), dried over $Na_2SO_4$, filtered and concentrated. The solid was stirred with hexanes using a wire stir blade to powderize the solid. The solid was removed by filtration and washed with hexanes (2×250 mL). The solid was dissolved in hexanes/EtOAc (1:1, 450 mL) using a steam bath to warm the mixture. An off white precipitate formed on cooling and was filtered off (182 g). The remaining mother liquor was purified via flash chromatography ($SiO_2$: 1:1 hexanes:EtOAc) to afford additional product (51.8 g) for an overall yield of 233.8 g (89% yield).

LCMS Conditions

Conditions A1:

Column: Agilent TC-C18 (2.1×50 mm) 5 μm; Mobile phase: A: 0.0375% Trifluoroacetic acid in water, B: 0.01875% Trifluoroacetic acid in acetonitrile; Gradient: 100:0 (A:B) for 0.4 min, 100:0 to 20:80 (A:B) over 3 min, 20:80 to 0:100 (A:B) over 0.6 min; Flow rate: 0.6 mL/min; UV detection: 254 and 220 nm; Mass spectrometer: Agilent 6110 quadrupole.

Conditions A2:

Column: Agilent TC-C18 (2.1×50 mm) 5 μm; Mobile phase: A: 0.0375% Trifluoroacetic acid in water, B: 0.01875% Trifluoroacetic acid in acetonitrile; Gradient: 99:1 (A:B) for 0.4 min, 99:1 to 10:90 (A:B) over 3 min, 10:90 to 0:100 (A:B) over 0.6 min; Flow rate: 0.8 mL/min; UV detection: 254 and 220 nm; Mass spectrometer: Agilent 6110 quadrupole Assays Protocols that may be used to determine the recited potency values for the compounds of the invention are described below.

BACE1 HTRF FRET Assay

Reagents $Na^+$-Acetate pH 5.0; 1% Brij-35; Glycerol; Dimethyl Sulfoxide (DMSO); Recombinant human soluble BACE1 catalytic domain (>95% pure); APP Swedish mutant peptide substrate (QSY7-APP$^{swe}$-Eu): QSY7-EISEVNLDAEFC-Europium-amide.

A homogeneous time-resolved FRET assay can be used to determine $IC_{50}$ values for inhibitors of the soluble human BACE1 catalytic domain. This assay monitors the increase of 620 nm fluorescence that resulted from BACE1 cleavage of an APPswedish APP$^{swe}$ mutant peptide FRET substrate (QSY7-EISEVNLDAEFC-Europium-amide). This substrate contains an N-terminal QSY7 moiety that serves as a quencher of the C-terminal Europium fluorophore (620 nm Em). In the absence of enzyme activity, 620 nm fluorescence is low in the assay and increased linearly over 3 hours in the presence of uninhibited BACE1 enzyme Inhibition of BACE1 cleavage of the QSY7-APP$^{swe}$-Eu substrate by inhibitors is manifested as a suppression of 620 nm fluorescence.

Varying concentrations of inhibitors at 3× the final desired concentration in a volume of 10 ul are preincubated with purified human BACE1 catalytic domain (3 nM in 10 μl) for 30 minutes at 30° C. in reaction buffer containing 20 mM Na-Acetate pH 5.0, 10% glycerol, 0.1% Brij-35 and 7.5% DSMO. Reactions are initiated by addition of 10 μl of 600 nM QSY7-APP$^{swe}$-Eu substrate (200 nM final) to give a final reaction volume of 30 μl in a 384 well Nunc HTRF plate. The reactions are incubated at 30° C. for 1.5 hours. The 620 nm fluorescence is then read on a Rubystar HTRF plate reader (BMG Labtechnologies) using a 50 milisecond delay followed by a 400 millisecond acquisition time window. Inhibitor $IC_{50}$ values are derived from non-linear regression analysis of concentration response curves. $K_i$ values are then calculated from $IC_{50}$ values using the Cheng-Prusoff equation using a previously determined μm value of 8 μM for the QSY7-APP$^{swe}$-Eu substrate at BACE1.

BACE-2 Assay

Inhibitor $IC_{50s}$ at purified human autoBACE-2 are determined in a time-resolved endpoint proteolysis assay that measures hydrolysis of the QSY7-EISEVNLDAEFC-Eu-amide FRET peptide substrate (BACE-HTRF assay). BACE-mediated hydrolysis of this peptide results in an increase in relative fluorescence (RFU) at 620 nm after excitation with 320 nm light. Inhibitor compounds, prepared at 3× the desired final concentration in 1×BACE assay buffer (20 mM sodium acetate pH 5.0, 10% glycerol, 0.1% Brij-35) supplemented with 7.5% DMSO are pre-incubated with an equal volume of autoBACE-2 enzyme diluted in 1×BACE assay buffer (final enzyme concentration 1 nM) in black 384-well NUNC plates for 30 minutes at 30° C. The assay is initiated by addition of an equal volume of the QSY7-EISEVNLDAEFC-Eu-amide substrate (200 nM final concentration, $\overline{K}_m$=8 μM for 4 μM for autoBACE-2) prepared in 1×BACE assay buffer supplemented with 7.5% DMSO and incubated for 90 minutes at 30° C. DMSO is present at 5% final concentration in the assay. Following laser excitation of sample wells at 320 nm, the fluorescence signal at 620 nm is collected for 400 ms following a 50 μs delay on a RUBYstar HTRF plate reader (BMG Labtechnologies). Raw RFU data is normalized to maximum (1.0 nM BACE/DMSO) and minimum (no enzyme/DMSO) RFU values. $IC_{50s}$ are determined by nonlinear regression analysis (sigmoidal dose response, variable slope) of percent inhibition data with minimum and maximum values set to 0 and 100 percent respectively. Similar $IC_{50s}$ are obtained when using raw RFU data. The $K_i$ values are calculated from the $IC_{50}$ using the Cheng-Prusoff equation.

BACE Inhibitor Whole Cell IC50 Determination Using HEK293-APP$^{swe/lon}$ Cells

HEK293 cells are obtained from the American Type Culture Collection (ATCC) and stably transfected with the human amyloid precursor protein cDNA containing the FAD Swedish (enhances β-secretase processing) and London (enhances Aβ42 cleavage) mutations. A HEK293 stable clone with Aβ expression (HEK293-APP$^{swe/lon}$) is identified and maintained at 37° C., 5% $CO_2$ in the ATCC-recommended growth media supplemented with hygromycin. Determination of compound $IC_{50}$ values for inhibition of APP processing (reduction of Aβ1-40, Aβ1-42 and sAPPβ levels) in HEK293-APP$^{swe/lon}$ cells is accomplished by treatment of cells with various concentrations of compounds diluted in fresh complete growth media for 4 hours at 37° C., 5% $CO_2$. Aβ40 or Aβ42 are measured in 15 μl of media using a mesoscale based ELISA assay. Full length Aβ40 and Aβ42 peptides are captured with the N-terminal specific biotinylated-WO2 monoclonal antibody and detected using either the ruthenylated Aβ40 C-terminal specific monoclonal antibody, G2-10 or the ruthenylated Aβ42 C-terminal specific monoclonal antibody G2-11 respectively. Raw electrochemiluminescence values are measured using a Mesoscale Sector Imager plate reader and are plotted as a function of compound concentration. $IC_{50}$ values are interpolated from the data using nonlinear regression analysis (Sigmoidal dose response fit with variable slope) of the data using GraphPad Prism software.

What is claimed:

1. A compound, or a stereoisomer of said compound, or a pharmaceutically acceptable salt of said compound or said stereoisomer, said compound having the structural Formula (I):

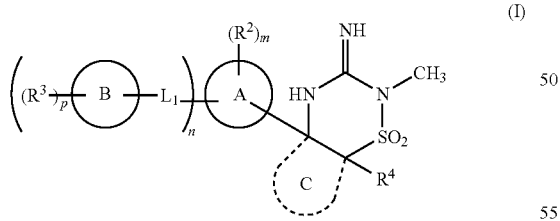

or a tautomer thereof having the structural Formula (I'):

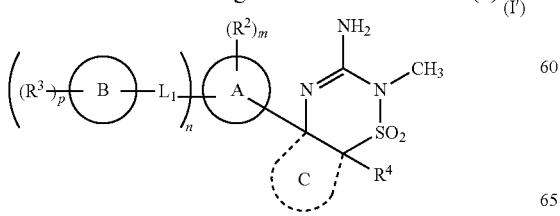

or pharmaceutically acceptable salt thereof, wherein:

ring C is selected from the group consisting of:

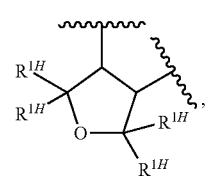

(C1)

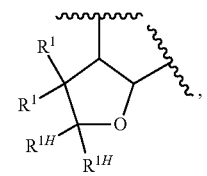

(C2)

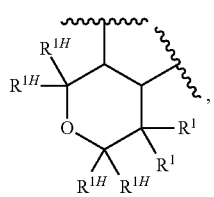

(C3)

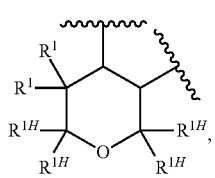

(C4)

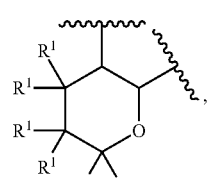

(C5)

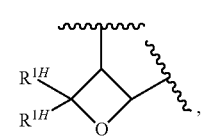

(C6)

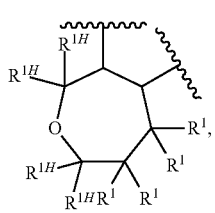

(C7)

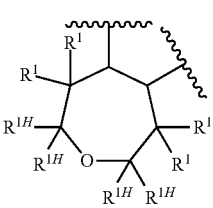

(C8)

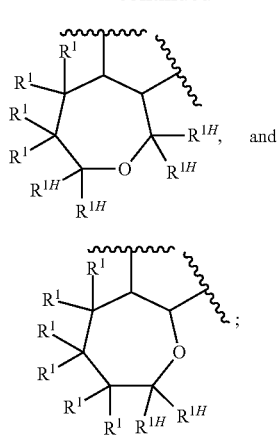

ring A is selected from the group consisting of aryl, monocyclic heteroaryl, monocyclic cycloalkyl, monocyclic cycloalkenyl, monocyclic heterocycloalkyl, monocyclic heterocycloalkenyl, and a multicyclic group;

each ring B (when present) is independently selected from the group consisting of aryl, monocyclic heteroaryl, monocyclic cycloalkyl, monocyclic cycloalkenyl, monocyclic heterocycloalkyl, monocyclic heterocycloalkenyl, and a multicyclic group;

-$L_1$- (when present) independently represents a bond or a divalent moiety selected from the group consisting of -alkyl-, -haloalkyl-, -heteroalkyl-, -alkenyl-, -alkynyl-, —N($R^6$)—, —NHC(O)—, —C(O)NH—, NHS(O)$_2$—, —S(O)$_2$NH—, —O—CH$_2$—, —CH$_2$—O—, —NHCH$_2$—, —CH$_2$NH—, and —CH(CF$_3$)NH—, —NHCH(CF$_3$)—;

m, n, and p are each independently selected integers, wherein:

m is 0 or more;

n is 0 or 1; and p is 0 or more, wherein the maximum value of m is the maximum number of available substitutable hydrogen atoms on ring A, and wherein the maximum value of p is the maximum number of available substitutable hydrogen atoms on ring B;

each $R^1$ (when present) is independently selected from the group consisting of: H, halogen, —OH, —CN, —SF$_5$, —OSF$_5$, —Si($R^5$)$_3$, —N($R^6$)$_2$, —NR$^7$C(O)R$^6$, —NR$^7$S(O)$_2$R$^6$, —NR$^7$C(O)N(R$^6$)$_2$, —NR$^7$C(O)OR$^6$, —OR$^6$, —SR$^6$, —C(O)R$^6$, —C(O)$_2$R$^6$, —C(O)N(R$^6$)$_2$, —P(O)(OR$^5$)$_2$, —P(O)(OR$^5$)(R$^5$), —S(O)R$^6$, —S(O)$_2$R$^6$, —S(O)$_2$N(R$^6$)$_2$, alkyl, haloalkyl, heteroalkyl, alkenyl, alkynyl, aryl, -alkyl-aryl, monocyclic heteroaryl, -alkyl-(monocyclic heteroaryl), monocyclic cycloalkyl, -alkyl-(monocyclic cycloalkyl), monocyclic heterocycloalkyl, a multicyclic group, and -alkyl-(multicyclic group);

wherein said alkyl, said haloalkyl, said heteroalkyl, said alkenyl, said alkynyl, said aryl, said -alkyl-aryl, said monocyclic heteroaryl, said -alkyl-(monocyclic heteroaryl), said monocyclic cycloalkyl, said -alkyl-(monocyclic cycloalkyl), said monocyclic heterocycloalkyl, said multicyclic group, and said -alkyl-(multicyclic group) of $R^1$ is optionally unsubstituted or substituted with one or more groups independently selected from $R^8$;

each $R^{1H}$ is independently selected from the group consisting of: H, alkyl, haloalkyl, heteroalkyl, alkenyl, alkynyl, aryl, -alkyl-aryl, monocyclic heteroaryl, -alkyl-(monocyclic heteroaryl), monocyclic cycloalkyl, -alkyl-(monocyclic cycloalkyl), monocyclic heterocycloalkyl, a multicyclic group, -alkyl-(multicyclic group), —C(O)R$^6$, —C(O)$_2$R$^6$, —C(O)N(R$^6$)$_2$, —P(O)(OR$^5$)$_2$, —P(O)(OR$^5$)(R$^5$), —S(O)R$^6$, —S(O)$_2$R$^6$, and —S(O)$_2$N(R$^6$)$_2$ wherein said alkyl, said haloalkyl, said heteroalkyl, said alkenyl, said alkynyl, said aryl, said -alkyl-aryl, said monocyclic heteroaryl, said -alkyl-(monocyclic heteroaryl), said monocyclic cycloalkyl, said -alkyl-(monocyclic cycloalkyl), said monocyclic heterocycloalkyl, said multicyclic group, and said -alkyl-(multicyclic group), of $R^{1H}$ is optionally unsubstituted or substituted with one or more groups independently selected from $R^8$;

each $R^2$ (when present) is independently selected from the group consisting of: halogen, —OH, —CN, —SF$_5$, —OSF$_5$, —NO$_2$, —Si($R^5$)$_3$, —P(O)(OR$^5$)$_2$, —P(O)(OR$^5$)(R$^5$), —N(R$^6$)$_2$, —NR$^7$C(O)R$^6$, —NR$^7$S(O)$_2$R$^6$, —NR$^7$C(O)N(R$^6$)$_2$, —NR$^7$C(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, alkyl, haloalkyl, heteroalkyl, alkenyl, alkynyl, cycloalkyl, -alkyl-cycloalkyl, aryl, -alkyl-aryl, heteroaryl, -alkyl-heteroaryl, and heterocycloalkyl, wherein said alkyl, haloalkyl, heteroalkyl, alkenyl, alkynyl, cycloalkyl, -alkyl-cycloalkyl, aryl, -alkyl-aryl, heteroaryl, -alkyl-heteroaryl, and heterocycloalkyl of $R^2$ are each optionally unsubstituted or substituted with one or more groups independently selected from $R^8$;

each $R^3$ (when present) is independently selected from the group consisting of: halogen, —OH, —CN, —SF$_5$, —OSF$_5$, —NO$_2$, —Si($R^5$)$_3$, —P(O)(OR$^5$)$_2$, —P(O)(OR$^5$)(R$^5$), —N(R$^6$)$_2$, —NR$^7$C(O)R$^6$, —NR$^7$S(O)$_2$R$^6$, —NR$^7$C(O)N(R$^6$)$_2$, —NR$^7$C(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, alkyl, haloalkyl, heteroalkyl, alkenyl, alkynyl, cycloalkyl, -alkyl-cycloalkyl, aryl, -alkyl-aryl, heteroaryl, -alkyl-heteroaryl, and heterocycloalkyl, wherein said alkyl, haloalkyl, heteroalkyl, alkenyl, alkynyl, cycloalkyl, -alkyl-cycloalkyl, aryl, -alkyl-aryl, heteroaryl, -alkyl-heteroaryl, and heterocycloalkyl of $R^2$ are each optionally unsubstituted or substituted with one or more groups independently selected from $R^8$;

$R^4$ is selected from the group consisting of H, halogen, optionally substituted alkyl, optionally substituted -alkyl-OH, optionally substituted heteroalkyl, optionally substituted -alkyl-cycloalkyl, optionally substituted -alkyl-aryl, and optionally substituted -alkyl-heteroaryl, wherein said optional substituents are each independently selected from $R^8$;

each $R^5$ (when present) is independently selected from the group consisting of H, alkyl, aryl, arylalkyl-, haloalkyl, cycloalkyl, -alkyl-cycloalkyl, heteroaryl, and heteroarylalkyl-;

each $R^6$ (when present) is independently selected from the group consisting of H, alkyl, -alkyl-OH, alkenyl, heteroalkyl, -heteroalkyl-OH, haloalkyl, -haloalkyl-OH, cycloalkyl, lower alkyl-substituted cycloalkyl, lower alkyl-substituted -alkyl-cycloalkyl, aryl, -alkyl-aryl, heteroaryl, and -alkyl-heteroaryl, wherein each said aryl, -alkyl-aryl, heteroaryl, and -alkyl-heteroaryl of $R^6$ is unsubstituted or substituted with one or more groups independently selected from halogen, alkyl, heteroalkyl, haloalkyl, alkoxy, heteroalkoxy, and haloalkoxy;

each R[7] (when present) is independently selected from the group consisting of H, alkyl, cycloalkyl, -alkyl-cycloalkyl, aryl, -alkyl-aryl, heteroaryl, and -alkyl-heteroaryl; and each R[8] (when present) is independently selected from the group consisting of halogen, —OH, —CN, —SF$_5$, —OSF$_5$, alkyl, alkoxy, haloalkyl, haloalkoxy, cycloalkyl, -alkyl-cycloalkyl, —O-cycloalkyl, —O-alkyl-cycloalkyl, heteroalkyl, —O-heteroalkyl, and -alkyl-OH;

wherein each said multicyclic group (when present) is selected from the group consisting of bicyclic aryl, bicyclic heteroaryl, bicyclic cycloalkyl, bicyclic cycloalkenyl, bicyclic heterocycloalkyl, bicyclic heterocycloalkenyl, tricyclic aryl, tricyclic heteroaryl, tricyclic cycloalkyl, tricyclic cycloalkenyl, tricyclic heterocycloalkyl, and tricyclic heterocycloalkenyl.

2. A compound of claim 1, or a tautomer thereof, or a stereoisomer of said compound or said tautomer, or a pharmaceutically acceptable salt of said compound, said tautomer, or said stereoisomer, wherein:

R[4] is H.

3. A compound of claim 2, or a tautomer thereof, or a stereoisomer of said compound or said tautomer, or a pharmaceutically acceptable salt of said compound, said tautomer, or said stereoisomer, wherein:

each R[1H] is selected from the group consisting of H, methyl, cyclopropyl, —CH$_2$-cyclopropyl, —CH$_2$OCH$_3$, trifluoromethyl, —CH$_2$F, and —CHF$_2$.

4. A compound of claim 3, or a tautomer thereof, or a stereoisomer of said compound or said tautomer, or a pharmaceutically acceptable salt of said compound, said tautomer, or said stereoisomer, wherein:

n is 1;

ring A is selected from the group consisting of phenyl, thienyl, and pyridyl;

m is 0 or 1;

each R[2] group (when present) is independently selected from the group consisting of halogen, —CN, —SF$_5$, —NHCH$_3$, —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, and OCHF$_2$ -L$_1$- is a bond or a divalent moiety selected from the group consisting of —NHC(O)— and —C(O)NH—;

ring B is selected from the group consisting of phenyl, monocyclic heterocycloalkyl, and monocyclic heteroaryl;

p is 0 or more; and each R[3] group (when present) is independently selected from the group consisting of halogen, —OH, —CN, —SF$_5$, —NH$_2$, —NH(CH$_3$), —N(CH$_3$)$_2$, —OCH$_3$, —OCH$_2$CH$_3$, O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, —OCH$_2$CF$_3$, and —OCHF$_2$.

5. A compound of claim 3, or a tautomer thereof, or a stereoisomer of said compound or said tautomer, or a pharmaceutically acceptable salt of said compound, said tautomer, or said stereoisomer, wherein:

n is 0 and the moiety

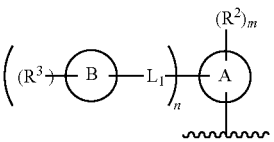

has the form

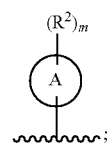

n is 0;

ring A is phenyl;

m is 0 to 4; and each R[2] group (when present) is independently selected from the group consisting of halogen, —CN, —SF$_5$, —NH$_2$, —NHCH$_3$, —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, and —OCHF$_2$.

6. A compound of claim 1, or a tautomer thereof, or a stereoisomer of said compound or said tautomer, or a pharmaceutically acceptable salt of said compound, said tautomer, or said stereoisomer, said compound selected from the group consisting of:

| Example |
|---|
| 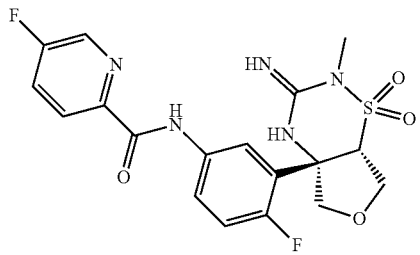 |
| 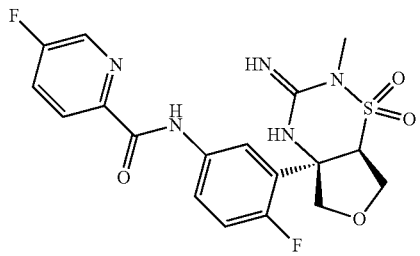 [SMILES: CN1C(=N)N[C@]2(c3cc(NC(=O)c4ccc(F)cn4)ccc3F)COC[C@@H]2S1(=O)=O] |
| 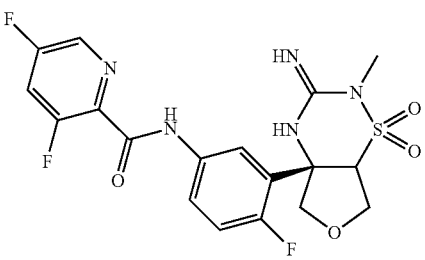 [SMILES: CN1C(=N)N[C@@]2(c3cc(NC(=O)c4ncc(F)cc4F)ccc3F)COCC2S1(=O)=O] |

| Example | Example |
|---|---|
| 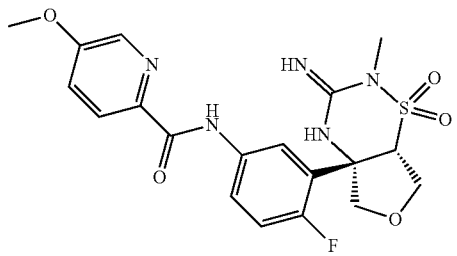 [SMILES: COc1ccc(C(=O)Nc2ccc(F)c([C@]34COC[C@H]3S(=O)(=O)N(C)C(=N)N4)c2)nc1] | 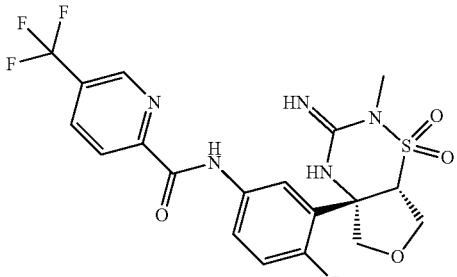 |
| 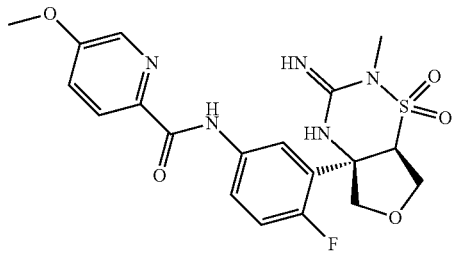 [SMILES: COc1ccc(C(=O)Nc2ccc(F)c([C@@]34COC[C@@H]3S(=O)(=O)N(C)C(=N)N4)c2)nc1] | 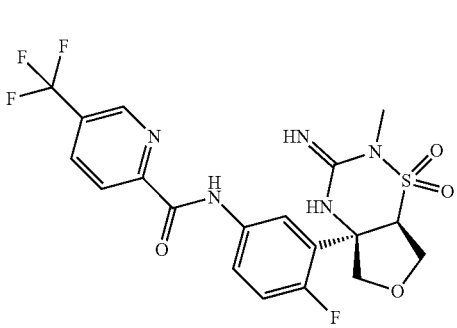 |
| 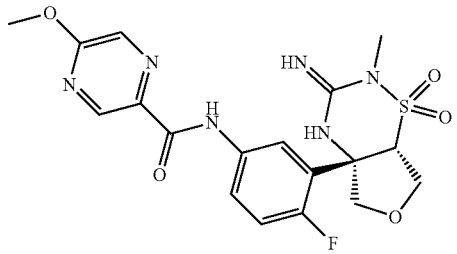 | 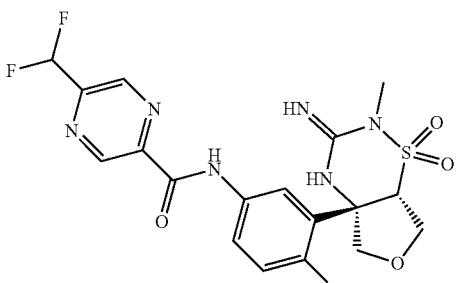 |
| 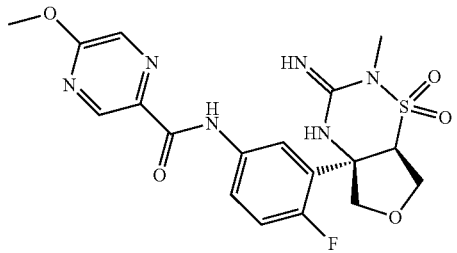 [SMILES: COc1cnc(C(=O)Nc2ccc(F)c([C@@]34COC[C@@H]3S(=O)(=O)N(C)C(=N)N4)c2)cn1] | 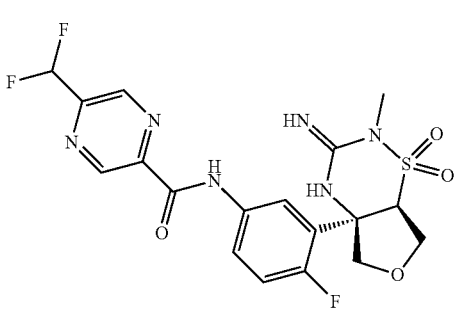 |
| 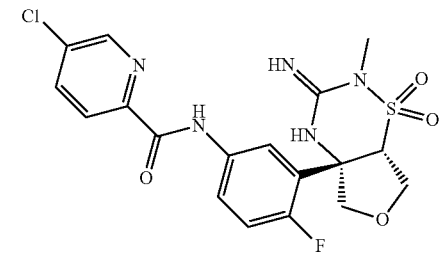 [SMILES: CN1C(=N)N[C@@]2(c3cc(NC(=O)c4ccc(Cl)cn4)ccc3F)COC[C@H]2S1(=O)=O] | 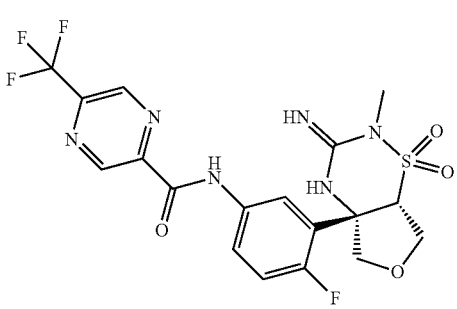 |
| 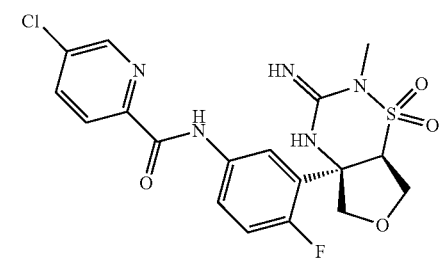 [SMILES: CN1C(=N)N[C@]2(c3cc(NC(=O)c4ccc(Cl)cn4)ccc3F)COC[C@@H]2S1(=O)=O] | |

| 171 -continued | 172 -continued |
|---|---|
| Example | Example |
| 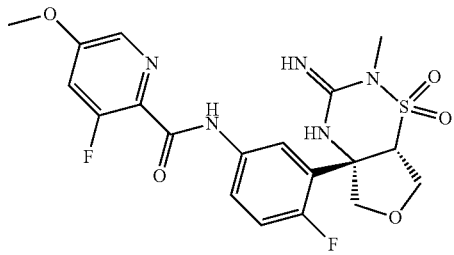 [SMILES: COc1cnc(C(=O)Nc2ccc(F)c([C@]34COC[C@H]3S(=O)(=O)N(C)C(=N)N4)c2)c(F)c1]<br>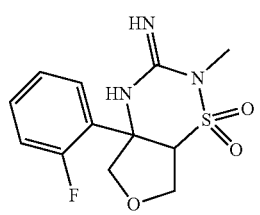 [SMILES: CN1C(=N)NC2(c3ccccc3F)COCC2S1(=O)=O]<br>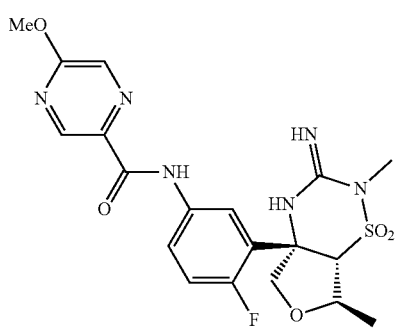<br>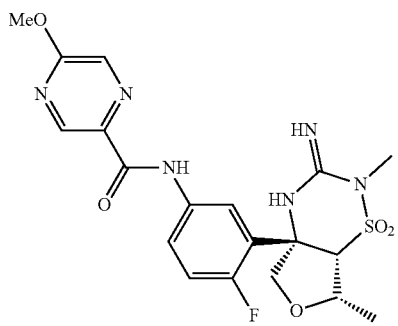 [SMILES: COc1cnc(C(=O)Nc2ccc(F)c([C@]34CO[C@@H](C)[C@H]3S(=O)(=O)N(C)C(=N)N4)c2)cn1]<br>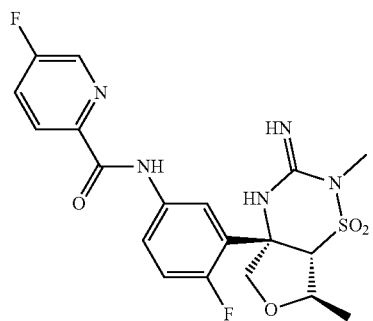 [SMILES: C[C@H]1OC[C@]2(c3cc(NC(=O)c4ccc(F)cn4)ccc3F)NC(=N)N(C)S(=O)(=O)[C@H]12] | 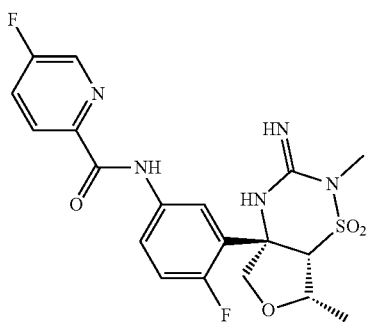 [SMILES: C[C@@H]1OC[C@]2(c3cc(NC(=O)c4ccc(F)cn4)ccc3F)NC(=N)N(C)S(=O)(=O)[C@H]12]<br>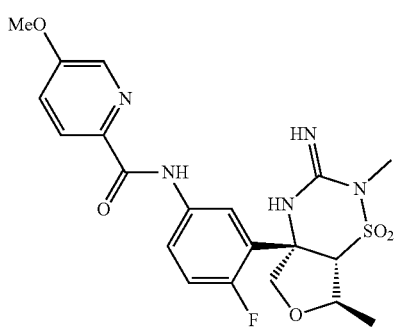 [SMILES: COc1ccc(C(=O)Nc2ccc(F)c([C@]34CO[C@H](C)[C@H]3S(=O)(=O)N(C)C(=N)N4)c2)nc1]<br>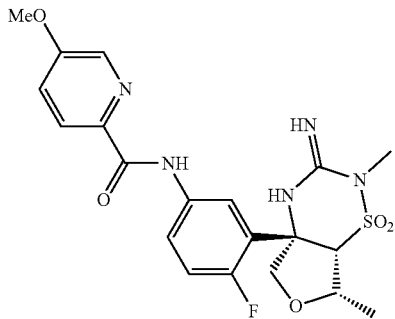 [SMILES: COc1ccc(C(=O)Nc2ccc(F)c([C@]34CO[C@@H](C)[C@H]3S(=O)(=O)N(C)C(=N)N4)c2)nc1]<br>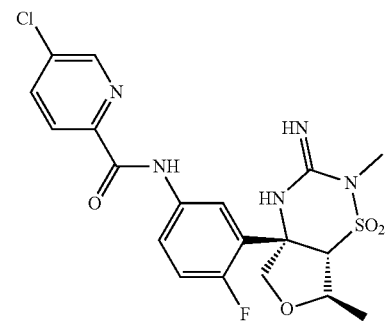 [SMILES: C[C@H]1OC[C@]2(c3cc(NC(=O)c4ccc(Cl)cn4)ccc3F)NC(=N)N(C)S(=O)(=O)[C@H]12] |

| Example | Example |
|---|---|
| 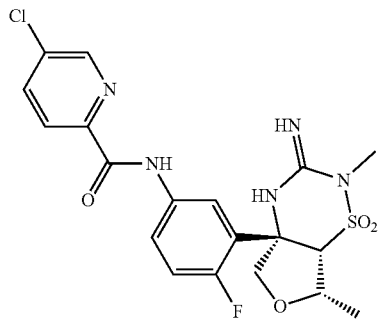 [SMILES: C[C@@H]1OC[C@]2(c3cc(NC(=O)c4ccc(Cl)cn4)ccc3F)NC(=N)N(C)S(=O)(=O)[C@H]12] | 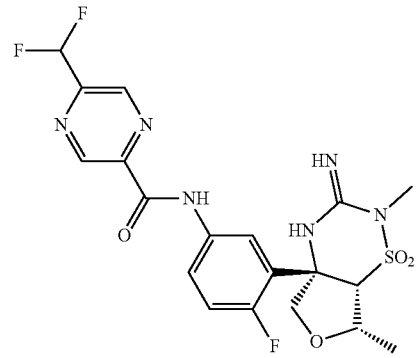 [SMILES: C[C@@H]1OC[C@]2(c3cc(NC(=O)c4cnc(C(F)F)cn4)ccc3F)NC(=N)N(C)S(=O)(=O)[C@H]12] |
| 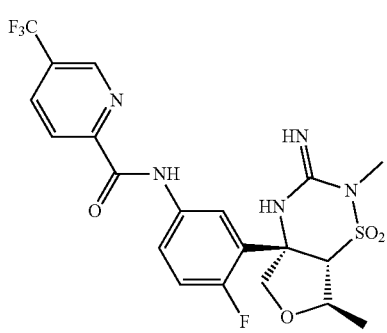 | 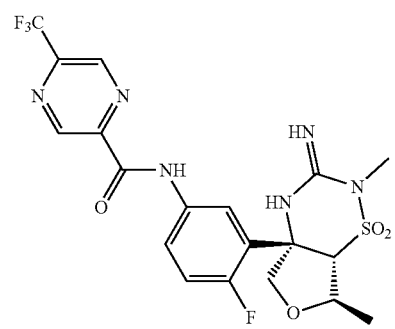 |
| 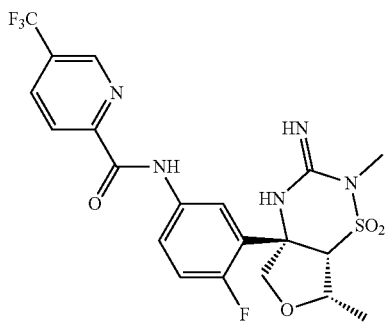 | 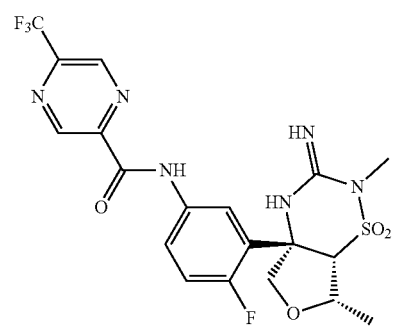 |
| 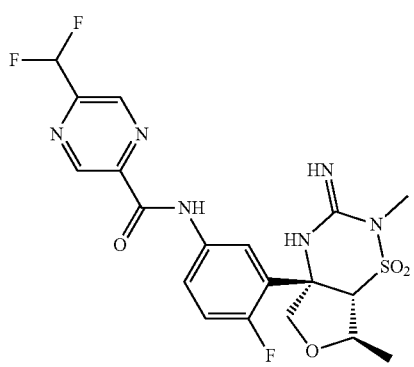 | 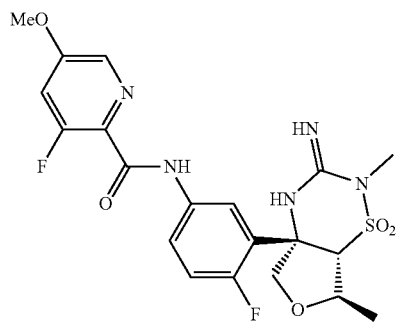 |

-continued
| Example |
|---|
| 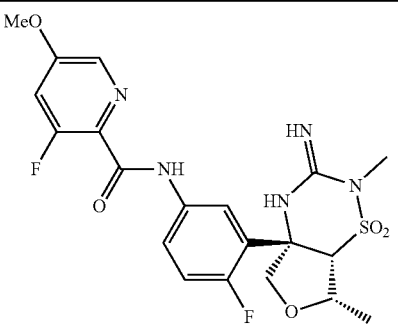 |
| 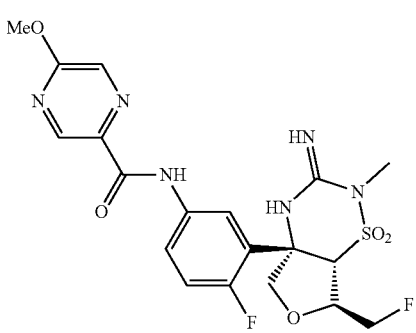 |
| 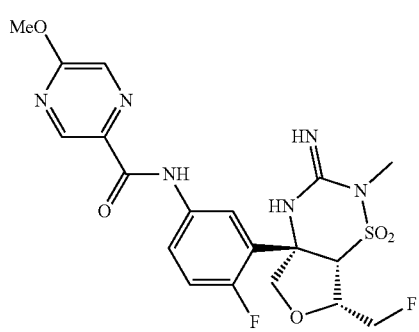 [SMILES: COc1cnc(C(=O)Nc2ccc(F)c([C@]34CO[C@@H](CF)[C@H]3S(=O)(=O)N(C)C(=N)N4)c2)cn1] |
| 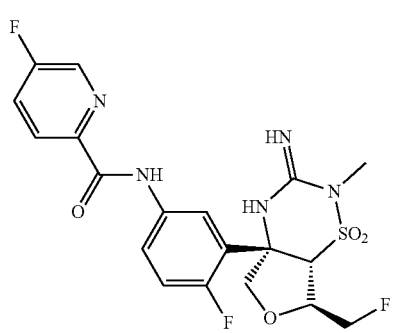 [SMILES: CN1C(=N)N[C@@]2(c3cc(NC(=O)c4ccc(F)cn4)ccc3F)CO[C@H](CF)[C@H]2S1(=O)=O] |
| 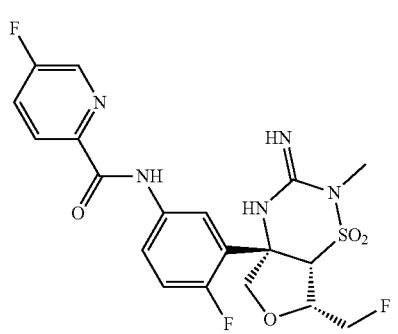 [SMILES: CN1C(=N)N[C@@]2(c3cc(NC(=O)c4ccc(F)cn4)ccc3F)CO[C@@H](CF)[C@H]2S1(=O)=O] |
-continued
| Example |
|---|
| 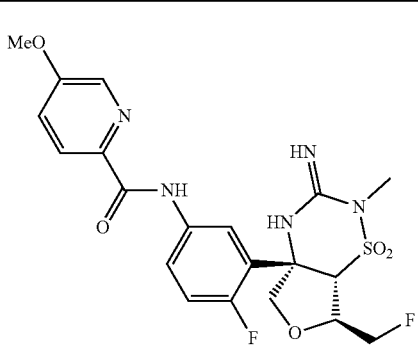 |
| 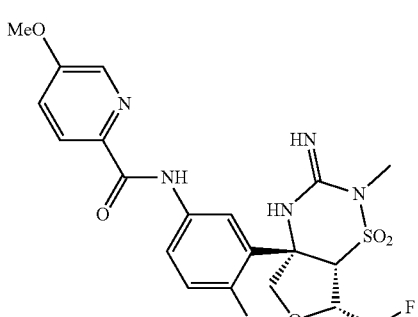 |
| 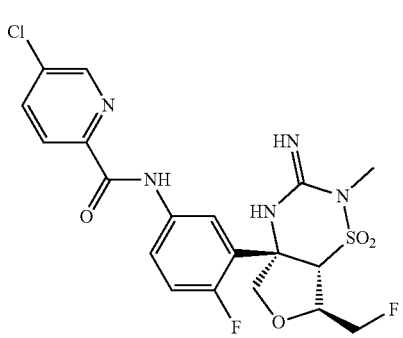 [SMILES: CN1C(=N)N[C@@]2(c3cc(NC(=O)c4ccc(Cl)cn4)ccc3F)CO[C@H](CF)[C@H]2S1(=O)=O] |
| 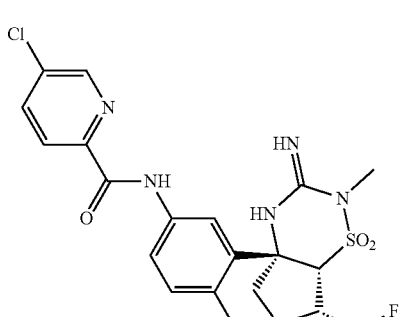 |

-continued
| Example |
|---|
| 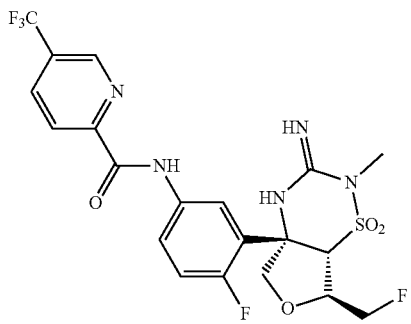 |
| 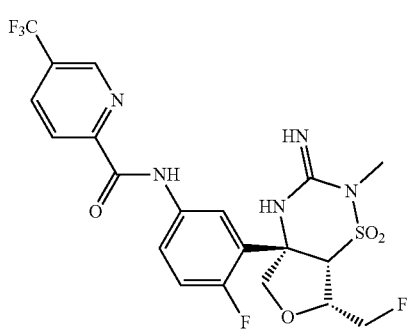 [SMILES: CN1C(=N)N[C@@]2(c3cc(NC(=O)c4ccc(C(F)(F)F)cn4)ccc3F)CO[C@@H](CF)[C@H]2S1(=O)=O] |
| 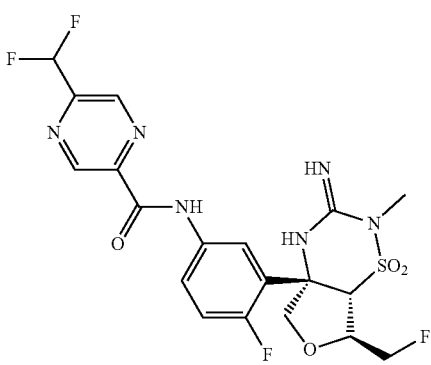 [SMILES: CN1C(=N)N[C@@]2(c3cc(NC(=O)c4cnc(C(F)F)cn4)ccc3F)CO[C@H](CF)[C@H]2S1(=O)=O] |
| 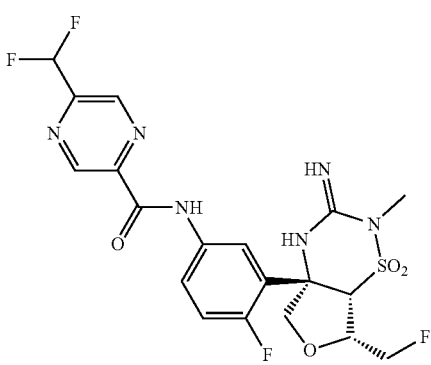 [SMILES: CN1C(=N)N[C@@]2(c3cc(NC(=O)c4cnc(C(F)F)cn4)ccc3F)CO[C@@H](CF)[C@H]2S1(=O)=O] |
-continued
| Example |
|---|
| 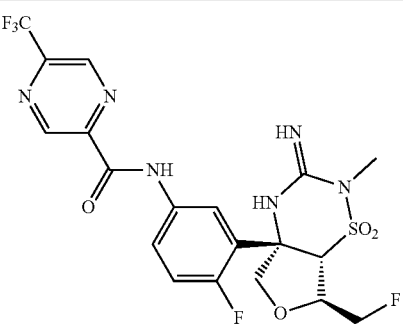 |
| 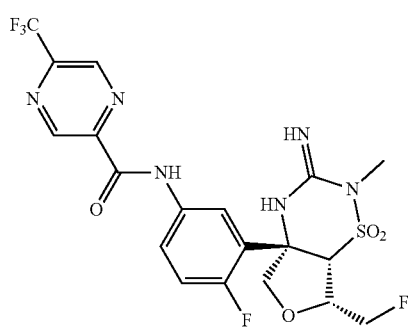 |
| 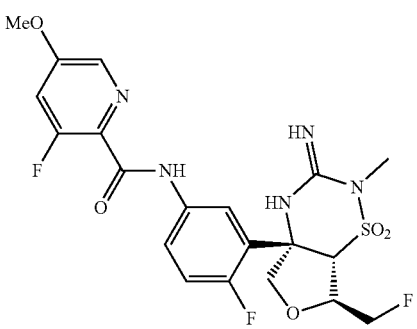 [SMILES: COc1cnc(C(=O)Nc2ccc(F)c([C@]34CO[C@H](CF)[C@H]3S(=O)(=O)N(C)C(=N)N4)c2)c(F)c1] |
| 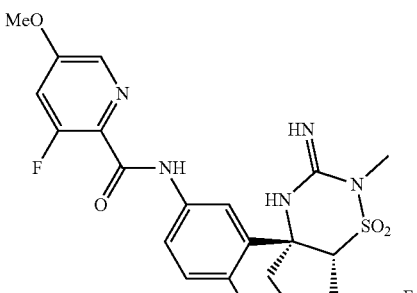 |
| 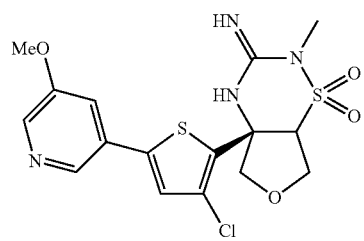 [SMILES: COc1cncc(-c2cc(Cl)c([C@]34COCC3S(=O)(=O)N(C)C(=N)N4)s2)c1] |

| 179 -continued | 180 -continued |
| --- | --- |
| Example | Example |
| 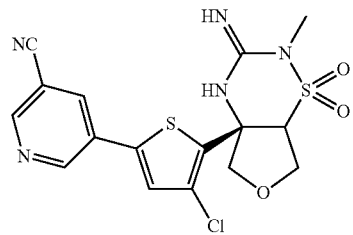 | 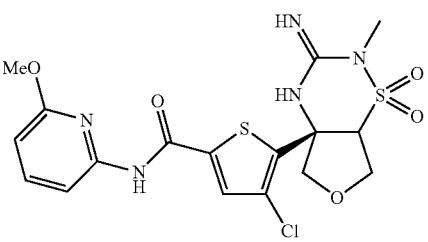 |
| 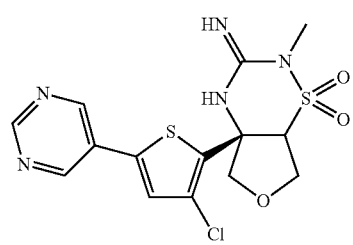 [SMILES: CN1C(=N)N[C@@]2(c3sc(-c4cncnc4)cc3Cl)COCC2S1(=O)=O] | 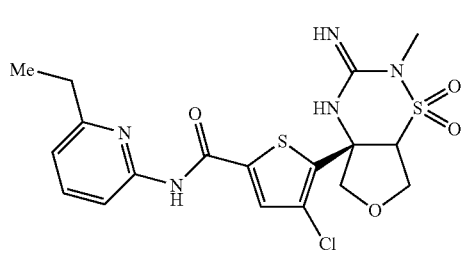 |
| 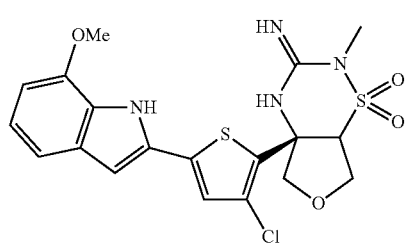 [SMILES: COc1cccc2cc(-c3cc(Cl)c([C@]45COCC4S(=O)(=O)N(C)C(=N)N5)s3)[nH]c12] | 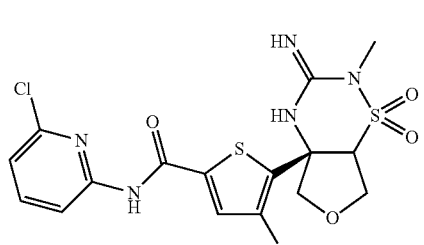 |
| 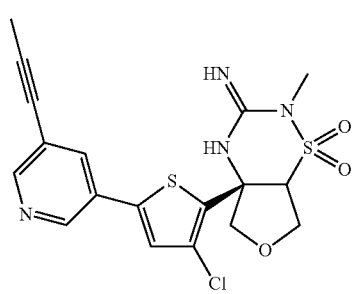 [SMILES: CC#Cc1cncc(-c2cc(Cl)c([C@]34COCC3S(=O)(=O)N(C)C(=N)N4)s2)c1] | 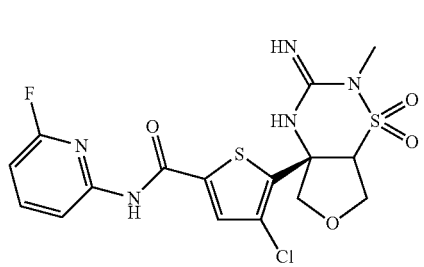 |
| 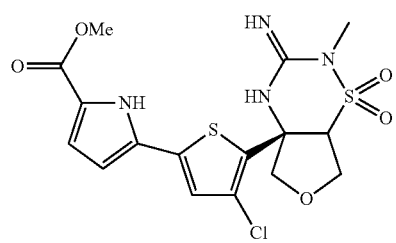 [SMILES: COC(=O)c1ccc(-c2cc(Cl)c([C@]34COCC3S(=O)(=O)N(C)C(=N)N4)s2)[nH]1] | 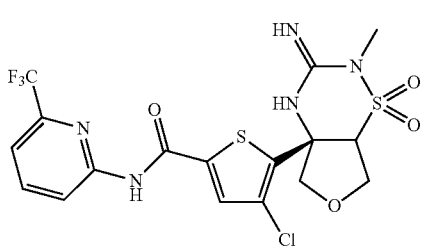 |
| 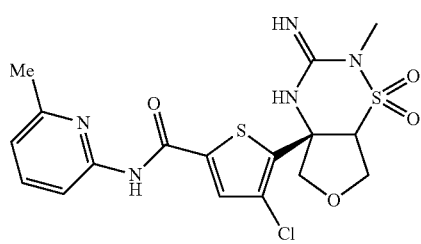 [SMILES: CN1C(=N)N[C@@]2(c3sc(C(=O)Nc4cccc(Cl)n4)cc3Cl)COCC2S1(=O)=O] | 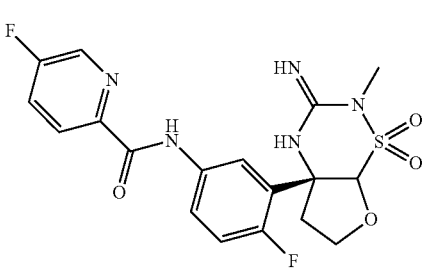 [SMILES: CN1C(=N)N[C@@]2(c3cc(NC(=O)c4ccc(F)cn4)ccc3F)CCOC2S1(=O)=O] |

| Example | Example |
|---|---|
| 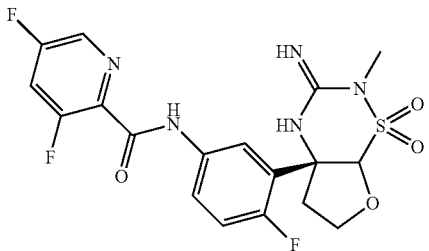 | 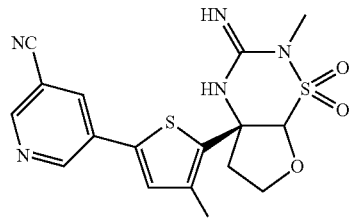 |
| 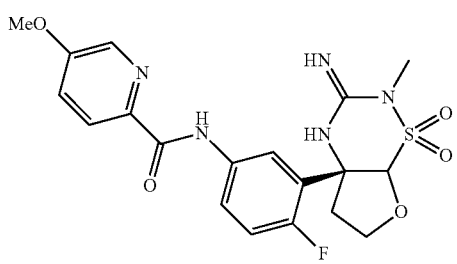 | 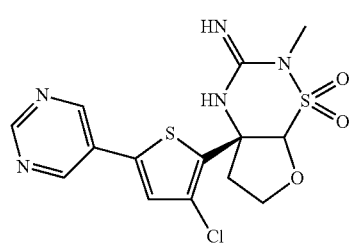 |
| 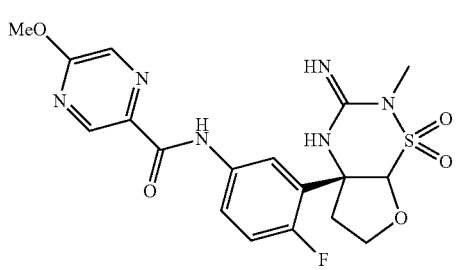 | 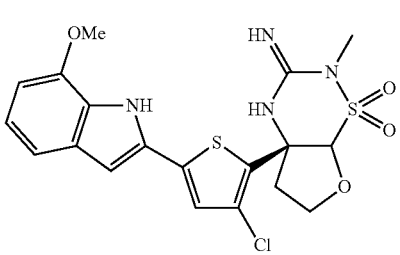 [SMILES: COc1cccc2cc(-c3cc(Cl)c([C@]45CCOC4S(=O)(=O)N(C)C(=N)N5)s3)[nH]c12] |
| 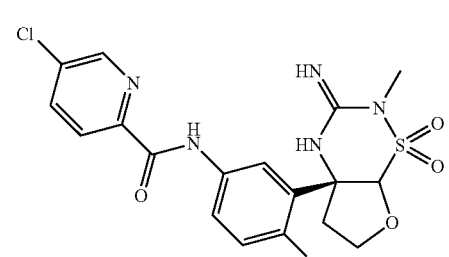 | 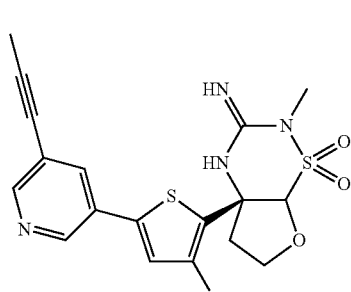 |
| 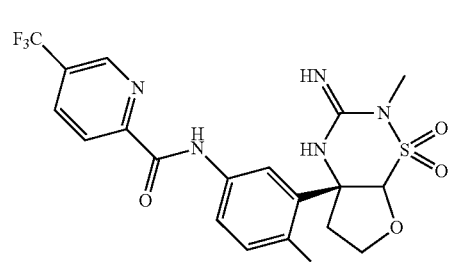 | 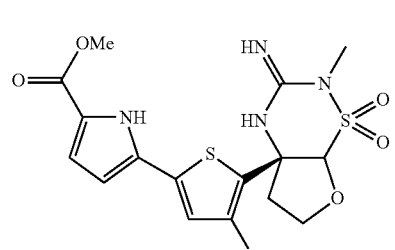 |
| 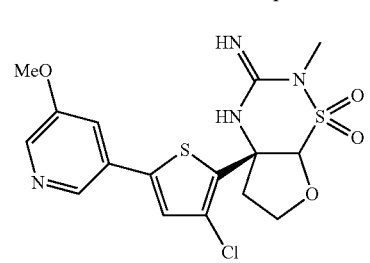 | 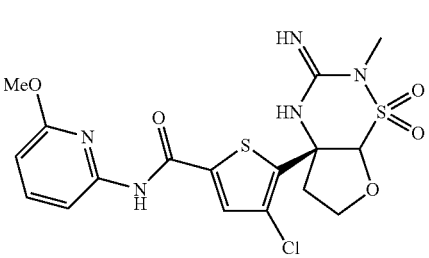 [SMILES: COc1cccc(NC(=O)c2cc(Cl)c([C@]34CCOC3S(=O)(=O)N(C)C(=N)N4)s2)n1] |

| 183 -continued | 184 -continued |
|---|---|
| Example | Example |
| 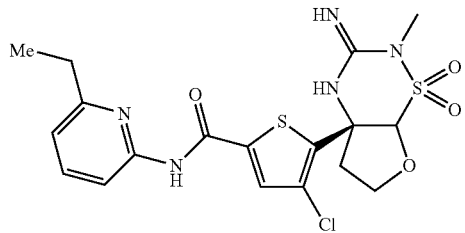 | 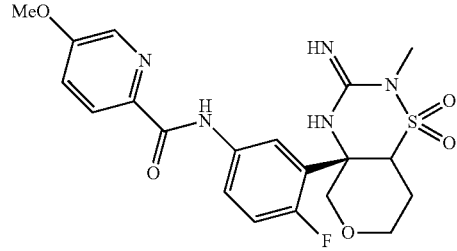 |
| 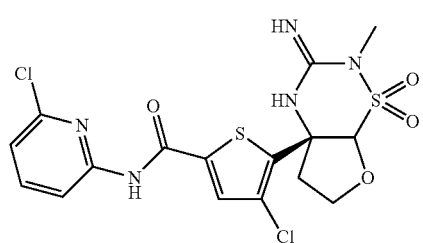 [SMILES: CN1C(=N)N[C@@]2(c3sc(C(=O)Nc4cccc(Cl)n4)cc3Cl)CCOC2S1(=O)=O] | 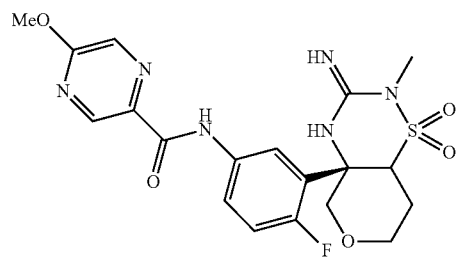 |
| 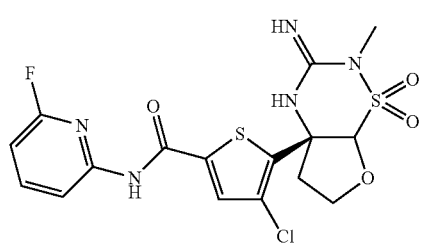 [SMILES: CN1C(=N)N[C@@]2(c3sc(C(=O)Nc4cccc(F)n4)cc3Cl)CCOC2S1(=O)=O] | 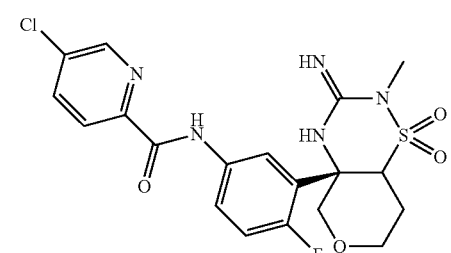 |
| 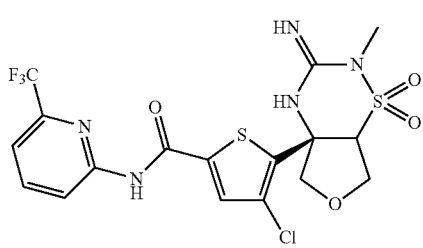 [SMILES: CN1C(=N)N[C@@]2(c3sc(C(=O)Nc4cccc(C(F)(F)F)n4)cc3Cl)COCC2S1(=O)=O] | 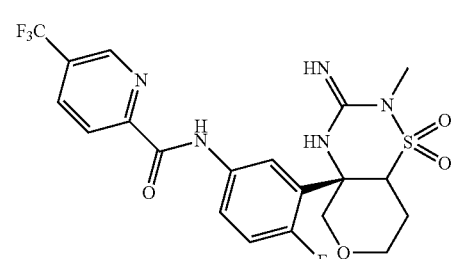 |
| 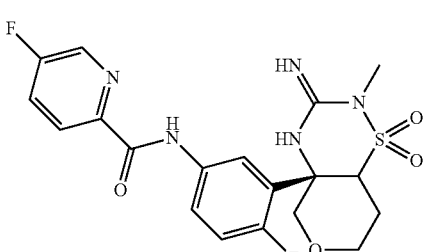 | 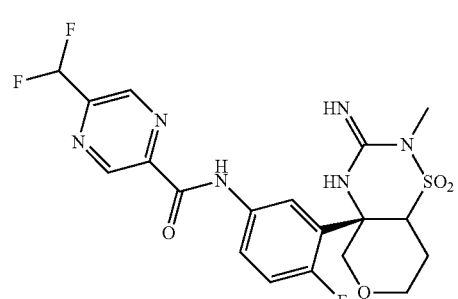 |
| 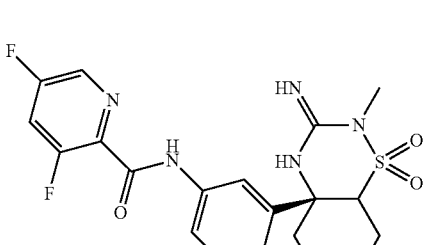 | 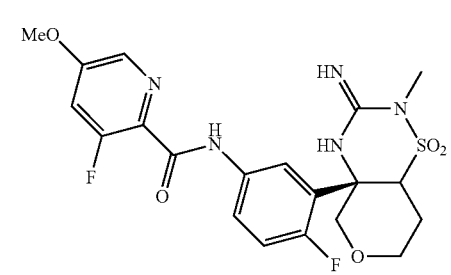 [SMILES: COc1cnc(C(=O)Nc2ccc(F)c([C@]34COCCC3S(=O)(=O)N(C)C(=N)N4)c2)c(F)c1] |

| 185 -continued | 186 -continued |
|---|---|
| Example | Example |
| 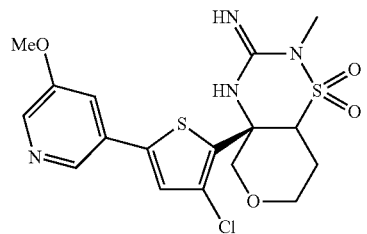 [SMILES: COc1cncc(-c2cc(Cl)c([C@]34COCCC3S(=O)(=O)N(C)C(=N)N4)s2)c1] | 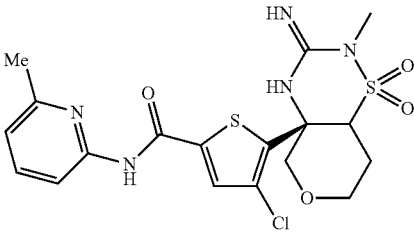 |
| 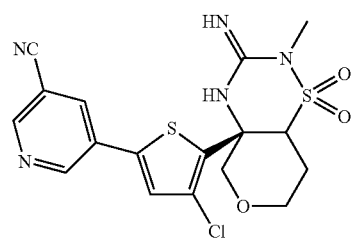 | 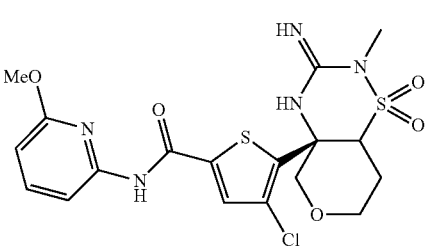 |
| 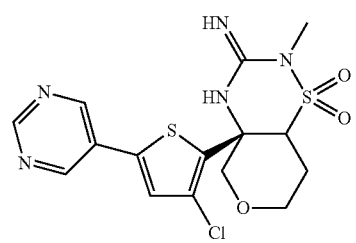 [SMILES: CN1C(=N)N[C@@]2(c3sc(-c4cncnc4)cc3Cl)COCCC2S1(=O)=O] | 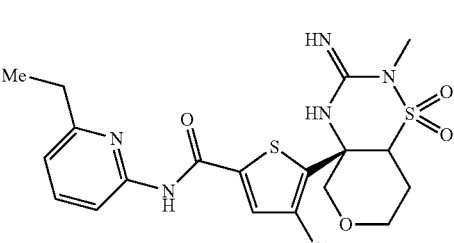 |
| 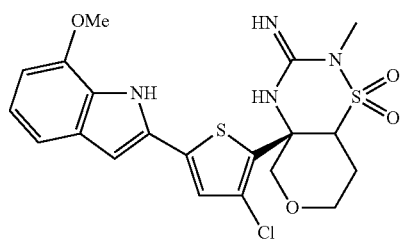 [SMILES: COc1cccc2cc(-c3cc(Cl)c([C@]45COCCC4S(=O)(=O)N(C)C(=N)N5)s3)[nH]c12] | 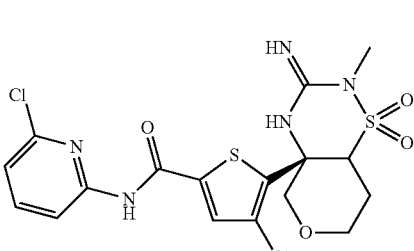 |
| 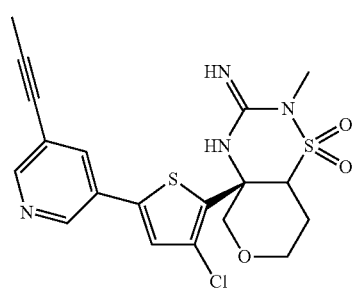 [SMILES: CC#Cc1cncc(-c2cc(Cl)c([C@]34COCCC3S(=O)(=O)N(C)C(=N)N4)s2)c1] | 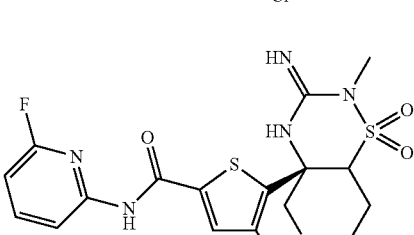 |
| 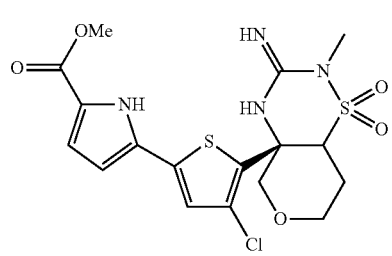 [SMILES: COC(=O)c1ccc(-c2cc(Cl)c([C@]34COCCC3S(=O)(=O)N(C)C(=N)N4)s2)[nH]1] | 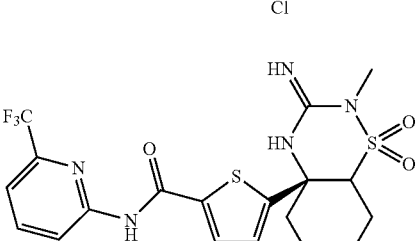 |

| Example |
|---|
| 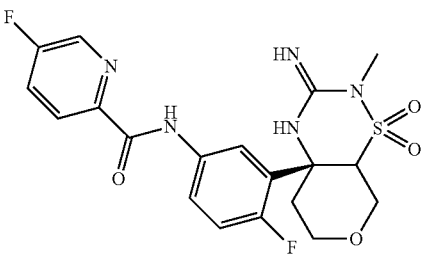 |
| 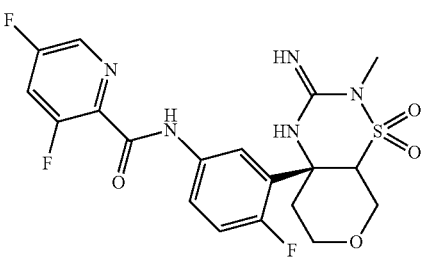 [SMILES: CN1C(=N)N[C@@]2(c3cc(NC(=O)c4ncc(F)cc4F)ccc3F)CCOCC2S1(=O)=O] |
| 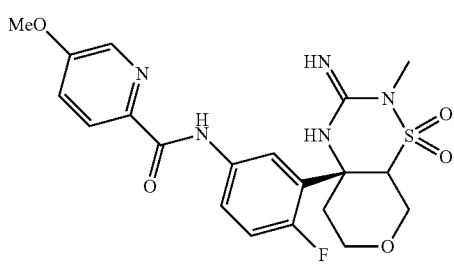 [SMILES: COc1ccc(C(=O)Nc2ccc(F)c([C@]34CCOCC3S(=O)(=O)N(C)C(=N)N4)c2)nc1] |
| 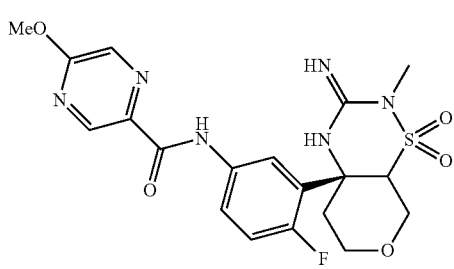 [SMILES: COc1cnc(C(=O)Nc2ccc(F)c([C@]34CCOCC3S(=O)(=O)N(C)C(=N)N4)c2)cn1] |
| 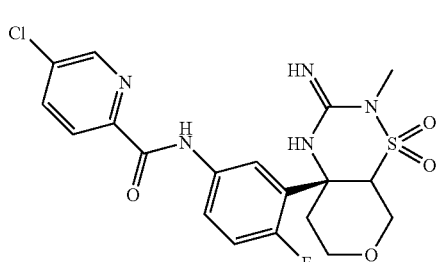 |
| 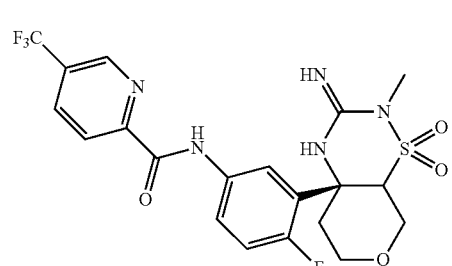 |
| Example |
|---|
| 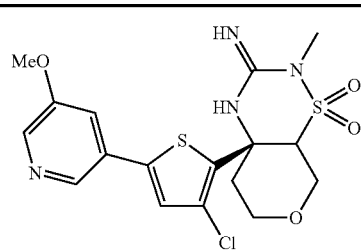 |
| 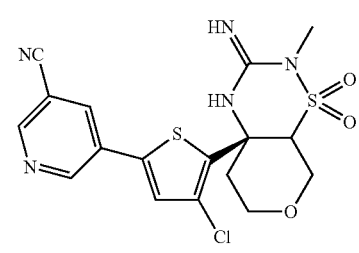 [SMILES: CN1C(=N)N[C@@]2(c3sc(-c4cncc(C#N)c4)cc3Cl)CCOCC2S1(=O)=O] |
| 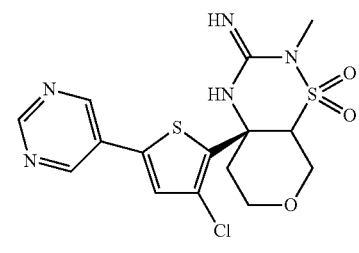 [SMILES: CN1C(=N)N[C@@]2(c3sc(-c4cncnc4)cc3Cl)CCOCC2S1(=O)=O] |
| 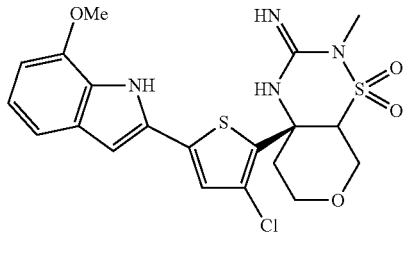 [SMILES: COc1cccc2cc(-c3cc(Cl)c([C@]45CCOCC4S(=O)(=O)N(C)C(=N)N5)s3)[nH]c12] |
| 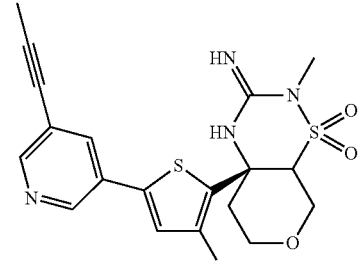 |
| 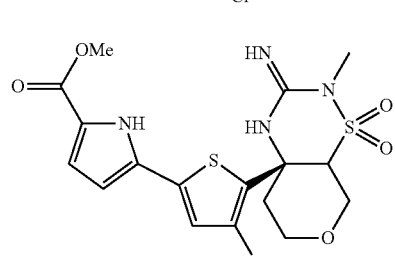 |

| Example | | Example |
|---|---|---|
| 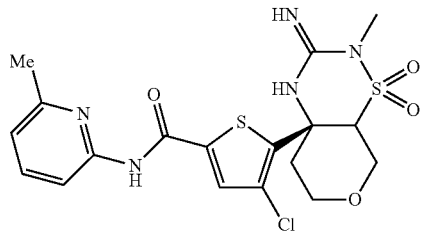 [SMILES: Cc1cccc(NC(=O)c2cc(Cl)c([C@]34CCOCC3S(=O)(=O)N(C)C(=N)N4)s2)n1] | 5 | 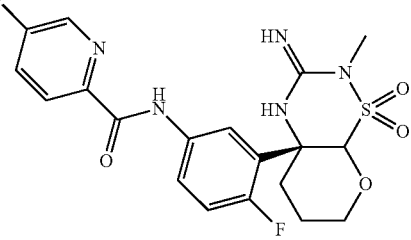 |
| 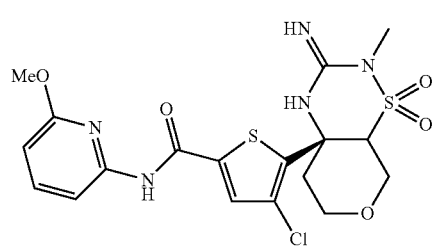 [SMILES: COc1cccc(NC(=O)c2cc(Cl)c([C@]34CCOCC3S(=O)(=O)N(C)C(=N)N4)s2)n1] | 10 15 20 | 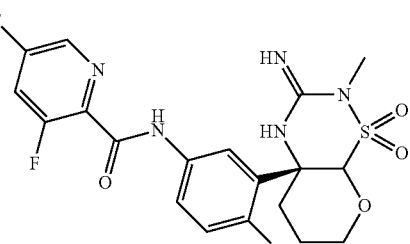 |
| 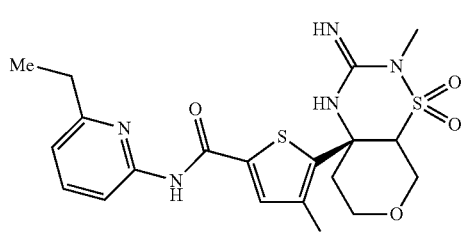 | 25 30 | 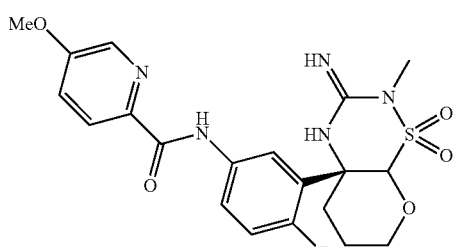 |
| 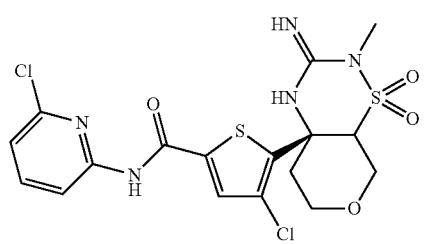 | 35 40 | 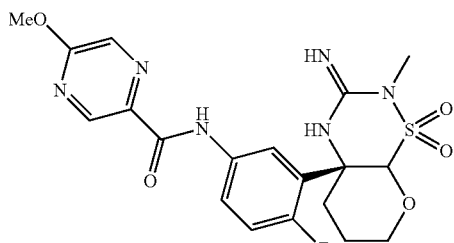 |
| 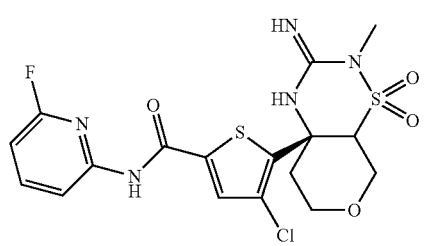 [SMILES: CN1C(=N)N[C@@]2(c3sc(C(=O)Nc4cccc(F)n4)cc3Cl)CCOCC2S1(=O)=O] | 45 50 55 | 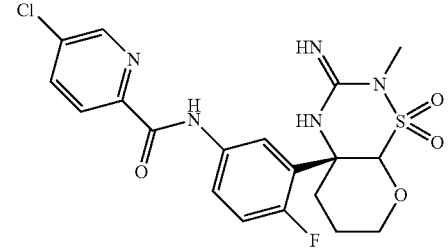 |
| 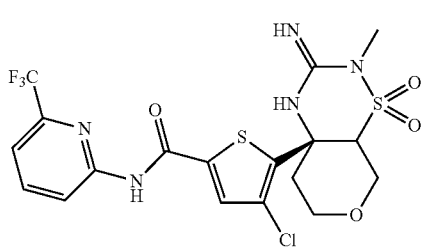 | 60 65 | 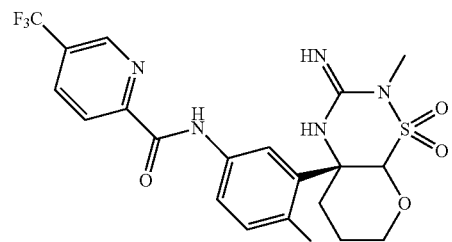 |

| Example |
|---|
| 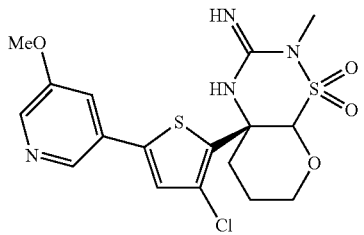 [SMILES: COc1cncc(-c2cc(Cl)c([C@]34CCCOC3S(=O)(=O)N(C)C(=N)N4)s2)c1] |
| 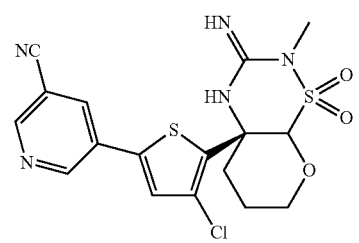 [SMILES: CN1C(=N)N[C@@]2(c3sc(-c4cncc(C#N)c4)cc3Cl)CCCOC2S1(=O)=O] |
| 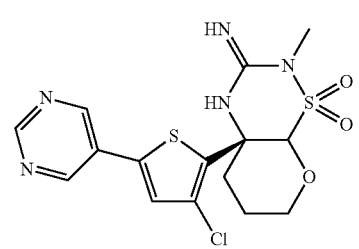 [SMILES: CN1C(=N)N[C@@]2(c3sc(-c4cncnc4)cc3Cl)CCCOC2S1(=O)=O] |
| 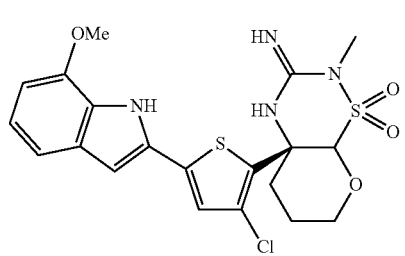 [SMILES: COc1cccc2cc(-c3cc(Cl)c([C@]45CCCOC4S(=O)(=O)N(C)C(=N)N5)s3)[nH]c12] |
| 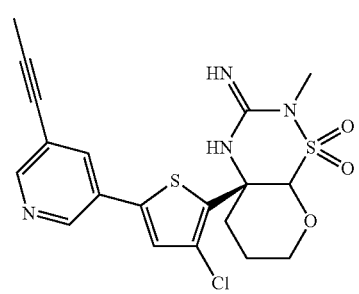 [SMILES: CC#Cc1cncc(-c2cc(Cl)c([C@]34CCCOC3S(=O)(=O)N(C)C(=N)N4)s2)c1] |
| 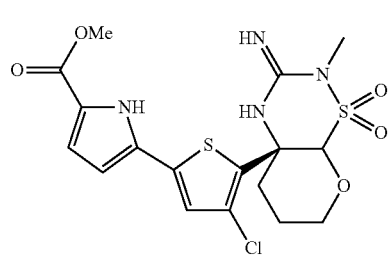 [SMILES: COC(=O)c1ccc(-c2cc(Cl)c([C@]34CCCOC3S(=O)(=O)N(C)C(=N)N4)s2)[nH]1] |
| Example |
|---|
| 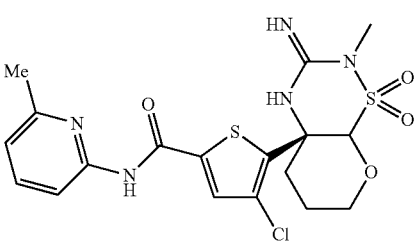 [SMILES: Cc1cccc(NC(=O)c2cc(Cl)c([C@]34CCCOC3S(=O)(=O)N(C)C(=N)N4)s2)n1] |
| 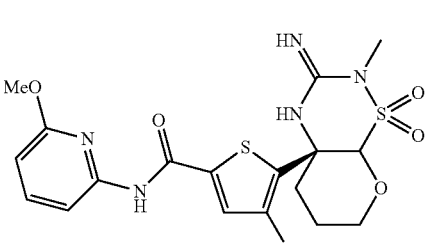 |
| 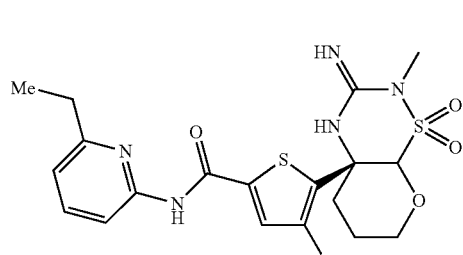 |
| 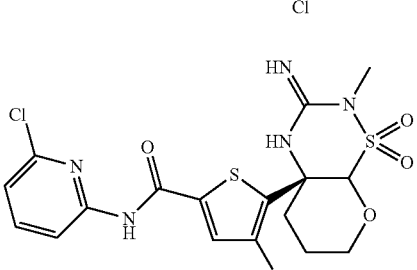 |
| 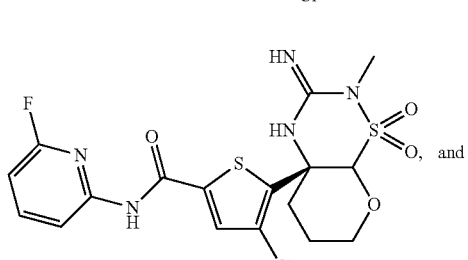, and |
| 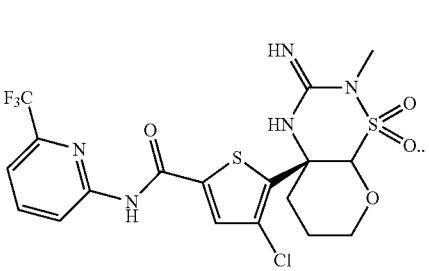 [SMILES: CN1C(=N)N[C@@]2(c3sc(C(=O)Nc4cccc(C(F)(F)F)n4)cc3Cl)CCCOC2S1(=O)=O] |

7. A compound of claim 1, or a tautomer thereof, or a stereoisomer of said compound or said tautomer, or a pharmaceutically acceptable salt of said compound, said tautomer, or said stereoisomer, said compound selected from the group consisting of:
| Example |
|---|
| 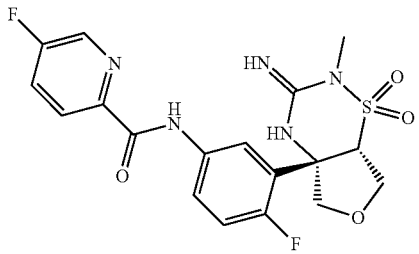 [SMILES: CN1C(=N)N[C@@]2(c3cc(NC(=O)c4ccc(F)cn4)ccc3F)COC[C@H]2S1(=O)=O] |
| 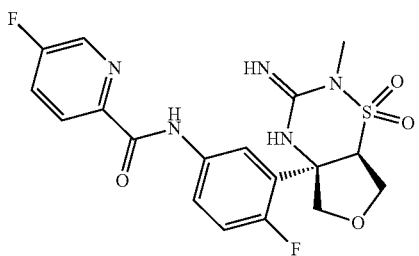 [SMILES: CN1C(=N)N[C@]2(c3cc(NC(=O)c4ccc(F)cn4)ccc3F)COC[C@@H]2S1(=O)=O] |
| 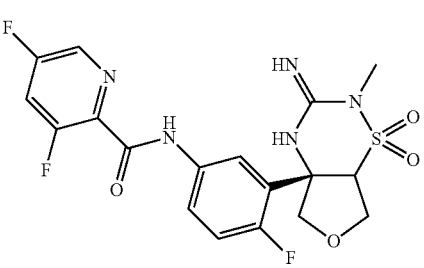 [SMILES: CN1C(=N)N[C@@]2(c3cc(NC(=O)c4ncc(F)cc4F)ccc3F)COCC2S1(=O)=O] |
| 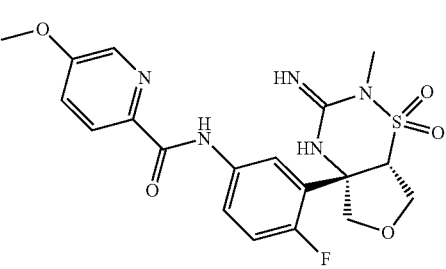 [SMILES: COc1ccc(C(=O)Nc2ccc(F)c([C@]34COC[C@H]3S(=O)(=O)N(C)C(=N)N4)c2)nc1] |
| 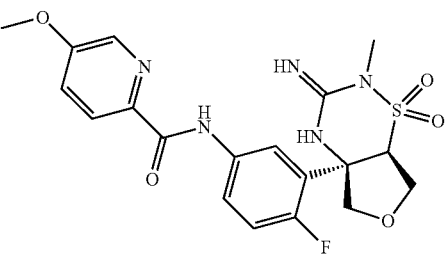 [SMILES: COc1ccc(C(=O)Nc2ccc(F)c([C@@]34COC[C@@H]3S(=O)(=O)N(C)C(=N)N4)c2)nc1] |
-continued
| Example |
|---|
| 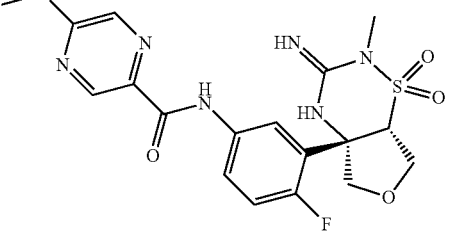 |
| 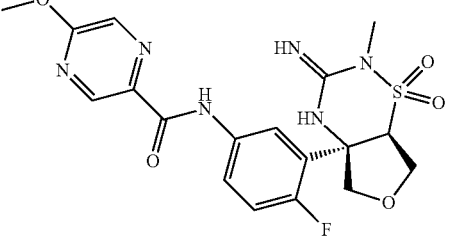 |
| 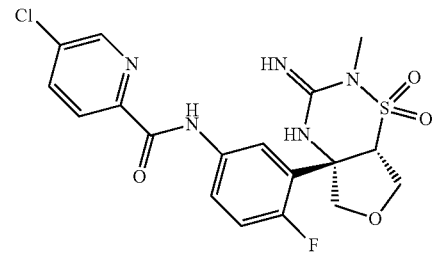 [SMILES: CN1C(=N)N[C@@]2(c3cc(NC(=O)c4ccc(Cl)cn4)ccc3F)COC[C@H]2S1(=O)=O] |
| 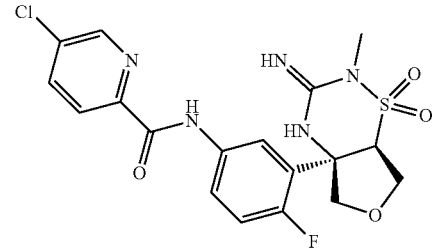 [SMILES: CN1C(=N)N[C@]2(c3cc(NC(=O)c4ccc(Cl)cn4)ccc3F)COC[C@@H]2S1(=O)=O] |
| 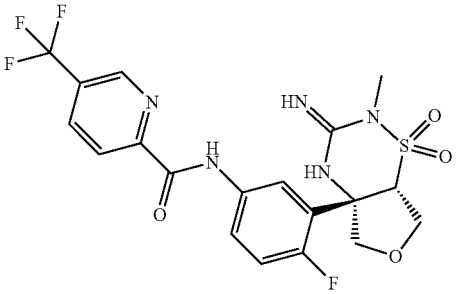 [SMILES: CN1C(=N)N[C@@]2(c3cc(NC(=O)c4ccc(C(F)(F)F)cn4)ccc3F)COC[C@H]2S1(=O)=O] |

| Example | Example |
|---|---|
| 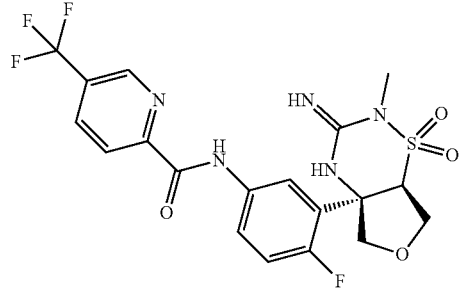 [SMILES: CN1C(=N)N[C@]2(c3cc(NC(=O)c4ccc(C(F)(F)F)cn4)ccc3F)COC[C@@H]2S1(=O)=O] | 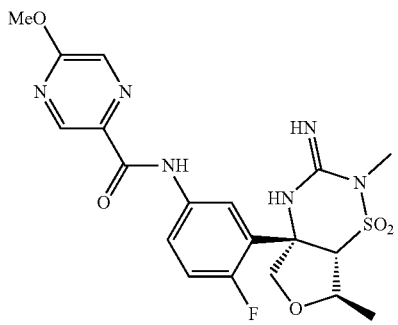 |
| 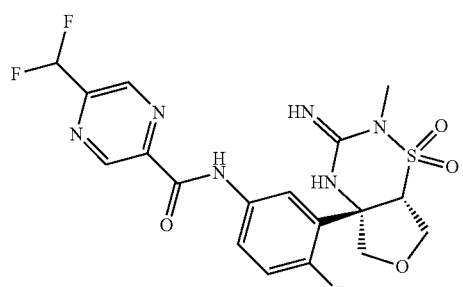 | 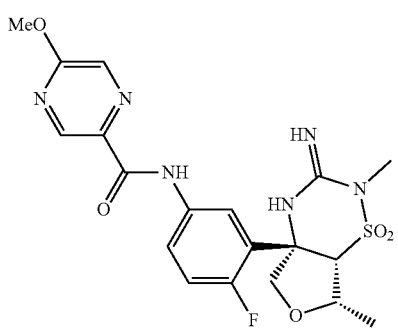 |
| 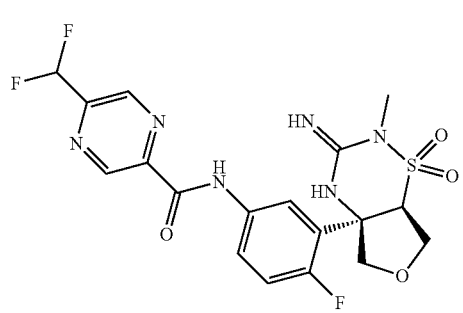 [SMILES: CN1C(=N)N[C@]2(c3cc(NC(=O)c4cnc(C(F)F)cn4)ccc3F)COC[C@@H]2S1(=O)=O] | 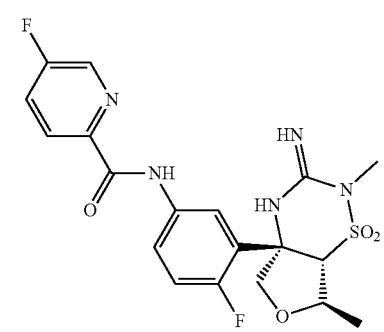 [SMILES: C[C@H]1OC[C@]2(c3cc(NC(=O)c4ccc(F)cn4)ccc3F)NC(=N)N(C)S(=O)(=O)[C@H]12] |
| 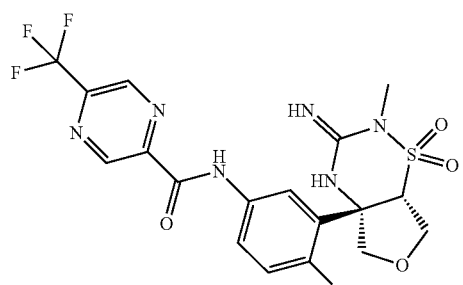 | 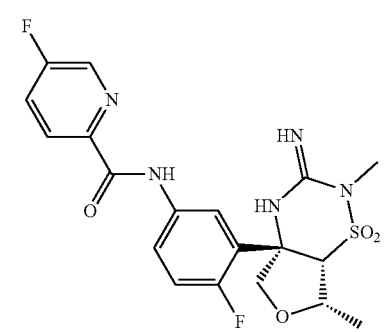 [SMILES: C[C@@H]1OC[C@]2(c3cc(NC(=O)c4ccc(F)cn4)ccc3F)NC(=N)N(C)S(=O)(=O)[C@H]12] |
| 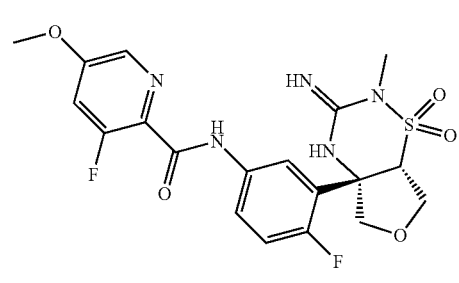 | |

| Example |
|---|
| 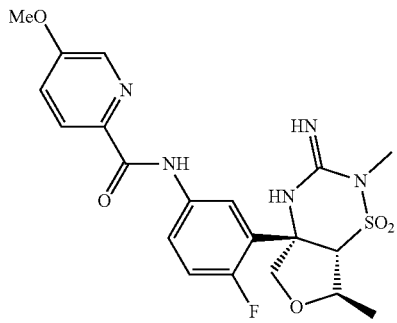 [SMILES: COc1ccc(C(=O)Nc2ccc(F)c([C@]34CO[C@H](C)[C@H]3S(=O)(=O)N(C)C(=N)N4)c2)nc1] |
| 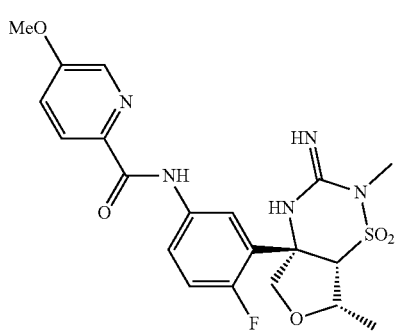 [SMILES: COc1ccc(C(=O)Nc2ccc(F)c([C@]34CO[C@@H](C)[C@H]3S(=O)(=O)N(C)C(=N)N4)c2)nc1] |
| 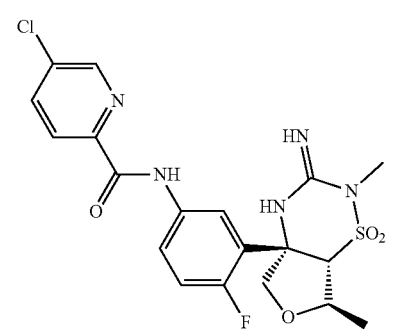 [SMILES: C[C@H]1OC[C@]2(c3cc(NC(=O)c4ccc(Cl)cn4)ccc3F)NC(=N)N(C)S(=O)(=O)[C@H]12] |
| 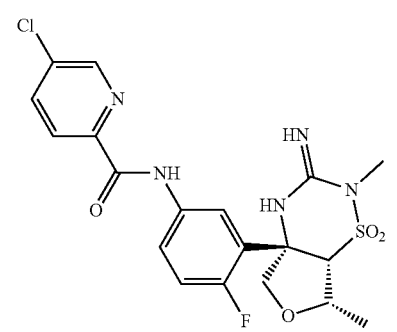 [SMILES: C[C@@H]1OC[C@]2(c3cc(NC(=O)c4ccc(Cl)cn4)ccc3F)NC(=N)N(C)S(=O)(=O)[C@H]12] |
| Example |
|---|
| 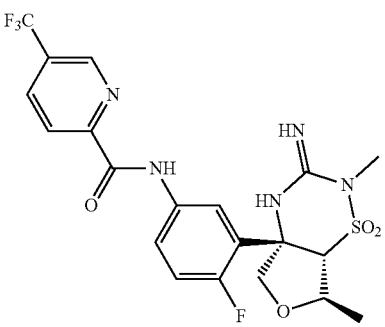 [SMILES: C[C@H]1OC[C@]2(c3cc(NC(=O)c4ccc(C(F)(F)F)cn4)ccc3F)NC(=N)N(C)S(=O)(=O)[C@H]12] |
| 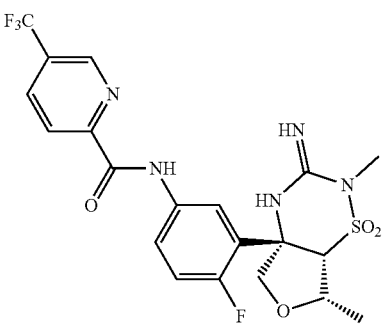 [SMILES: C[C@@H]1OC[C@]2(c3cc(NC(=O)c4ccc(C(F)(F)F)cn4)ccc3F)NC(=N)N(C)S(=O)(=O)[C@H]12] |
| 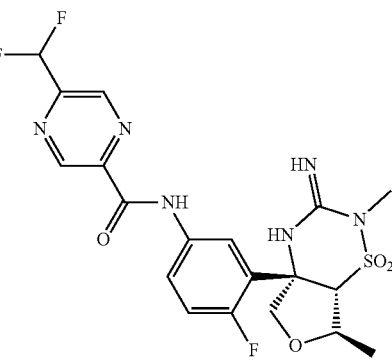 |
| 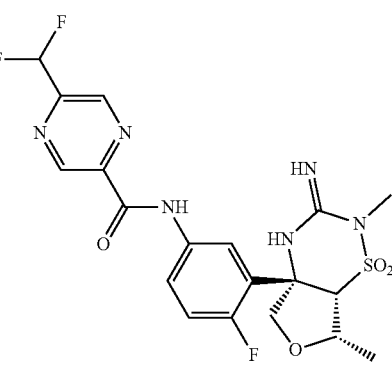 |

| Example |
|---|
| 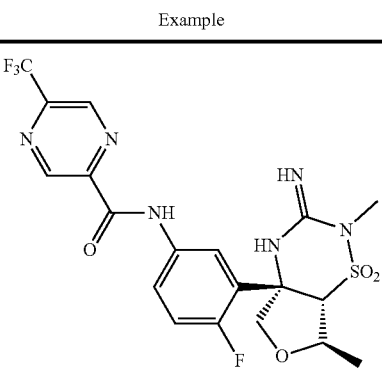 |
| 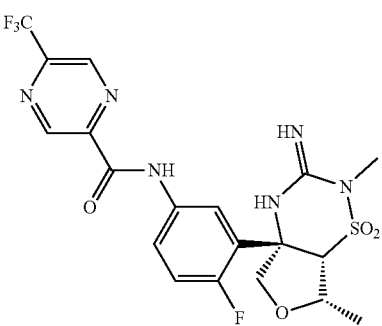 [SMILES: C[C@@H]1OC[C@]2(c3cc(NC(=O)c4cnc(C(F)(F)F)cn4)ccc3F)NC(=N)N(C)S(=O)(=O)[C@H]12] |
| 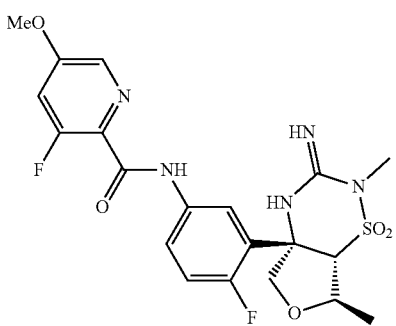 [SMILES: COc1cnc(C(=O)Nc2ccc(F)c([C@]34CO[C@H](C)[C@H]3S(=O)(=O)N(C)C(=N)N4)c2)c(F)c1] |
| 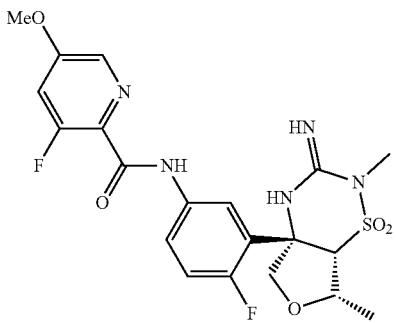 [SMILES: COc1cnc(C(=O)Nc2ccc(F)c([C@]34CO[C@@H](C)[C@H]3S(=O)(=O)N(C)C(=N)N4)c2)c(F)c1] |
| Example |
|---|
| 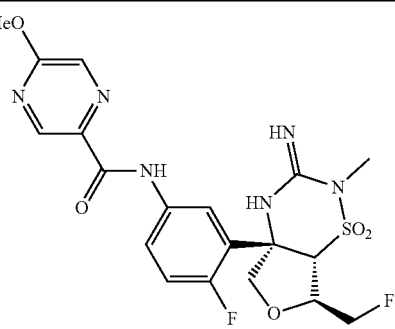 |
| 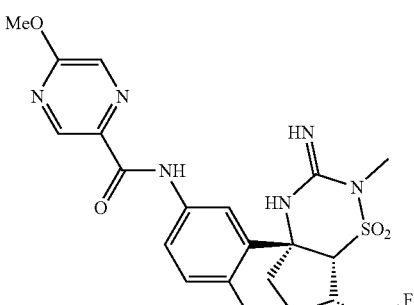 |
| 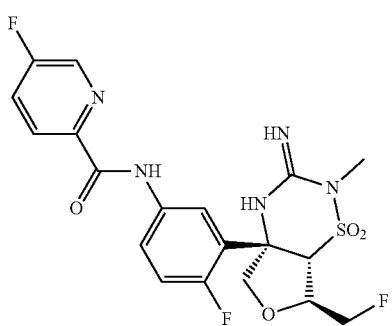 [SMILES: CN1C(=N)N[C@@]2(c3cc(NC(=O)c4ccc(F)cn4)ccc3F)CO[C@H](CF)[C@H]2S1(=O)=O] |
| 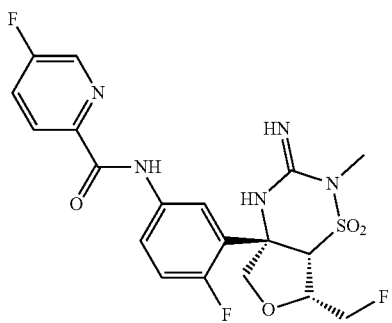 [SMILES: CN1C(=N)N[C@@]2(c3cc(NC(=O)c4ccc(F)cn4)ccc3F)CO[C@@H](CF)[C@H]2S1(=O)=O] |

| Example |
|---|
| 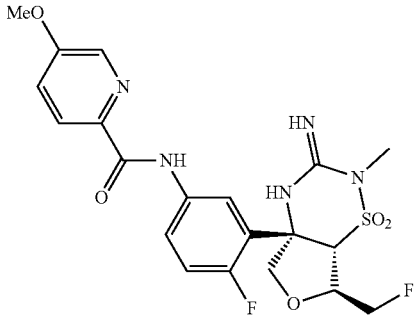 [SMILES: COc1ccc(C(=O)Nc2ccc(F)c([C@]34CO[C@H](CF)[C@H]3S(=O)(=O)N(C)C(=N)N4)c2)nc1] |
| 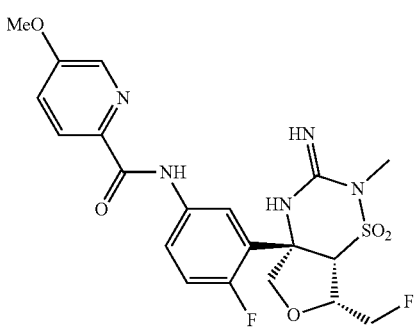 |
| 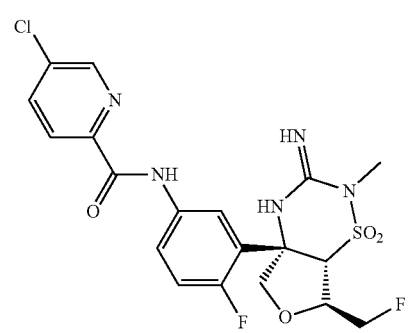 [SMILES: CN1C(=N)N[C@@]2(c3cc(NC(=O)c4ccc(Cl)cn4)ccc3F)CO[C@H](CF)[C@H]2S1(=O)=O] |
| 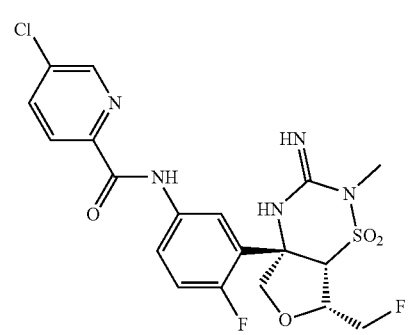 [SMILES: CN1C(=N)N[C@@]2(c3cc(NC(=O)c4ccc(Cl)cn4)ccc3F)CO[C@@H](CF)[C@H]2S1(=O)=O] |
| Example |
|---|
| 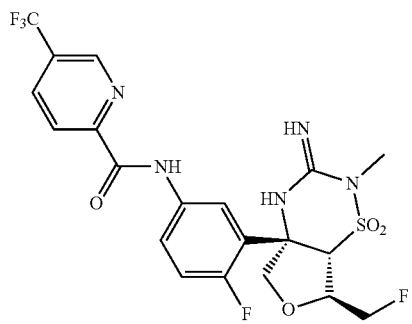 [SMILES: CN1C(=N)N[C@@]2(c3cc(NC(=O)c4ccc(C(F)(F)F)cn4)ccc3F)CO[C@H](CF)[C@H]2S1(=O)=O] |
| 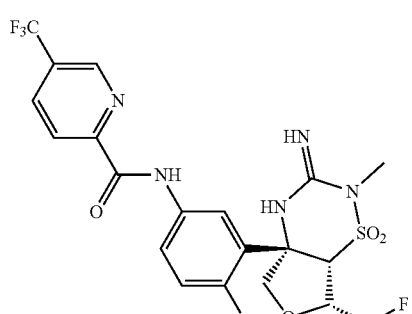 |
| 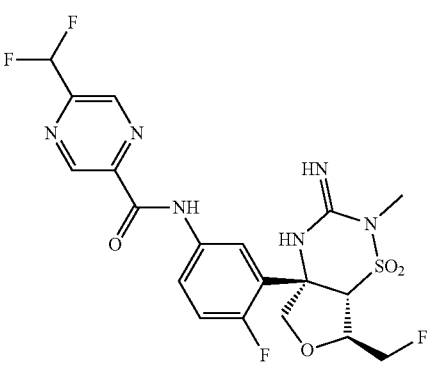 [SMILES: CN1C(=N)N[C@@]2(c3cc(NC(=O)c4cnc(C(F)F)cn4)ccc3F)CO[C@H](CF)[C@H]2S1(=O)=O] |
| 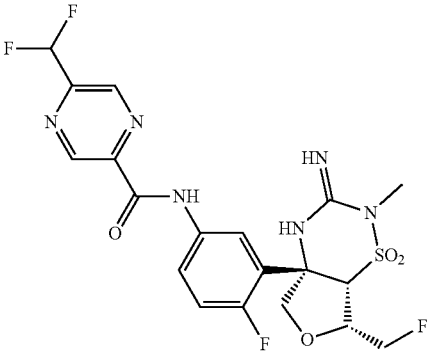 [SMILES: CN1C(=N)N[C@@]2(c3cc(NC(=O)c4cnc(C(F)F)cn4)ccc3F)CO[C@@H](CF)[C@H]2S1(=O)=O] |

| Example |
|---|
| 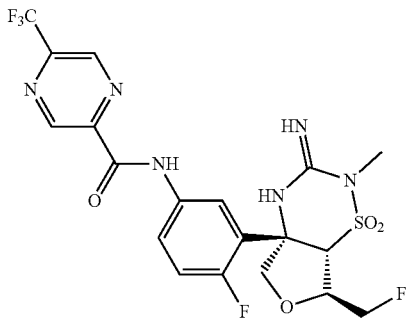 [SMILES: CN1C(=N)N[C@@]2(c3cc(NC(=O)c4cnc(C(F)(F)F)cn4)ccc3F)CO[C@H](CF)[C@H]2S1(=O)=O] |
| 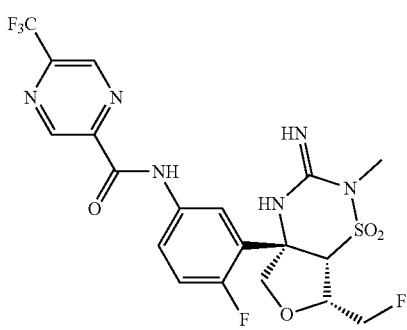 [SMILES: CN1C(=N)N[C@@]2(c3cc(NC(=O)c4cnc(C(F)(F)F)cn4)ccc3F)CO[C@@H](CF)[C@H]2S1(=O)=O] |
| 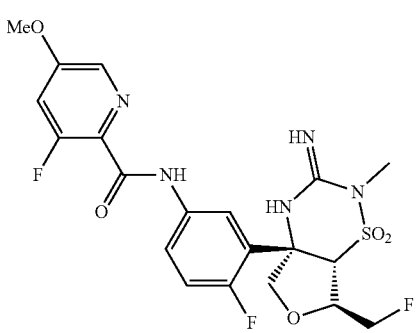 [SMILES: COc1cnc(C(=O)Nc2ccc(F)c([C@]34CO[C@H](CF)[C@H]3S(=O)(=O)N(C)C(=N)N4)c2)c(F)c1] |
| 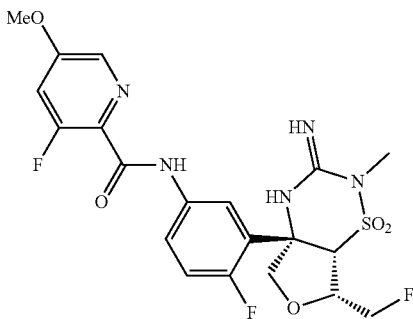 [SMILES: COc1cnc(C(=O)Nc2ccc(F)c([C@]34CO[C@@H](CF)[C@H]3S(=O)(=O)N(C)C(=N)N4)c2)c(F)c1] |
| 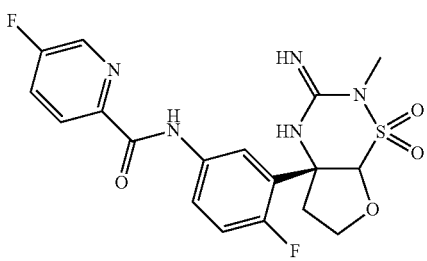 [SMILES: CN1C(=N)N[C@@]2(c3cc(NC(=O)c4ccc(F)cn4)ccc3F)CCOC2S1(=O)=O] |
| Example |
|---|
| 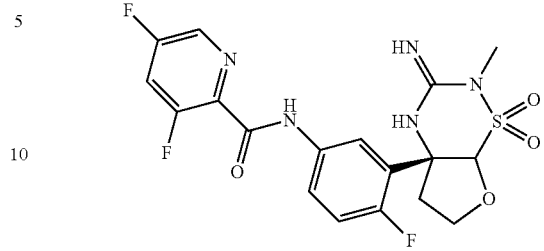 |
| 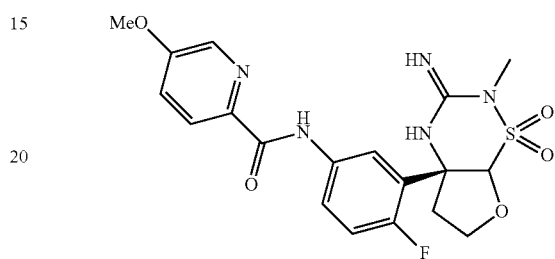 |
| 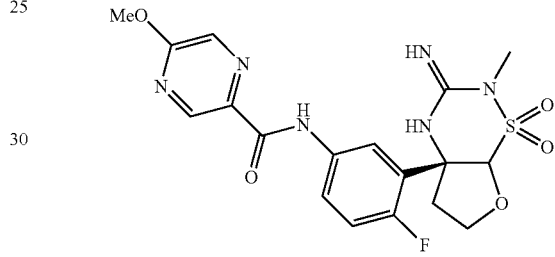 |
| 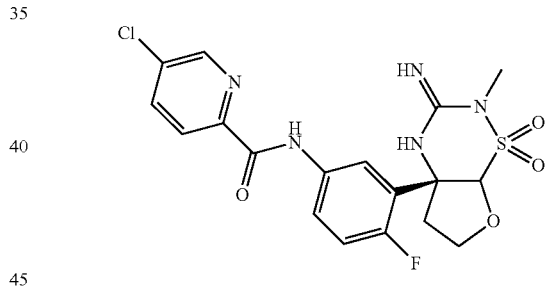 |
| 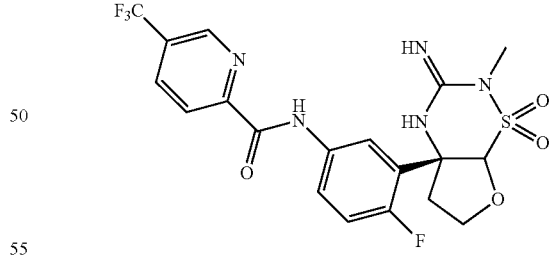 |
| 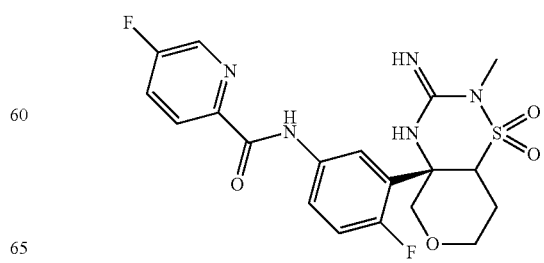 |

| Example |
|---|
| 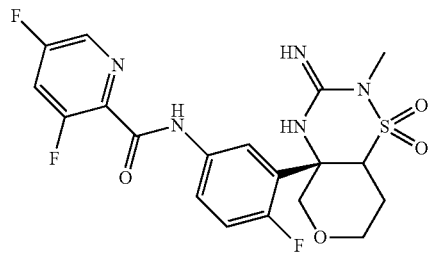 [SMILES: CN1C(=N)N[C@@]2(c3cc(NC(=O)c4ncc(F)cc4F)ccc3F)COCCC2S1(=O)=O] |
| 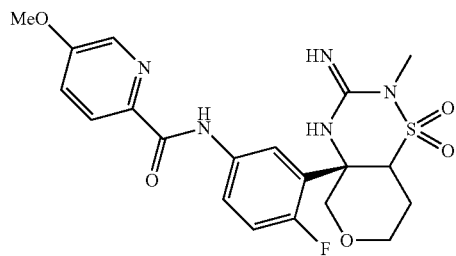 [SMILES: COc1ccc(C(=O)Nc2ccc(F)c([C@]34COCCC3S(=O)(=O)N(C)C(=N)N4)c2)nc1] |
| 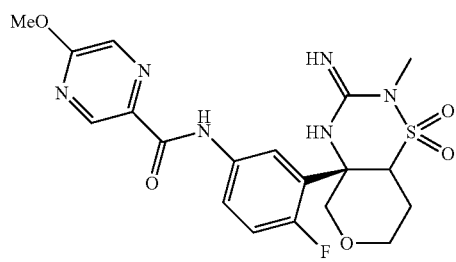 [SMILES: COc1cnc(C(=O)Nc2ccc(F)c([C@]34COCCC3S(=O)(=O)N(C)C(=N)N4)c2)cn1] |
| 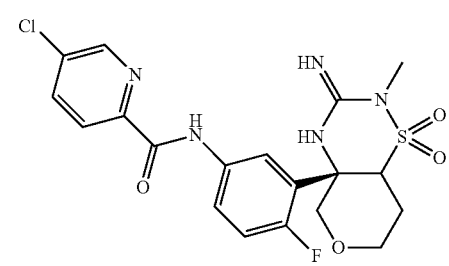 |
| 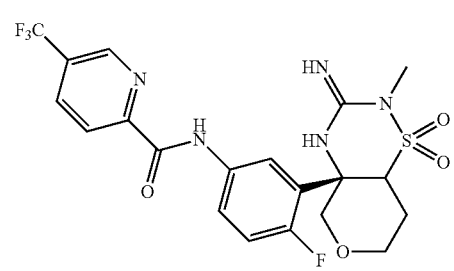 [SMILES: CN1C(=N)N[C@@]2(c3cc(NC(=O)c4ccc(C(F)(F)F)cn4)ccc3F)COCCC2S1(=O)=O] |
| 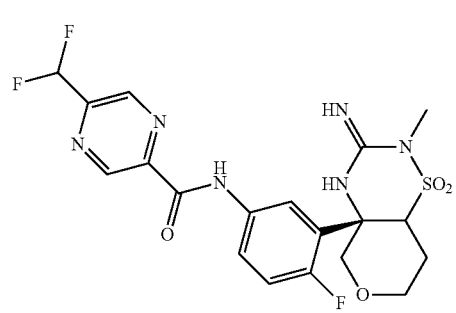 [SMILES: CN1C(=N)N[C@@]2(c3cc(NC(=O)c4cnc(C(F)F)cn4)ccc3F)COCCC2S1(=O)=O] |
| Example |
|---|
| 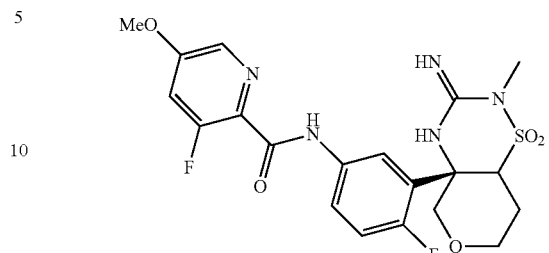 |
| 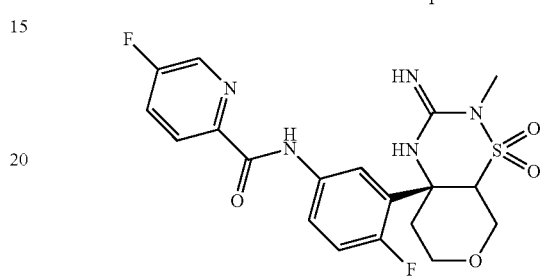 |
| 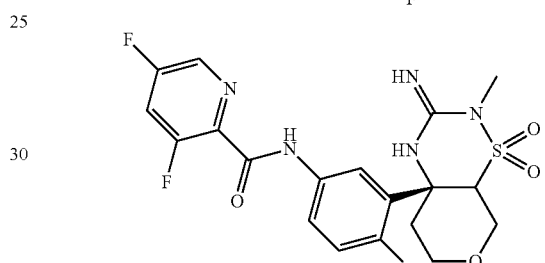 |
| 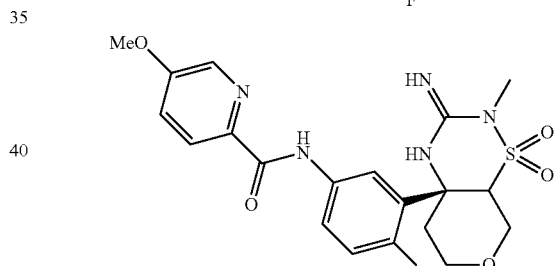 |
| 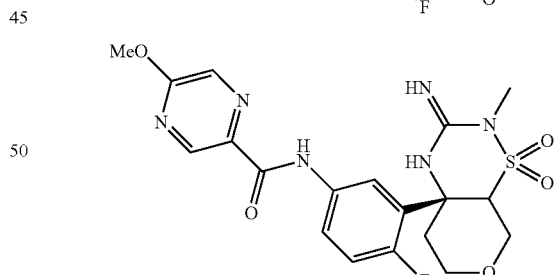 |
| 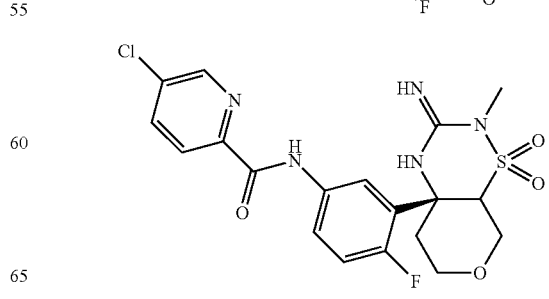 |

| Example |
|---|
| 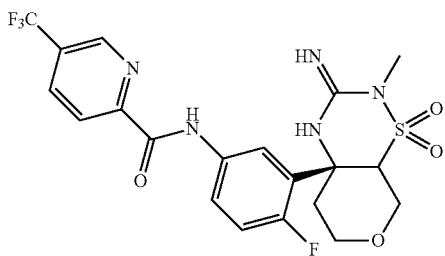 [SMILES: CN1C(=N)N[C@@]2(c3cc(NC(=O)c4ccc(C(F)(F)F)cn4)ccc3F)CCOCC2S1(=O)=O] |
| 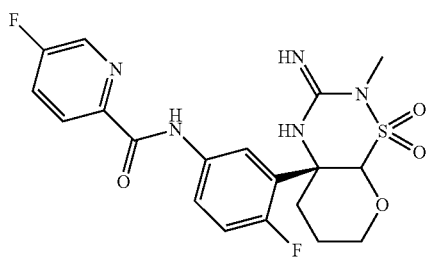 [SMILES: CN1C(=N)N[C@@]2(c3cc(NC(=O)c4ccc(F)cn4)ccc3F)CCCOC2S1(=O)=O] |
| 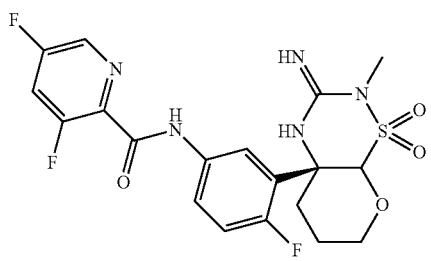 |
| 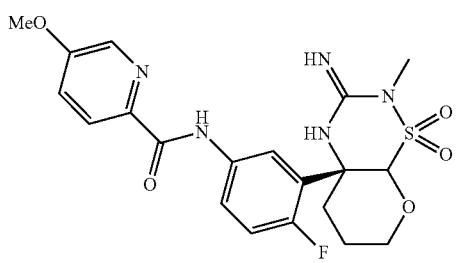 |
| 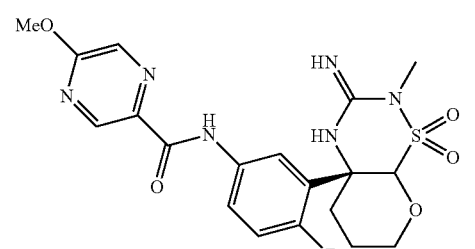 |
| 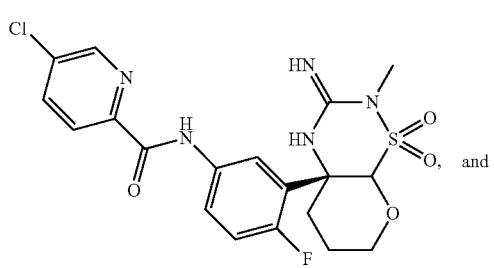 [SMILES: CN1C(=N)N[C@@]2(c3cc(NC(=O)c4ccc(Cl)cn4)ccc3F)CCCOC2S1(=O)=O], and |
| Example |
|---|
| 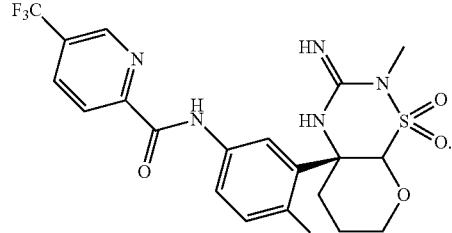 |
8. A compound of claim 1, or a tautomer thereof, or a stereoisomer of said compound or said tautomer, or a pharmaceutically acceptable salt of said compound, said tautomer, or said stereoisomer, said compound selected from the group consisting of:
| Example |
|---|
| 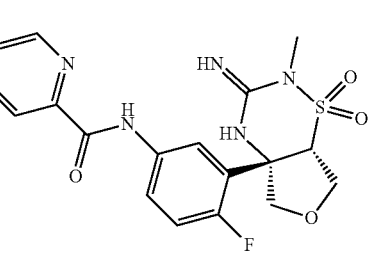 |
| 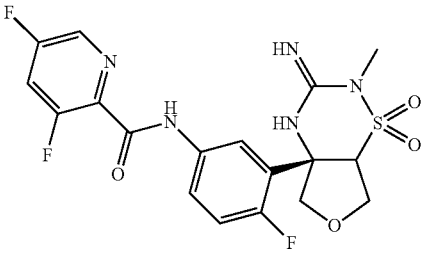 [SMILES: CN1C(=N)N[C@@]2(c3cc(NC(=O)c4ncc(F)cc4F)ccc3F)COCC2S1(=O)=O] |
| 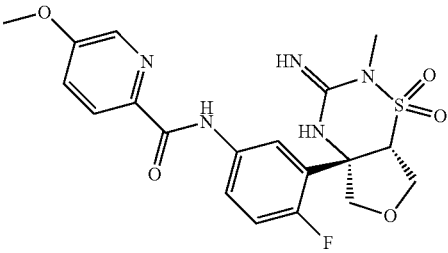 |
| 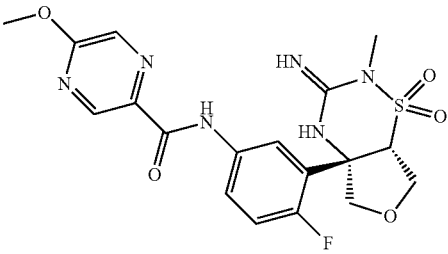 [SMILES: COc1cnc(C(=O)Nc2ccc(F)c([C@]34COC[C@H]3S(=O)(=O)N(C)C(=N)N4)c2)cn1] |

209
-continued
Example
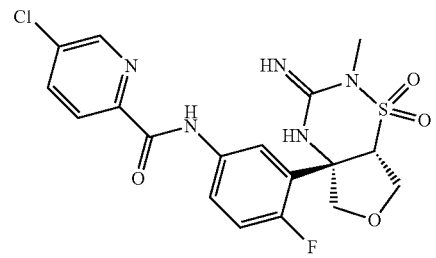 [SMILES: CN1C(=N)N[C@@]2(c3cc(NC(=O)c4ccc(Cl)cn4)ccc3F)COC[C@H]2S1(=O)=O]
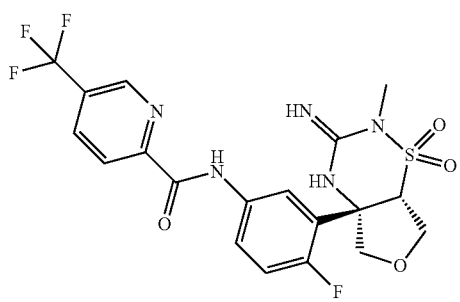 [SMILES: CN1C(=N)N[C@@]2(c3cc(NC(=O)c4ccc(C(F)(F)F)cn4)ccc3F)COC[C@H]2S1(=O)=O]
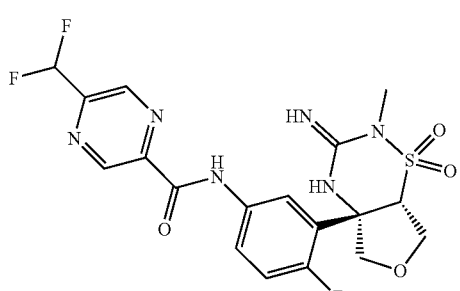
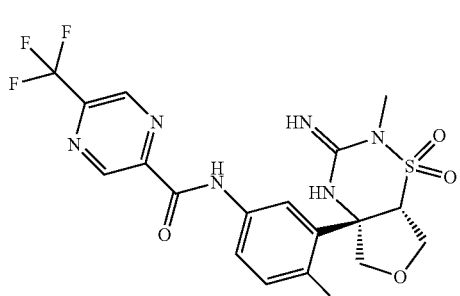
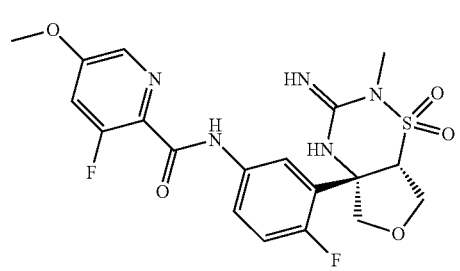 [SMILES: COc1cnc(C(=O)Nc2ccc(F)c([C@]34COC[C@H]3S(=O)(=O)N(C)C(=N)N4)c2)c(F)c1]
210
-continued
Example
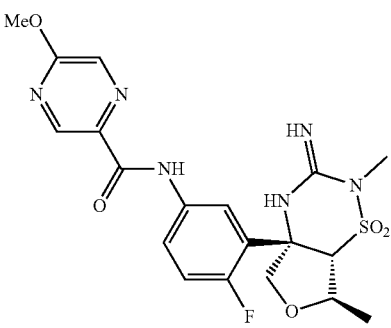 [SMILES: COc1cnc(C(=O)Nc2ccc(F)c([C@]34CO[C@H](C)[C@H]3S(=O)(=O)N(C)C(=N)N4)c2)cn1]
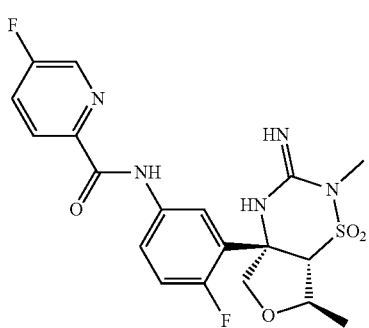 [SMILES: C[C@H]1OC[C@]2(c3cc(NC(=O)c4ccc(F)cn4)ccc3F)NC(=N)N(C)S(=O)(=O)[C@H]12]
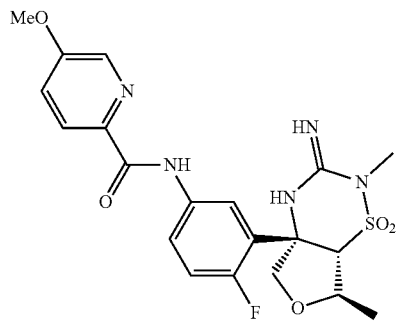 [SMILES: COc1ccc(C(=O)Nc2ccc(F)c([C@]34CO[C@H](C)[C@H]3S(=O)(=O)N(C)C(=N)N4)c2)nc1]
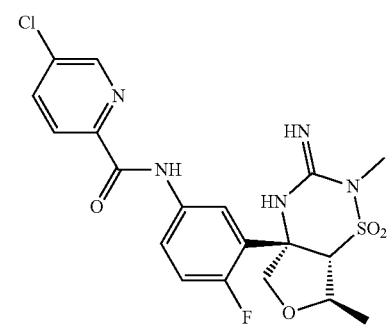 [SMILES: C[C@H]1OC[C@]2(c3cc(NC(=O)c4ccc(Cl)cn4)ccc3F)NC(=N)N(C)S(=O)(=O)[C@H]12]

| Example | Example |
|---|---|
| 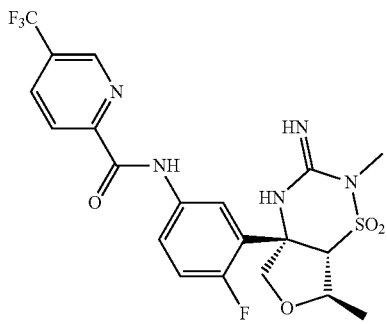 [SMILES: C[C@H]1OC[C@]2(c3cc(NC(=O)c4ccc(C(F)(F)F)cn4)ccc3F)NC(=N)N(C)S(=O)(=O)[C@H]12] | 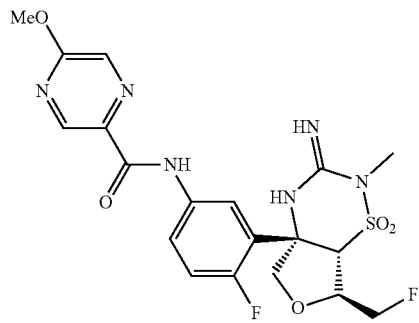 |
| 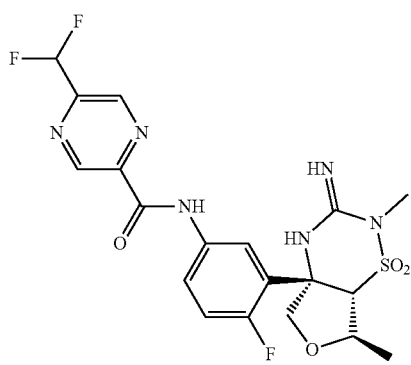 [SMILES: C[C@H]1OC[C@]2(c3cc(NC(=O)c4cnc(C(F)F)cn4)ccc3F)NC(=N)N(C)S(=O)(=O)[C@H]12] | 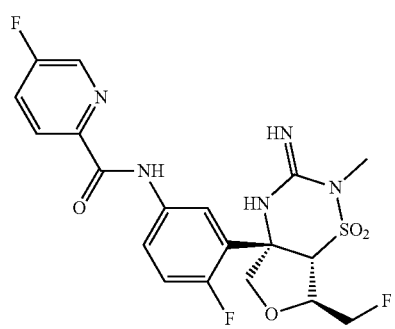 |
| 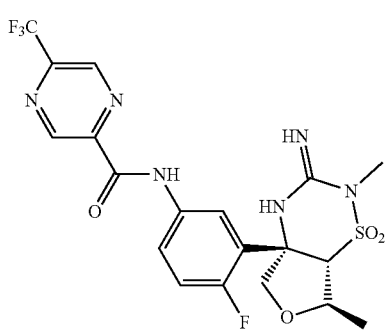 [SMILES: C[C@H]1OC[C@]2(c3cc(NC(=O)c4cnc(C(F)(F)F)cn4)ccc3F)NC(=N)N(C)S(=O)(=O)[C@H]12] | 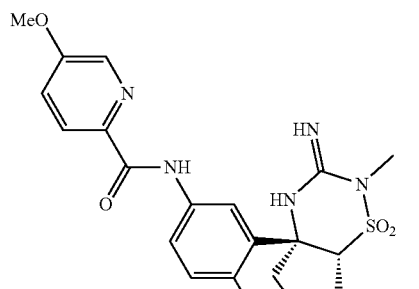 |
| 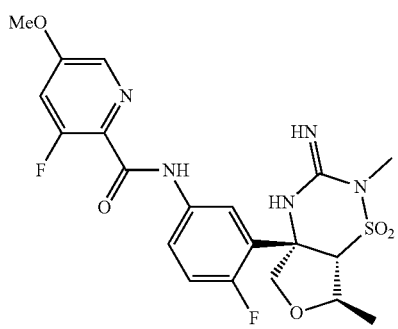 [SMILES: COc1cnc(C(=O)Nc2ccc(F)c([C@]34CO[C@H](C)[C@H]3S(=O)(=O)N(C)C(=N)N4)c2)c(F)c1] | 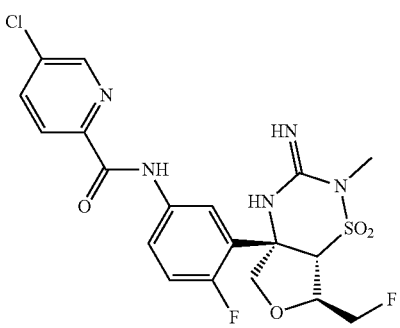 [SMILES: CN1C(=N)N[C@@]2(c3cc(NC(=O)c4ccc(Cl)cn4)ccc3F)CO[C@H](CF)[C@H]2S1(=O)=O] |

| 213 -continued | 214 -continued |
|---|---|
| Example | Example |
| 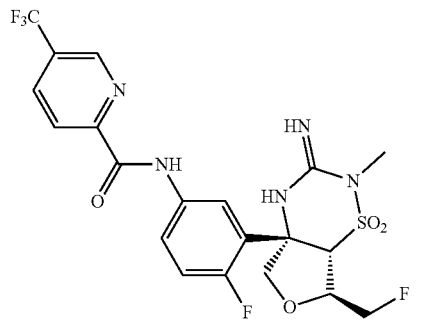 [SMILES: CN1C(=N)N[C@@]2(c3cc(NC(=O)c4ccc(C(F)(F)F)cn4)ccc3F)CO[C@H](CF)[C@H]2S1(=O)=O] | 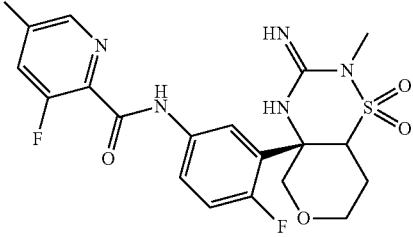 |
| 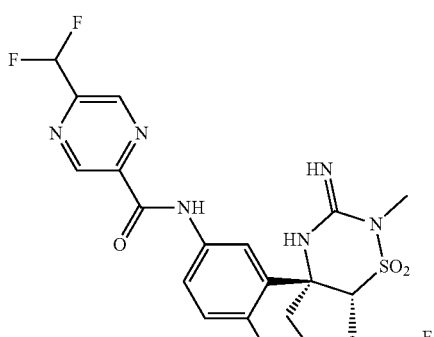 | 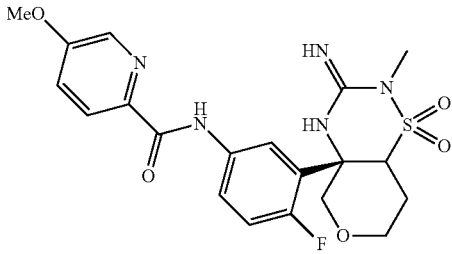 |
| 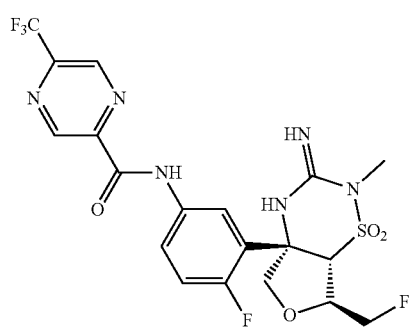 | 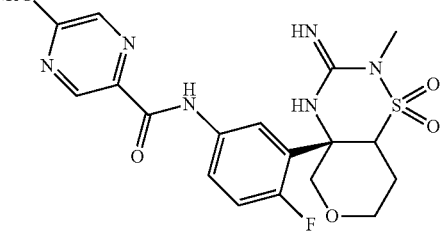 |
| 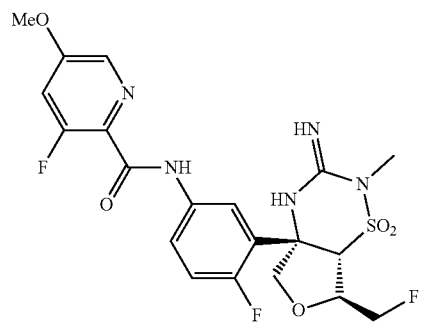 [SMILES: COc1cnc(C(=O)Nc2ccc(F)c([C@]34CO[C@H](CF)[C@H]3S(=O)(=O)N(C)C(=N)N4)c2)c(F)c1] | 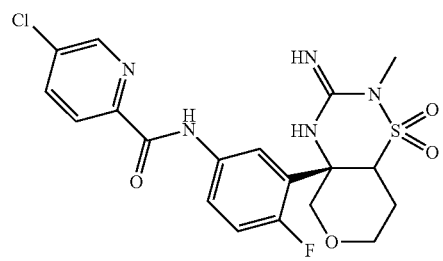 |
| 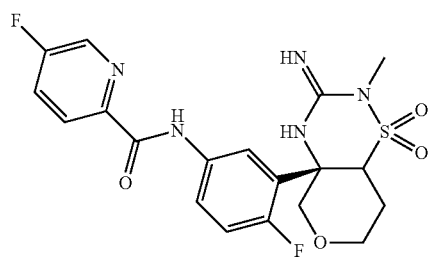 [SMILES: CN1C(=N)N[C@@]2(c3cc(NC(=O)c4ccc(F)cn4)ccc3F)COCCC2S1(=O)=O] | 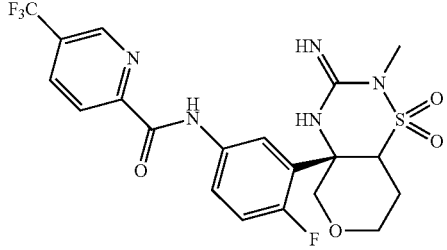 [SMILES: CN1C(=N)N[C@@]2(c3cc(NC(=O)c4ccc(C(F)(F)F)cn4)ccc3F)COCCC2S1(=O)=O] |
| | 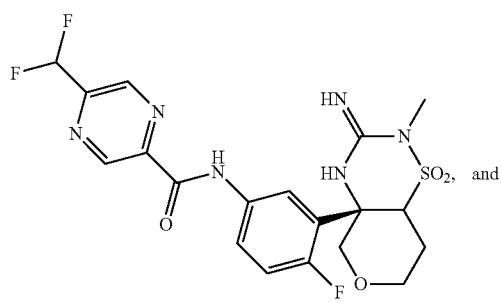 [SMILES: CN1C(=N)N[C@@]2(c3cc(NC(=O)c4cnc(C(F)F)cn4)ccc3F)COCCC2S1(=O)=O] |

Example

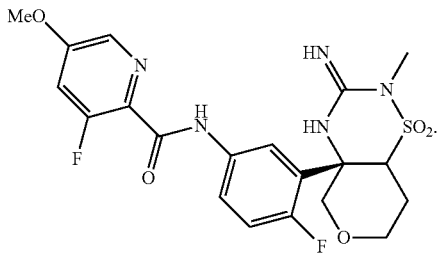 [SMILES: COc1cnc(C(=O)Nc2ccc(F)c([C@]34COCCC3S(=O)(=O)N(C)C(=N)N4)c2)c(F)c1]

9. A pharmaceutical composition comprising at least one compound of claim 1, or a tautomer thereof, or a stereoisomer of said compound or said tautomer, or a pharmaceutically acceptable salt thereof, and a pharmaceutically acceptable carrier or diluent.

10. A pharmaceutical composition of claim 9, wherein said at least one additional therapeutic agent is at least one agent selected from: $m_1$ agonists; $m_2$ antagonists; cholinesterase inhibitors; galantamine; rivastigimine; N-methyl-D-aspartate receptor antagonists; combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies; vitamin E; nicotinic acetylcholine receptor agonists; CB1 receptor inverse agonists; CB1 receptor antagonists; antibiotics; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Tau kinase inhibitors; Tau aggregation inhibitors; RAGE inhibitors; anti-Abeta vaccine; APP ligands; agents that upregulate insulin, cholesterol lowering agents; cholesterol absorption inhibitors; combinations of HMG-CoA reductase inhibitors and cholesterol absorption inhibitors; fibrates; combinations of fibrates and cholesterol lowering agents and/or cholesterol absorption inhibitors; nicotinic receptor agonists; niacin; combinations of niacin and cholesterol absorption inhibitors and/or cholesterol lowering agents; LXR agonists; LRP mimics; H3 receptor antagonists; histone deacetylase inhibitors; hsp90 inhibitors; 5-HT4 agonists; 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux; Metal-protein attenuating compound; GPR3 modulators; and antihistamines.

11. A method of treating and/or delaying the onset of a disease or pathology, wherein said disease or pathology is selected from the group consisting of Alzheimer's disease, Down's syndrome, Parkinson's disease, stroke, microgliosis, brain inflammation, pre-senile dementia, senile dementia, progressive supranuclear palsy, cortical basal degeneration, olfactory impairment associated with Alzheimer's disease, olfactory impairment associated with Parkinson's disease, olfactory impairment associated with Down's syndrome, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, and Creutzfeld-Jakob disease, said method comprising administering to a patient in need thereof a compound according to claim 1, or a tautomer thereof, or a pharmaceutically acceptable salt of said compound or said tautomer.

12. The method of claim 11, wherein said disease or pathology is Alzheimer's disease.

* * * * *